(12) United States Patent
Sircar et al.

(10) Patent No.: US 7,375,118 B2
(45) Date of Patent: May 20, 2008

(54) PHENYL-INDOLE COMPOUNDS FOR MODULATING IGE AND INHIBITING CELLULAR PROLIFERATION

(75) Inventors: Jagadish C. Sircar, San Diego, CA (US); Jailall Ramnauth, Toronto (CA); Mark L. Richards, La Jolla, CA (US)

(73) Assignee: Avanir Pharmaceuticals, San Diego, CA (US)

( * ) Notice: Subject to any disclaimer, the term of this patent is extended or adjusted under 35 U.S.C. 154(b) by 614 days.

(21) Appl. No.: 10/661,139

(22) Filed: Sep. 12, 2003

(65) Prior Publication Data

US 2004/0180946 A1 Sep. 16, 2004

Related U.S. Application Data

(60) Provisional application No. 60/410,777, filed on Sep. 12, 2002.

(51) Int. Cl.
*A61K 31/44* (2006.01)
*A61K 31/404* (2006.01)
*C07D 209/04* (2006.01)
*C07D 401/12* (2006.01)

(52) U.S. Cl. ............... 514/339; 548/465; 548/469; 548/490; 548/491; 546/268.1; 546/277.4; 514/336; 514/415

(58) Field of Classification Search ............... 548/465, 548/469, 490, 491; 546/268.1, 277.4; 514/415, 514/336, 339
See application file for complete search history.

(56) References Cited

U.S. PATENT DOCUMENTS

| | | | |
|---|---|---|---|
| 4,510,158 A | 4/1985 | Bailey | |
| 4,582,837 A | 4/1986 | Hauel et al. | |
| 4,696,931 A | 9/1987 | Hauel et al. | |
| 5,017,467 A | 5/1991 | Masukawa et al. | |
| 5,124,336 A | 6/1992 | Bru-Magniez et al. | |
| 5,322,847 A | 6/1994 | Marfat et al. | |
| 5,380,865 A | 1/1995 | Cramp et al. | |
| 5,643,893 A | 7/1997 | Benson et al. | |
| 5,712,392 A | 1/1998 | Thurkauf et al. | |
| 5,821,258 A | 10/1998 | Matsunanaga et al. | |
| 5,935,983 A | 8/1999 | Muller-Gliemann et al. | |
| 6,093,728 A | 7/2000 | McMahon et al. | |
| 6,100,282 A | 8/2000 | Alig et al. | |
| 6,100,283 A | 8/2000 | Griffin et al. | |
| 6,153,631 A | 11/2000 | Petrie et al. | |
| 6,271,249 B1 | 8/2001 | Romine et al. | |
| 6,271,390 B1 | 8/2001 | Sircar et al. | |
| 6,288,101 B1 | 9/2001 | Glennon | |
| 6,303,645 B1 | 10/2001 | Sircar et al. | |
| 6,369,091 B1 | 4/2002 | Sircar et al. | |
| 6,387,938 B1 | 5/2002 | Mizuguchi et al. | |
| 6,451,829 B2 | 9/2002 | Sircar et al. | |
| 6,486,153 B1 | 11/2002 | Castro Pineiro et al. | |
| 6,503,938 B1 | 1/2003 | Von Angerer et al. | |
| 6,509,365 B1 | 1/2003 | Lubisch et al. | |
| 6,537,994 B2 | 3/2003 | Ashwell et al. | |
| 6,759,425 B2 | 7/2004 | Sircar et al. | |
| 6,911,462 B2 | 6/2005 | Sircar et al. | |
| 6,919,366 B2 | 7/2005 | Sircar et al. | |
| 2002/0010343 A1 | 1/2002 | Sircar et al. | |
| 2002/0132808 A1 | 9/2002 | Sircar et al. | |
| 2003/0004203 A1 | 1/2003 | Sircar et al. | |
| 2003/0100582 A1 | 5/2003 | Sircar et al. | |
| 2004/0116466 A1 | 6/2004 | Sircar et al. | |
| 2004/0214821 A1 | 10/2004 | Sircar et al. | |
| 2004/0229927 A1 | 11/2004 | Sircar et al. | |
| 2005/0075343 A1 | 4/2005 | Sircar et al. | |
| 2005/0197375 A1 | 9/2005 | Sircar et al. | |
| 2005/0256179 A1 | 11/2005 | Sircar et al. | |
| 2005/0277686 A1 | 12/2005 | Sircar et al. | |

FOREIGN PATENT DOCUMENTS

| | | |
|---|---|---|
| EP | 0 221 146 A1 | 5/1987 |
| EP | 0 221 346 A1 | 5/1987 |
| EP | 0 232 199 A2 | 8/1987 |
| EP | 0 353 606 A2 | 2/1990 |
| EP | 0 415 886 A2 | 8/1990 |
| EP | 0 385 850 A2 | 9/1990 |
| EP | 0 469 477 A1 | 2/1992 |
| EP | 0 497 564 A1 | 8/1992 |

(Continued)

OTHER PUBLICATIONS

Related pending U.S. Appl. No. 10/661,296, filed Sep. 12, 2003. Title: Phenyl-Aza-Benzimidazole Compounds for Modulating IgE and Inhibiting Cellular Proliferation. Inventors: Jagadish C. Sircar et al.

(Continued)

*Primary Examiner*—Golam M. M. Shameem
(74) *Attorney, Agent, or Firm*—Knobbe Martens Olson & Bear LLP

(57) ABSTRACT

The present invention is directed to small molecule inhibitors of the IgE response to allergens, which are useful in the treatment of allergy and/or asthma or any diseases where IgE is pathogenic. This invention also relates to phenyl-indole molecules that are cellular proliferation inhibitors and thus are useful as anticancer agents. This invention further relates to small molecules which suppress cytokines and leukocytes.

15 Claims, No Drawings

FOREIGN PATENT DOCUMENTS

| | | |
|---|---|---|
| EP | 0 694 535 A1 | 1/1996 |
| EP | 0 700 906 A1 | 3/1996 |
| EP | 0 719 765 A2 | 7/1996 |
| EP | 1 077 700 A1 | 2/2001 |
| EP | 1 123 295 | 8/2001 |
| EP | 1 125 936 A2 | 8/2001 |
| JP | 06 263993 A | 9/1994 |
| SU | 1316559 | 6/1983 |
| WO | WO 89 06975 | 8/1989 |
| WO | WO 90 09989 | 9/1990 |
| WO | WO 92/02500 | 2/1992 |
| WO | WO 93 25517 | 12/1993 |
| WO | WO 98 17267 | 4/1998 |
| WO | WO 98 47890 | 10/1998 |
| WO | WO 98 56761 | 12/1998 |
| WO | WO 99 61020 A1 | 2/1999 |
| WO | WO 99 61013 A1 | 12/1999 |
| WO | WO 99 61019 A1 | 12/1999 |
| WO | WO 00 26192 A1 | 5/2000 |
| WO | WO 00 29384 A1 | 5/2000 |
| WO | WO 00 32579 A1 | 6/2000 |
| WO | WO 00 64878 A1 | 11/2000 |
| WO | WO 00 68206 A1 | 11/2000 |
| WO | WO 01 12169 A2 | 2/2001 |
| WO | WO 01 14342 A1 | 3/2001 |
| WO | WO 01 72737 A1 | 10/2001 |
| WO | WO 02 072090 | 9/2002 |
| WO | WO 02 072539 A1 | 9/2002 |
| WO | WO 02 072574 A1 | 9/2002 |

OTHER PUBLICATIONS

Related pending U.S. Appl. No. 10/795,006, filed Mar. 5, 2004. Title: Benzimidazole Compounds for Modulating IgE and Inhibiting Cellular Proliferation. Inventors: Jagadish C. Sircar et al.

Related pending U.S. Appl. No. 10/821,667, filed Apr. 9, 2004. Title: Imidazole Derivatives for Treatment of Allergic and Hyperproliferative Disorders. Inventors: Jagadish C. Sircar et al.

Related pending U.S. Appl. No. 10/915,722, filed Aug. 9, 2004. Title: Selective Pharmacologic Inhibition of Protein Trafficking and Related Methods of Treating Human Diseases. Inventors: Jagadish C. Sircar et al.

Related pending U.S. Appl. No. 10/508,968, filed Sep. 24, 2004. Title: Use of Benzimidazole Analogs in the Treatment of Cell Proliferation. Inventors: Jagadish C. Sircar et al.

Related pending U.S. Appl. No. 10/951,515, filed Sep. 28, 2004. Title: Benzimidazole Derivatives as Modulators of IgE. Inventors: Jagadish C. Sircar et al.

Related pending U.S. Appl. No. 11/168,711, filed Jun. 28, 2005. Title: Benzimidazole Compounds for Regulating IgE. Inventors: Jagadish C. Sircar et al.

Manecke et al., Ü ber Polyamide mit 2,4-Imidazolidiyl-Bausteinen, Die Makromolekulare Chemie 176, pp. 3551-3563, Apr. 29, 1975, Institut für Organische Chemie der Freien Universität Berline, D-1 Berlin 33.

Cheney B V, et al., "Structure-activity Correlations for a Series of Antiallergy Agents. 3. Development of a Quantitative Model," Journal of Medicinal Chemistry, vol. 26, No. 5, 1983, pp. 726-737.

Pozdnyakov et al., "Mass Spectrometric Study of Dissociative Ionization of Low-molecular Models of Aromatic Polyamides," Khim. Vys. Energ. (1987), 21(1), 38-44 Coden; Khvkao; ISSN: 0023-1193, 1987.

English language abstract of Pozdnyakov, et al. (1987) "Mass spectrometric study of dissociative ionization of low-molecular models of aromatic polyamides," vol. 21 (1), pp. 38-44.

Database Crossifre Beilstein 'Online!, Beilstein Institut zur Forderung der Chemischen Wissenchaften, Frankfurt am Main, DE; Beilstein Registry No. 563073 & Khim. Farm. ZH., vol. 22, No. 6, 1988, pp. 697-699.

Karag'ozov S, "Synthesis of N-acyl Derivatives of 6-amio-1-4-benzodioXane," STN International, vol. 39, No. 1989, pp. 5-8, Abstract only.

Masukawa et al., Calplus 111:31259 (EP 304856, Mar. 1, 1989).

Denny W A et al., "Potential antitumor agents. 59. Structure-activity relationships for 2-phenylbenzimidazole-4-carboXamides, a new class of "minimal" DNA-intercalating agents which may not act via topoisomerase II", Journal of Medicinal Chemistry, vol. 33, No. 2, Feb. 1990, pp. 814-819.

Yildir I, "Synthesis of 32-(subtitutephenyl) Benzimidazole Derivatives and their Sedative Activity: Structure-activity Relationships," Journal FaX. Pharm. Gazi Uni., vol. 7, No. 2, 1990, pp. 111-114.

Timothy F. Gallagher, et al., "2,4,5-Triarylimidazole Inhibitors of IL-1 Biosynthesis," Bioorganic & Medicinal Chemistry Letters, vol. 5, No. 11, pp. 1171-1176, 1995.

Ashton et al., "New Low-Density Lipoprotein Receptor Upregulators Acting via a Novel Mechanism," Journal of Medicinal Chemistry, vol. 39, Jan. 1, 1996, pp. 3343-3356.

Krieg et al., ber einige neue Imizazolderivative, Chem. Ber. 100, pp. 4042-4049 (1967), Jun. 28, 1997, Jahrg. 100, Aus dem Institut für Organische Chemie der Freien Universität Berlin, Berlinn-Dahlem.

Kreimeyer A et al., "Suramin analogues with a 2-phenylbenzimidazole moiety as partyial structure; potential anti HIV-and angiostic drugs, 2: Sulfanilic acid, benzendisulfonic, and naphthalenetrisulfonic acid analogues" Archi Der Pharmazie, vol. 331, No. 3, Mar. 1998, pp. 97-103.

Japanese Application No. 10273013, entitled Antagonist for Gonadotrophic Hormone-Releasing Hormone, filed on Sep. 28, 1998, English abstract only.

Database Caplus 'Online! Chemical Abstracts Service, Columbus, Ohio, US; Databse accession No. 2000:214835 & JP 2000 095767 (Takeda Chemical Industries, Ltd.), Apr. 4, 2000.

White A W et al., "Resistance-modifying agents. 9. Synthesis and biological properties of benzimidazole inhibitors of the DNA repair enzyme poly(ADP-ribose) polymerase", Journal of Medicinal Chemistry, vol. 43, No. 2, Nov. 2, 2000, pp. 4084-4097.

Golub et al., Science, vol. 286, Oct. 15, 1999, pp. 531-537.

Farina, et al., IL Farmaco, 2001, "Novel bone antiresorptive agents tht selectively inhibit the osteoclast V-H+-ATPase", vol. 56, pp. 113-116.

Viscardi et al., Journal of Heterocyclic Chemistry, 1990, "Heterocyclic X-azolopyridine intermediates", vol. 27, pp. 1825-1829.

PHENYL-INDOLE COMPOUNDS FOR MODULATING IGE AND INHIBITING CELLULAR PROLIFERATION

RELATED APPLICATIONS

This application claims priority under 35 U.S.C.§119(e) to Provisional Appl. No. 60/410,777 filed on Sep. 12, 2002.

BACKGROUND OF THE INVENTION

1. Field of the Invention

This invention relates to small molecule inhibitors of the IgE response to allergens that are useful in the treatment of allergy and/or asthma or any diseases where IgE is pathogenic. This invention also relates to small molecules that are proliferation inhibitors and thus they are useful as anticancer agents. This invention further relates to small molecules which suppress cytokines and leukocytes.

2. Description of the Related Art

An estimated 10 million persons in the United States have asthma, about 5% of the population. The estimated cost of asthma in the United States exceeds $6 billion. About 25% of patients with asthma who seek emergency care require hospitalization, and the largest single direct medical expenditure for asthma has been inpatient hospital services (emergency care), at a cost of greater than $1.6 billion. The cost for prescription medications, which increased 54% between 1985 and 1990, was close behind at $1.1 billion (Kelly, *Pharmacotherapy* 12:13S–21S (1997)).

According to the National Ambulatory Medical Care Survey, asthma accounts for 1% of all ambulatory care visits, and the disease continues to be a significant cause of missed school days in children. Despite improved understanding of the disease process and better drugs, asthma morbidity and mortality continue to rise in this country and worldwide (U.S. Department of Health and Human Services; 1991, publication no. 91-3042). Thus, asthma constitutes a significant public health problem.

The pathophysiologic processes that attend the onset of an asthmatic episode can be broken down into essentially two phases, both marked by bronchoconstriction, that causes wheezing, chest tightness, and dyspnea. The first, early phase asthmatic response is triggered by allergenis, irritants, or exercise. Allergens cross-link immunoglobulin E (IgE) molecules bound to receptors on mast cells, causing them to release a number of pre-formed inflammatory mediators, including histamine. Additional triggers include the osmotic changes in airway tissues following exercise or the inhalation of cold, dry air. The second, late phase response that follows is characterized by infiltration of activated eosinophils and other inflammatory cells into airway tissues, epithelial desquamonon, and by the presence of highly viscous mucus within the airways. The damage caused by this inflammatory response leaves the airways "primed" or sensitized, such that smaller triggers are required to elicit subsequent asthma symptoms.

A number of drugs are available for the palliative treatment of asthma; however, their efficacies vary markedly. Short-acting $\beta_2$-adrenergic agonists, terbutaline and albuterol, long the mainstay of asthma treatment, act primarily during the early phase as bronchodilators. The newer long-acting $\beta_2$-agonists, salmeterol and formoterol, may reduce the bronchoconstrictive component of the late response. However, because the $\beta_2$-agonists do not possess significant antiinflammatory activity, they have no effect on bronchial hyperreactivity.

Numerous other drugs target specific aspects of the early or late asthmatic responses. For example, antihistamines, like loratadine, inhibit early histamine-mediated inflammatory responses. Some of the newer antihistamines, such as azelastine and ketotifen, may have both antiinflammatory and weak bronchodilatory effects, but they currently do not have any established efficacy in asthma treatment. Phosphodiesterase inhibitors, like theophylline/xanthines, may attenuate late inflammatory responses, but there is no evidence that these compounds decrease bronchial hyperreactivity. Anticholinergics, like ipratopium bromide, which are used in cases of acute asthma to inhibit severe bronchoconstriction, have no effect on early or late phase inflammation, no effect on bronchial hyperreactivity, and therefore, essentially no role in chronic therapy.

The corticosteroid drugs, like budesonide, are the most potent antiinflammatory agents. Inflammatory mediator release inhibitors, like cromolyn and nedocromil, act by stabilizing mast cells and thereby inhibiting the late phase inflammatory response to allergen. Thus, cromolyn and nedocromil, as well as the corticosteroids, all reduce bronchial hyperreactivity by minimizing the sensitizing effect of inflammatory damage to the airways. Unfortunately, these antiinflammatory agents do not produce bronchodilation.

Several new agents have been developed that inhibit specific aspects of asthmatic inflammation. For instance, leukotriene receptor antagonists (ICI-204, 219, accolate), specifically inhibit leukotriene-mediated actions. The leukotrienes have been implicated in the production of both airway inflammation and bronchoconstriction.

Thus, while numerous drugs are currently available for the treatment of asthma, these compounds are primarily palliative and/or have significant side effects. Consequently, new therapeutic approaches which target the underlying cause rather than the cascade of symptoms would be highly desirable. Asthma and allergy share a common dependence on IgE-mediated events. Indeed, it is known that excess IgE production is the underlying cause of allergies in general and allergic asthma in particular (Duplantier and Cheng, *Ann. Rep. Med. Chem.* 29:73–81 (1994)). Thus, compounds that lower IgE levels may be effective in treating the underlying cause of asthma and allergy.

None of the current therapies eliminate the excess circulating IgE. The hypothesis that lowering plasma IgE may reduce the allergic response, was confirmed by recent clinical results with chimeric anti-IgE antibody, CGP-51901, and recombinant humanized monoclonal antibody, rhuMAB-E25. Indeed, three companies, Tanox Biosystems, Inc., Genentech Inc. and Novartis AG are collaborating in the development of a humanized anti-IgE antibody (BioWorld® Today, Feb. 26, 1997, p. 2) which will treat allergy and asthma by neutralizing excess IgE. Tanox has already successfully tested the anti-IgE antibody, CGP-51901, which reduced the severity and duration of nasal symptoms of allergic rhinitis in a 155-patient Phase II trial (Scrip #2080, Nov. 24, 1995, p. 26). Genentech recently disclosed positive results from a 536 patient phase-II/III trials of its recombinant humanized monoclonal antibody, rhuMAB-E25 (BioWorld® Today, Nov. 10, 1998, p. 1). The antibody, rhuMAB-E25, administered by injection (highest dose 300 mg every 2 to 4 weeks as needed) provided a 50% reduction in the number of days a patient required additional "rescue" medicines (antihistimines and decongestants), compared to placebo. More recently, Dr. Henry Milgrom et. al. of the National Jewish Medical and Research Center in Denver, Colo., published the clinical results of rhuMAB-25 in moderate to severe asthma patients (317 patients for 12 weeks, iv injection every two weeks) and concluded that this drug is "going to be a breakthrough" (New England Journal of Medicine, Dec. 23, 1999). A Biologics License Application (BLA) for this product has been submitted to the FDA in June, 2000 jointly by Novartis Pharmaceuticals Corporation, Tanox Inc., and Genentech, Inc. The positive results from anti-IgE antibody trials suggest that therapeutic strategies aimed at IgE down-regulation may be effective.

Cancer and Hyperproliferation Disorders

Cellular proliferation is a normal process that is vital to the normal functioning of most biological processes. Cellular proliferation occurs in all living organisms and involves two main processes: nuclear division (mitosis), and cytoplasmic division (cytokinesis). Because organisms are continually growing and replacing cells, cellular proliferation is essential to the vitality of the healthy cell. The disruption of normal cellular proliferation can result in a variety of disorders. For example, hyperproliferation of cells may cause psoriasis, thrombosis, atherosclerosis, coronary heart disease, myocardial infarction, stroke, smooth muscle neoplasms, uterine fibroid or fibroma, and obliterative diseases of vascular grafts and transplanted organs. Abnormal cell proliferation is most commonly associated with tumor formation and cancer.

Cancer is a major disease and is one of the leading causes of mortality both in the United States and internationally. Indeed, cancer is the second leading cause of death in the United States. According to the National Institute of Health, the overall annual cost for cancer is approximately $107 billion, which includes $37 billion for direct medical costs, $11 billion for indirect costs of lost productivity due to illness and $59 billion for indirect costs of lost productivity due to premature death. Not surprisingly, considerable efforts are underway to develop new treatments and preventative measures to combat this devastating illness.

Currently, cancer is primarily treated using a combination of surgery, radiation and chemotherapy. Chemotherapy involves the use of chemical agents to disrupt the replication and metabolism of cancerous cells. Chemotherapeutic agents which are currently being used to treat cancer can be classified into five main groups: natural products and their derivatives; anthacyclines; alkylating agents; antiproliferatives and hormonal agents.

SUMMARY OF THE INVENTION

It is one object of several embodiments of the present invention to provide phenyl-indole compounds and methods thereof to modulate IgE. It is another object to provide phenyl-indole compositions and methods to inhibit cell proliferation. It is yet another object of several embodiments of the current invention to inhibit cytokines and leukocytes, including but not limited to IL-4, IL-5, eosinophils and lymphocytes.

One family of small molecules of the several embodiments is defined by the following genus (Genus I):

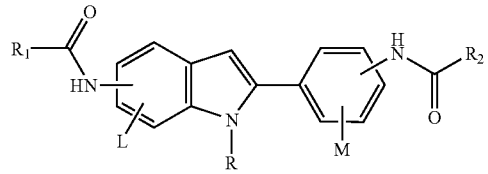

Genus I wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, $CONHR$ and $NHCOR_1$;

wherein R is selected from the group consisting of H, $C_1$–$C_5$ alkyl, benzyl, p-fluorobenzyl and di-alkylamino alkyl, wherein said $C_1$–$C_5$ alkyl is selected from the group consisting of a straight chain, branched or cyclic alkyl;

wherein $R_1$ and $R_2$ are independently selected from the group consisting of H, alkyl, substituted alyl, $C_3$–$C_9$ cycloalkyl, substituted $C_3$–$C_9$ cycloalkyl, polycyclic aliphatic groups, substituted polycyclic aliphatic groups, phenyl, substituted phenyl, naphthyl, substituted naphthyl, heterocyclic, polycyclic heterocyclic, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1–3 substituents, wherein said substituent is selected from the group consisting of H, halogens, polyhalogens, alkoxy group, substituted alkoxy, alkyl, substituted alkyl, dialkylaminoalkyl, hydroxyalkyl, hydroxyamino, alkoxyamino, carbonyl, OH, $OCH_3$, COOH, COOR' COR', CN, $CF_3$, $OCF_3$, $NO_2$, NR'R', NHCOR', and CONR'R'; and wherein R' is selected from the group consisting of H, alkyl, substituted alkyl, $C_3$–$C_9$ cycloalkyl, substituted $C_3$–$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur.

Preferred embodiments include species of Genus I, as shown by formulas S-1 to S-123.

One family of small molecule IgE inhibitors of the preferred embodiments is defined by the following genus (Genus II):

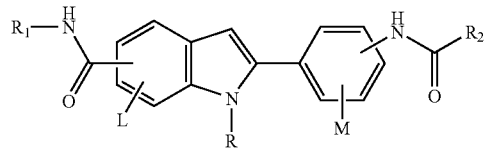

Genus II wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$–$C_5$ alkyl, benzyl, p-fluorobenzyl and di-alkylamino alkyl, wherein said $C_1$–$C_5$ alkyl is selected from the group consisting of a straight chain, branched or cyclic alkyl;

wherein $R_1$ and $R_2$ are independently selected from the group consisting of H, alkyl, substituted alkyl, $C_3$–$C_9$ cycloalkyl, substituted $C_3$–$C_9$ cycloalkyl, polycyclic aliphatic groups, substituted polycyclic aliphatic groups, phenyl, substituted phenyl, naphthyl, substituted naphthyl, heterocyclic, polycyclic heterocyclic, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1–3 substituents, wherein said substituent is selected from the group consisting of H, halogens, polyhalogens, alkoxy group, substituted alkoxy, alkyl, substituted alkyl, dialkylaminoalkyl, hydroxyalkyl, hydroxyamino, alkoxyamino, carbonyl, OH, $OCH_3$, COOH, COOR' COR', CN, $CF_3$, $OCF_3$, $NO_2$, NR'R', NHCOR', and CONR'R'; and wherein R' is selected from the group consisting of H, alkyl, substituted alkyl, $C_3$–$C_9$ cycloalkyl, substituted $C_3$–$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur.

Preferred embodiments include species of Genus II, as shown by formulas T-1 to T-102.

One family of small molecule IgE inhibitors of the preferred embodiments is defined by the following genus (Genus III):

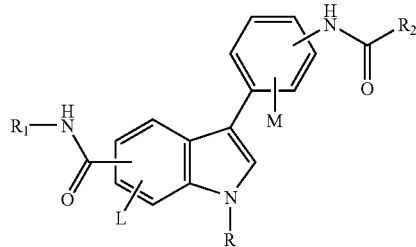

Genus III wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$–$C_5$ alkyl, benzyl, p-fluorobenzyl and di-alkylamino alkyl, wherein said $C_1$–$C_5$ alkyl is selected from the group consisting of a straight chain, branched or cyclic alkyl;

wherein $R_1$ and $R_2$ are independently selected from the group consisting of H, alkyl, substituted alkyl, $C_3$–$C_9$ cycloalkyl, substituted $C_3$–$C_9$ cycloalkyl, polycyclic aliphatic groups, substituted polycyclic aliphatic groups, phenyl, substituted phenyl, naphthyl, substituted naphthyl, heterocyclic, polycyclic heterocyclic, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1–3 substituents, wherein said substituent is selected from the group consisting of H, halogens, polyhalogens, alkoxy group, substituted alkoxy, alkyl, substituted alkyl, dialkylaminoalkyl, hydroxyalkyl, hydroxyamino, alkoxyamino, carbonyl, OH, $OCH_3$, COOH, COOR' COR', CN, $CF_3$, $OCF_3$, $NO_2$, NR'R', NHCOR', and CONR'R'; and wherein R' is selected from the group consisting of H, alkyl, substituted alkyl, $C_3$–$C_9$ cycloalkyl, substituted $C_3$–$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur.

Preferred embodiments include species of Genus III, as shown by formulas U-1 to U-18.

One family of small molecule IgE inhibitors of the preferred embodiments is defined by the following genus (Genus IV):

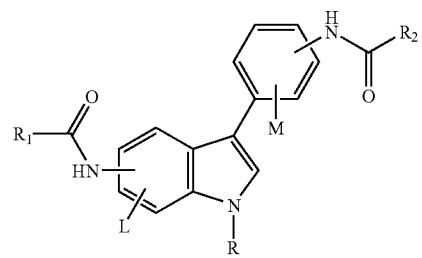

Genus IV wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$–$C_5$ alkyl, benzyl, p-fluorobenzyl and di-alkylamino alkyl, wherein said $C_1$–$C_5$ alkyl is selected from the group consisting of a straight chain, branched or cyclic alkyl;

wherein $R_1$ and $R_2$ are independently selected from the group consisting of H, alkyl, substituted alky, $C_3$–$C_9$ cycloalkyl, substituted $C_3$–$C_9$ cycloalkyl, polycyclic aliphatic groups, substituted polycyclic aliphatic groups, phenyl, substituted phenyl, naphthyl, substituted naphthyl, heterocyclic, polycyclic heterocyclic, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1–3 substituents, wherein said substituent is selected from the group consisting of H, halogens, polyhalogens, alkoxy group, substituted alkoxy, alkyl, substituted alkyl, dialkylaminoalkyl, hydroxyalkyl, hydroxyamino, alkoxyamino, carbonyl, OH, $OCH_3$, COOH, COOR' COR', CN, $CF_3$, $OCF_3$, $NO_2$, NR'R', NHCOR', and CONR'R'; and wherein R' is selected from the group consisting of H, alkyl, substituted alkyl, $C_3$–$C_9$ cycloalkyl, substituted $C_3$–$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur.

Preferred embodiments include species of Genus IV, as shown by formulas V-1 to V-28.

One family of small molecule IgE inhibitors of the preferred embodiments is defined by the following genus (Genus V):

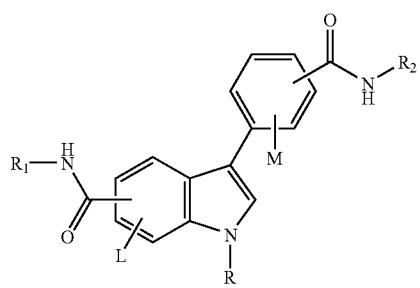

Genus V wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$–$C_5$ alkyl, benzyl, p-fluorobenzyl and di-alkylamino alkyl, wherein said $C_1$–$C_5$ alkyl is selected from the group consisting of a straight chain, branched or cyclic alkyl;

wherein $R_1$ and $R_2$ are independently selected from the group consisting of H, alkyl, substituted alky, $C_3$–$C_9$ cycloalkyl, substituted $C_3$–$C_9$ cycloalkyl, polycyclic aliphatic groups, substituted polycyclic aliphatic groups, phenyl, substituted phenyl, naphthyl, substituted naphthyl, heterocyclic, polycyclic heterocyclic, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1–13 substituents, wherein said substituent is selected from the group consisting of H, halogens, polyhalogens, alkoxy group, substituted alkoxy, alkyl, substituted alkyl, dialkylaminoalkyl, hydroxyalkyl, hydroxyamino, alkoxyamino, carbonyl, OH, $OCH_3$, COOH, COOR' COR', CN, $CF_3$, $OCF_3$, $NO_2$, NR'R', NHCOR', and CONR'R'; and wherein R' is selected from the group consisting of H, alkyl, substituted alkyl, $C_3$–$C_9$ cycloalkyl, substituted $C_3$–$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur.

One family of small molecule IgE inhibitors of the preferred embodiments is defined by the following genus (Genus VI):

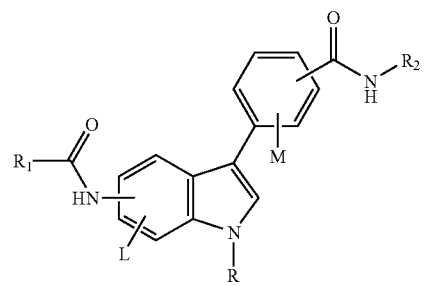

Genus VI wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$–$C_5$ alkyl, benzyl, p-fluorobenzyl and di-alkylamino alkyl, wherein said $C_1$–$C_5$ alkyl is selected from the group consisting of a straight chain, branched or cyclic alkyl;

wherein $R_1$ and $R_2$ are independently selected from the group consisting of H, alkyl, substituted alkyl, $C_3$–$C_9$ cycloalkyl, substituted $C_3$–$C_9$ cycloalkyl, polycyclic aliphatic groups, substituted polycyclic aliphatic groups, phenyl, substituted phenyl, naphthyl, substituted naphthyl, heterocyclic, polycyclic heterocyclic, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1–3 substituents, wherein said substituent is selected from the group consisting of H, halogens, polyhalogens, alkoxy group, substituted alkoxy, alkyl, substituted alkyl, dialkylaminoalkyl, hydroxyalkyl, hydroxyamino, alkoxyamino, carbonyl, OH, $OCH_3$, COOH, COOR' COR', CN, $CF_3$, $OCF_3$, $NO_2$, NR'R', NHCOR', and CONR'R'; and wherein R' is selected from the group consisting of H, alkyl, substituted alkyl, $C_3$–$C_9$ cycloalkyl, substituted $C_3$–$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur.

One family of small molecule IgE inhibitors of the preferred embodiments is defined by the following genus (Genus VII):

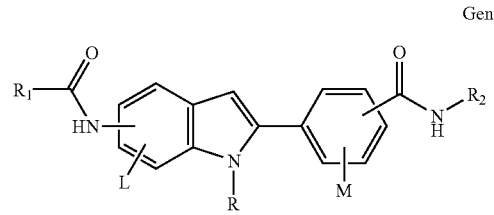

Genus VII wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$–$C_5$ alkyl, benzyl, p-fluorobenzyl and di-alkylamino alkyl, wherein said $C_1$–$C_5$ alkyl is selected from the group consisting of a straight chain, branched or cyclic alkyl;

wherein $R_1$ and $R_2$ are independently selected from the group consisting of H, alkyl, substituted alkyl, $C_3$–$C_9$ cycloalkyl, substituted $C_3$–$C_9$ cycloalkyl, polycyclic aliphatic groups, substituted polycyclic aliphatic groups, phenyl, substituted phenyl, naphthyl, substituted naphthyl, heterocyclic, polycyclic heterocyclic, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1–3 substituents, wherein said substituent is selected from the group consisting of H, halogens, polyhalogens, alkoxy group, substituted alkoxy, alkyl, substituted alkyl, dialkylaminoalkyl, hydroxyalkyl, hydroxyamino, alkoxyamino, carbonyl, OH, $OCH_3$, COOH, COOR' COR', CN, $CF_3$, $OCF_3$, $NO_2$, NR'R', NHCOR', and CONR'R'; and wherein R' is selected from the group consisting of H, alkyl, substituted alkyl, $C_3$–$C_9$ cycloalkyl, substituted $C_3$–$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur.

One family of small molecule IgE inhibitors of the preferred embodiments is defined by the following genus (Genus VIII):

Genus VIII

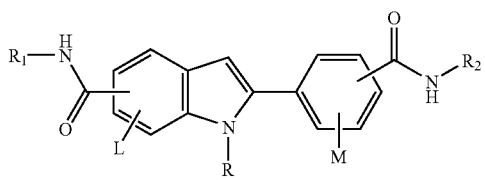

wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$–$C_5$ alkyl, benzyl, p-fluorobenzyl and di-alkylamino alkyl, wherein said $C_1$–$C_5$ alkyl is selected from the group consisting of a straight chain, branched or cyclic alkyl;

wherein $R_1$ and $R_2$ are independently selected from the group consisting of H, alkyl, substituted alkyl, $C_3$–$C_9$ cycloalkyl, substituted $C_3$–$C_9$ cycloalkyl, polycyclic aliphatic groups, substituted polycyclic aliphatic groups, phenyl, substituted phenyl, naphthyl, substituted naphthyl, heterocyclic, polycyclic heterocyclic, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1–3 substituents, wherein said substituent is selected from the group consisting of H, halogens, polyhalogens, alkoxy group, substituted alkoxy, alkyl, substituted alkyl, dialkylaminoalkyl, hydroxyalkyl, hydroxyamino, alkoxyamino, carbonyl, OH, $OCH_3$, COOH, COOR' COR', CN, $CF_3$, $OCF_3$, $NO_2$, NR'R', NHCOR', and CONR'R'; and wherein R' is selected from the group consisting of H, alkyl, substituted alkyl, $C_3$–$C_9$ cycloalkyl, substituted $C_3$–$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur.

One subgenus of small molecule IgE inhibitors of the preferred embodiments is defined by the following formula, as Subgenus Ia:

Subgenus Ia

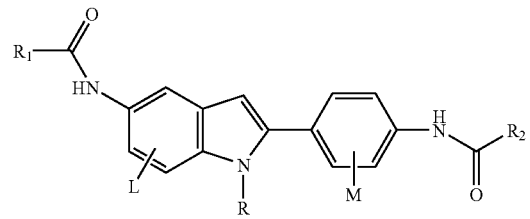

wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$–$C_5$ alkyl, benzyl, p-fluorobenzyl and di-alkylamino alkyl, wherein said $C_1$–$C_5$ alkyl is selected from the group consisting of a straight chain, branched or cyclic alkyl;

wherein $R_1$ and $R_2$ are independently selected from the group consisting of H, alkyl, substituted alkyl, $C_3$–$C_9$ cycloalkyl, substituted $C_3$–$C_9$ cycloalkyl, polycyclic aliphatic groups, substituted polycyclic aliphatic groups, phenyl, substituted phenyl, naphthyl, substituted naphthyl, heterocyclic, polycyclic heterocyclic, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1–3 substituents, wherein said substituent is selected from the group consisting of H, halogens, polyhalogens, alkoxy group, substituted alkoxy, alkyl, substituted alkyl, dialkylaminoalkyl, hydroxyalkyl, hydroxyamino, alkoxyamino, carbonyl, OH, $OCH_3$, COOH, COOR' COR', CN, $CF_3$, $OCF_3$, $NO_2$, NR'R', NHCOR', and CONR'R'; and wherein R' is selected from the group consisting of H, alkyl, substituted alkyl, $C_3$–$C_9$ cycloalkyl, substituted $C_3$–$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur.

One subgenus of small molecule IgE inhibitors of the preferred embodiments is defined by the following formula, as Subgenus IIa:

Subgenus IIa

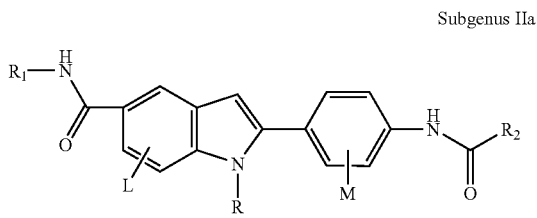

wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$–$C_5$ alkyl, benzyl, p-fluorobenzyl and di-alkylamino alkyl, wherein said $C_1$–$C_5$ alkyl is selected from the group consisting of a straight chain, branched or cyclic alkyl;

wherein $R_1$ and $R_2$ are independently selected from the group consisting of H, alkyl, substituted alkyl, $C_3$–$C_9$ cycloalkyl, substituted $C_3$–$C_9$ cycloalkyl, polycyclic aliphatic groups, substituted polycyclic aliphatic groups, phenyl, substituted phenyl, naphthyl, substituted naphthyl, heterocyclic, polycyclic heterocyclic, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1–3 substituents, wherein said substituent is selected from the group consisting of H, halogens, polyhalogens, alkoxy group, substituted alkoxy, alkyl, substituted alkyl, dialkylaminoalkyl, hydroxyalkyl, hydroxyamino, alkoxyamino, carbonyl, OH, $OCH_3$, COOH, COOR' COR', CN, $CF_3$, $OCF_3$, $NO_2$, NR'R', NHCOR', and CONR'R'; and wherein R' is selected from the group consisting of H, alkyl, substituted alkyl, $C_3$–$C_9$ cycloalkyl, substituted $C_3$–$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur.

One subgenus of small molecule IgE inhibitors of the preferred embodiments is defined by the following formula, as Subgenus IIb:

Subgenus IIb

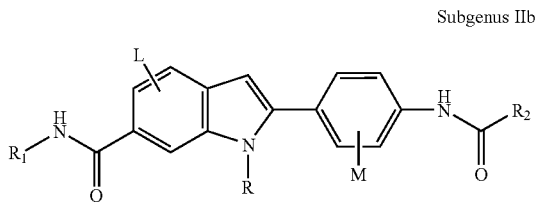

wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$–$C_5$ alkyl, benzyl, p-fluorobenzyl and di-alkylamino alkyl, wherein said $C_1$–$C_5$ alkyl is selected from the group consisting of a straight chain, branched or cyclic alkyl;

wherein $R_1$ and $R_2$ are independently selected from the group consisting of H, alkyl, substituted alkyl, $C_3$–$C_9$ cycloalkyl, substituted $C_3$–$C_9$ cycloalkyl, polycyclic aliphatic groups, substituted polycyclic aliphatic groups, phenyl, substituted phenyl, naphthyl, substituted naphthyl, heterocyclic, polycyclic heterocyclic, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1–3 substituents, wherein said substituent is selected from the group consisting of H, halogens, polyhalogens, alkoxy group, substituted alkoxy, alkyl, substituted alkyl, dialkylaminoalkyl, hydroxyalkyl, hydroxyamino, alkoxyamino, carbonyl, OH, $OCH_3$, COOH, COOR' COR', CN, $CF_3$, $OCF_3$, $NO_2$, NR'R', NHCOR', and CONR'R'; and wherein R' is selected from the group consisting of H, alkyl, substituted alkyl, $C_3$–$C_9$ cycloalkyl, substituted $C_3$–$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur.

For each chemical structure disclosed herein, the hydrogen atoms on the heteroatoms have been omitted for clarity purposes. Where open valences on heteroatoms are indicated, it is assumed that these valences are filled by hydrogen atoms.

A method for treating a disease condition associated with excess IgE and/or abnormal cell proliferation (e.g. cancer) in a mammal is also disclosed. In one aspect, the method comprises the step of administering to the mammal an IgE-suppressing amount or anti-cell proliferation amount of a pharmaceutical formulation comprising at least one phenyl-indole compound from the above-disclosed small molecule families.

In accordance with a variation of the method of treatment, the small molecule IgE-suppressing compound may be administered in conjunction with at least one additional agent, which is active in reducing a symptom associated with an allergic reaction. In one embodiment, the small molecule inhibitor may be mixed with at least one additional active ingredient to form a pharmaceutical composition. Alternatively, the small molecule inhibitor may be co-administered at the same time or according to different treatment regimens with the at least one additional active agent.

The at least one additional active ingredient may be a short-acting $β_2$-adrenergic agonist selected from the group consisting of terbutaline and albuterol; a long-acting $β_2$-adrenergic agonist selected from the group consisting of salmeterol and formoterol; an antihistamine selected from the group consisting of loratadine, azelastine and ketotifen; a phosphodiesterase inhibitor, an anticholinergic agent, a corticosteroid, an inflammatory mediator release inhibitor or a leukotriene receptor antagonist.

In another embodiment, the phenyl-indole compound may be administered in conjunction with at least one additional active agent. These active agents include antifungals, antivirals, antibiotics, anti-inflammatories, and anticancer agents. Anticancer agents include, but are not limited to, alkylating agents (lomustine, carmustine, streptozocin, mechlorethamine, melphalan, uracil nitrogen mustard, chlorambucil cyclophosphamide, iphosphamide, cisplatin, carboplatin mitomycin thiotepa dacarbazine procarbazine, hexamethyl melamine, triethylene melamine, busulfan, pipobroman, and mitotane); antimetabolites (methotrexate, trimetrexate pentostatin, cytarabine, ara-CMP, fludarabine phosphate, hydroxyurea, fluorouracil, floxuridine, chlorodeoxyadenosine, gemcitabine, thioguanine, and 6-mercaptopurine); DNA cutters (bleomycin); topoisomerase I poisons (topotecan irinotecan and camptothecin); topoisomerase II poisons (daunorubicin, doxorubicin, idarubicin, mitoxantrone, teniposide, and etoposide); DNA binders (dactinomycin, and mithramycin); and spindle poisons (vinblastine, vincristine, navelbine, paclitaxel, and docetaxel).

In another embodiment, the phenyl-indole compounds of the preferred embodiments are administered in conjunction with one or more other therapies. These therapies include, but are not limited to radiation, immunotherapy, gene therapy and surgery. These combination therapies may be administered simultaneously or sequentially. For example, radiation may be administered along with the administration of phenyl-indole compounds, or may be administered at any time before or after administration of phenyl-indole compounds.

A dose of about 0.01 mg to about 100 mg per kg body weight per day of the small molecule IgE inhibitory compound is preferably administered in divided doses daily.

A method for treating a disease condition associated with excess IgE or abnormal cell proliferation in a mammal is also disclosed which comprises the step of administering to the mammal an therapeutic amount of a pharmaceutical formulation comprising at least one compound selected from Genus I, Genus II, Genus III, Genus IV, Genus V, Genus VI, Genus VII, or Genus VIII. In another preferred embodiment, a method is disclosed for treating a disease condition associated with excess IgE or abnormal cell proliferation in a mammal is also disclosed which comprises the step of administering to the mammal an therapeutic amount of a pharmaceutical formulation comprising at least one compound selected from Subgenus Ia, IIa, or IIb.

The methods provided herein for treating diseases and processes mediated by undesired, uncontrolled or abnormal cell proliferation, such as cancer, involve administering to a mammal a composition of the phenyl-indole compounds disclosed herein to inhibit cell proliferation. The method is particularly useful for preventing or treating tumor formation and progression. In the preferred embodiments, the compounds and methods disclosed are especially useful in treating estrogen receptor positive and estrogen receptor negative type breast cancers.

Other variations within the scope of the present invention may be more fully understood with reference to the following detailed description.

DETAILED DESCRIPTION OF THE PREFERRED EMBODIMENT

The preferred embodiments are directed to small molecule inhibitors of IgE which are useful in the treatment of allergy and/or asthma or any diseases where IgE is pathogenic. The inhibitors may affect the synthesis, activity, release, metabolism, degradation, clearance and/or pharmacokinetics of IgE. The particular compounds disclosed herein were identified by their ability to suppress IgE levels in both ex vivo and in vivo assays. The compounds disclosed in the preferred embodiments are also useful in the treatment of diseases associated with abnormal cellular proliferation, including, but not limited to, tumorgenesis and other proliferative diseases such as cancers, inflammatory disorders and circulatory diseases. Development and optimization of clinical treatment regimens can be monitored by those of skill in the art by reference to the ex vivo and in vivo assays described below. In addition, several embodiments of the current invention are directed to phenyl-indole compounds that inhibit cytokines and leukocytes, including but not limited to IL-4, IL-5, eosinophils and lymphocytes.

Ex Vivo Assay

This system begins with in vivo antigen priming and measures secondary antibody responses in vitro. The basic protocol was documented and optimized for a range of parameters including: antigen dose for priming and time span following priming, number of cells cultured in vitro, antigen concentrations for eliciting secondary IgE (and other Ig's) response in vitro, fetal bovine serum (FBS) batch that will permit optimal IgE response in vitro, the importance of primed CD4+ T cells and hapten-specific B cells, and specificity of the ELISA assay for IgE (Marcelletti and Katz, *Cellular Immunology* 135:471–489 (1991); incorporated herein by reference).

The actual protocol utilized for this project was adapted for a more high throughput analyses. BALB/cByj mice were immunized i.p. with 10 µg DNP-KLH adsorbed onto 4 mg alum and sacrificed after 15 days. Spleens were excised and homogenized in a tissue grinder, washed twice, and maintained in DMEM supplemented with 10% FBS, 100 U/ml penicillin, 100 µg/ml streptomycin and 0.0005% 2-mercaptoethanol. Spleen cell cultures were established (2–3 million cells/ml, 0.2 ml/well in quadruplicate, 96-well plates) in the presence or absence of DNP-KLH (10 ng/ml). Test compounds (2 µg/ml and 50 ng/ml) were added to the spleen cell cultures containing antigen and incubated at 37° C. for 8 days in an atmosphere of 10% $CO_2$.

Culture supernatants were collected after 8 days and Ig's were measured by a modification of the specific isotype-selective ELISA assay described by Marcelletti and Katz (supra). The assay was modified to facilitate high throughput. ELISA plates were prepared by coating with DNP-KLH or DNP-OVA overnight. After blocking with bovine serum albumin (BSA), an aliquot of each culture supernatant was diluted (1:4 in phosphate buffered saline (PBS) with BSA, sodium azide and Tween 20), added to the ELISA plates, and incubated overnight in a humidified box at 4° C. IgE levels were quantitated following successive incubations with biotinylated-goat antimouse IgE (b-GAME), AP-streptavidin and substrate.

Antigen-specific IgG1 was measured similarly, except that culture supernatants were diluted 200-fold and biotinylated-goat antimouse IgG1 (b-GAMG1) was substituted for b-GAME. IgG2a was measured in ELISA plates that were coated with DNP-KLH following a 1:20 dilution of culture supernatants and incubation with biotinylated-goat antimouse IgG2a (b-GAMG2a). Quantitation of each isotype was determined by comparison to a standard curve. The level of detectability of all antibody was about 200–400 pg/ml and there was less than 0.001% cross-reactivity with any other Ig isotype in the ELISA for IgE.

In Vivo Assay

Compounds found to be active in the ex vivo assay (above) were further tested for their activity in suppressing IgE responses in vivo. Mice receiving low-dose radiation prior to immunization with a carrier exhibited an enhanced IgE response to challenge with antigen 7 days later. Administration of the test compounds immediately prior to and after antigen sensitization, measured the ability of that drug to suppress the IgE response. The levels of antigen specific IgE, IgG1 and IgG2a in serum were compared.

Female BALB/cByj mice were irradiated with 250 rads 7 hours after initiation of the daily light cycle. Two hours later, the mice were immunized i.p. with 2 μg of KLH in 4 mg alum. Two to seven consecutive days of drug injections were initiated 6 days later on either a once or twice daily basis. Typically, i.p. injections and oral gavages were administered as suspensions (150 μl/injection) in saline with 10% ethanol and 0.25% methylcellulose. Each treatment group was composed of 5–6 mice. On the second day of drug administration, 2 μg of DNP-KLH was administered i.p. in 4 mg alum, immediately following the morning injection of drug. Mice were bled 7–21 days following DNP-KLH challenge.

Antigen-specific IgE, IgG1 and IgG2a antibodies were measured by ELISA. Periorbital bleeds were centrifuged at 14,000 rpm for 10 min, the supernatants were diluted 5-fold in saline, and centrifuged again. Antibody concentrations of each bleed were determined by ELISA of four dilutions (in triplicate) and compared to a standard curve: anti-DNP IgE (1:100 to 1:800), anti-DNP IgG2a (1:100 to 1:800), and anti-DNP IgG1 (1:1600 to 1:12800).

Active Compounds of Preferred Embodiments

The following series of compounds, identified under subheadings Genus I, Genus II, Genus III, Genus IV, Genus V, Genus VI, Genus VII, and Genus VIII were found to be potent inhibitors of IgE in both ex-vivo and in vivo models. These compounds also exhibit anti-proliferative effects, and, as such, may be used as agents to treat hyperproliferation disorders, including cancer.

Compounds of Genus I

One family of small molecule IgE inhibitors is defined by the following genus (Genus I):

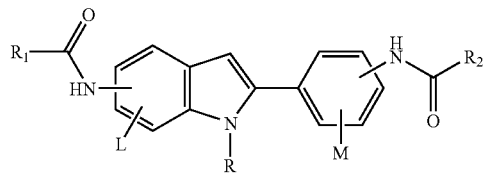

Genus I wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$–$C_5$ alkyl, benzyl, p-fluorobenzyl and di-alkylamino alkyl, wherein said $C_1$–$C_5$ alkyl is selected from the group consisting of a straight chain, branched or cyclic alkyl;

wherein $R_1$ and $R_2$ are independently selected from the group consisting of H, alkyl, substituted alkyl, $C_3$–$C_9$ cycloalkyl, substituted $C_3$–$C_9$ cycloalkyl, polycyclic aliphatic groups, substituted polycyclic aliphatic groups, phenyl, substituted phenyl, naphthyl, substituted naphthyl, heterocyclic, polycyclic heterocyclic, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1–3 substituents, wherein said substituent is selected from the group consisting of H, halogens, polyhalogens, alkoxy group, substituted alkoxy, alkyl, substituted alkyl, dialkylaminoalkyl, hydroxyalkyl, hydroxyamino, alkoxyamino, carbonyl, OH, $OCH_3$, COOH, COOR' COR', CN, $CF_3$, $OCF_3$, $NO_2$, NR'R', NHCOR', and CONR'R'; and wherein R' is selected from the group consisting of H, alkyl, substituted alkyl, $C_3$–$C_9$ cycloalkyl, substituted $C_3$–$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur.

One subgenus of small molecule IgE inhibitors of the preferred embodiments is defined by the following formula, as Subgenus Ia:

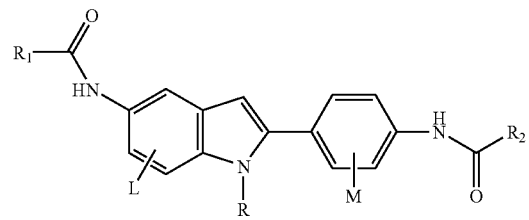

Subgenus Ia wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$–$C_5$ alkyl, benzyl, p-fluorobenzyl and di-alkylamino alkyl, wherein said $C_1$–$C_5$ alkyl is selected from the group consisting of a straight chain, branched or cyclic alkyl;

wherein $R_1$ and $R_2$ are independently selected from the group consisting of H, alkyl, substituted alkyl, $C_3$–$C_9$ cycloalkyl, substituted $C_3$–$C_9$ cycloalkyl, polycyclic aliphatic groups, substituted polycyclic aliphatic groups, phenyl, substituted phenyl, naphthyl, substituted naphthyl, heterocyclic, polycyclic heterocyclic, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1–3 substituents, wherein said substituent is selected from the group consisting of H, halogens, polyhalogens, alkoxy group, substituted alkoxy, alkyl, substituted alkyl, dialkylaminoalkyl, hydroxyalkyl, hydroxyamino, alkoxyamino, carbonyl, OH, $OCH_3$, COOH, COOR' COR', CN, $CF_3$, $OCF_3$, $NO_2$, NR'R', NHCOR', and CONR'R'; and wherein R' is selected from the group consisting of H, alkyl, substituted alkyl, $C_3$–$C_9$ cycloalkyl, substituted $C_3$–$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur.

The following specific compounds were synthesized as described below and found to be active in both ex vivo and in vivo assays. They are encompassed within the definition of Genus I:
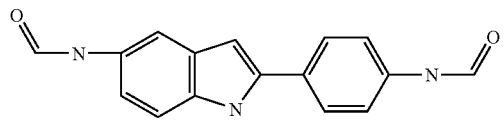
MOL NUMBER   MOLSTRUCTURE
S-1
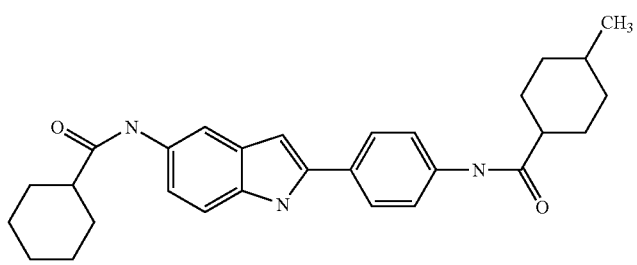
S-2
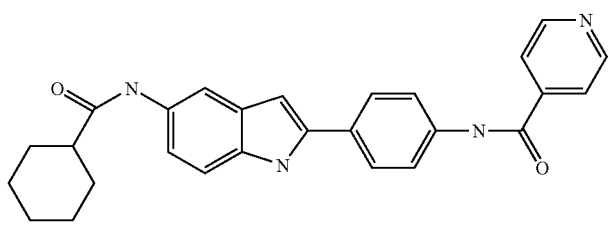
S-3
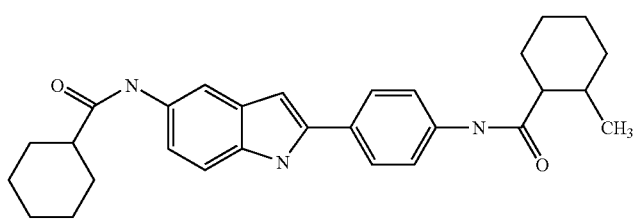
S-4
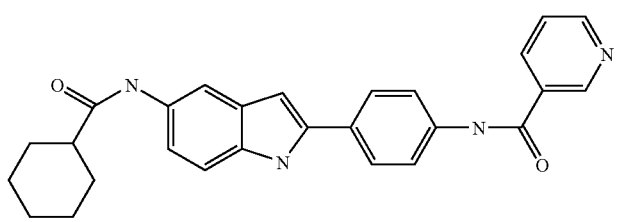
S-5
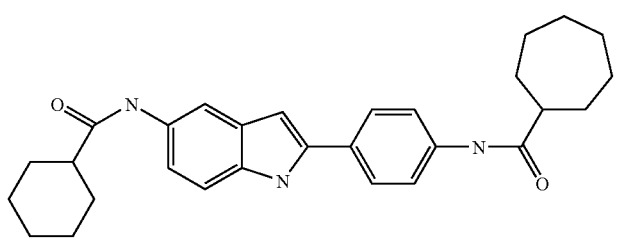

-continued
S-6
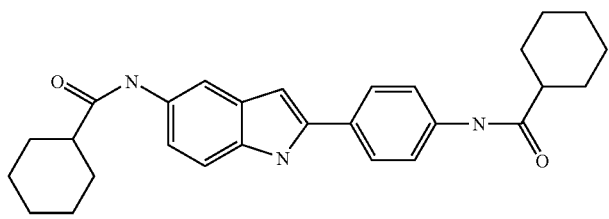
S-7
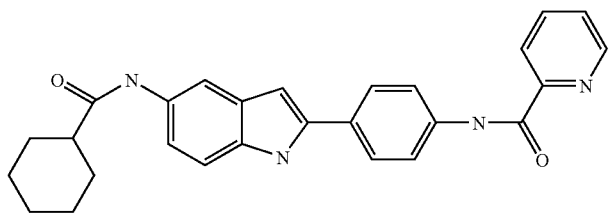
S-8
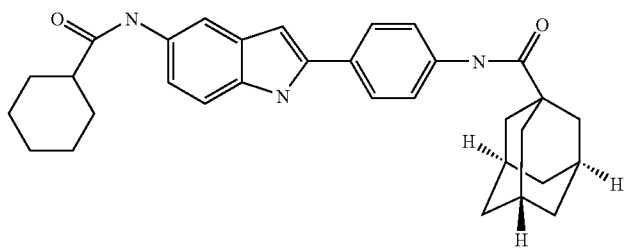
S-9
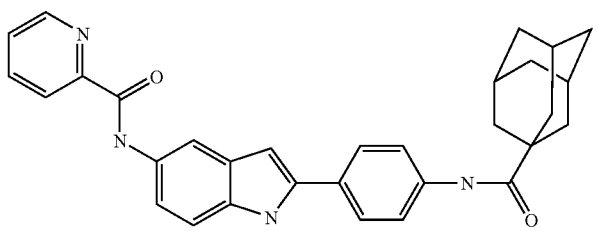
S-10
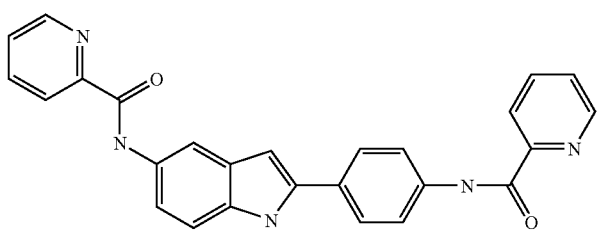
S-11
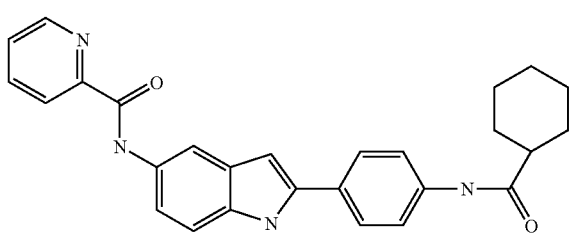

-continued
S-12
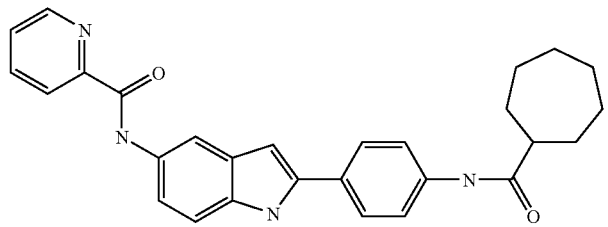
S-13
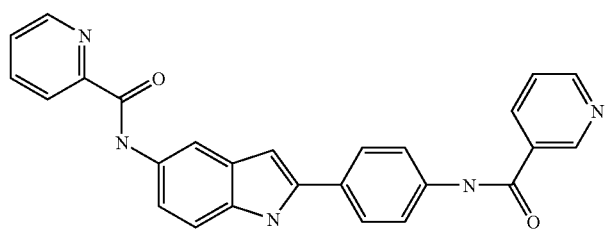
S-14
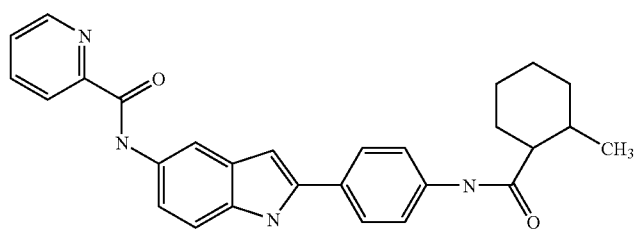
S-15
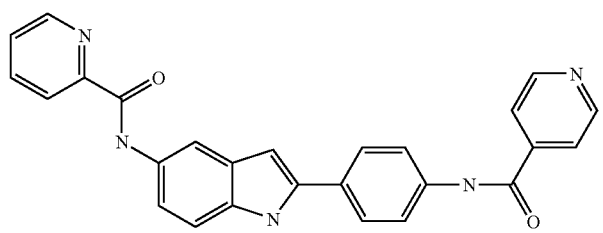
S-16
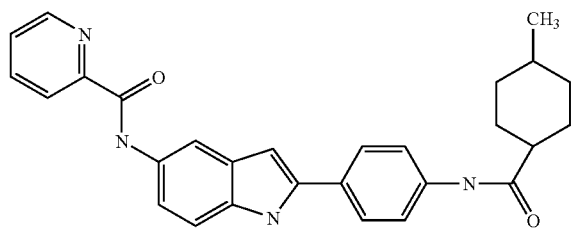
S-17
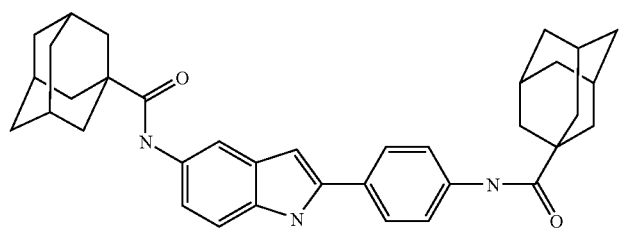

S-18
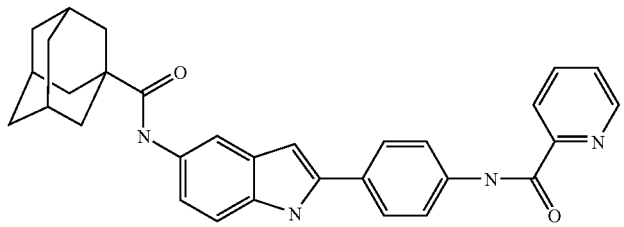
S-19
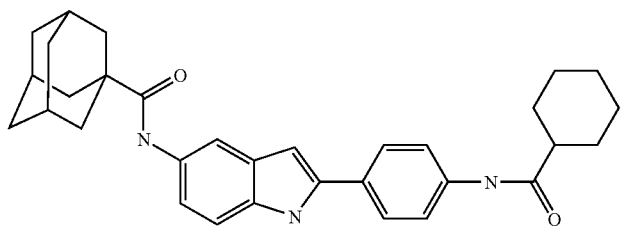
S-20
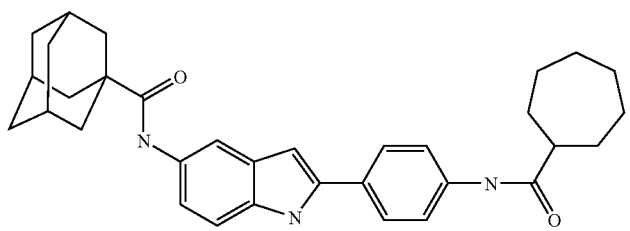
S-21
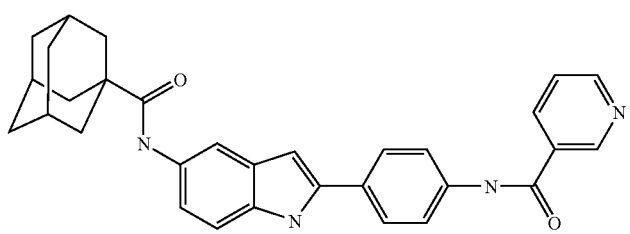
S-22
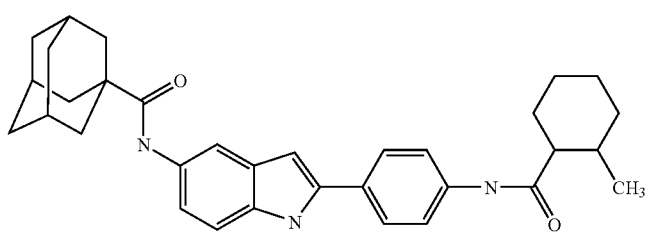
S-23
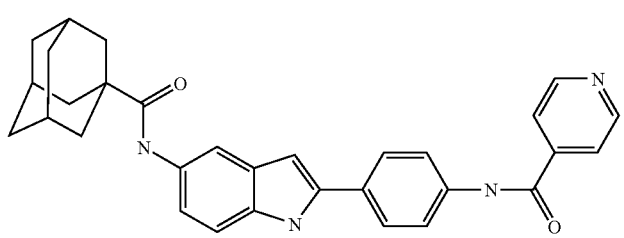

-continued
S-24
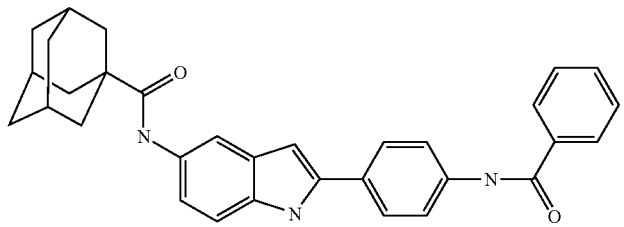
S-25
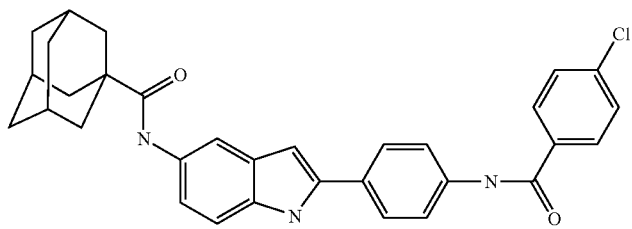
S-26
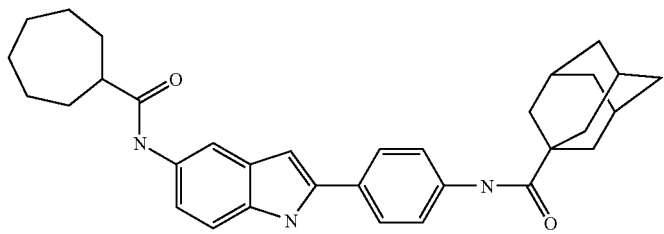
S-27
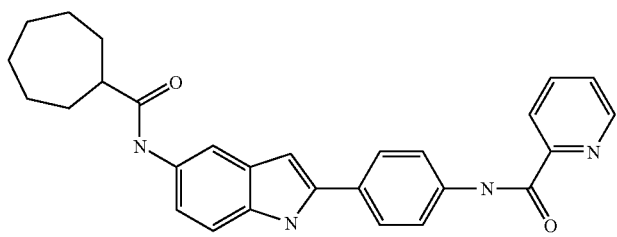
S-28
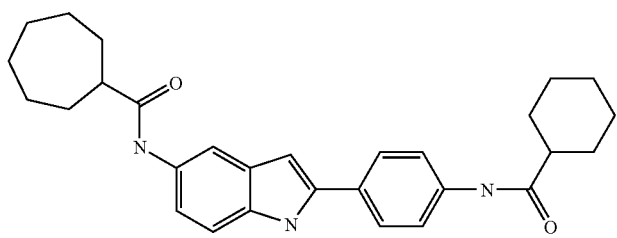
S-29
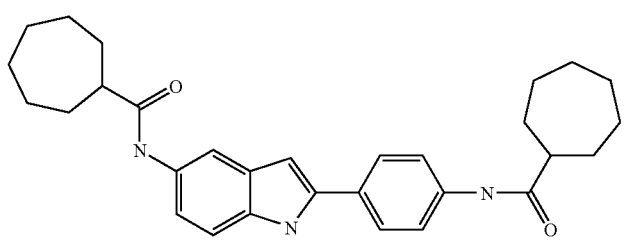

-continued
S-30
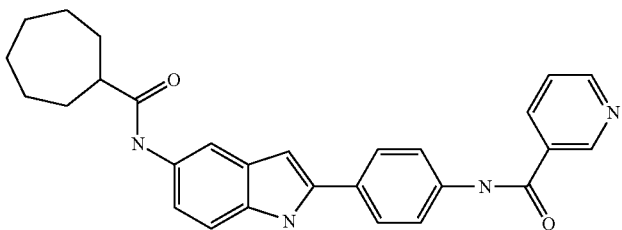
S-31
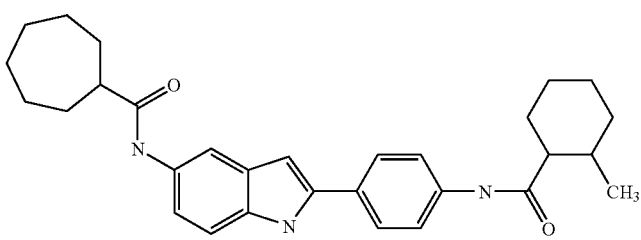
S-32
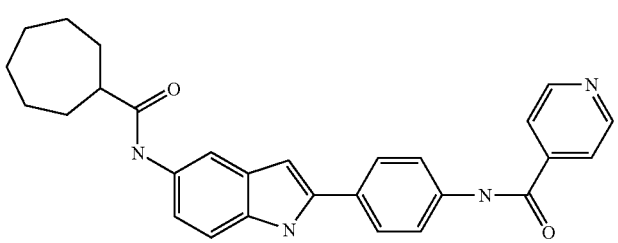
S-33
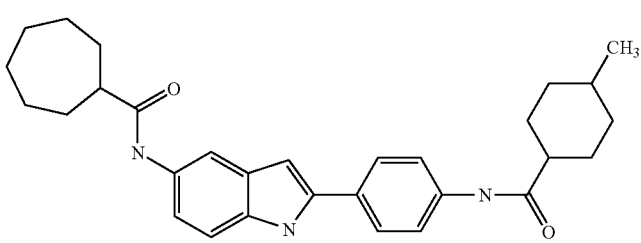
S-34
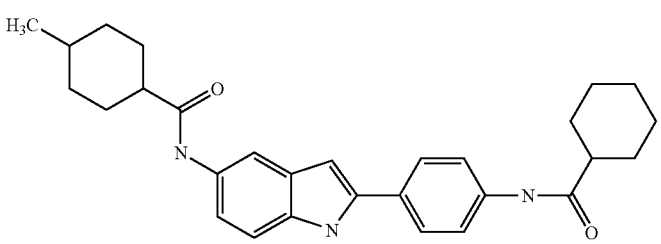
S-35
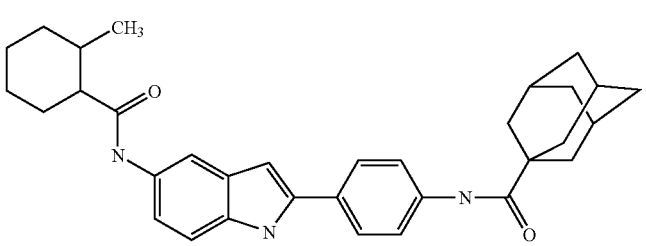

-continued
S-36 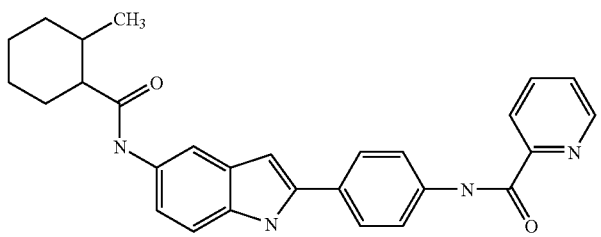
S-37 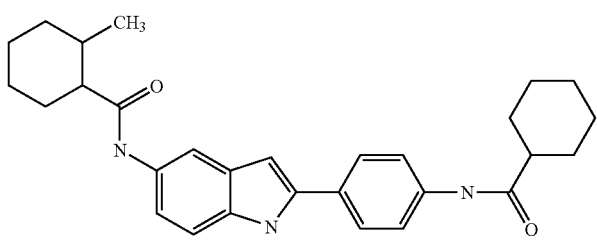
S-38 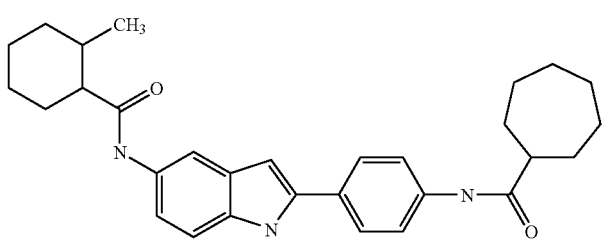
S-39 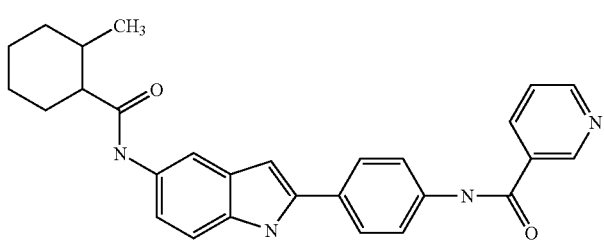
S-40 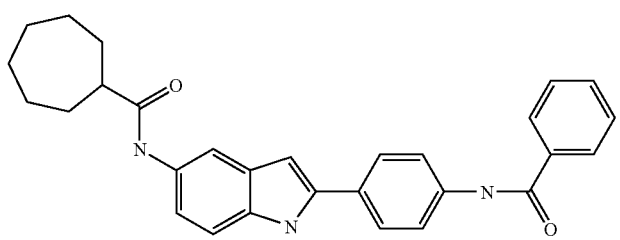
S-41 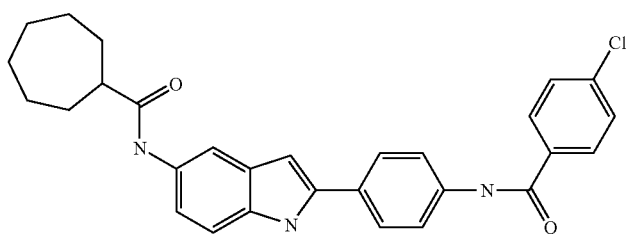

-continued
S-42
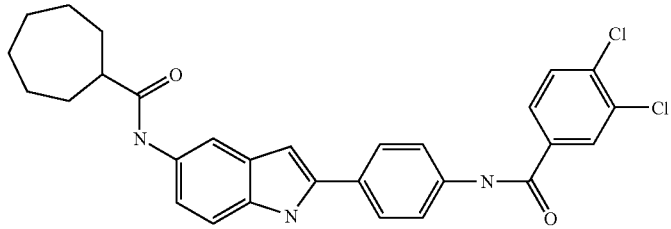
S-43
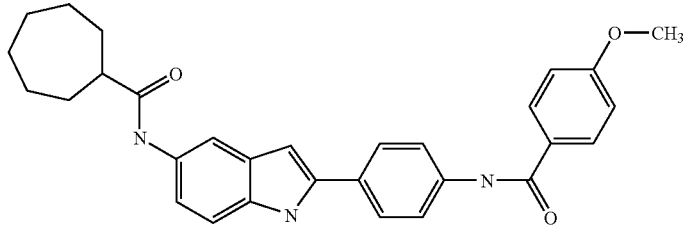
S-44
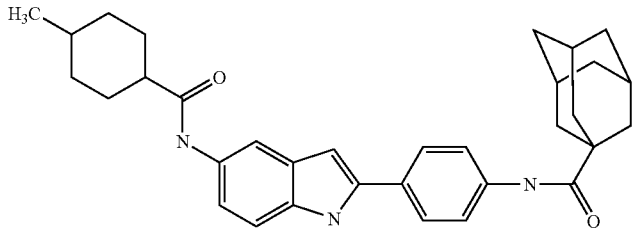
S-45
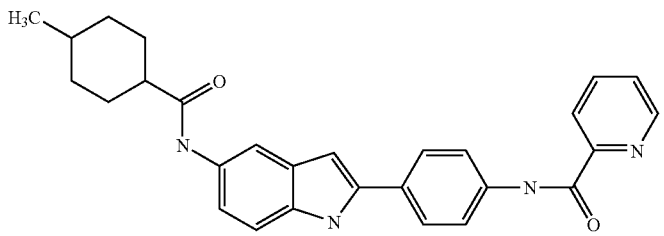
S-46
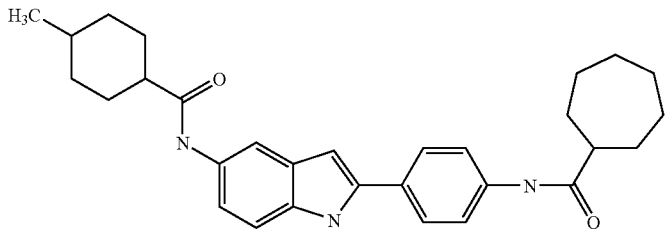
S-47
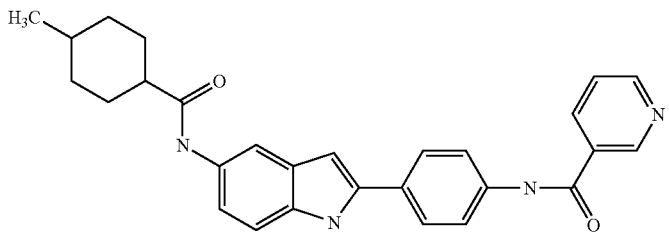

-continued
S-48 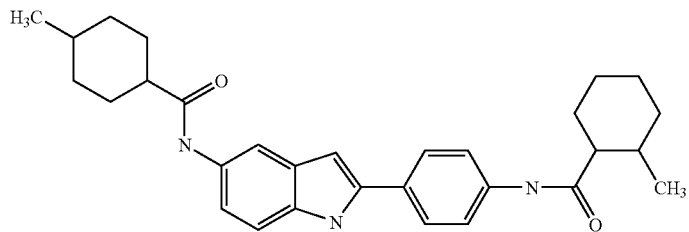
S-49 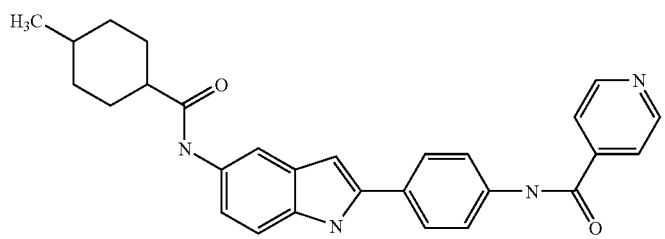
S-50 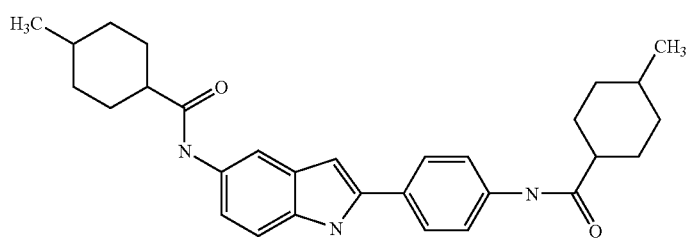
S-51 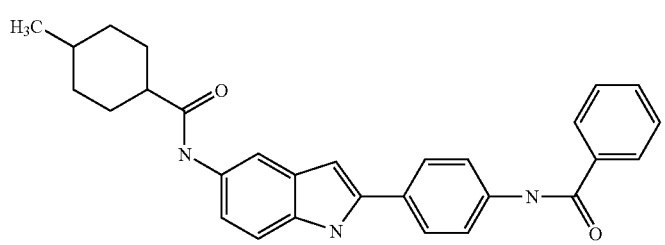
S-52 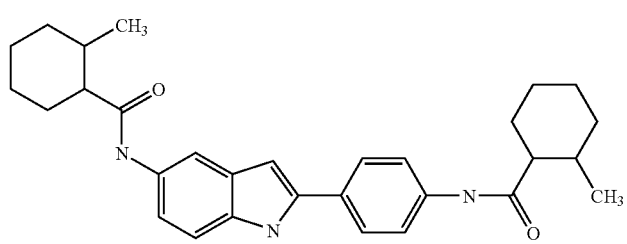
S-53 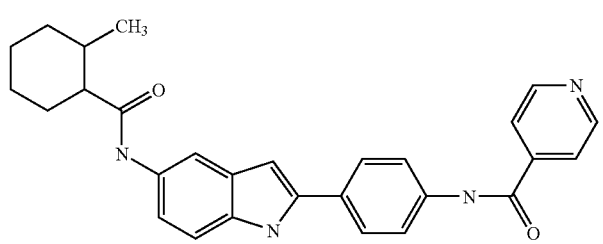

-continued
S-54 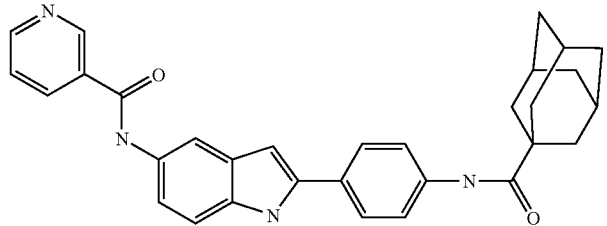
S-55 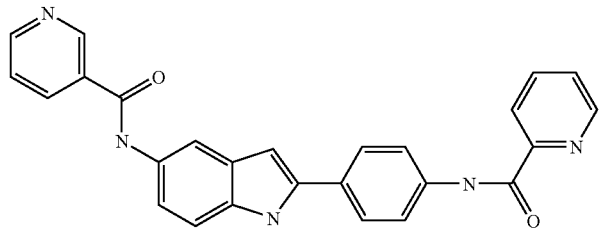
S-56 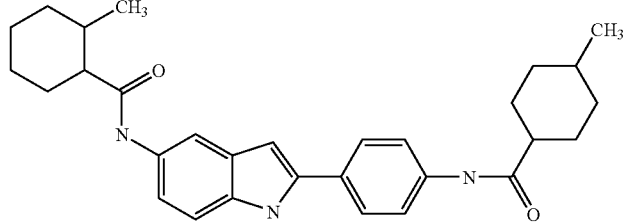
S-57 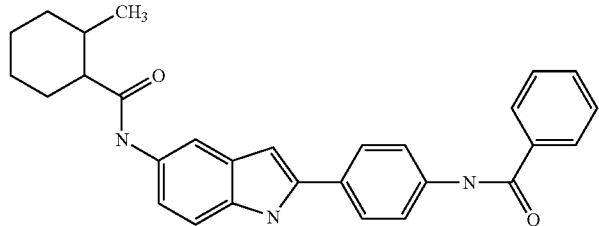
S-58 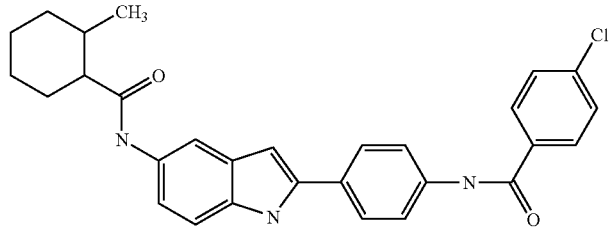
S-59 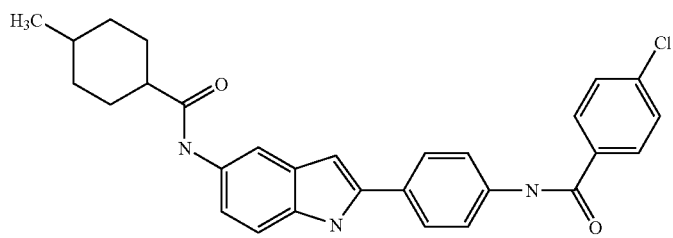

-continued
S-60 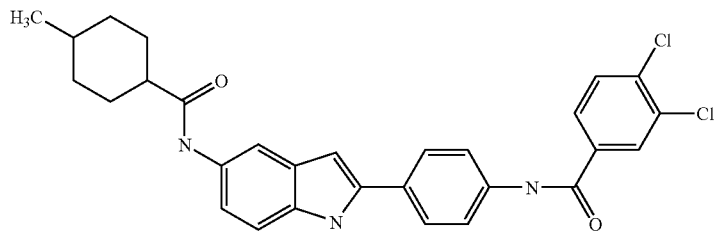
S-61 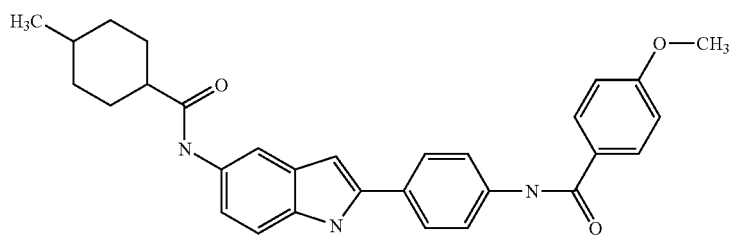
S-62 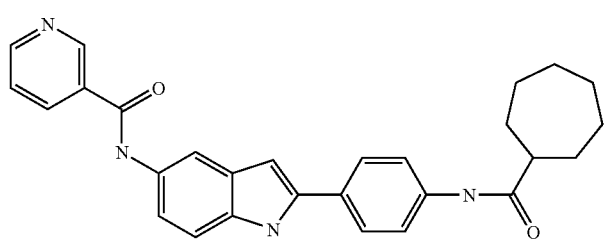
S-63 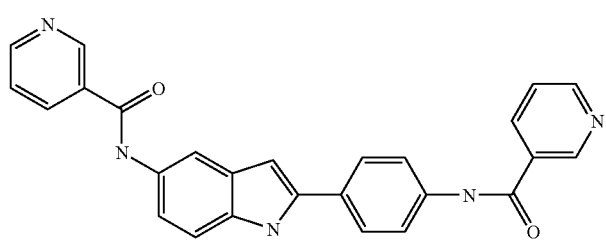
S-64 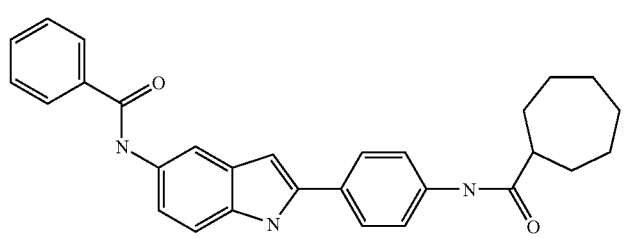
S-65 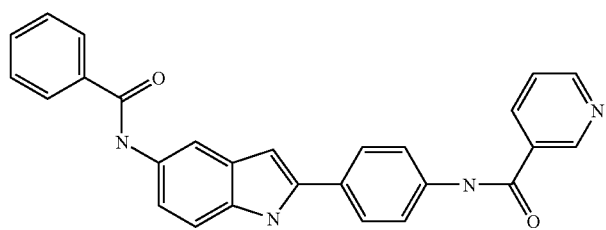

-continued
S-66 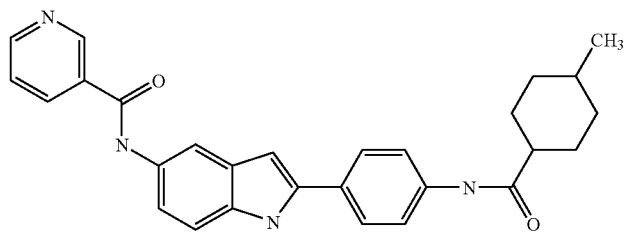
S-67 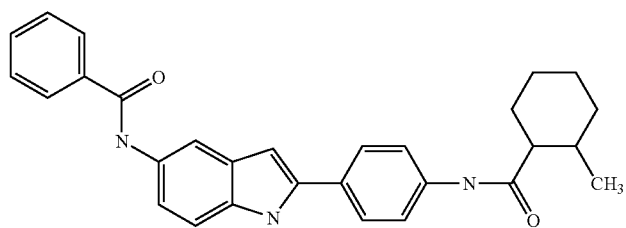
S-68 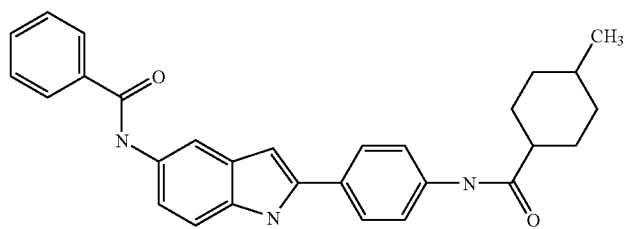
S-69 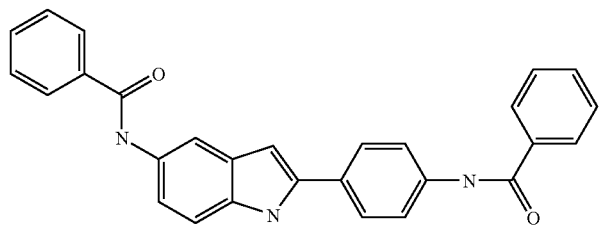
S-70 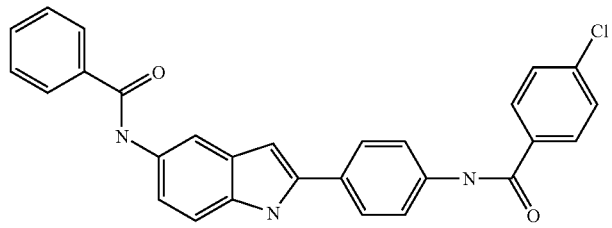
S-71 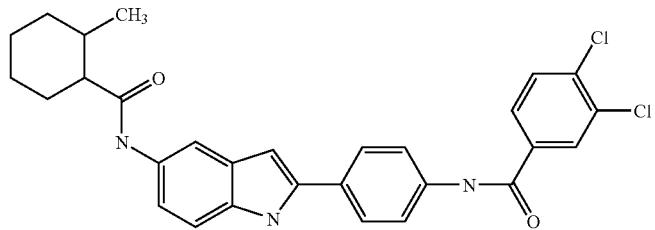

-continued
S-72 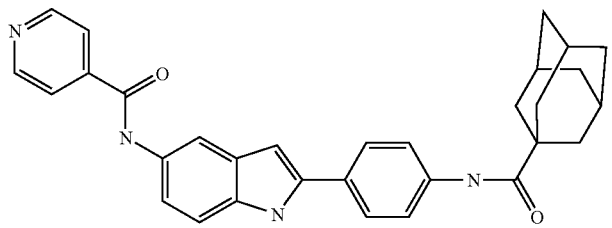
S-73 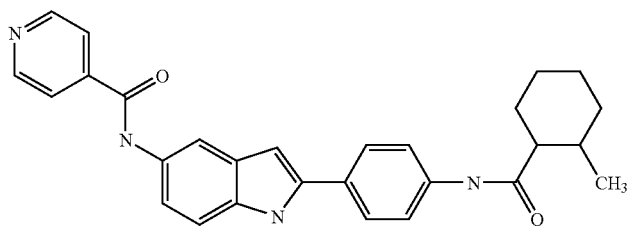
S-74 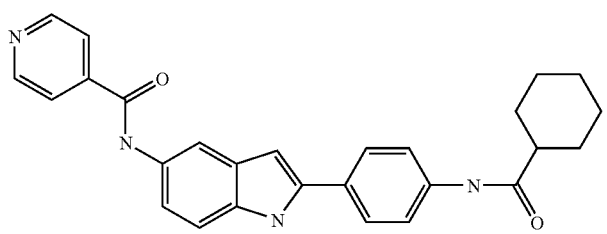
S-75 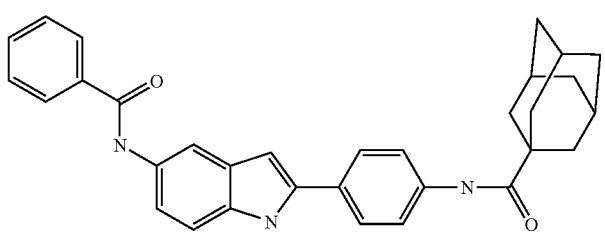
S-76 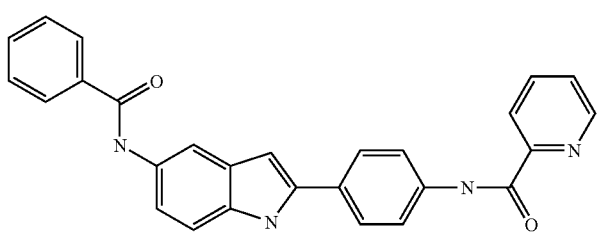
S-77 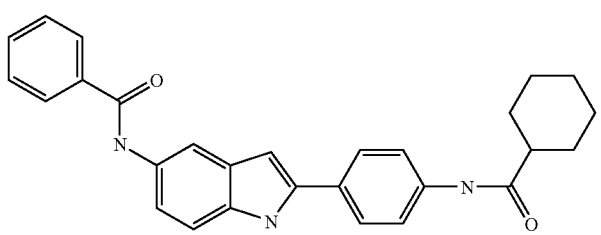

-continued
S-78 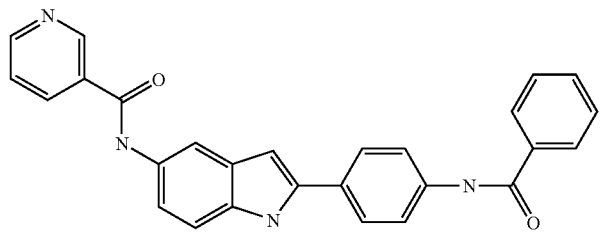
S-79 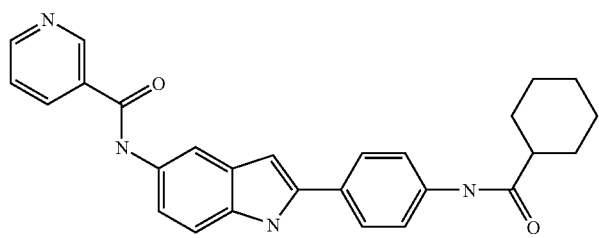
S-80 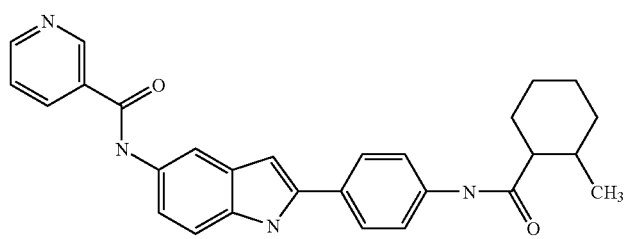
S-81 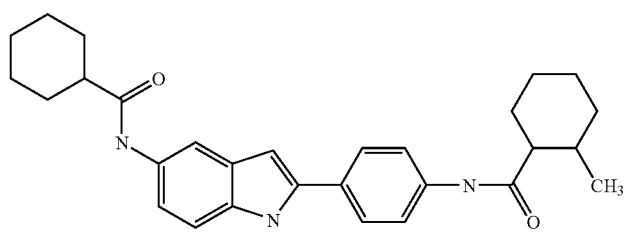
S-82 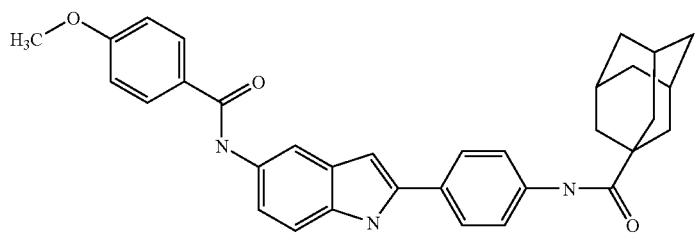
S-83 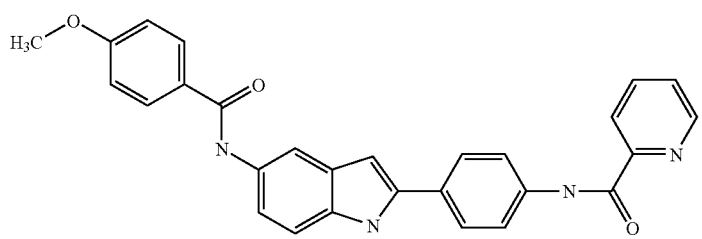

-continued
S-84
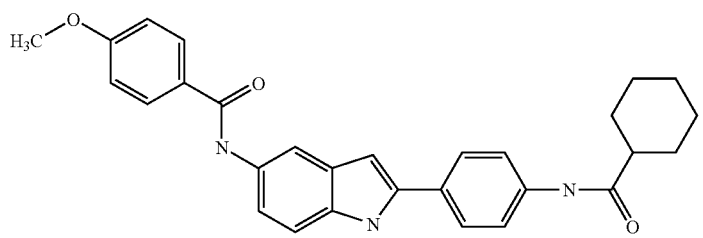
S-85
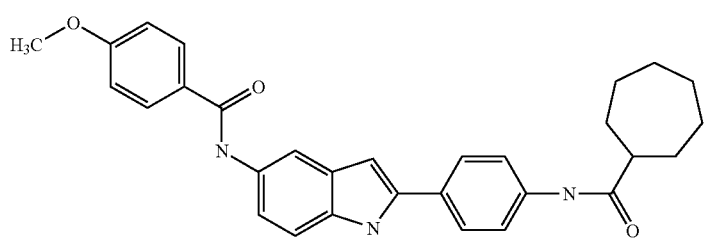
S-86
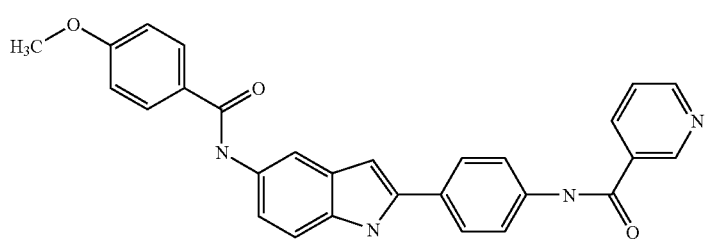
S-87
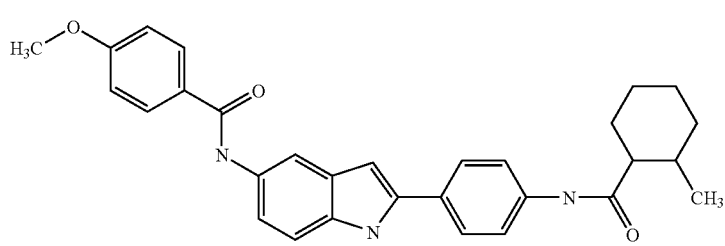
S-88
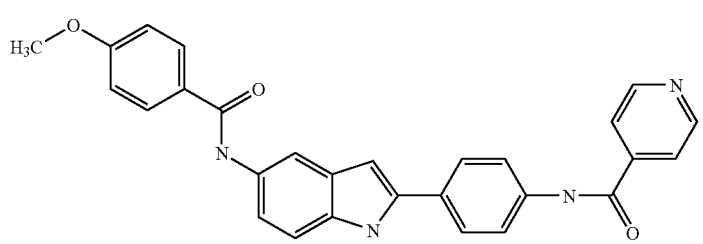
S-89
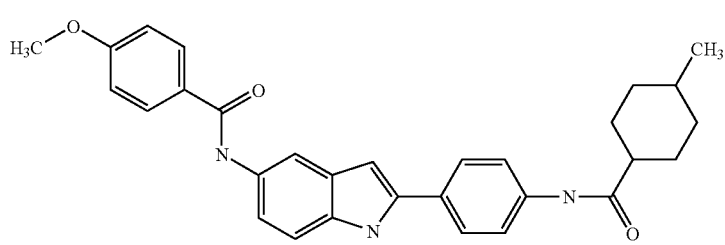

-continued
S-90
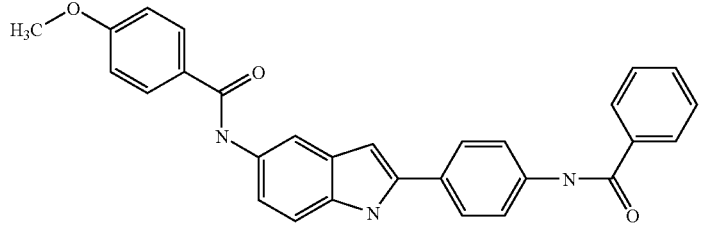
S-91
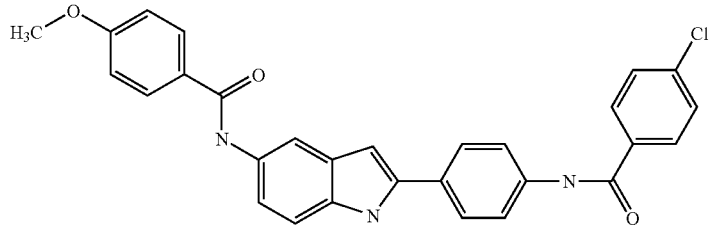
S-92
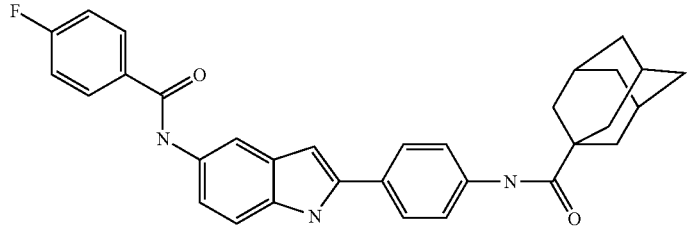
S-93
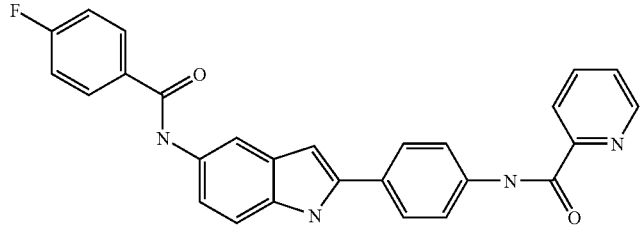
S-94
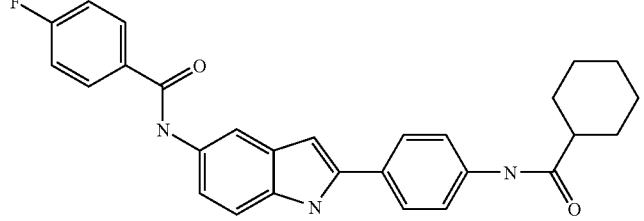
S-95
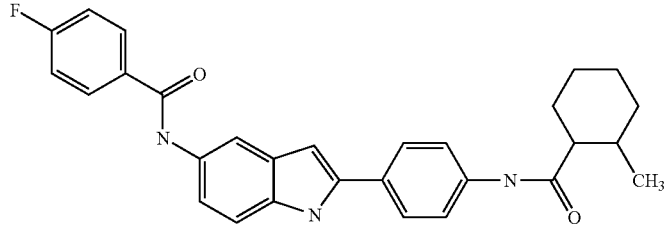

-continued
S-96
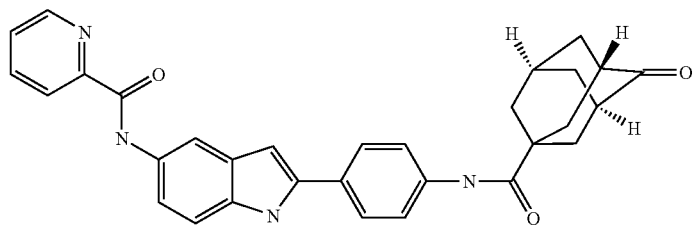
S-97
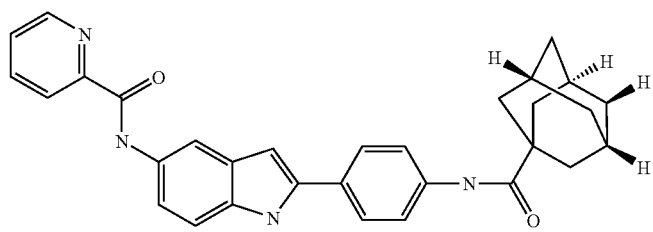
S-98
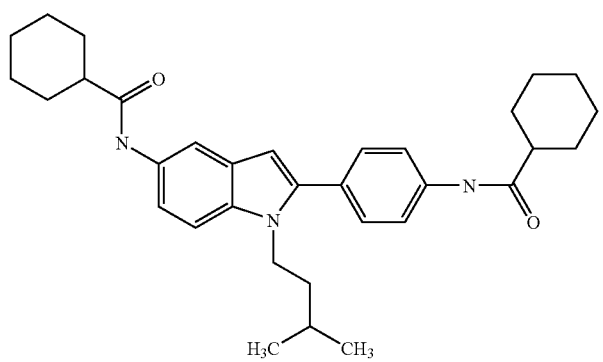
S-99
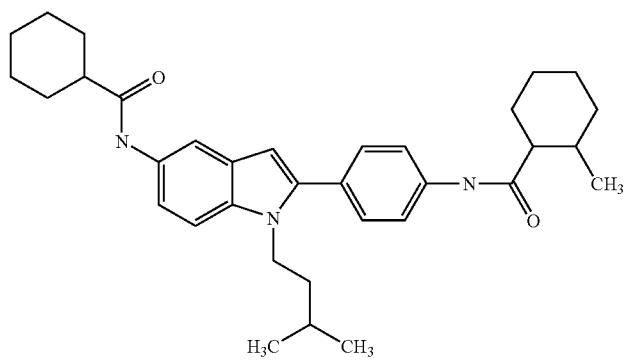
S-100
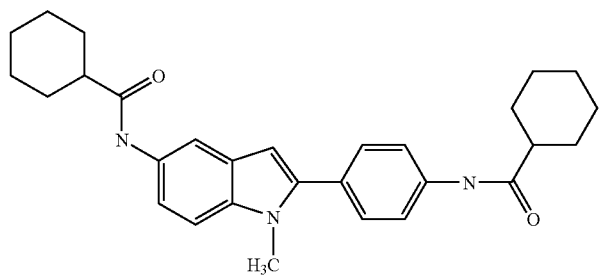

-continued
S-101 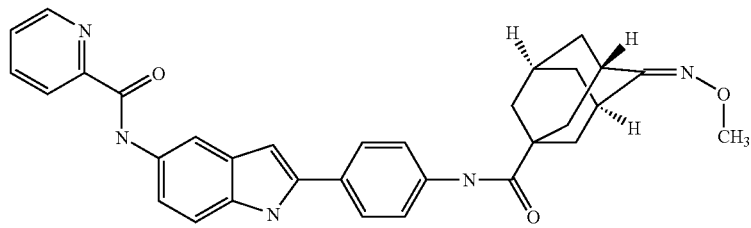
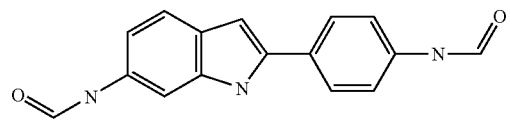
MOL NUMBER    MOLSTRUCTURE
S-102 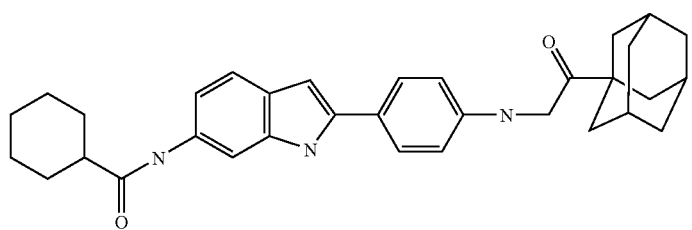
S-103 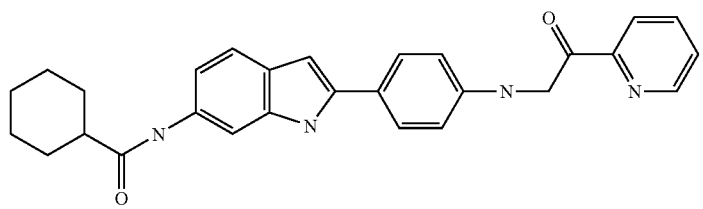
S-104 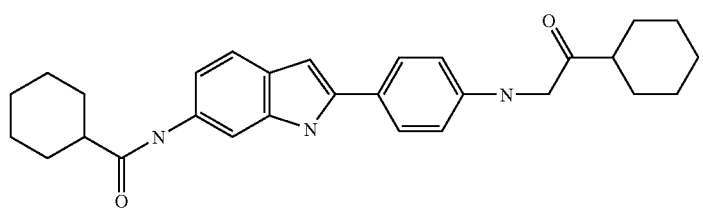
S-105 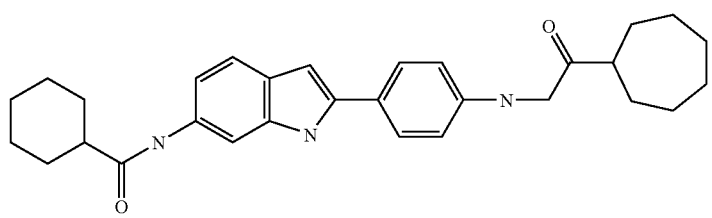
S-106 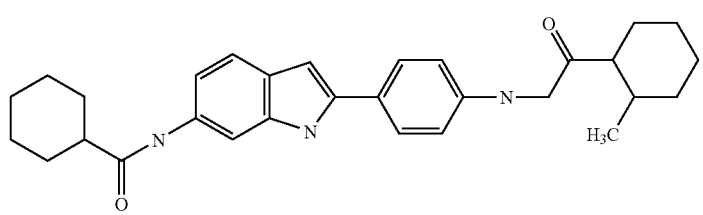

-continued
S-107
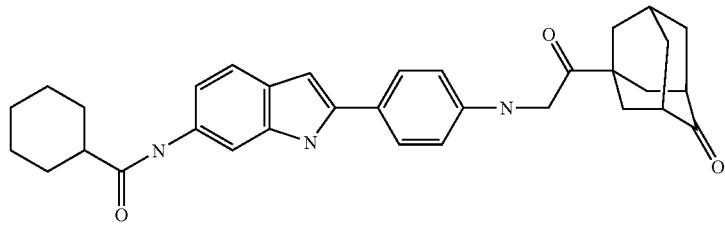
S-108
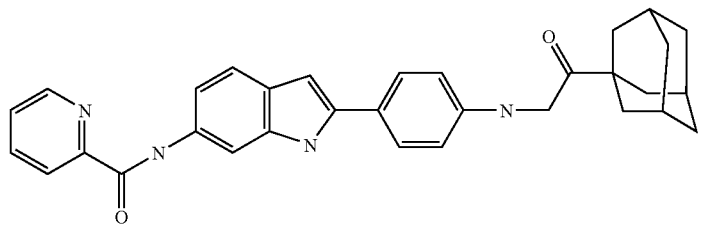
S-109
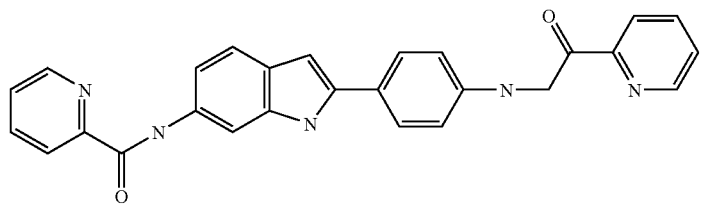
S-110
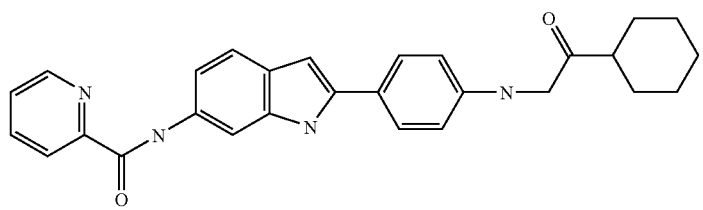
S-111
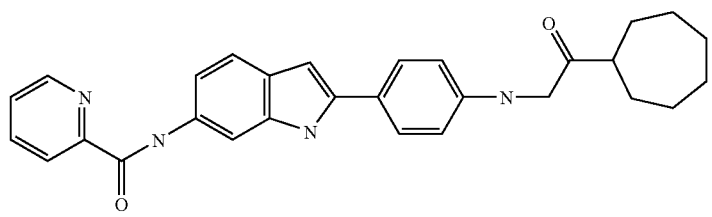
S-112
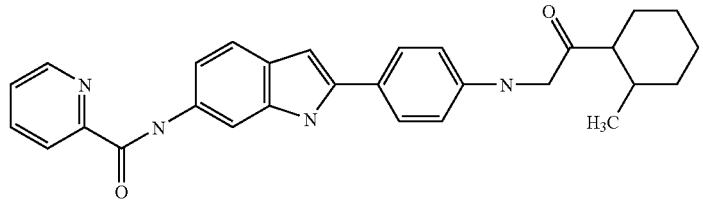
S-113
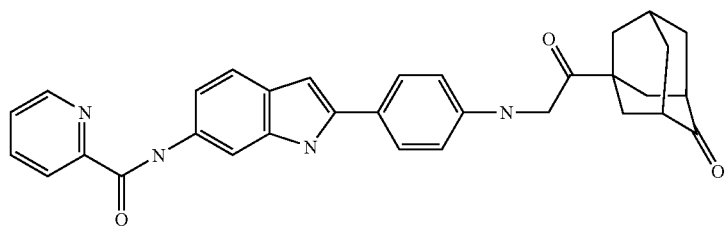

-continued
S-114
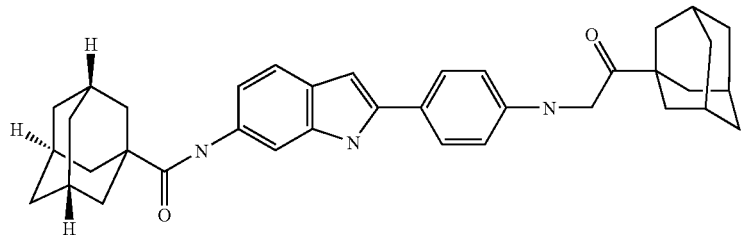
S-115
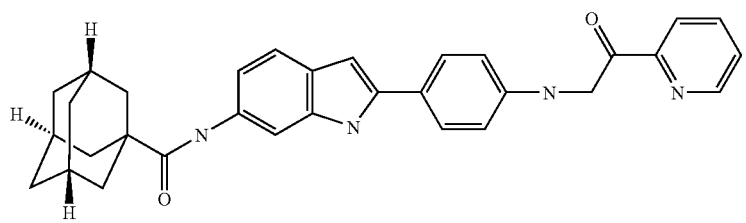
S-116
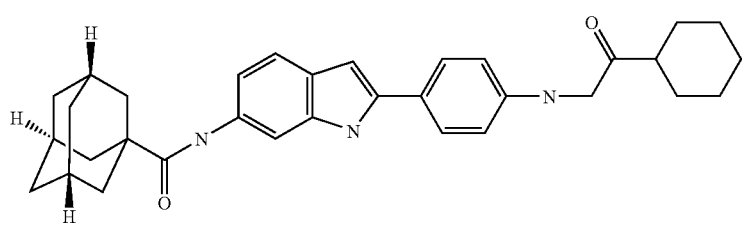
S-117
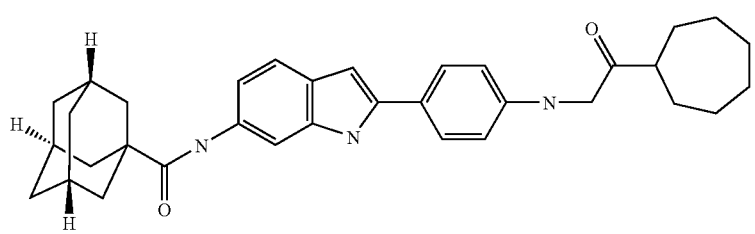
S-118
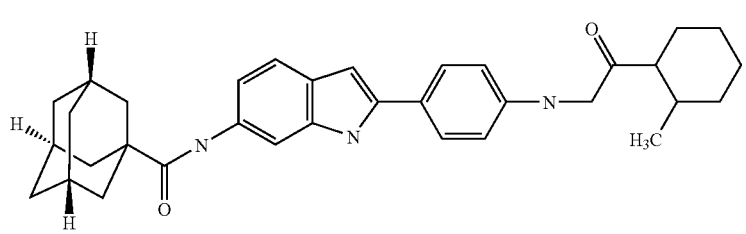
S-119
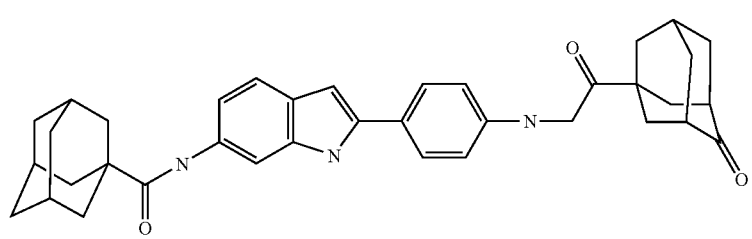
S-120
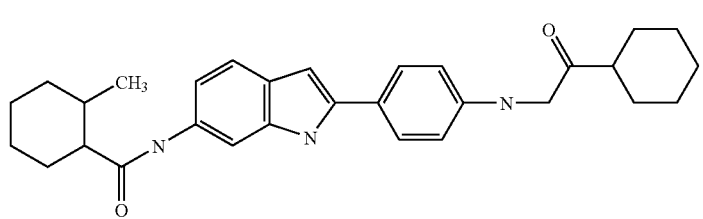

S-121

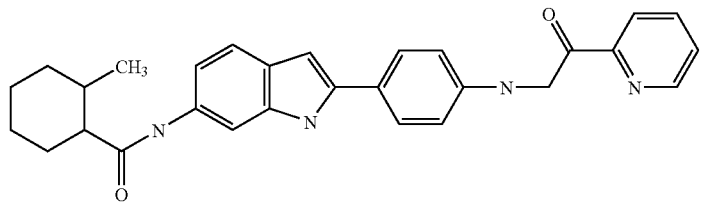

S-122

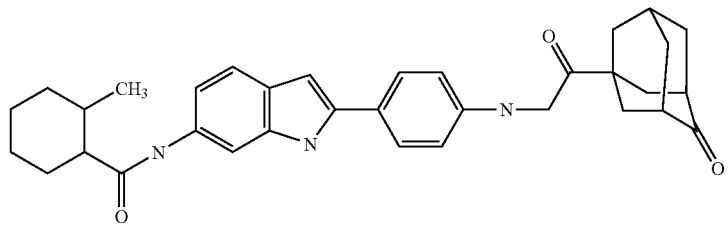

S-123

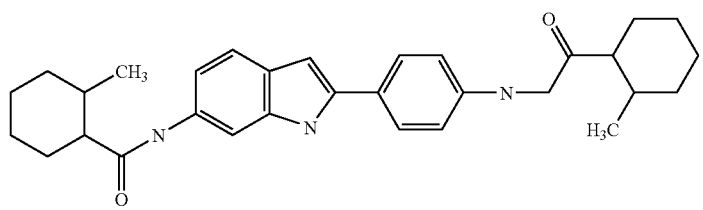

Compounds of Genus I may be synthesized by any conventional reactions known in the art. Examples of syntheses include the following reactions, designated Synthetic Scheme I:

Synthesis of the Compounds of Genus I

Synthetic Scheme I shows one method that can be used to prepare the compounds of Genus I. One skilled in the art will appreciate that a number of different synthetic reaction

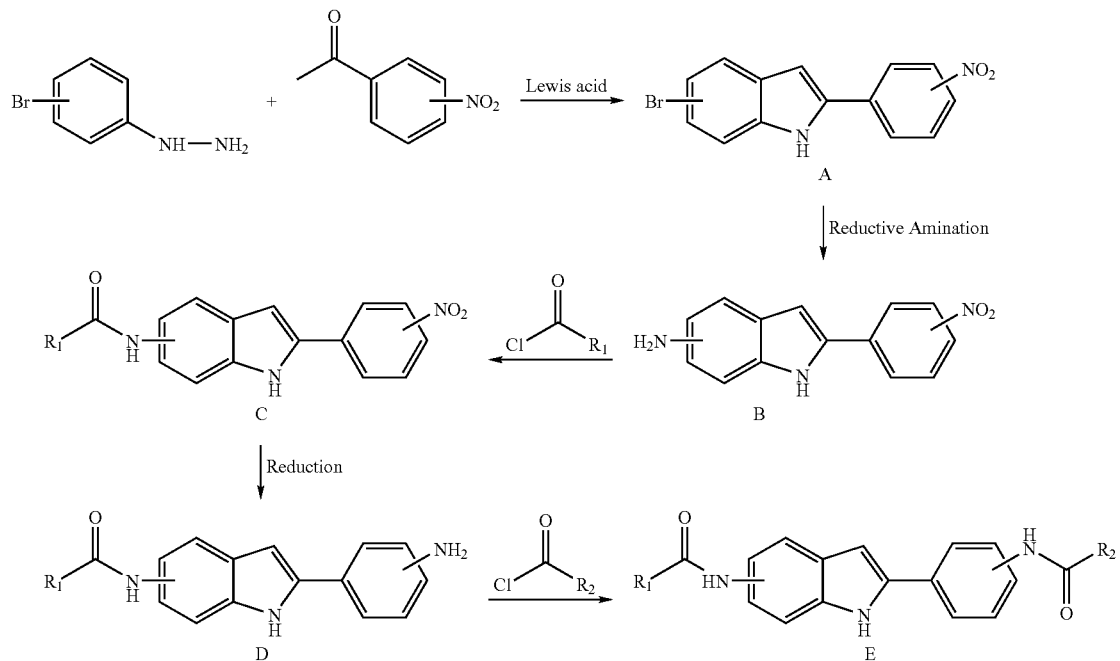

schemes may be used to synthesize the compounds of Genus I. Further, one skilled in the art will understand that a number of different solvents, coupling agents and reaction conditions can be used in the syntheses reactions to yield comparable results.

Compound E is representative of the compounds in Genus I.

One skilled in the art will appreciate variations in the sequence and further, will recognize variations in the appropriate reaction conditions from the analogous reactions shown or otherwise known which may be appropriately used in the processes above to make compounds A–E.

In the processes described herein for the preparation of compounds A–E of preferred embodiments, the requirements for protective groups are generally well recognized by one skilled in the art of organic chemistry, and accordingly the use of appropriate protecting groups is necessarily implied by the processes of the schemes herein, although such groups may not be expressly illustrated. Introduction and removal of such suitable protecting groups are well known in the art of organic chemistry; see for example, T. W. Greene, "Protective Groups in Organic Synthesis", Wiley (New York), 1981.

The products of the reactions described herein are isolated by conventional means such as extraction, distillation, chromatography, and the like.

Starting materials not described herein are available commercially, are known, or can be prepared by methods known in the art.

The salts of compounds A–E described above are prepared by reacting the appropriate base or acid with a stoichiometric equivalent of compounds A–E.

Compounds of Genus II

One family of small molecule IgE inhibitors is defined by the following genus (Genus II):

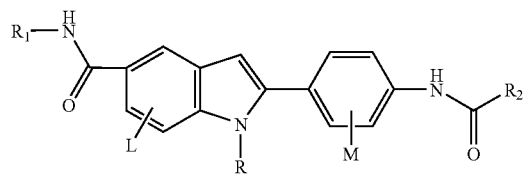

Genus II wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$–$C_5$ alkyl, benzyl, p-fluorobenzyl and di-alkylamino alkyl, wherein said $C_1$–$C_5$ alkyl is selected from the group consisting of a straight chain, branched or cyclic alkyl;

wherein $R_1$ and $R_2$ are independently selected from the group consisting of H, alkyl, substituted alkyl, $C_3$–$C_9$ cycloalkyl, substituted $C_3$–$C_9$ cycloalkyl, polycyclic aliphatic groups, substituted polycyclic aliphatic groups, phenyl, substituted phenyl, naphthyl, substituted naphthyl, heterocyclic, polycyclic heterocyclic, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1–3 substituents, wherein said substituent is selected from the group consisting of H, halogens, polyhalogens, alkoxy group, substituted alkoxy, alkyl, substituted alkyl, dialkylaminoalkyl, hydroxyalkyl, hydroxyamino, alkoxyamino, carbonyl, OH, $OCH_3$, COOH, COOR' COR', CN, $CF_3$, $OCF_3$, $NO_2$, NR'R', NHCOR', and CONR'R'; and wherein R' is selected from the group consisting of H, alkyl, substituted alkyl, $C_3$–$C_9$ cycloalkyl, substituted $C_3$–$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur.

One subgenus of small molecule IgE inhibitors of the preferred embodiments is defined by the following formula, as Subgenus IIa:

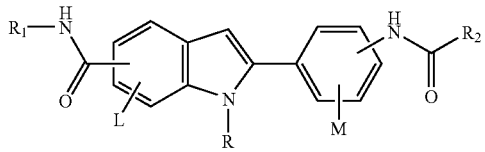

Subgenus IIa wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$–$C_5$ alkyl, benzyl, p-fluorobenzyl and di-alkylamino alkyl, wherein said $C_1$–$C_5$ alkyl is selected from the group consisting of a straight chain, branched or cyclic alkyl;

wherein $R_1$ and $R_2$ are independently selected from the group consisting of H, alkyl, substituted alkyl, $C_3$–$C_9$ cycloalkyl, substituted $C_3$–$C_9$ cycloalkyl, polycyclic aliphatic groups, substituted polycyclic aliphatic groups, phenyl, substituted phenyl, naphthyl, substituted naphthyl, heterocyclic, polycyclic heterocyclic, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1–3 substituents, wherein said substituent is selected from the group consisting of H, halogens, polyhalogens, alkoxy group, substituted alkoxy, alkyl, substituted alkyl, dialkylaminoalkyl, hydroxyalkyl, hydroxyamino, alkoxyamino, carbonyl, OH, $OCH_3$, COOH, COOR' COR', CN, $CF_3$, $OCF_3$, $NO_2$, NR'R', NHCOR', and CONR'R'; and wherein R' is selected from the group consisting of H, alkyl, substituted alkyl, $C_3$–$C_9$ cycloalkyl, substituted $C_3$–$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur.

One subgenus of small molecule IgE inhibitors of the preferred embodiments is defined by the following formula, as Subgenus IIb:

Subgenus IIb

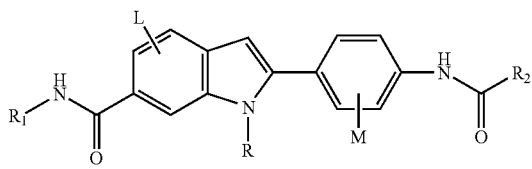

wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$–$C_5$ alkyl, benzyl, p-fluorobenzyl and di-alkylamino alkyl, wherein said $C_1$–$C_5$ alkyl is selected from the group consisting of a straight chain, branched or cyclic alkyl;

wherein $R_1$ and $R_2$ are independently selected from the group consisting of H, alkyl, substituted alkyl, $C_3$–$C_9$ cycloalkyl, substituted $C_3$–$C_9$ cycloalkyl, polycyclic aliphatic groups, substituted polycyclic aliphatic groups, phenyl, substituted phenyl, naphthyl, substituted naphthyl, heterocyclic, polycyclic heterocyclic, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1–3 substituents, wherein said substituent is selected from the group consisting of H, halogens, polyhalogens, alkoxy group, substituted alkoxy, alkyl, substituted alkyl, dialkylaminoalkyl, hydroxyalkyl, hydroxyamino, alkoxyamino, carbonyl, OH, $OCH_3$, COOH, COOR' COR', CN, $CF_3$, $OCF_3$, $NO_2$, NR'R', NHCOR', and CONR'R'; and wherein R' is selected from the group consisting of H, alkyl, substituted alkyl, $C_3$–$C_9$ cycloalkyl, substituted $C_3$–$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur.

The following specific compounds were synthesized as described below and found to be active in both ex vivo and in vivo assays. They are encompassed within the definition of Genus II:

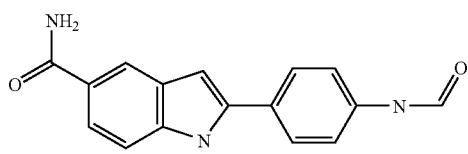

| MOL NUMBER | MOLSTRUCTURE |
|---|---|
| T-1 | 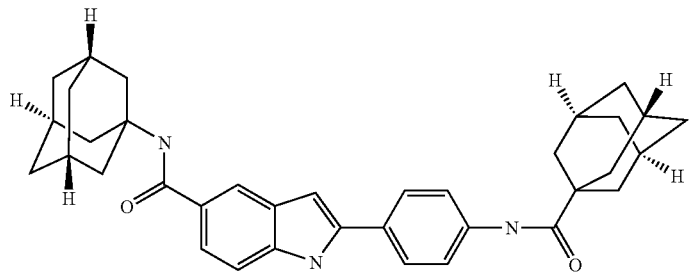 |
| T-2 | 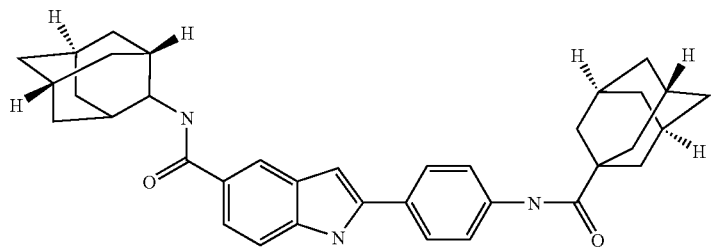 |
| T-3 | 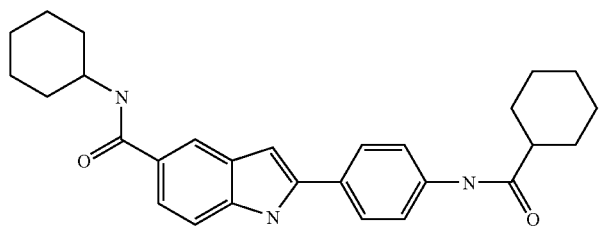 |

-continued
T-4 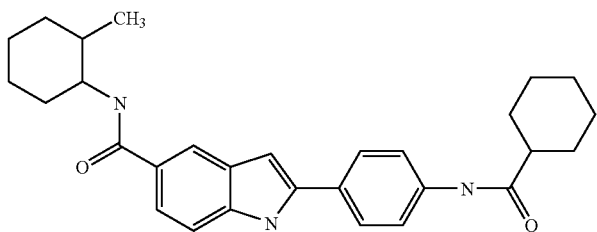
T-5 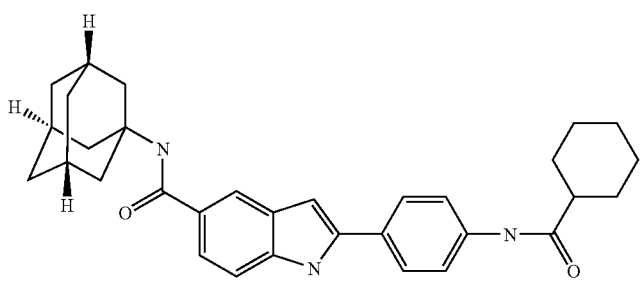
T-6 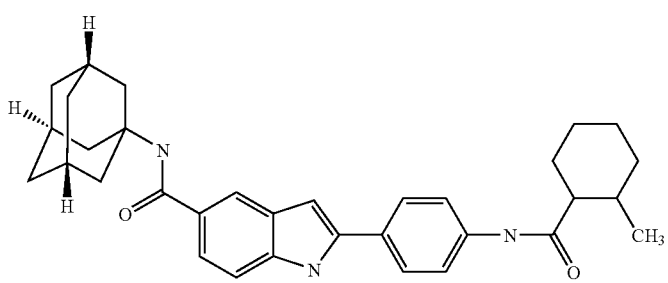
T-7 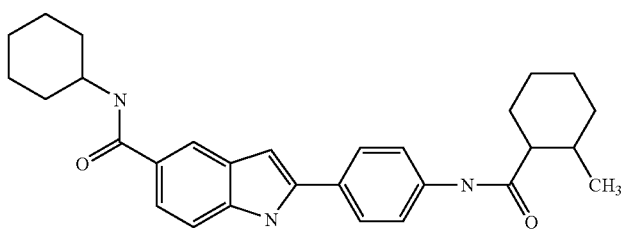
T-8 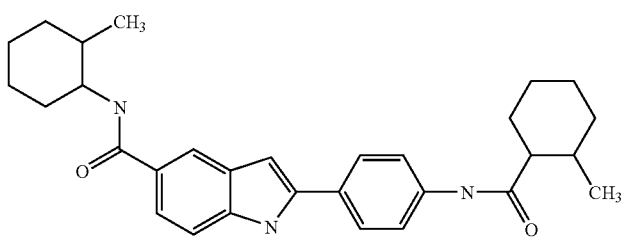
T-9 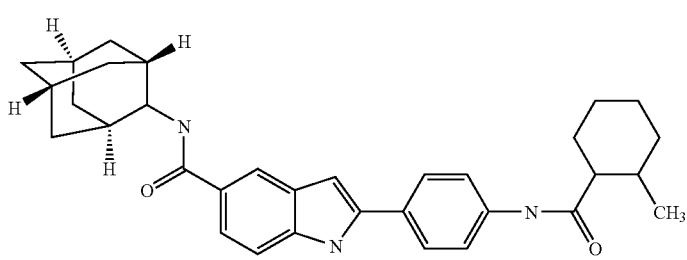

-continued
T-10 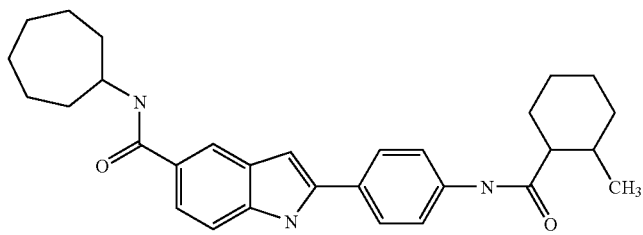
T-11 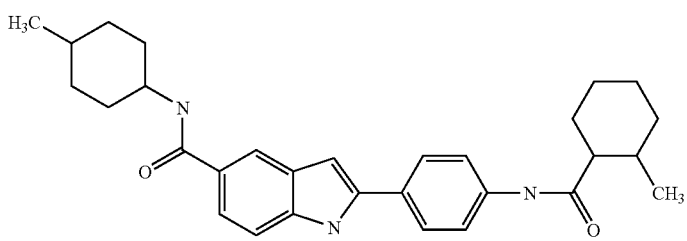
T-12 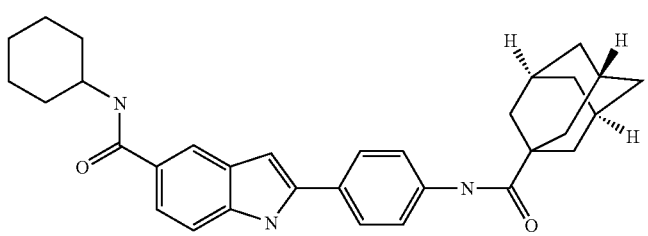
T-13 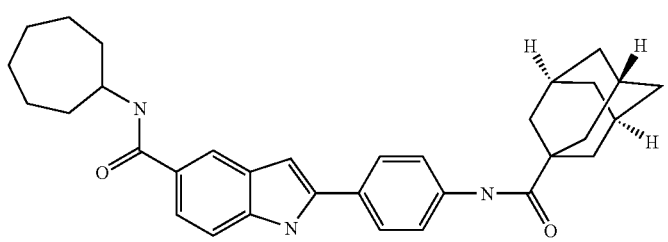
T-14 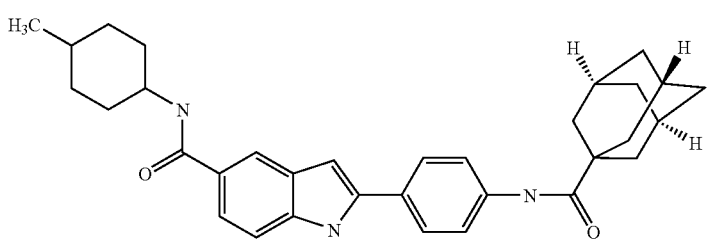
T-15 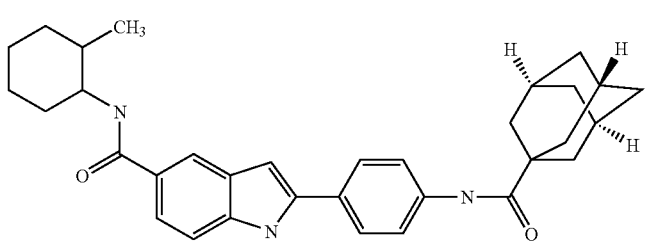

-continued
T-16
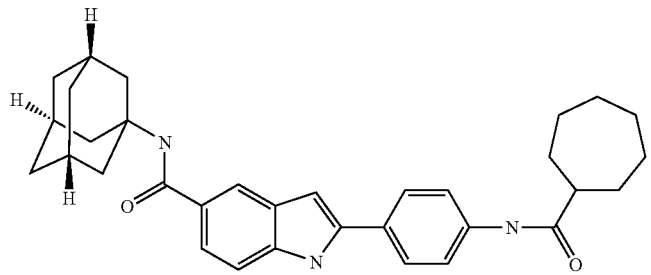
T-17
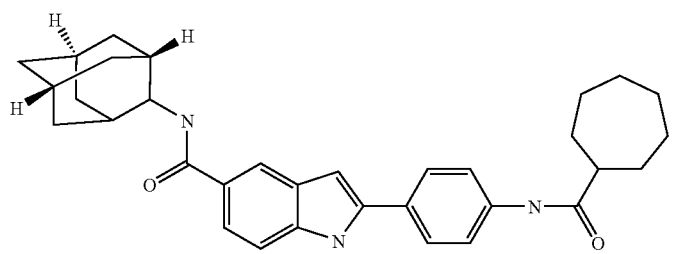
T-18
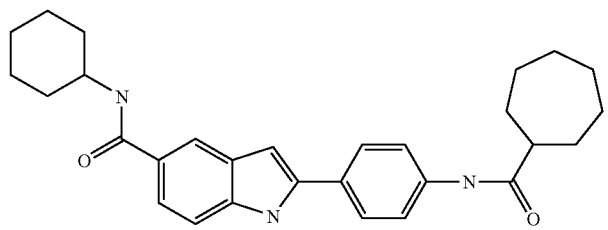
T-19
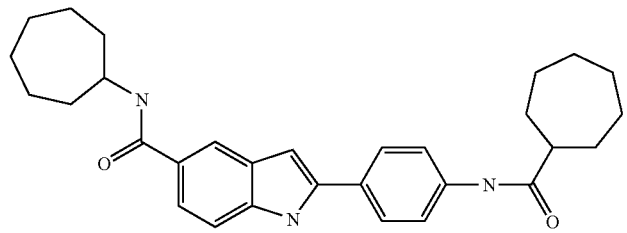
T-20
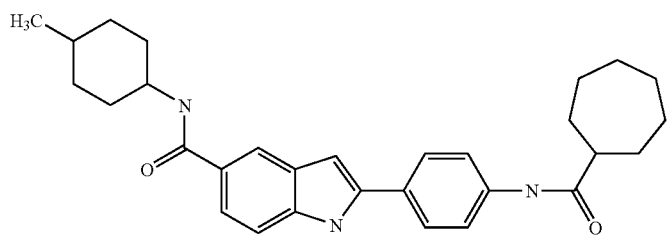
T-21
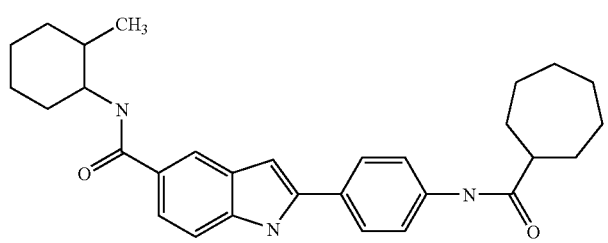

-continued
T-22 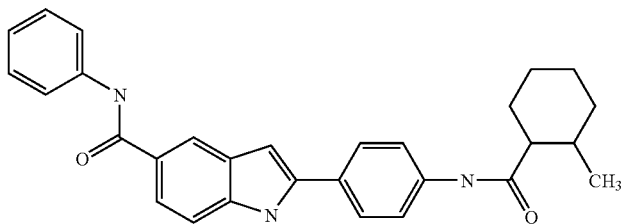
T-23 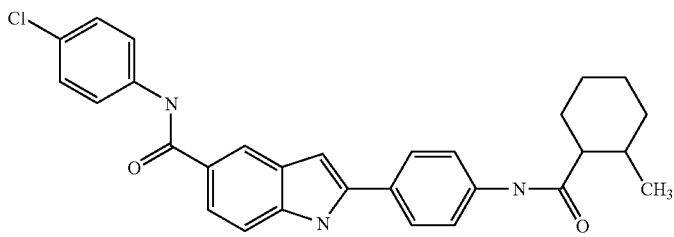
T-24 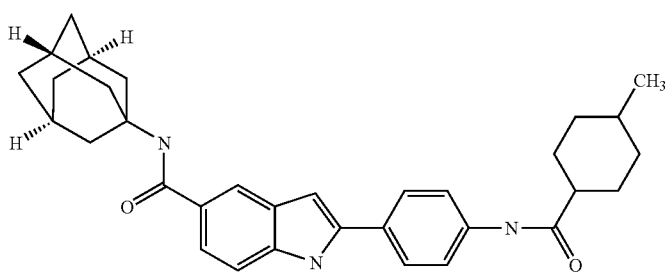
T-25 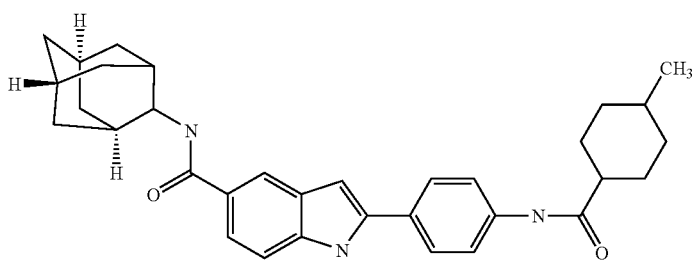
T-26 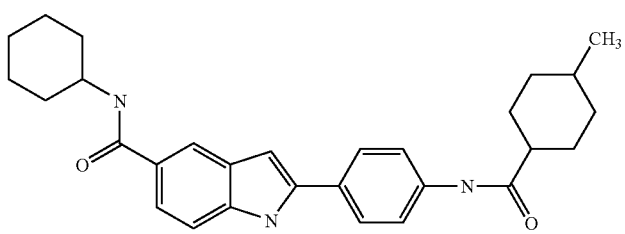
T-27 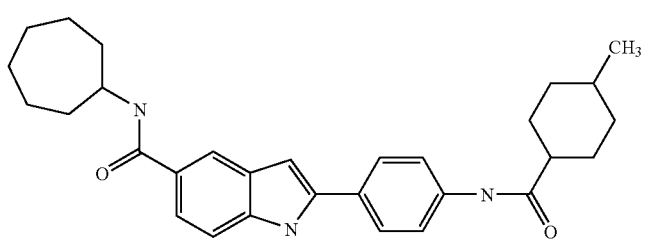

-continued
T-28 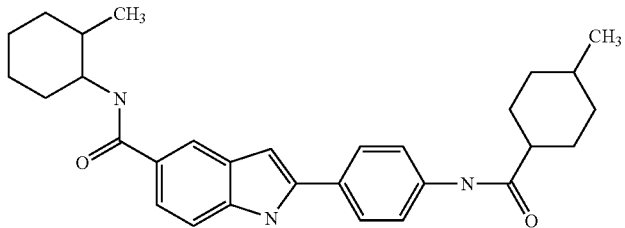
T-29 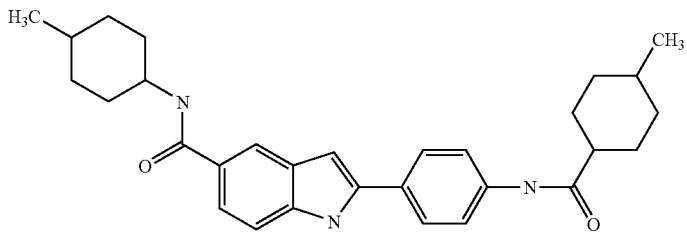
T-30 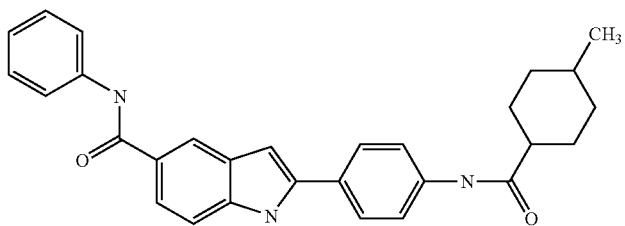
T-31 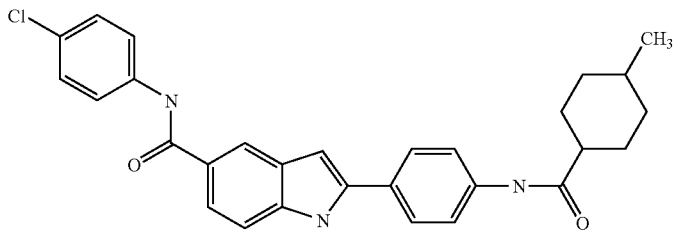
T-32 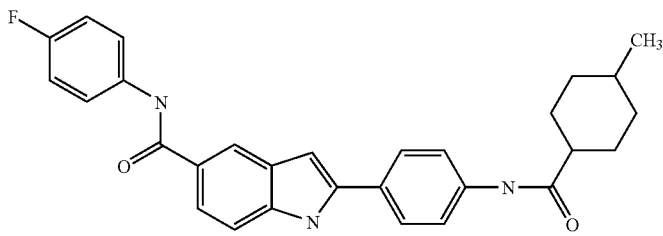
T-33 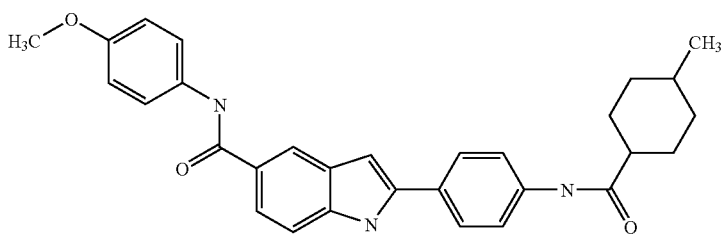

-continued
T-34 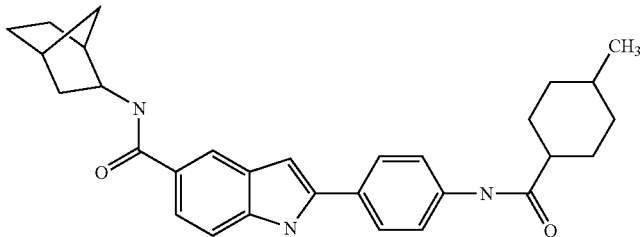
T-35 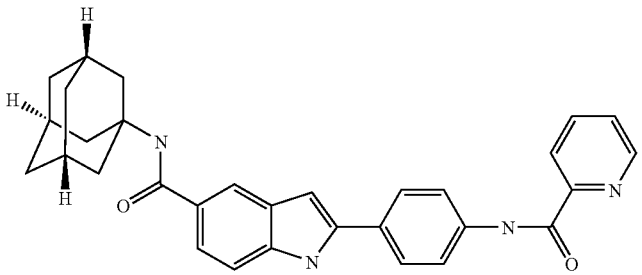
T-36 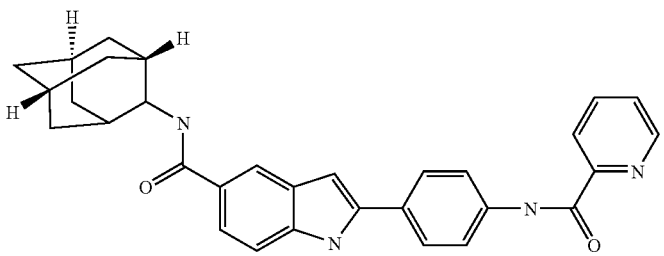
T-37 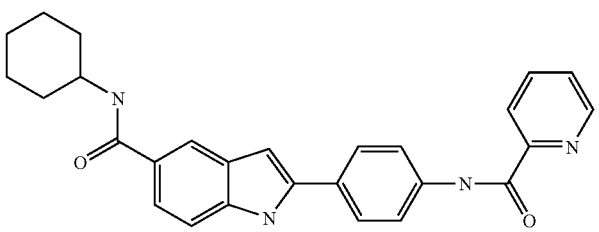
T-38 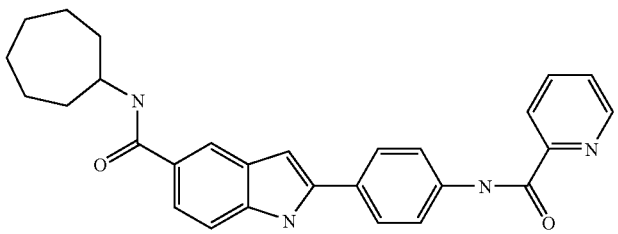
T-39 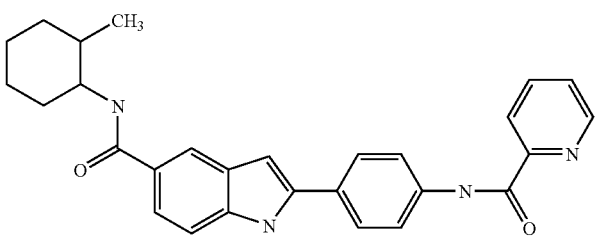

-continued
T-40 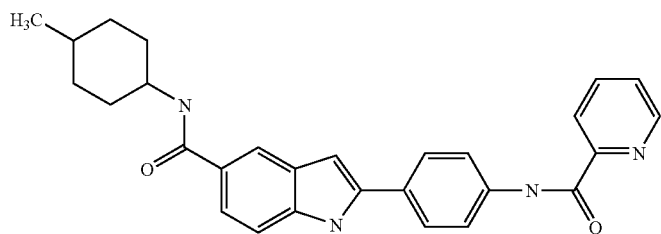
T-41 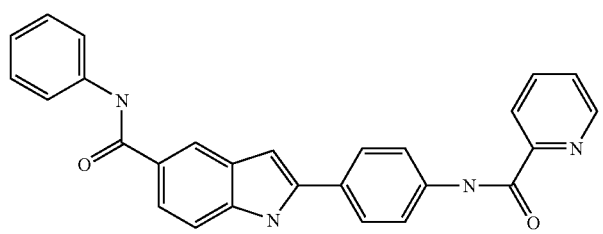
T-42 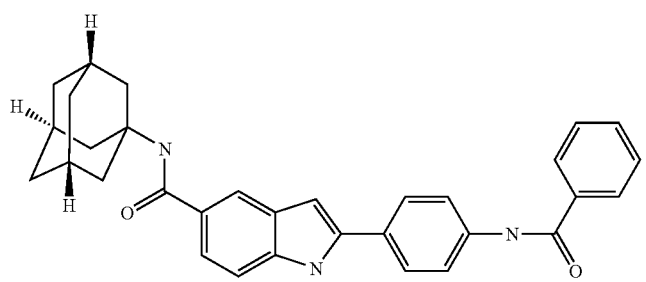
T-43 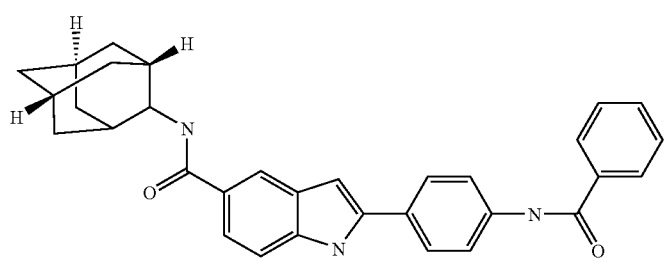
T-44 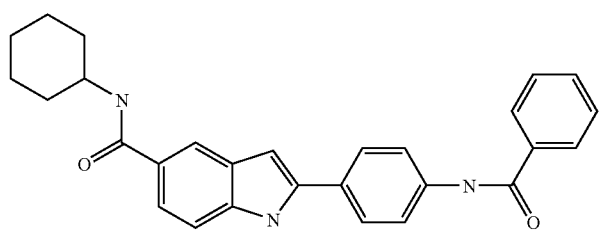
T-45 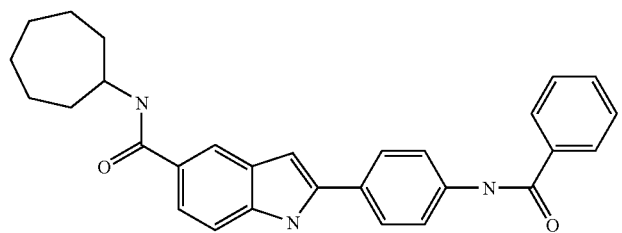

-continued
T-46 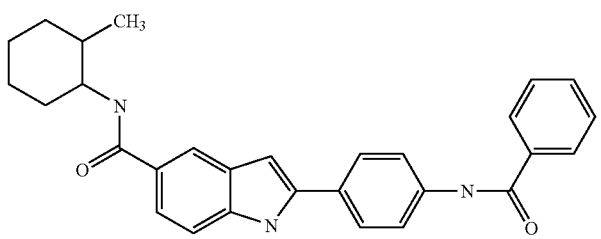
T-47 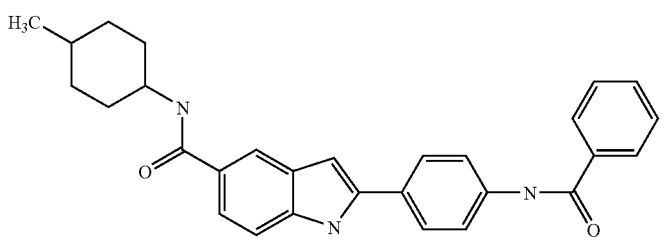
T-48 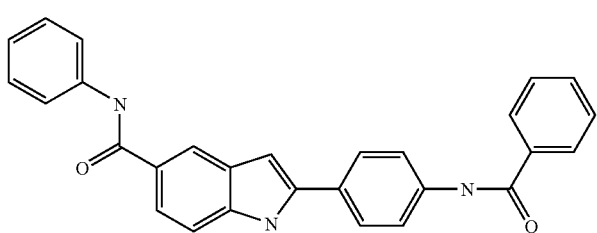
T-49 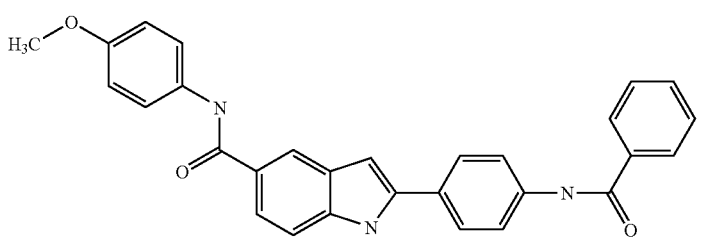
T-50 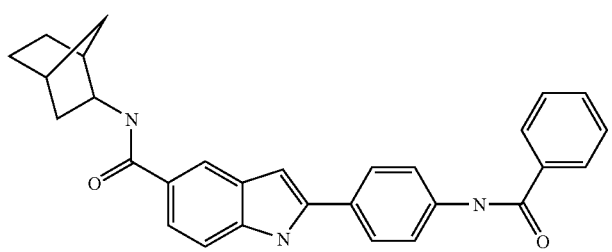
T-51 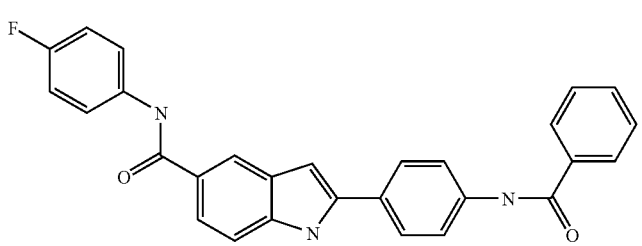

-continued
T-52
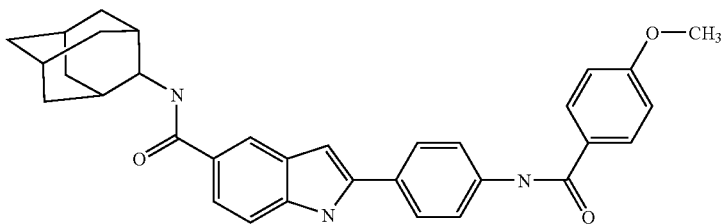
T-53
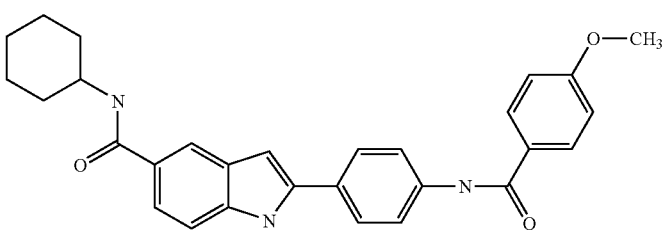
T-54
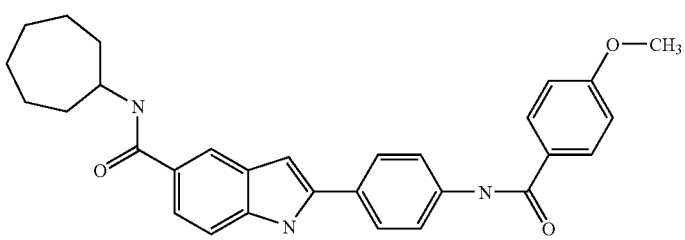
T-55
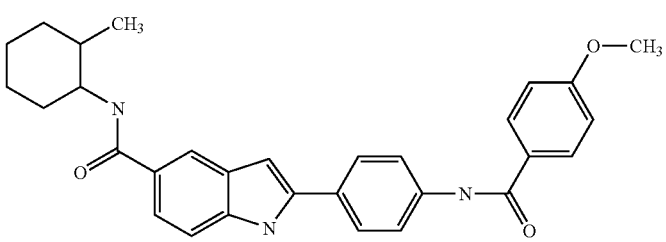
T-56
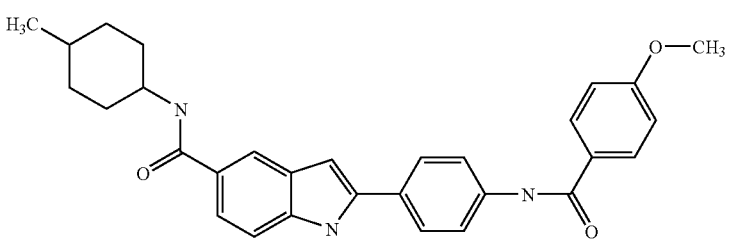
T-57
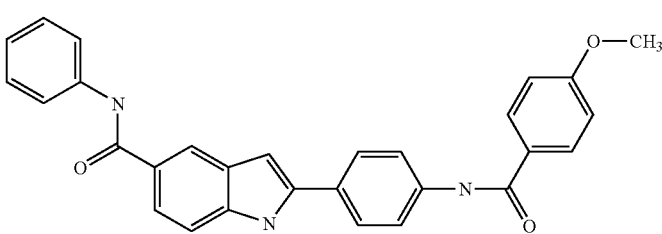

-continued
T-58 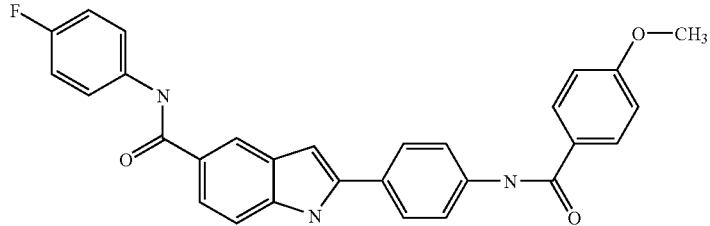
T-59 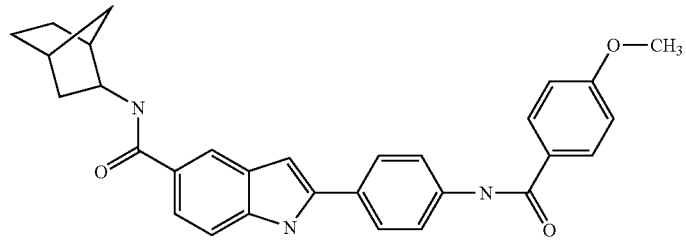
T-60 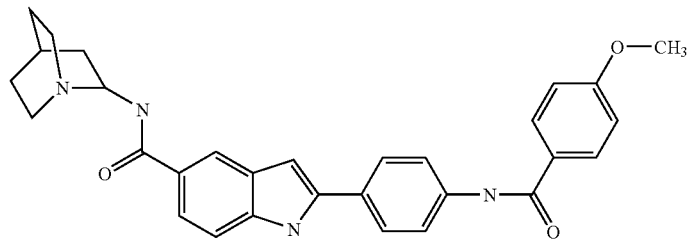
T-61 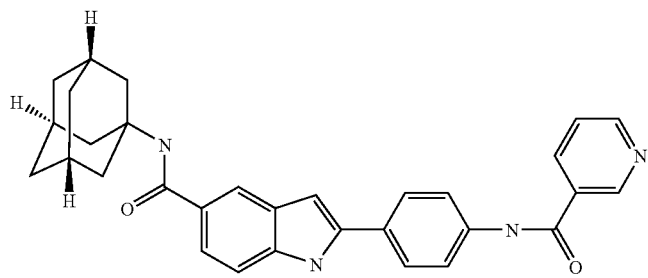
T-62 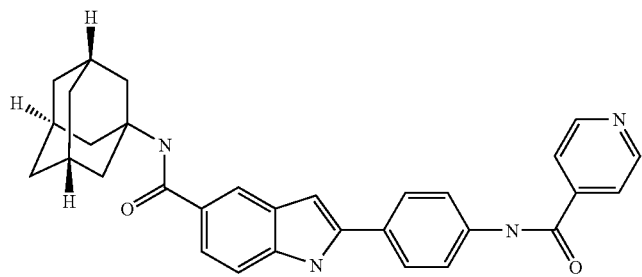
T-63 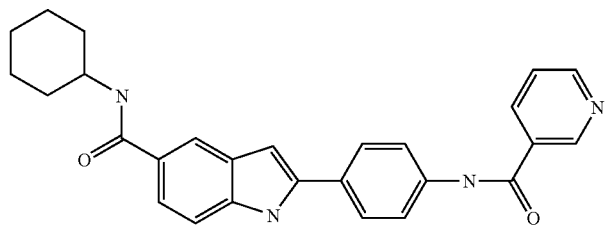

-continued
T-64 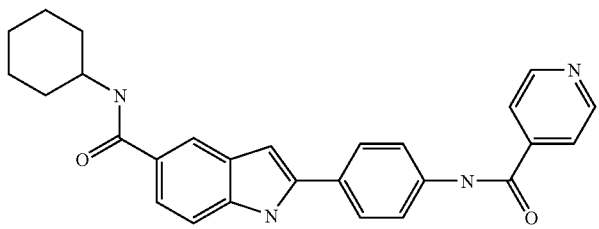
T-65 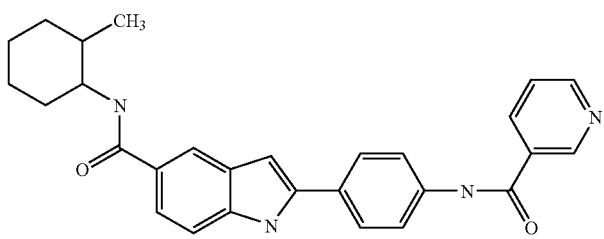
T-66 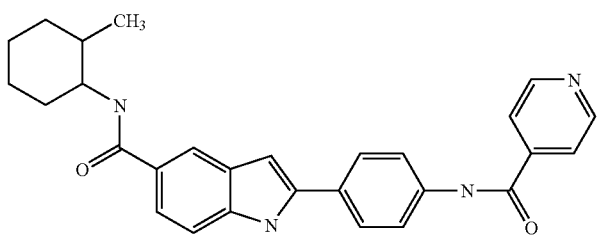
T-67 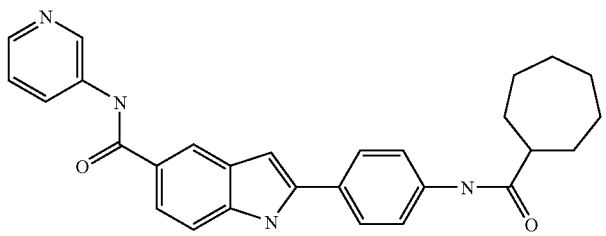
T-68 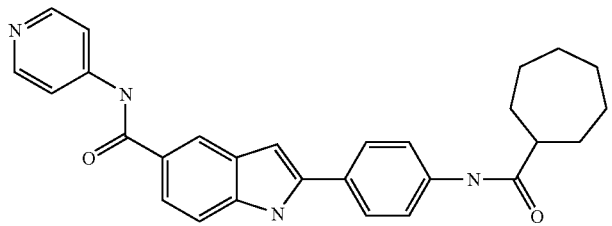
T-69 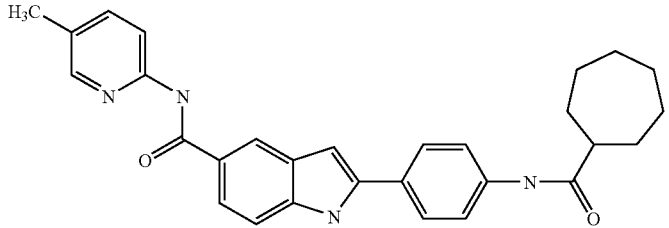

T-70
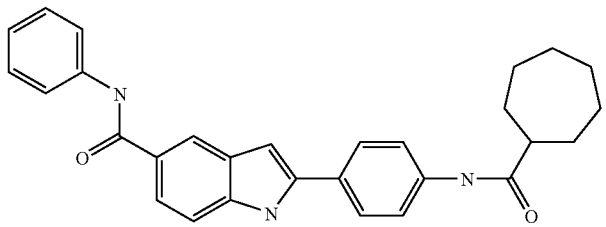
T-71
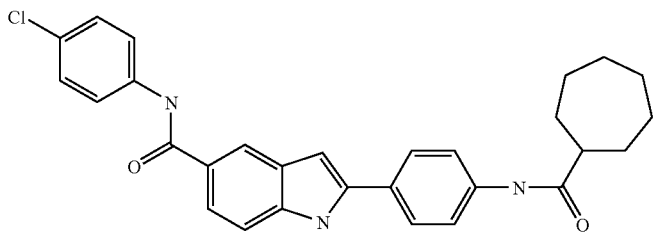
T-72
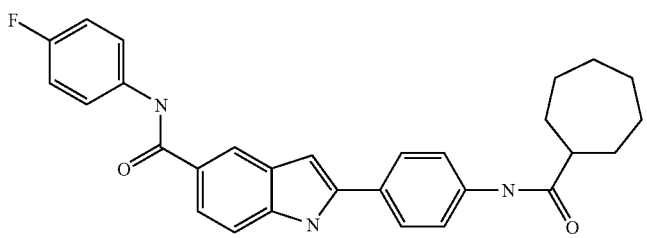
T-73
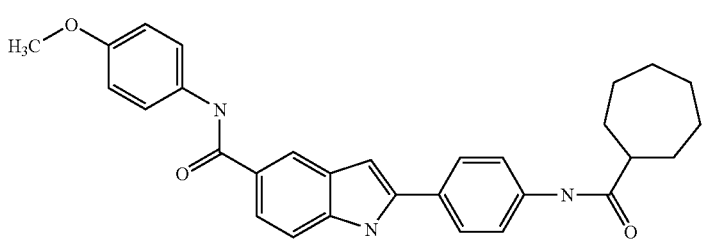
T-74
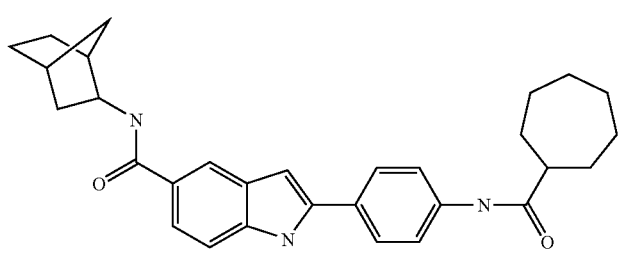
T-75
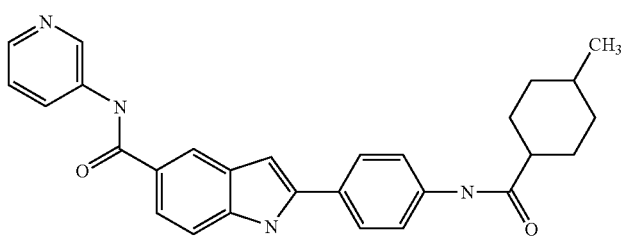

-continued
T-76 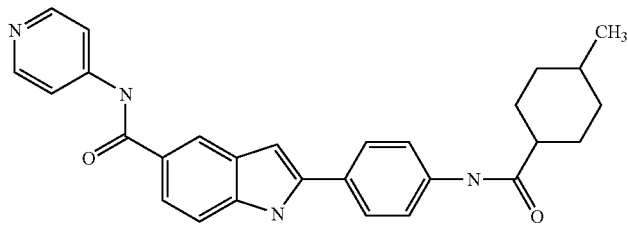
T-77 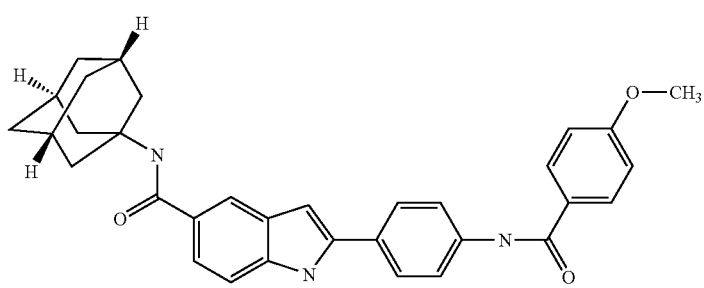
T-78 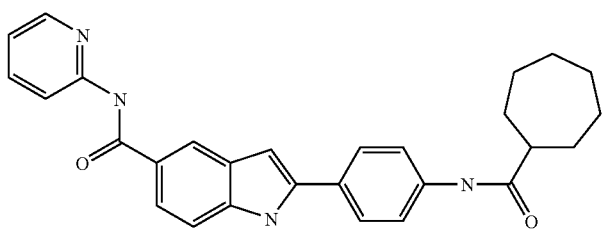
T-79 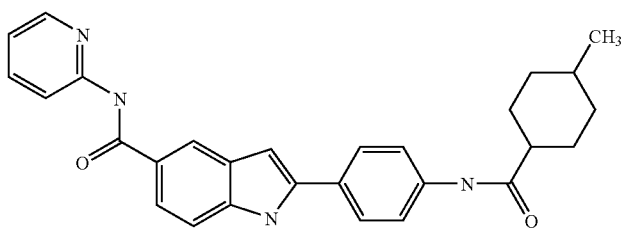
T-80 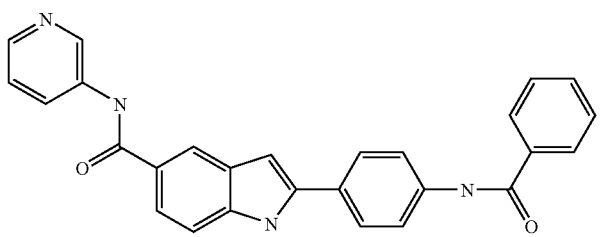
T-81 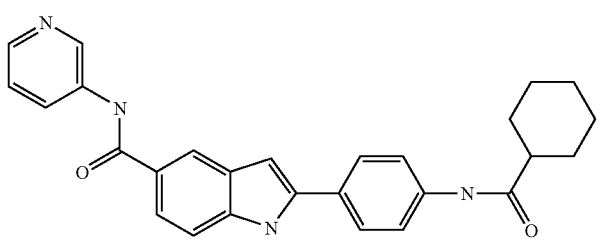

-continued
T-82 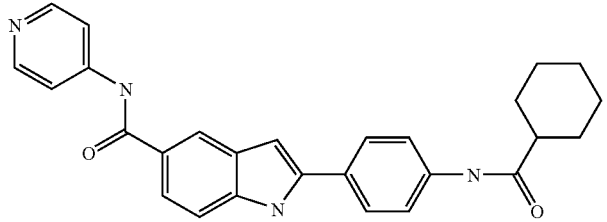
T-83 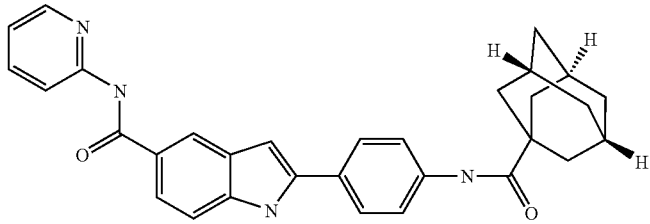
T-84 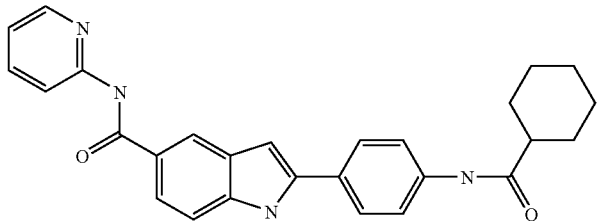
T-85 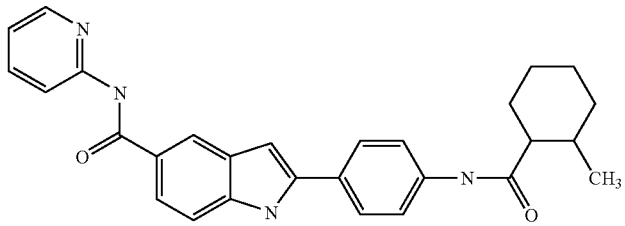
T-86 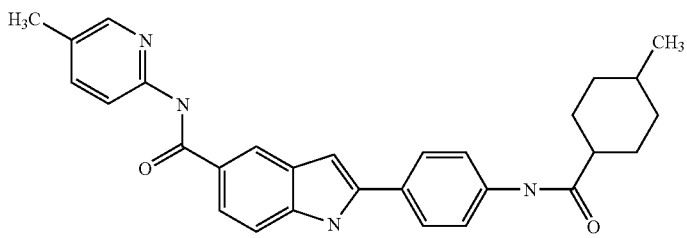
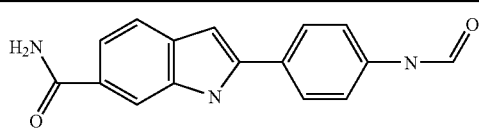
| MOL NUMBER | MOLSTRUCTURE |
| --- | --- |
T-87 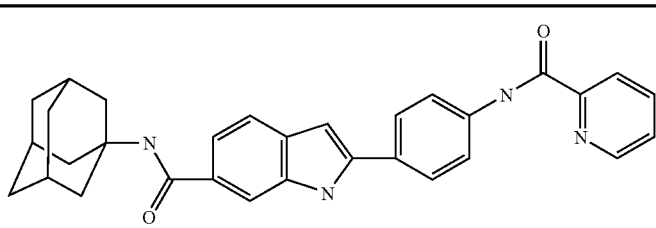

-continued
T-88 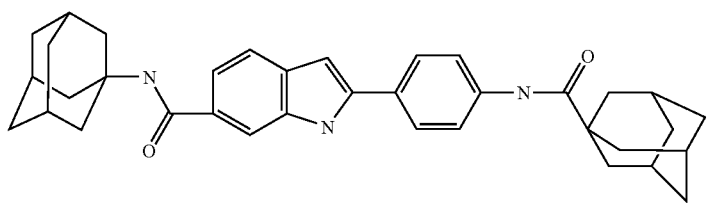
T-89 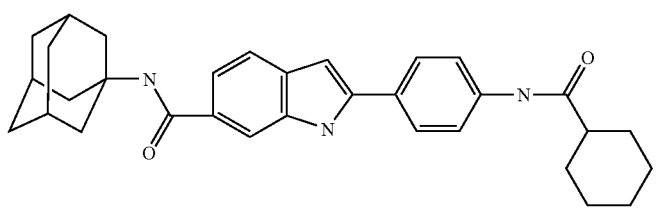
T-90 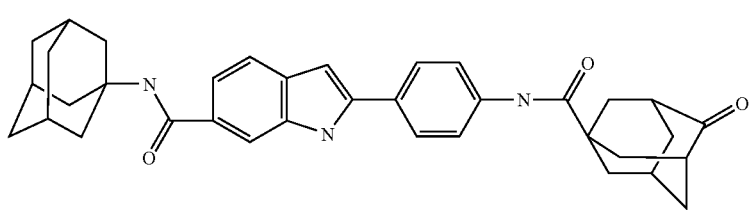
T-91 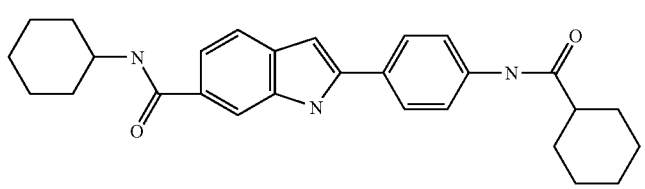
T-92 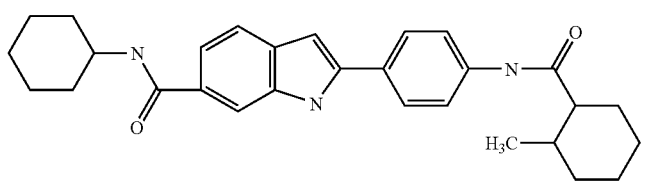
T-93 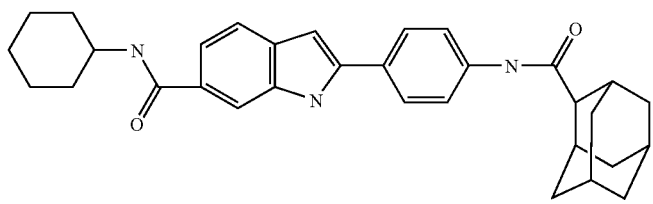
T-94 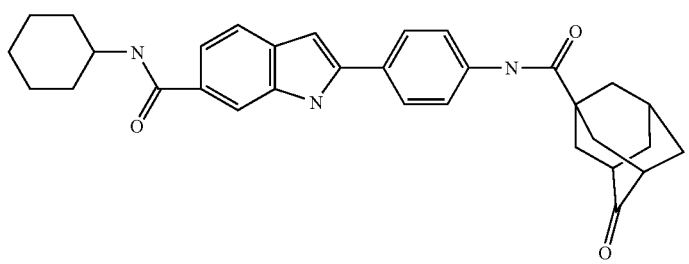

-continued
T-95 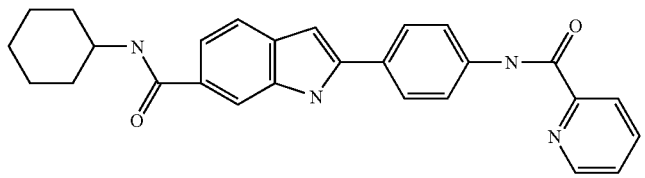
T-96 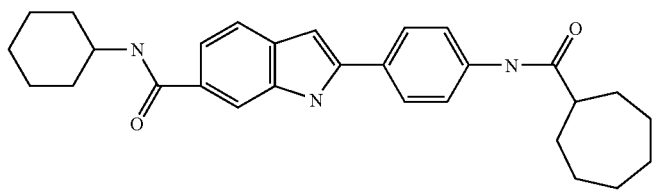
T-97 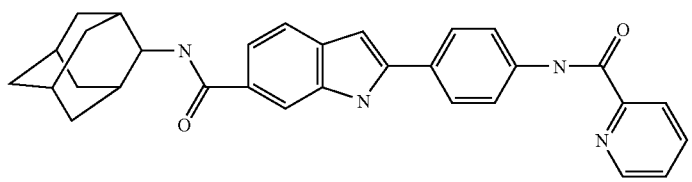
T-98 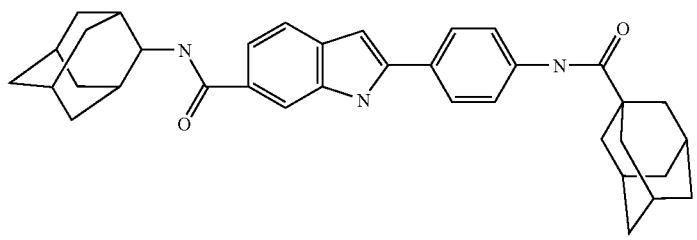
T-99 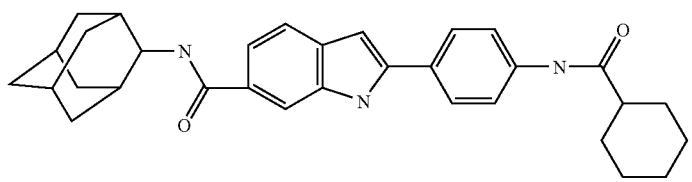
T-100 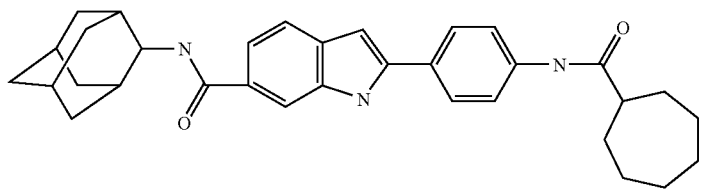
T-101 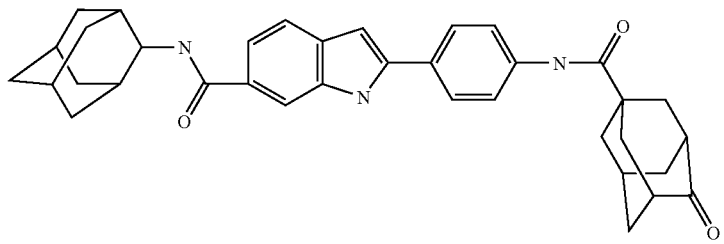

T-102
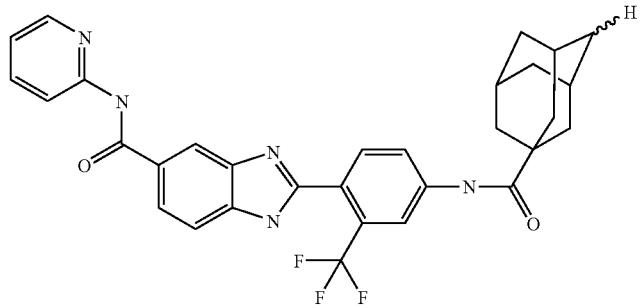
Compounds of Genus II may be synthesized by any conventional reactions known in the art. Examples of syntheses include the following reactions, designated Synthetic Scheme II:
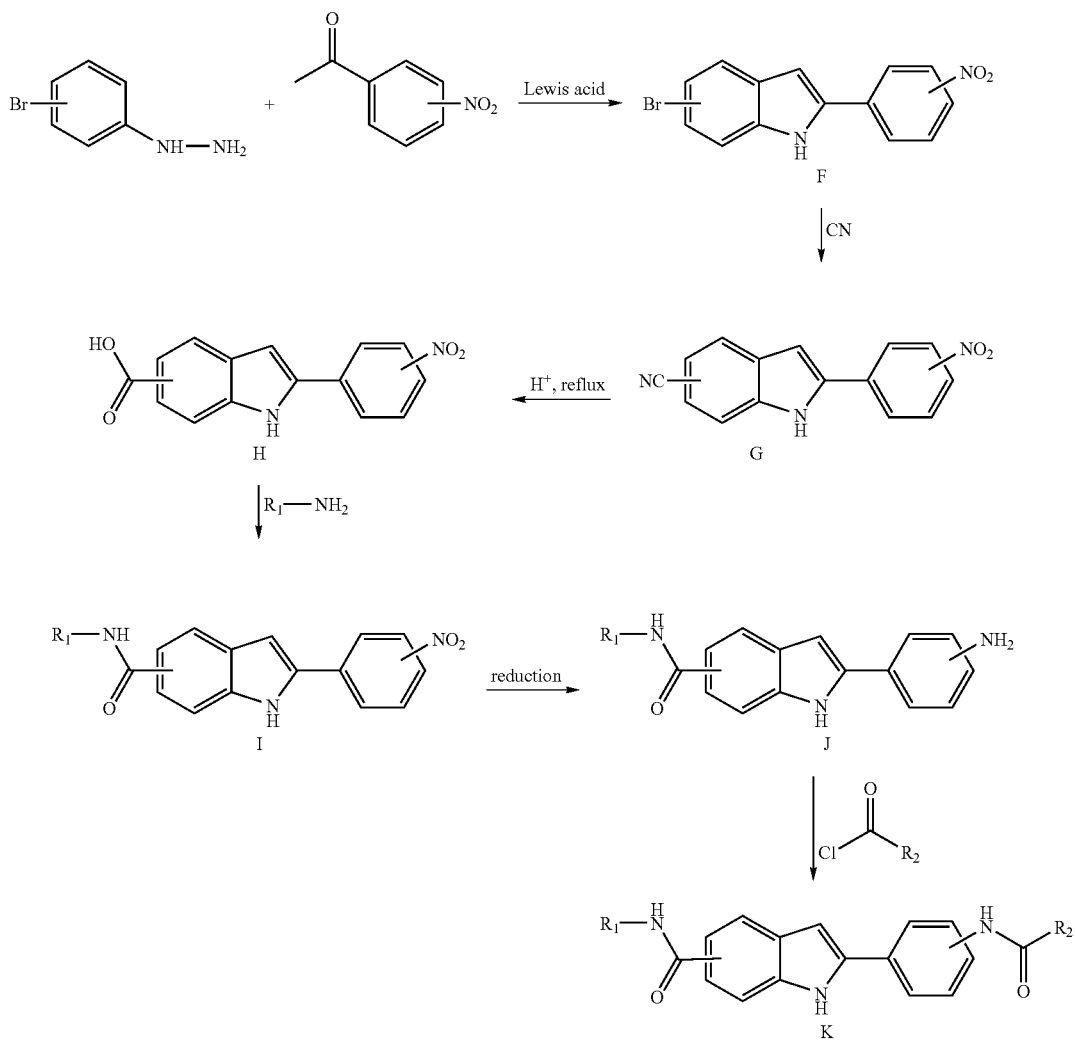

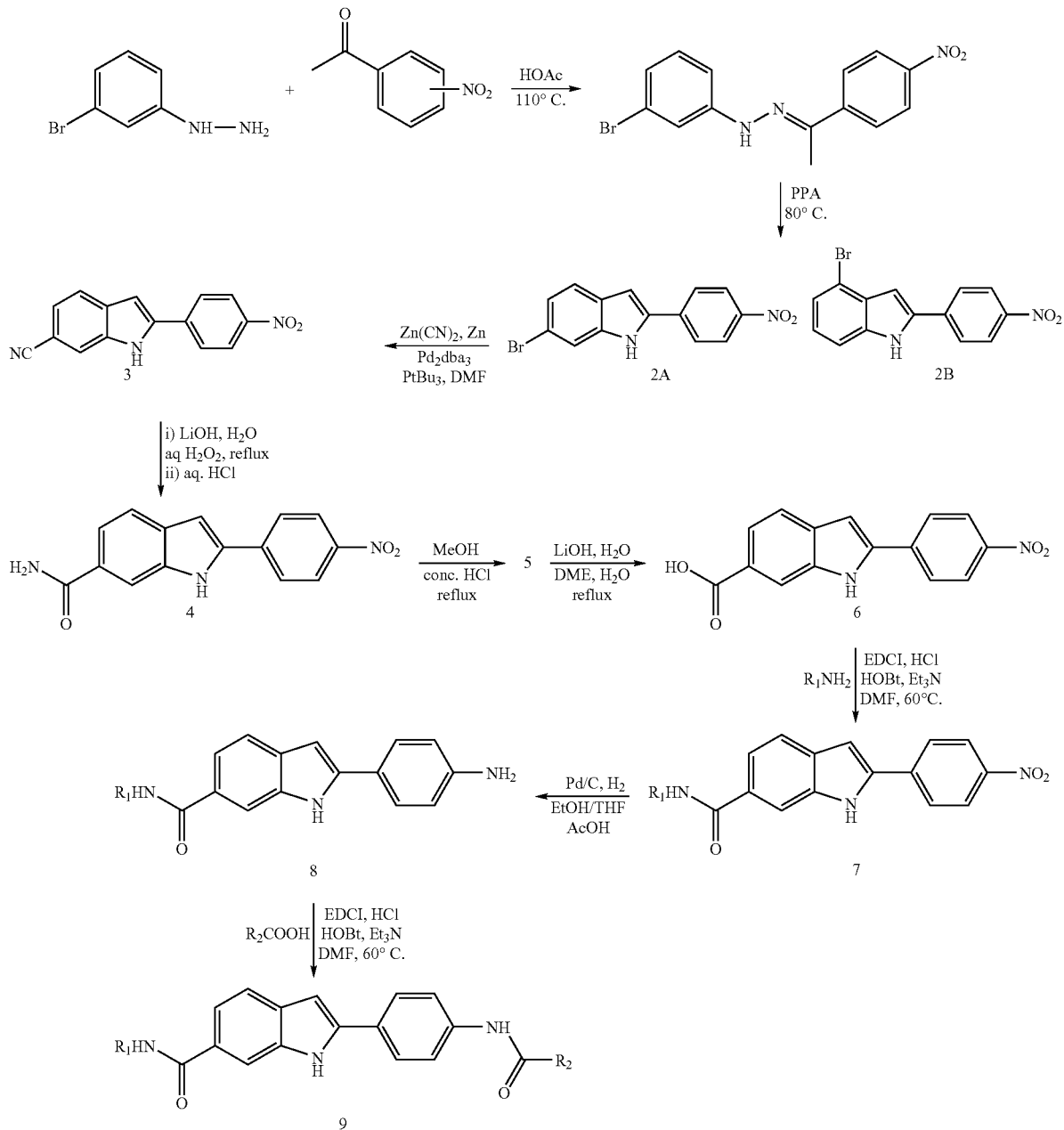

Synthetic Scheme IIa

Synthesis of the Compounds of Genus II

Synthetic Scheme II shows one method that can be used to prepare the compounds of Genus II. Synthetic Scheme IIa shows a certain embodiment of a method that can be used to prepare the compounds of Genus II. One skilled in the art will appreciate that a number of different synthetic reaction schemes may be used to synthesize the compounds of Genus II. Further, one skilled in the art will understand that a number of different solvents, coupling agents and reaction conditions can be used in the syntheses reactions to yield comparable results.

Compound K is representative of the compounds in Genus II.

One skilled in the art will appreciate variations in the sequence and further, will recognize variations in the appropriate reaction conditions from the analogous reactions shown or otherwise known which may be appropriately used in the processes above to make compounds F–K.

In the processes described herein for the preparation of compounds F–K of the preferred embodiments, the requirements for protective groups are generally well recognized by one skilled in the art of organic chemistry, and accordingly the use of appropriate protecting groups is necessarily implied by the processes of the schemes herein, although such groups may not be expressly illustrated. Introduction and removal of such suitable protecting groups are well known in the art of organic chemistry; see for example, T. W. Greene, "Protective Groups in Organic Synthesis", Wiley (New York), 1981.

The products of the reactions described herein are isolated by conventional means such as extraction, distillation, chromatography, and the like.

Starting materials not described herein are available commercially, are known, or can be prepared by methods known in the art.

The salts of compounds F–K described above are prepared by reacting the appropriate base or acid with a stoichiometric equivalent of the compounds of compounds F–K.

Examples of compounds of Genus II are shown below in an array. Preferred compounds can be synthesized according to the above methods.

-continued

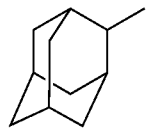

3

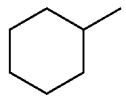

4

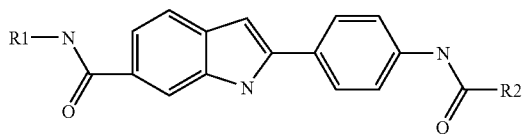

Project-I

| R2 | R1 | | | | | | | | | | | | | | | | | | | |
|---|---|---|---|---|---|---|---|---|---|---|---|---|---|---|---|---|---|---|---|---|
|  | 1 | 2 | 3 | 4 | 5 | 6 | 7 | 8 | 9 | 10 | 11 | 12 | 13 | 14 | 15 | 16 | 17 | 18 | 19 | 20 |
| 1 | | | | | | | | | | | | | | | | | | | | |
| 2 | | | | | | | | | | | | | | | | | | | | |
| 3 | | | | | | | | | | | | | | | | | | | | |
| 4 | | | | | | | | | | | | | | | | | | | | |
| 5 | | | | | | | | | | | | | | | | | | | | |
| 6 | | | | | | | | | | | | | | | | | | | | |
| 7 | | | | | | | | | | | | | | | | | | | | |
| 8 | | | | | | | | | | | | | | | | | | | | |
| 9 | | | | | | | | | | | | | | | | | | | | |
| 10 | | | | | | | | | | | | | | | | | | | | |
| 11 | | | | | | | | | | | | | | | | | | | | |
| 12 | | | | | | | | | | | | | | | | | | | | |
| 13 | | | | | | | | | | | | | | | | | | | | |
| 14 | | | | | | | | | | | | | | | | | | | | |
| 15 | | | | | | | | | | | | | | | | | | | | |
| 16 | | | | | | | | | | | | | | | | | | | | |
| 17 | | | | | | | | | | | | | | | | | | | | |
| 18 | | | | | | | | | | | | | | | | | | | | |
| 19 | | | | | | | | | | | | | | | | | | | | |
| 20 | | | | | | | | | | | | | | | | | | | | |

A family of compounds can be made with the formula shown in Project I. The substituents $R_1$ and $R_2$ can be chosen from Substituents 1–20, as shown below.

-continued

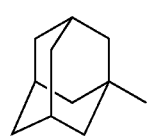

2

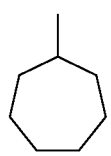

5

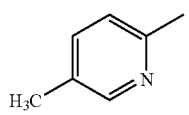

6

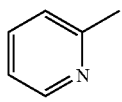

1

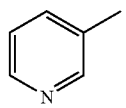

7

-continued

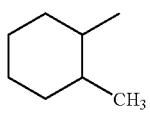
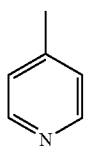
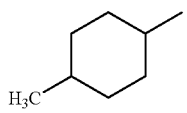
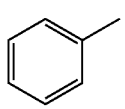
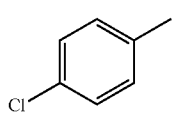
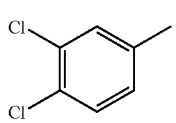
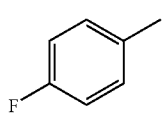
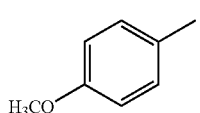
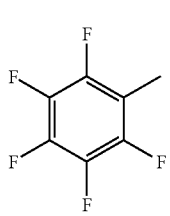
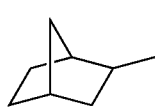
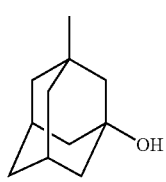

-continued

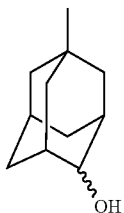
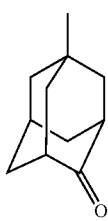

Compounds of Genus III

One family of small molecule IgE inhibitors is defined by the following genus (Genus III):

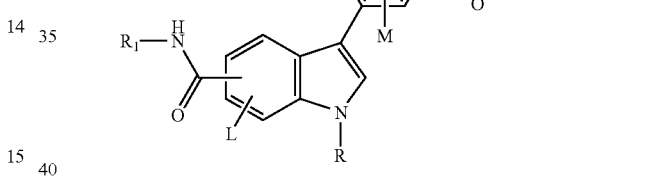

Genus III wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$–$C_5$ alkyl, benzyl, p-fluorobenzyl and di-alkylamino alkyl, wherein said $C_1$–$C_5$ alkyl is selected from the group consisting of a straight chain, branched or cyclic alkyl;

wherein $R_1$ and $R_2$ are independently selected from the group consisting of H, alkyl, substituted alkyl, $C_3$–$C_9$ cycloalkyl, substituted $C_3$–$C_9$ cycloalkyl, polycyclic aliphatic groups, substituted polycyclic aliphatic groups, phenyl, substituted phenyl, naphthyl, substituted naphthyl, heterocyclic, polycyclic heterocyclic, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1–3 substituents, wherein said substituent is selected from the group consisting of H, halogens, polyhalogens, alkoxy group, substituted alkoxy, alkyl, substituted alkyl, dialkylaminoalkyl, hydroxyalkyl, hydroxyamino, alkoxyamino, carbonyl, OH, $OCH_3$, COOH, COOR' COR', CN, $CF_3$, $OCF_3$, $NO_2$, NR'R', NHCOR', and CONR'R'; and wherein R' is selected from the group consisting of H, alkyl, substituted alkyl, $C_3$–$C_9$ cycloalkyl, substituted $C_3$–$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur.

The following specific compounds were synthesized as described below and found to be active in both ex vivo and in vivo assays. They are encompassed within the definition of Genus III:

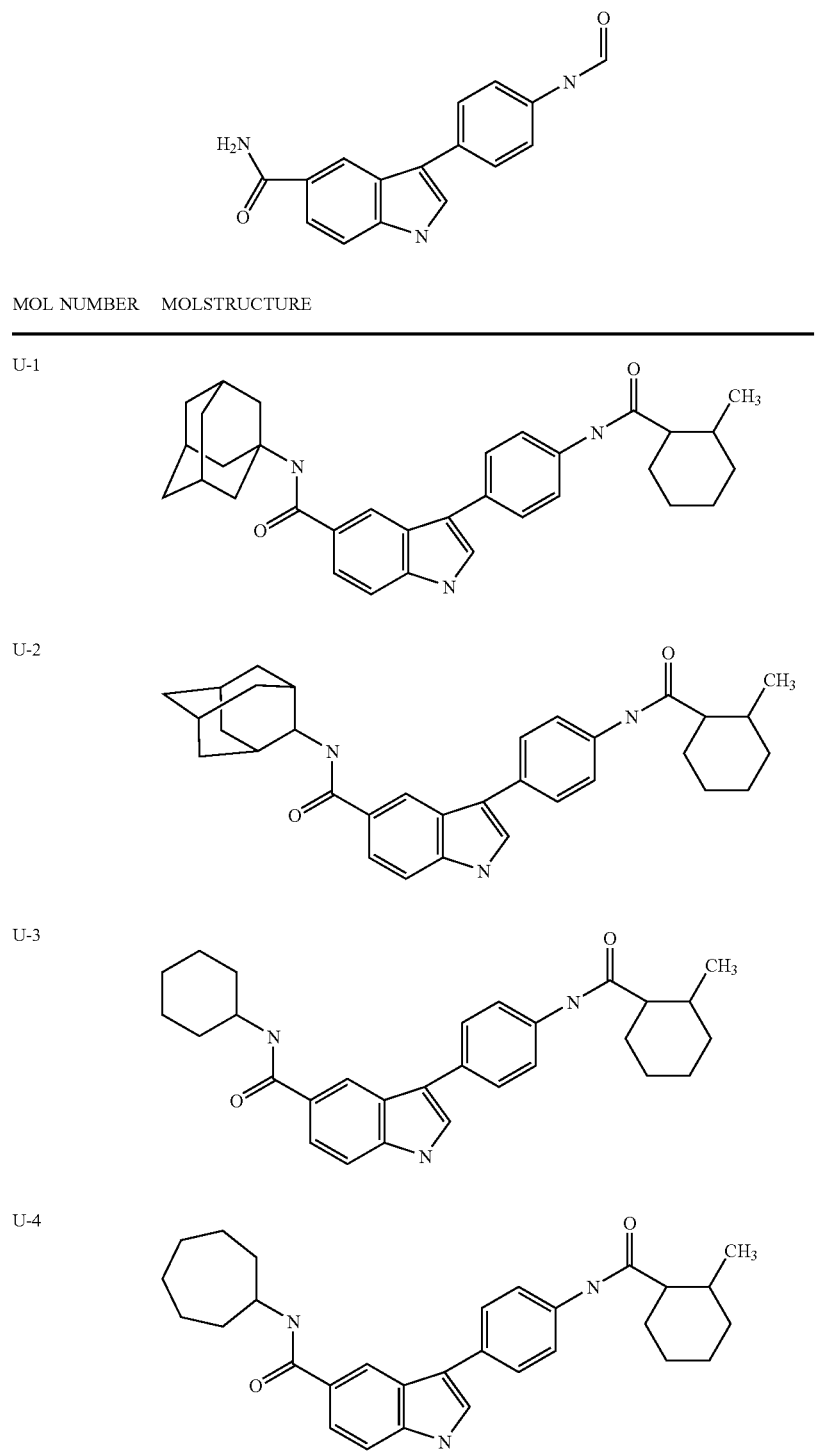

-continued
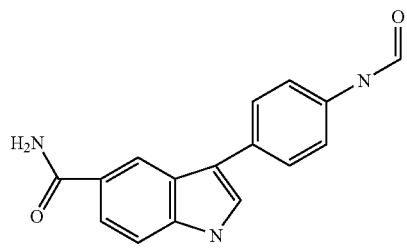
MOL NUMBER  MOLSTRUCTURE
U-5
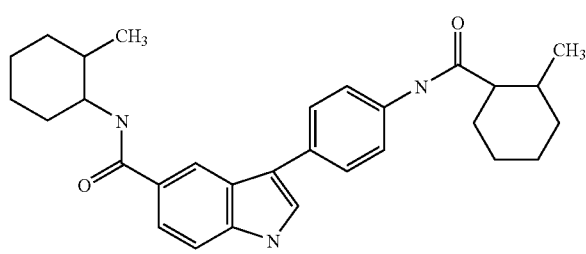
U-6
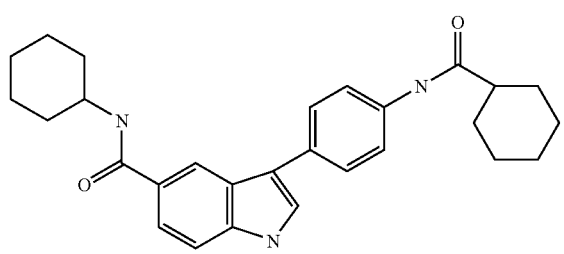
U-7
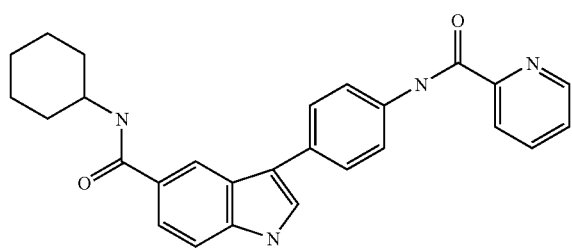
U-8
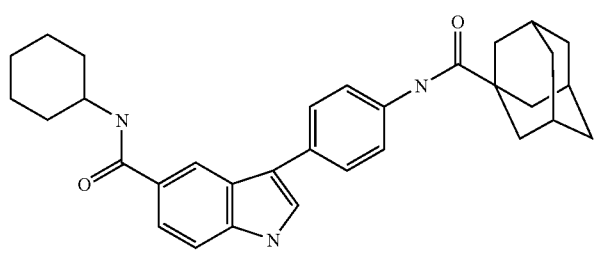
U-9
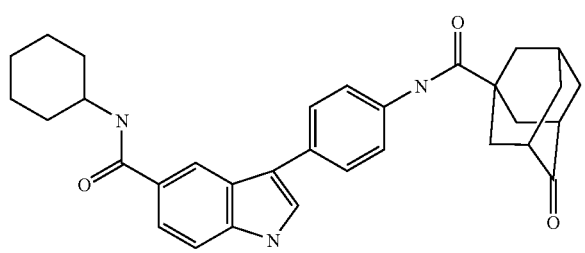

-continued
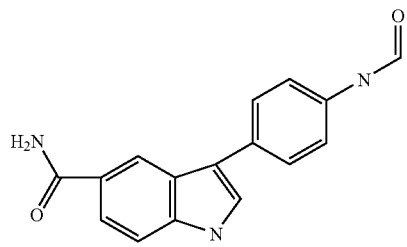
MOL NUMBER    MOLSTRUCTURE
U-10
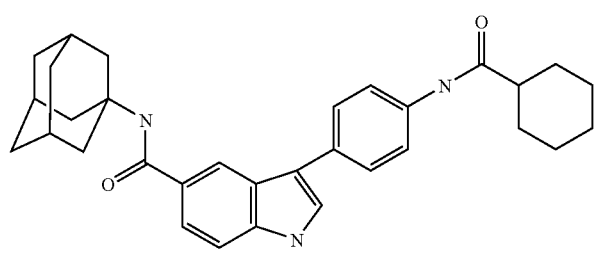
U-11
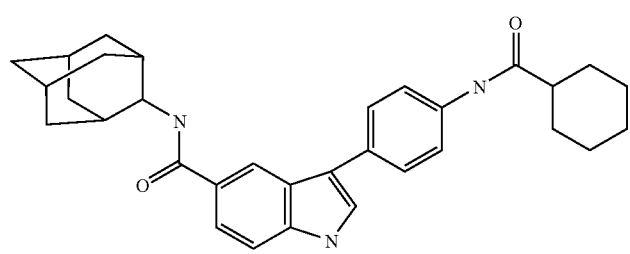
U-12
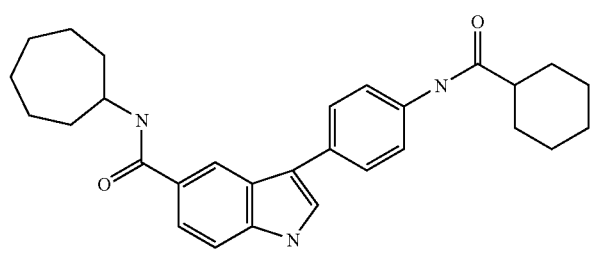
U-13
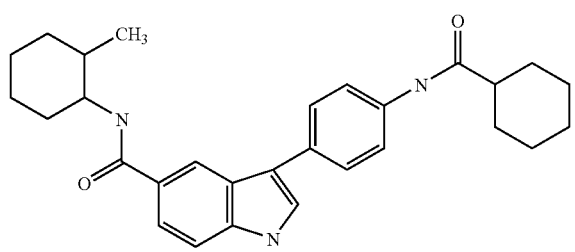
U-14
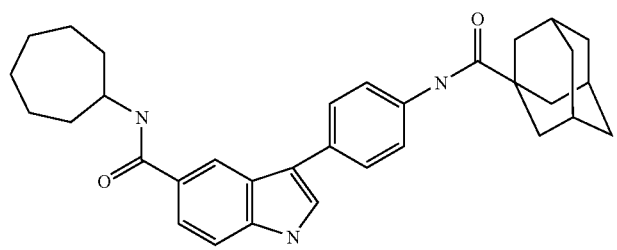

-continued
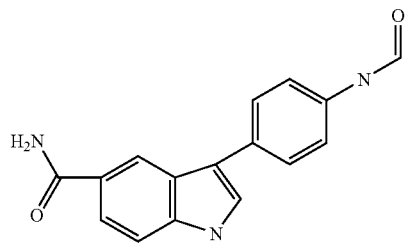
| MOL NUMBER | MOLSTRUCTURE |
|---|---|
| U-15 | 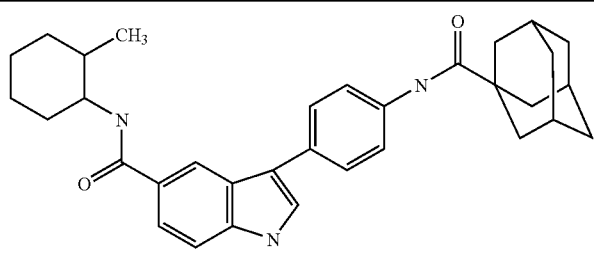 |
| U-16 | 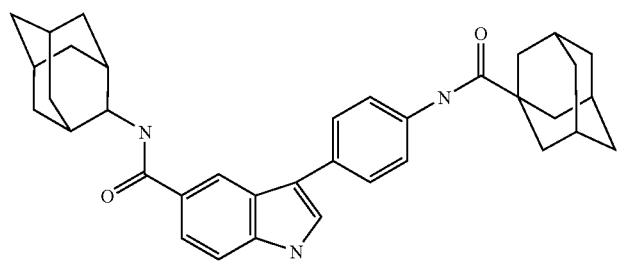 |
| U-17 | 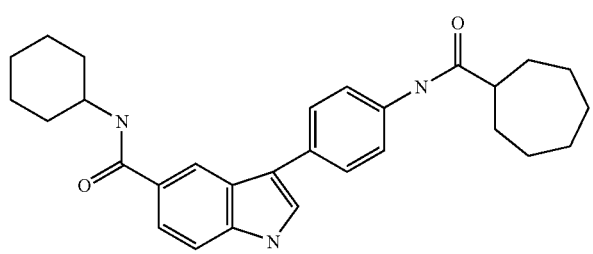 |
| U-18 | 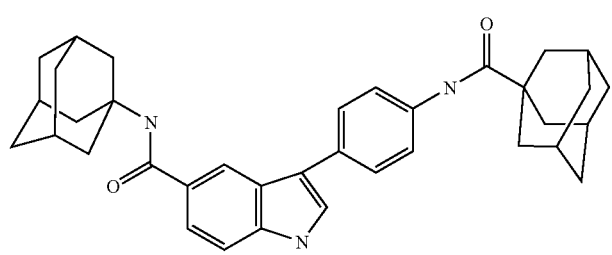 |
Compounds of Genus III may be synthesized by any conventional reactions known in the art. Examples of syntheses include the following reactions, designated Synthetic Scheme III:

Synthetic Scheme III

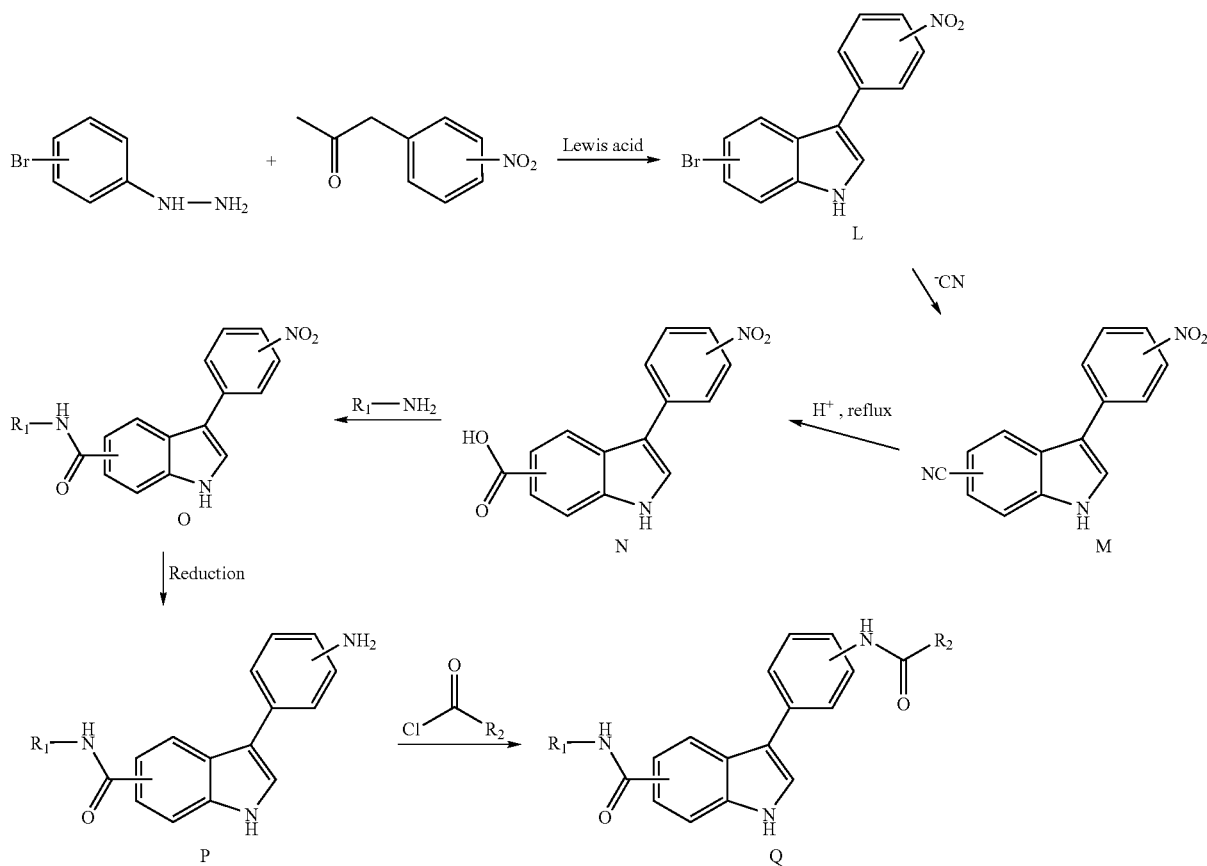

Synthesis of the Compounds of Genus III

Synthetic Scheme III shows one method that can be used to prepare the compounds of Genus III. One skilled in the art will appreciate that a number of different synthetic reaction schemes may be used to synthesize the compounds of Genus III. Further, one skilled in the art will understand that a number of different solvents, coupling agents and reaction conditions can be used in the syntheses reactions to yield comparable results.

Compound Q is representative of the compounds in Genus III.

One skilled in the art will appreciate variations in the sequence and further, will recognize variations in the appropriate reaction conditions from the analogous reactions shown or otherwise known which may be appropriately used in the processes above to make compounds L–Q.

In the processes described herein for the preparation of compounds L–Q of the preferred embodiments, the requirements for protective groups are generally well recognized by one skilled in the art of organic chemistry, and accordingly the use of appropriate protecting groups is necessarily implied by the processes of the schemes herein, although such groups may not be expressly illustrated. Introduction and removal of such suitable protecting groups are well known in the art of organic chemistry; see for example, T. W. Greene, "Protective Groups in Organic Synthesis", Wiley (New York), 1981.

The products of the reactions described herein are isolated by conventional means such as extraction, distillation, chromatography, and the like.

Starting materials not described herein are available commercially, are known, or can be prepared by methods known in the art.

The salts of compounds L–Q described above are prepared by reacting the appropriate base or acid with a stoichiometric equivalent of the compounds of compounds L–Q.

Compounds of Genus IV

One family of small molecule IgE inhibitors is defined by the following genus (Genus IV):

Genus IV

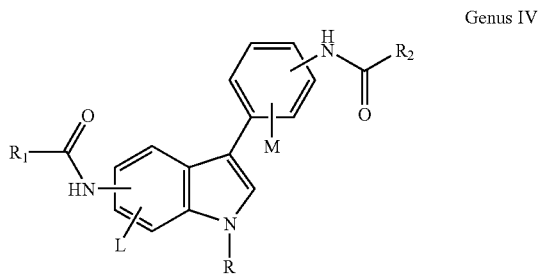

wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$–$C_5$ alkyl, benzyl, p-fluorobenzyl and di-alkylamino alkyl, wherein said $C_1$–$C_5$ alkyl is selected from the group consisting of a straight chain, branched or cyclic alkyl;

wherein $R_1$ and $R_2$ are independently selected from the group consisting of H, alkyl, substituted alkyl, $C_3$–$C_9$ cycloalkyl, substituted $C_3$–$C_9$ cycloalkyl, polycyclic aliphatic groups, substituted polycyclic aliphatic groups, phenyl, substituted phenyl, naphthyl, substituted naphthyl, heterocyclic, polycyclic heterocyclic, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1–3 substituents, wherein said substituent is selected from the group consisting of H, halogens, polyhalogens, alkoxy group, substituted alkoxy, alkyl, substituted alkyl, dialkylaminoalkyl, hydroxyalkyl, hydroxyamino, alkoxyamino, carbonyl, OH, $OCH_3$, COOH, COOR' COR', CN, $CF_3$, $OCF_3$, $NO_2$, NR'R', NHCOR', and CONR'R'; and wherein R' is selected from the group consisting of H, alkyl, substituted alkyl, $C_3$–$C_9$ cycloalkyl, substituted $C_3$–$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur.

The following specific compounds were synthesized as described below and found to be active in both ex vivo and in vivo assays. They are encompassed within the definition of Genus IV:

| MOL NUMBER | MOLSTRUCTURE |
|---|---|
| V-1 | 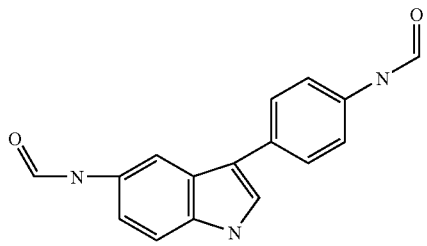 |
| V-2 | 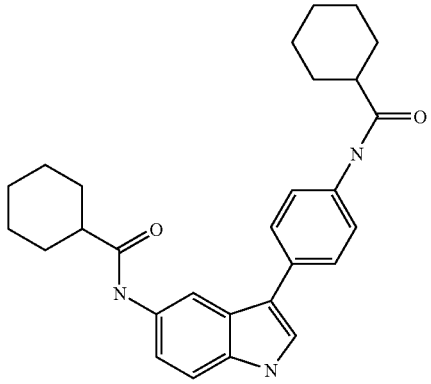 |
| | 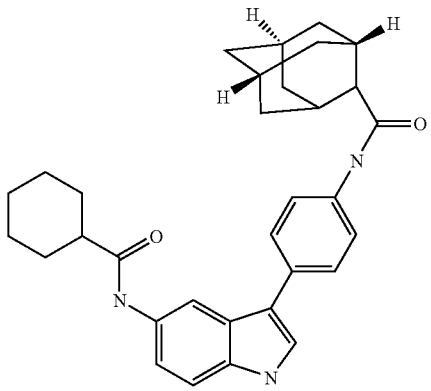 |

-continued
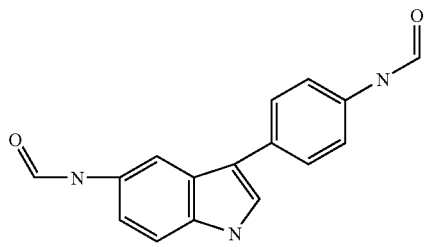
| MOL NUMBER | MOLSTRUCTURE |
|---|---|
| V-3 | 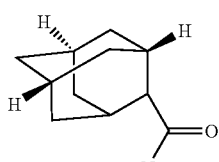 |
| V-4 | 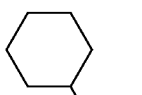 |
| V-5 | 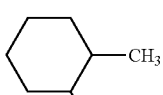 |
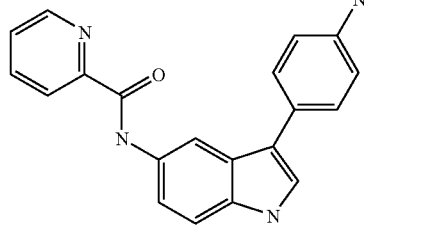
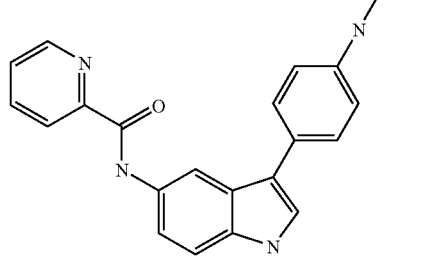
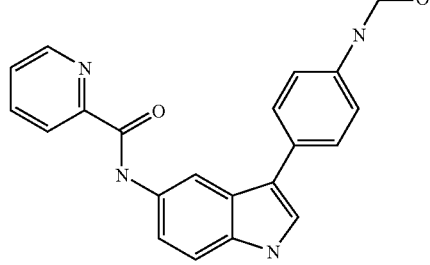

-continued
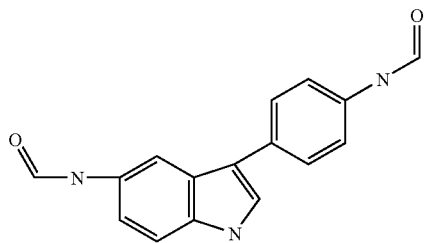
MOL NUMBER  MOLSTRUCTURE
V-6
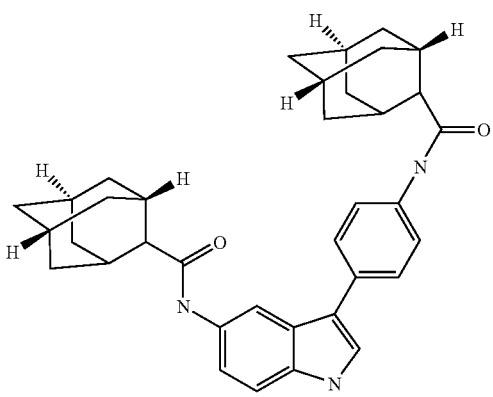
V-7
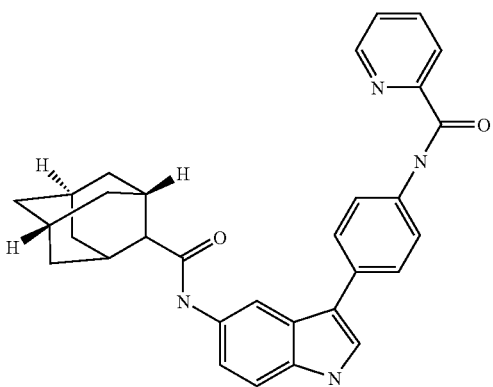
V-8
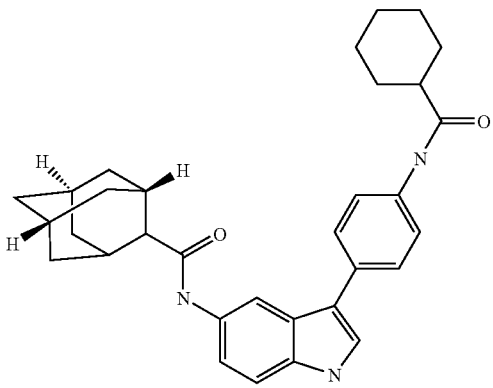

-continued
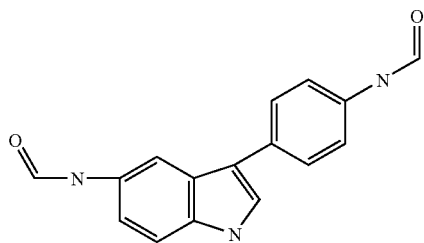
| MOL NUMBER | MOLSTRUCTURE |
|---|---|
| V-9 | 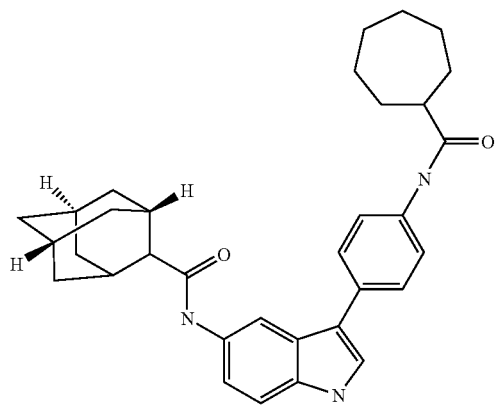 |
| V-10 | 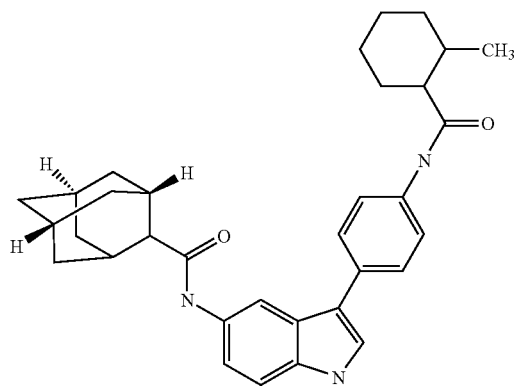 |
| V-11 | 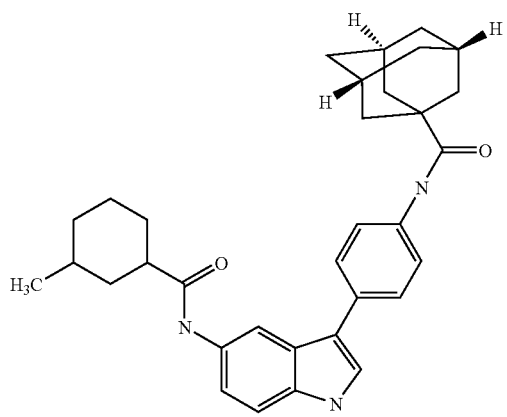 |

-continued
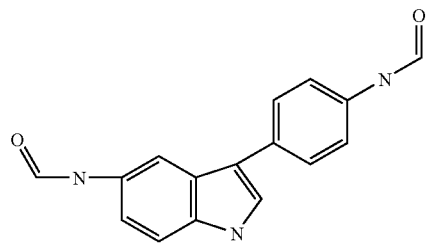
| MOL NUMBER | MOLSTRUCTURE |
|---|---|
| V-12 | 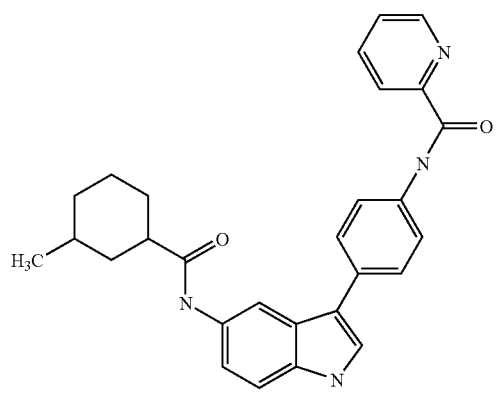 |
| V-13 | 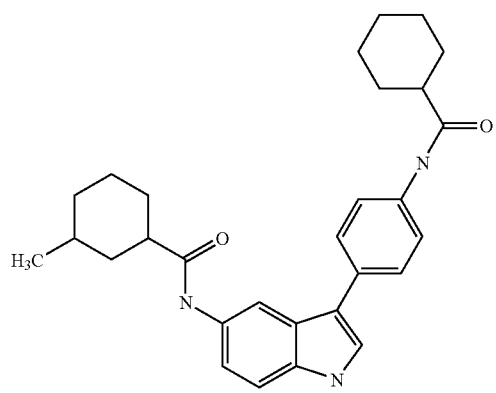 |
| V-14 | 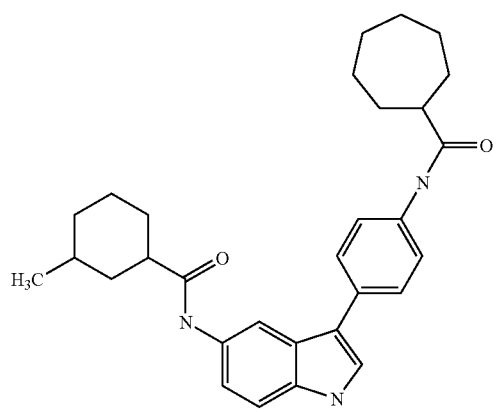 |

-continued
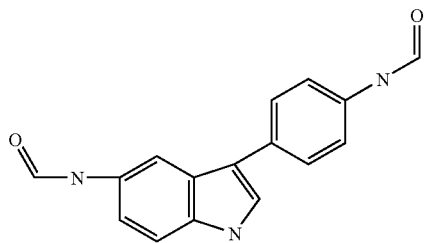
| MOL NUMBER | MOLSTRUCTURE |
| --- | --- |
| V-15 | 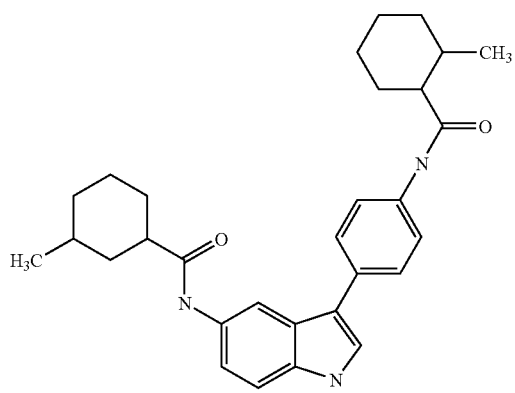 |
| V-16 | 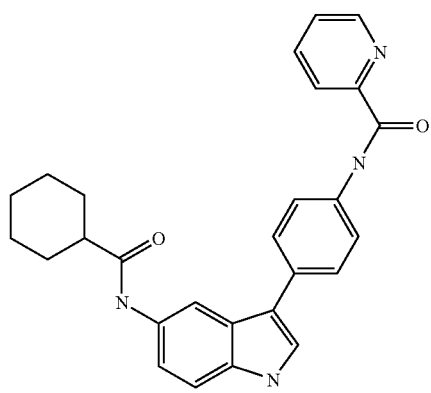 |
| V-17 | 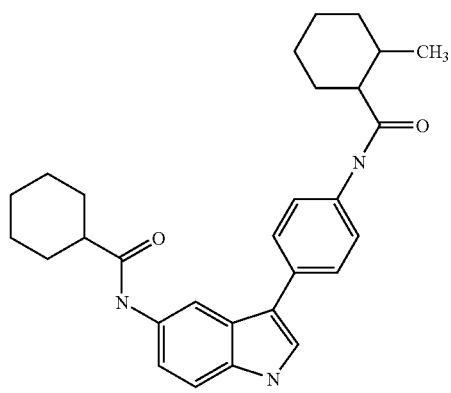 |

-continued
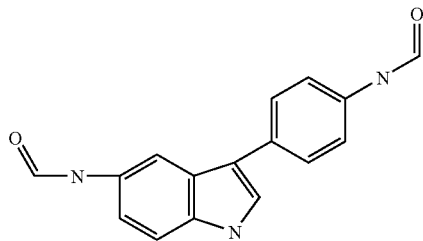
| MOL NUMBER | MOLSTRUCTURE |
|---|---|
| V-18 | 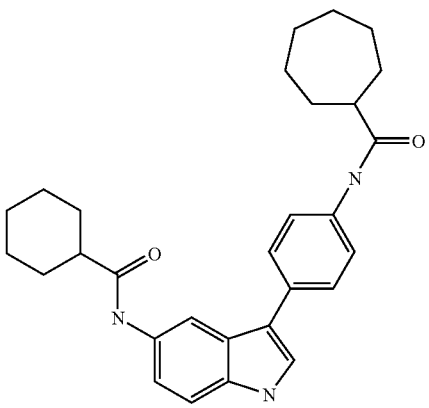 |
| V-19 | 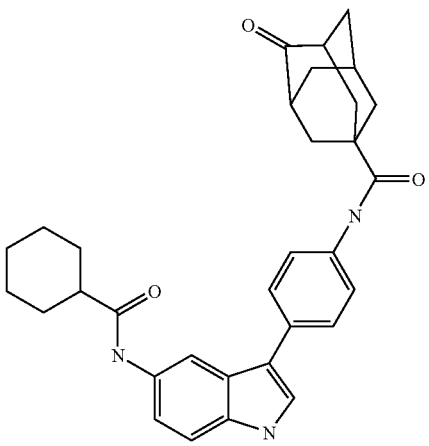 |
| V-20 | 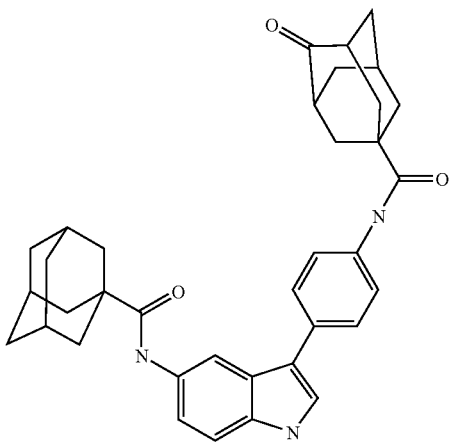 |

-continued
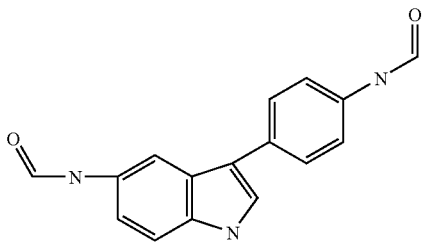
| MOL NUMBER | MOLSTRUCTURE |
|---|---|
| V-21 | 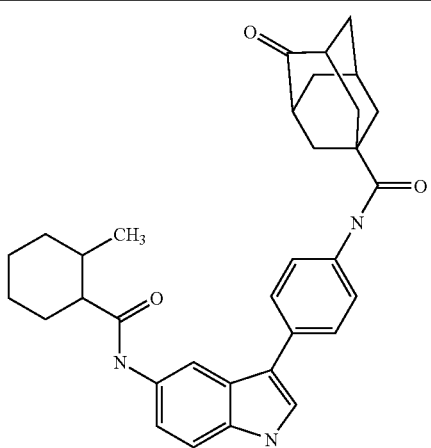 |
| V-22 | 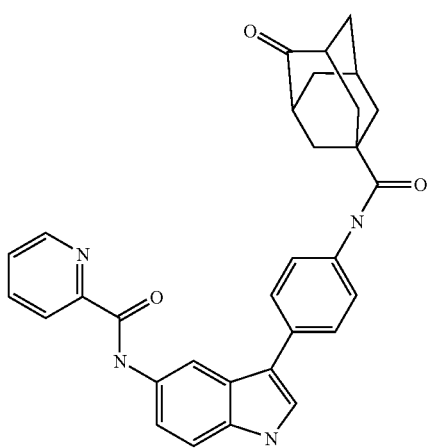 |
| V-23 | 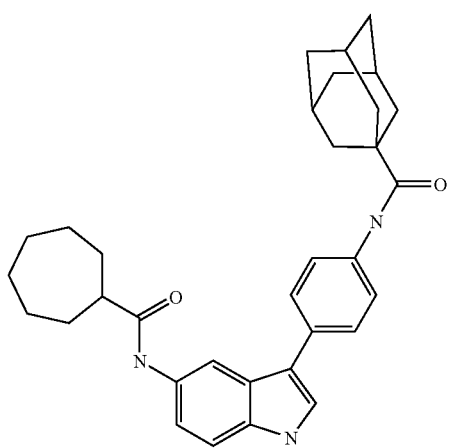 |

-continued
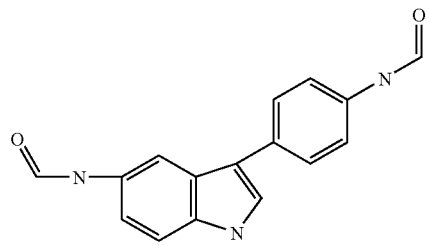
| MOL NUMBER | MOLSTRUCTURE |
|---|---|
| V-24 | 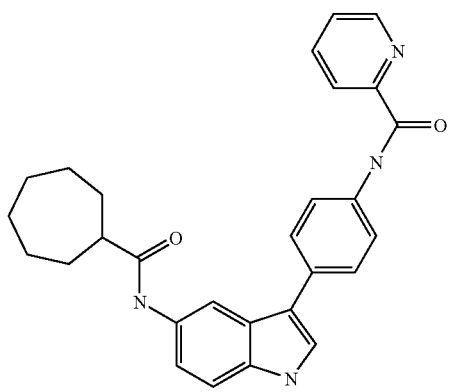 |
| V-25 | 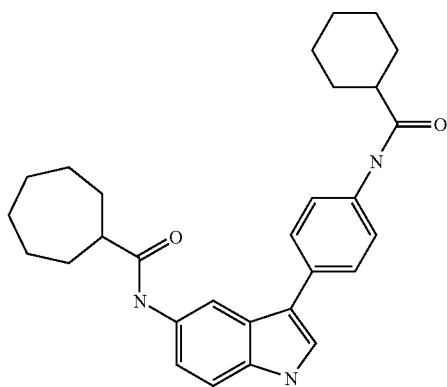 |
| V-26 | 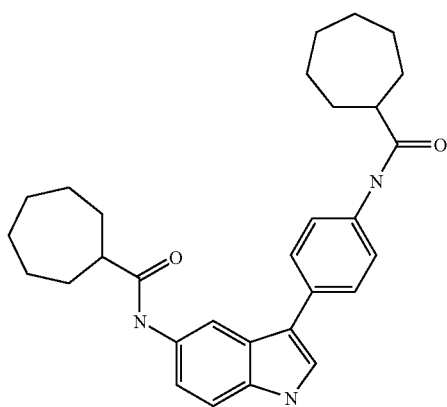 |

-continued
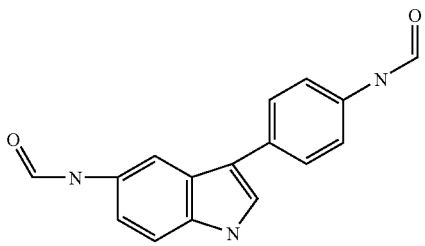
| MOL NUMBER | MOLSTRUCTURE |
|---|---|
| V-27 | 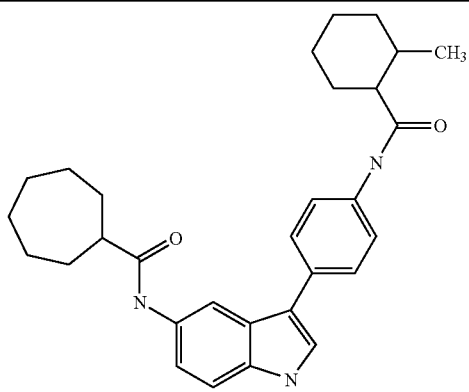 |
| V-28 | 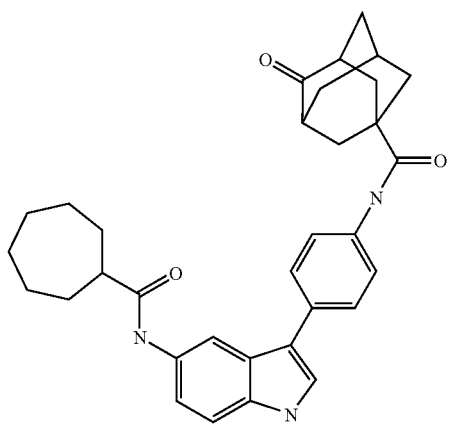 |
Compounds of Genus IV may be synthesized by any conventional reactions known in the art. Examples of syntheses include the following reactions, designated Synthetic Scheme IV:

Synthetic Scheme IV

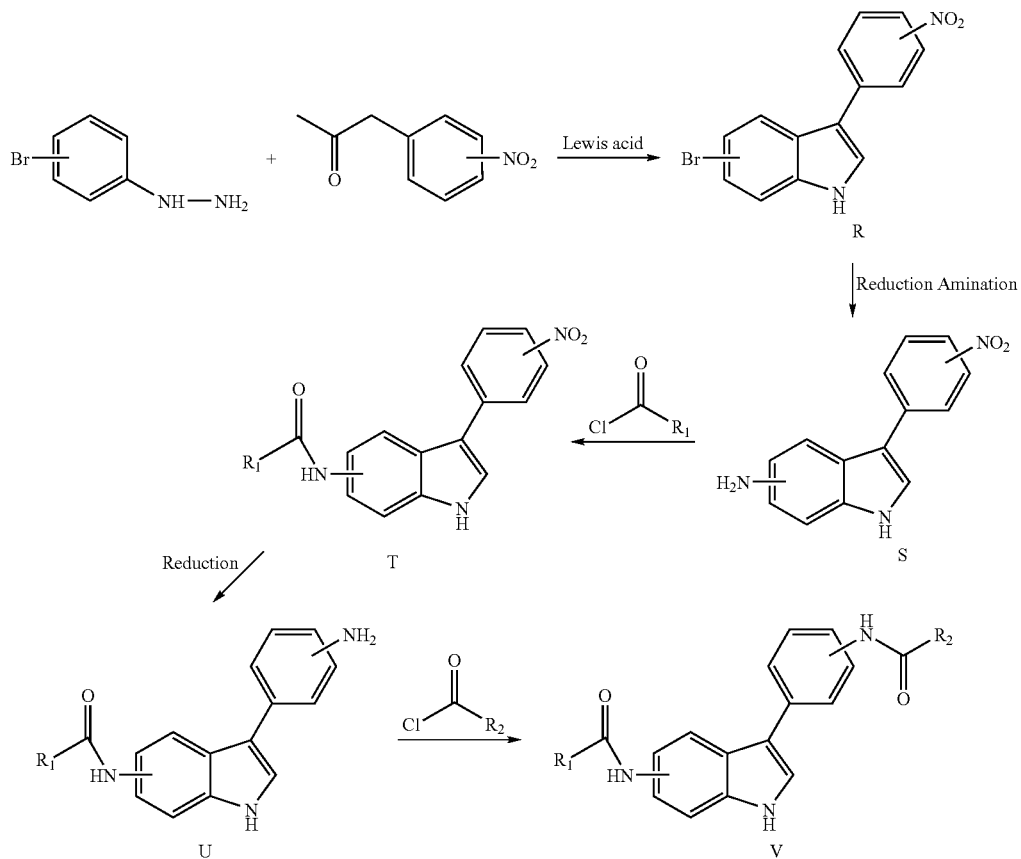

Synthesis of the Compounds of Genus IV

Synthetic Scheme IV shows one method that can be used to prepare the compounds of Genus IV. One skilled in the art will appreciate that a number of different synthetic reaction schemes may be used to synthesize the compounds of Genus IV. Further, one skilled in the art will understand that a number of different solvents, coupling agents and reaction conditions can be used in the syntheses reactions to yield comparable results.

Compound V is representative of the compounds in Genus IV.

One skilled in the art will appreciate variations in the sequence and further, will recognize variations in the appropriate reaction conditions from the analogous reactions shown or otherwise known which may be appropriately used in the processes above to make compounds R–V.

In the processes described herein for the preparation of compounds R–V of the preferred embodiments, the requirements for protective groups are generally well recognized by one skilled in the art of organic chemistry, and accordingly the use of appropriate protecting groups is necessarily implied by the processes of the schemes herein, although such groups may not be expressly illustrated. Introduction and removal of such suitable protecting groups are well known in the art of organic chemistry; see for example, T. W. Greene, "Protective Groups in Organic Synthesis", Wiley (New York), 1981.

The products of the reactions described herein are isolated by conventional means such as extraction, distillation, chromatography, and the like.

Starting materials not described herein are available commercially, are known, or can be prepared by methods known in the art.

The salts of compounds R–V described above are prepared by reacting the appropriate base or acid with a stoichiometric equivalent of the compounds of compounds R–V.

Compounds of Genus V

One family of small molecule IgE inhibitors is defined by the following genus (Genus V):

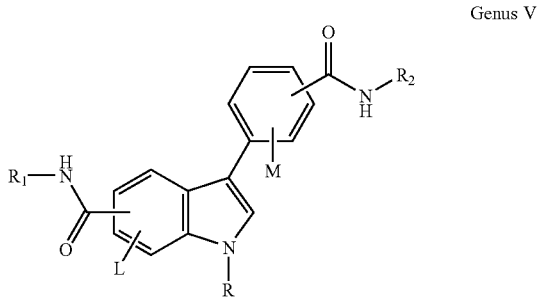

Genus V wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliwherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur.

Compounds of Genus V may be synthesized by any conventional reactions known in the art. Examples of syntheses include the following reactions, designated Synthetic Scheme V:

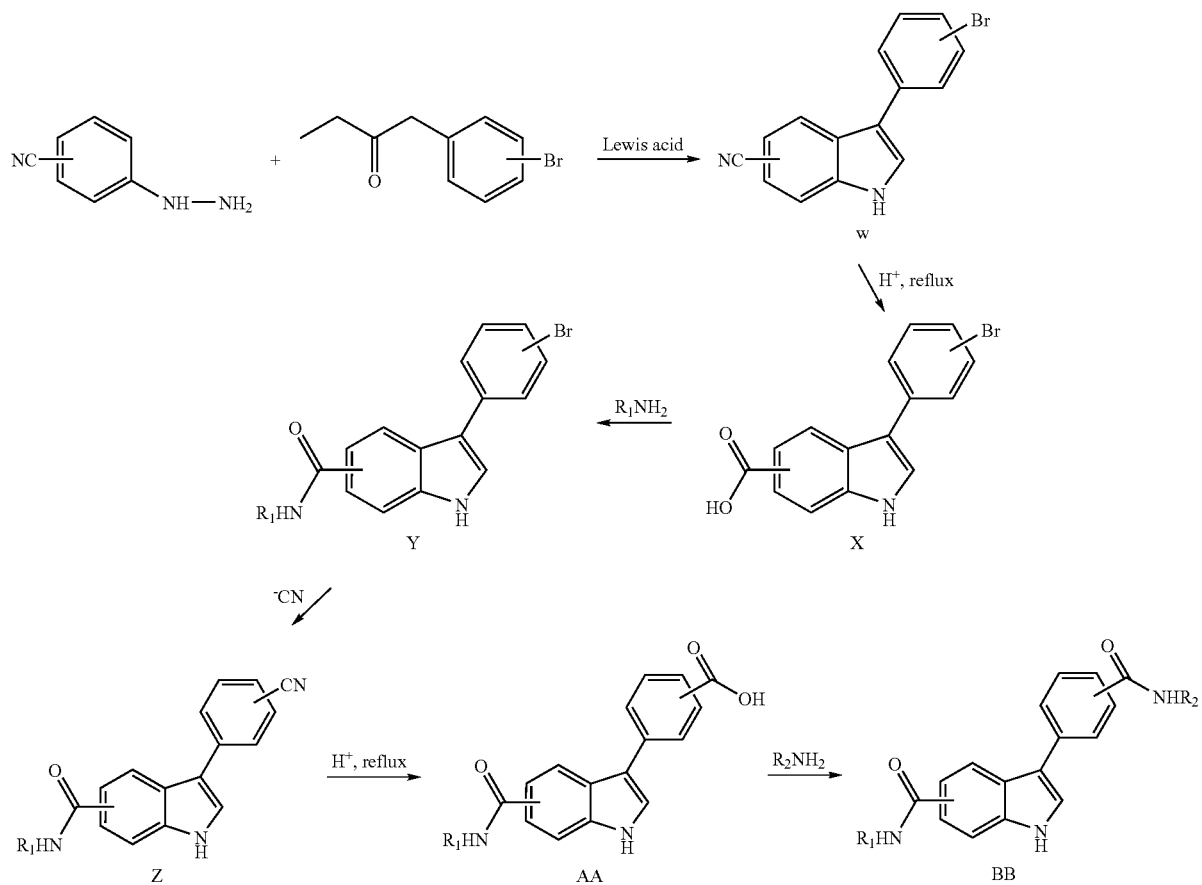

phatic groups, substituted polycyclic aliphatic groups, phenyl, substituted phenyl, naphthyl, substituted naphthyl, heterocyclic, polycyclic heterocyclic, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1–3 substituents, wherein said substituent is selected from the group consisting of H, halogens, polyhalogens, alkoxy group, substituted alkoxy, alkyl, substituted alkyl, dialkylaminoalkyl, hydroxyalkyl, hydroxyamino, alkoxyamino, carbonyl, OH, $OCH_3$, COOH, COOR' COR', CN, $CF_3$, $OCF_3$, $NO_2$, NR'R', NHCOR', and CONR'R'; and Synthesis of the Compounds of Genus V Synthetic Scheme V shows one method that can be used to prepare the compounds of Genus V. One skilled in the art will appreciate that a number of different synthetic reaction schemes may be used to synthesize the compounds of Genus V. Further, one skilled in the art will understand that a number of different solvents, coupling agents and reaction conditions can be used in the syntheses reactions to yield comparable results.

Compound BB is representative of the compounds in Genus V.

One skilled in the art will appreciate variations in the sequence and further, will recognize variations in the appropriate reaction conditions from the analogous reactions shown or otherwise known which may be appropriately used in the processes above to make compounds W–BB.

In the processes described herein for the preparation of compound W–BB of the preferred embodiments, the requirements for protective groups are generally well recognized by one skilled in the art of organic chemistry, and accordingly the use of appropriate protecting groups is necessarily implied by the processes of the schemes herein, although such groups may not be expressly illustrated. Introduction and removal of such suitable protecting groups are well known in the art of organic chemistry; see for example, T. W. Greene, "Protective Groups in Organic Synthesis", Wiley (New York), 1981.

The products of the reactions described herein are isolated by conventional means such as extraction, distillation, chromatography, and the like.

Starting materials not described herein are available commercially, are known, or can be prepared by methods known in the art.

The salts of compounds W–BB described above are prepared by reacting the appropriate base or acid with a stoichiometric equivalent of the compounds of compounds W–BB.

Compounds of Genus VI

One family of small molecule IgE inhibitors is defined by the following genus (Genus VI):

Genus VI

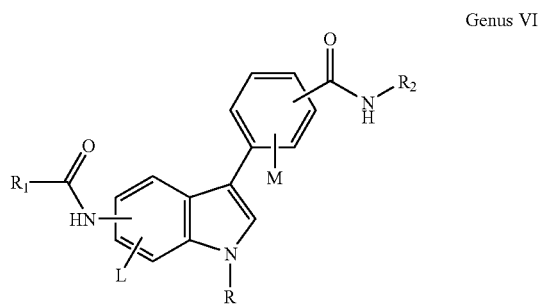

wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$–$C_5$ alkyl, benzyl, p-fluorobenzyl and di-alkylamino alkyl, wherein said $C_1$–$C_5$ alkyl is selected from the group consisting of a straight chain, branched or cyclic alkyl;

wherein $R_1$ and $R_2$ are independently selected from the group consisting of H, alkyl, substituted alkyl, $C_3$–$C_9$ cycloalkyl, substituted $C_3$–$C_9$ cycloalkyl, polycyclic aliphatic groups, substituted polycyclic aliphatic groups, phenyl, substituted phenyl, naphthyl, substituted naphthyl, heterocyclic, polycyclic heterocyclic, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1–3 substituents, wherein said substituent is selected from the group consisting of H, halogens, polyhalogens, alkoxy group, substituted alkoxy, alkyl, substituted alkyl, dialkylaminoalkyl, hydroxyalkyl, hydroxyamino, alkoxyamino, carbonyl, OH, $OCH_3$, COOH, COOR' COR', CN, $CF_3$, $OCF_3$, $NO_2$, NR'R', NHCOR', and CONR'R'; and wherein R' is selected from the group consisting of H, alkyl, substituted alkyl, $C_3$–$C_9$ cycloalkyl, substituted $C_3$–$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur.

Compounds of Genus VI may be synthesized by any conventional reactions known in the art. Examples of syntheses include the following reactions, designated Synthetic Scheme VI:

Synthetic Scheme VI

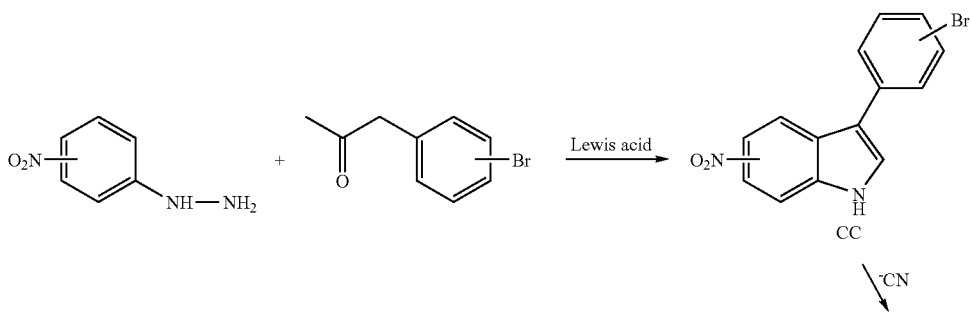

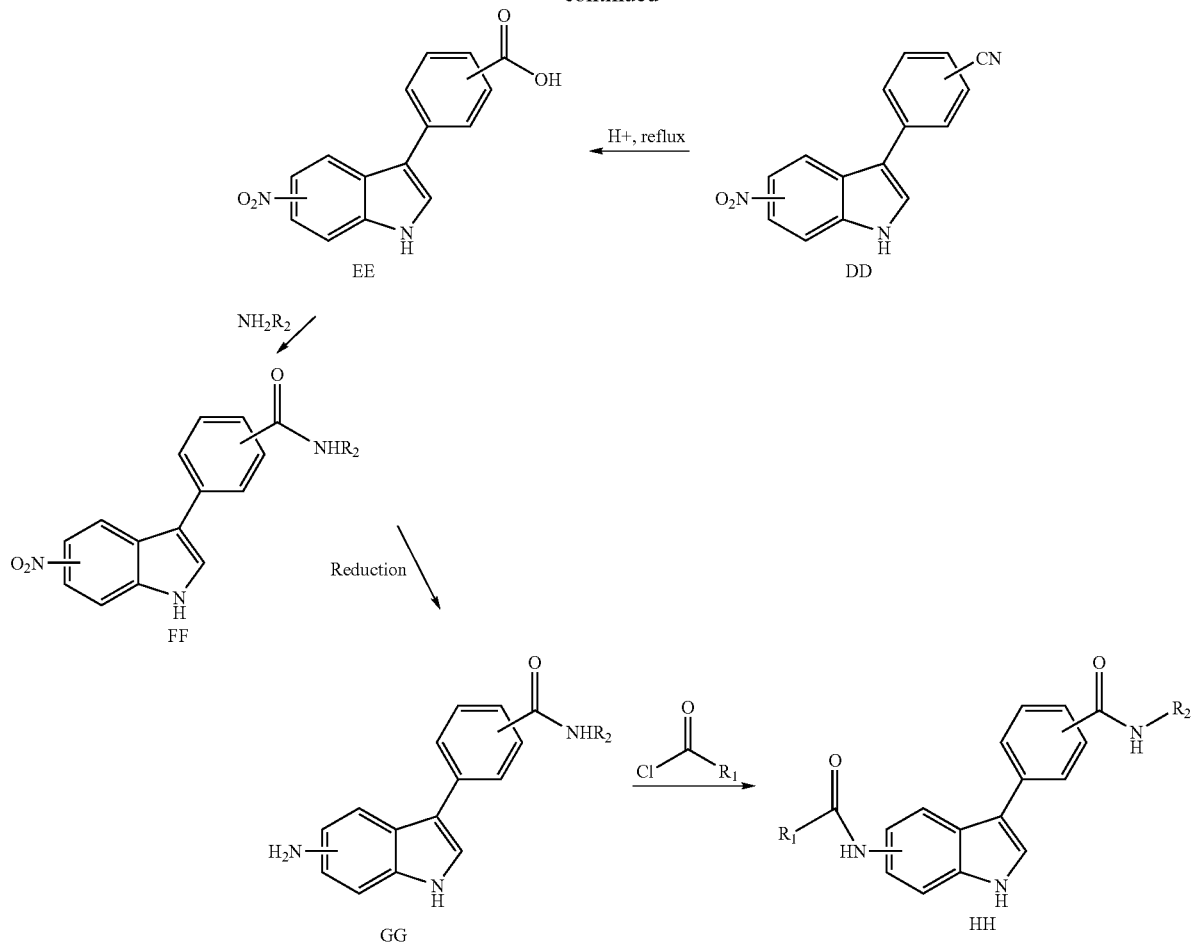

Synthesis of the Compounds of Genus VI

Synthetic Scheme VI shows one method that can be used to prepare the compounds of Genus VI. One skilled in the art will appreciate that a number of different synthetic reaction schemes may be used to synthesize the compounds of Genus VI. Further, one skilled in the art will understand that a number of different solvents, coupling agents and reaction conditions can be used in the syntheses reactions to yield comparable results.

Compound HH is representative of the compounds in Genus VI.

One skilled in the art will appreciate variations in the sequence and further, will recognize variations in the appropriate reaction conditions from the analogous reactions shown or otherwise known which may be appropriately used in the processes above to make compounds CC–HH.

In the processes described herein for the preparation of compounds CC–HH of the preferred embodiments, the requirements for protective groups are generally well recognized by one skilled in the art of organic chemistry, and accordingly the use of appropriate protecting groups is necessarily implied by the of the schemes herein, although such groups may not be expressly illustrated. Introduction and removal of such suitable protecting groups are well known in the art of organic chemistry; see for example, T. W. Greene, "Protective Groups in Organic Synthesis", Wiley (New York), 1981.

The products of the reactions described herein are isolated by conventional means such as extraction, distillation, chromatography, and the like.

Starting materials not described herein are available commercially, are known, or can be prepared by methods known in the art.

The salts of compounds CC–HH described above are prepared by reacting the appropriate base or acid with a stoichiometric equivalent of the compounds of compounds CC–HH.

Compounds of Genus VII

One family of small molecule IgE inhibitors is defined by the following genus (Genus VII):

Genus VII

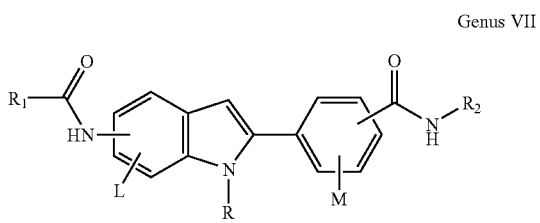

wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$–$C_5$ alkyl, benzyl, p-fluorobenzyl and di-alkylamino alkyl, wherein said $C_1$–$C_5$ alkyl is selected from the group consisting of a straight chain, branched or cyclic alkyl;

wherein $R_1$ and $R_2$ are independently selected from the group consisting of H, alkyl, substituted alkyl, $C_3$–$C_9$ cycloalkyl, substituted $C_3$–$C_9$ cycloalkyl, polycyclic aliphatic groups, substituted polycyclic aliphatic groups, phenyl, substituted phenyl, naphthyl, substituted naphthyl, heterocyclic, polycyclic heterocyclic, heteroaryl and wherein R' is selected from the group consisting of H, alkyl, substituted alkyl, $C_3$–$C_9$ cycloalkyl, substituted $C_3$–$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur.

Compounds of Genus VII may be synthesized by any conventional reactions known in the art. Examples of syntheses include the following reactions, designated Synthetic Scheme VII:

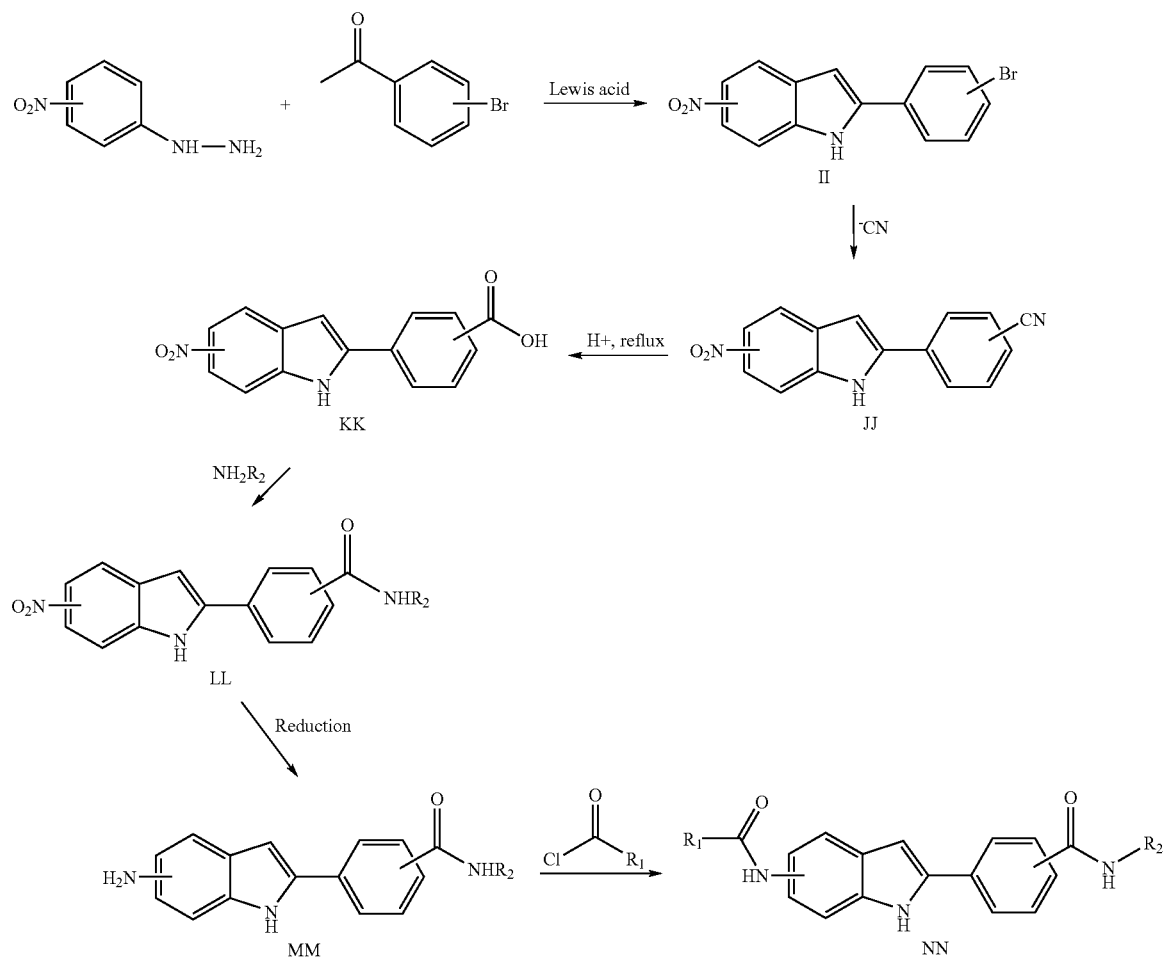

substituted heteroaryl, wherein said heteroaryl and said substituted heteroaryl contain 1–3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1–3 substituents, wherein said substituent is selected from the group consisting of H, halogens, polyhalogens, alkoxy group, substituted alkoxy, alkyl, substituted alkyl, dialkylaminoalkyl, hydroxyalkyl, hydroxyamino, alkoxyamino, carbonyl, OH, $OCH_3$, COOH, COOR' COR', CN, $CF_3$, $OCF_3$, $NO_2$, NR'R', NHCOR', and CONR'R'; and Synthesis of the Compounds of Genus VII Synthetic Scheme VII shows one method that can be used to prepare the compounds of Genus VII. One skilled in the art will appreciate that a number of different synthetic reaction schemes may be used to synthesize the compounds of Genus VII. Further, one skilled in the art will understand that a number of different solvents, coupling agents and reaction conditions can be used in the syntheses reactions to yield comparable results.

Compound NN is representative of the compounds in Genus VII.

One skilled in the art will appreciate variations in the sequence and further, will recognize variations in the appropriate reaction conditions from the analogous reactions shown or otherwise known which may be appropriately used in the processes above to make compounds II–NN.

In the processes described herein for the preparation of compounds II–NN of the preferred embodiments, the requirements for protective groups are generally well recognized by one skilled in the art of organic chemistry, and accordingly the use of appropriate protecting groups is necessarily implied by the processes of the schemes herein, although such groups may not be expressly illustrated. Introduction and removal of such suitable protecting groups are well known in the art of organic chemistry; see for example, T. W. Greene, "Protective Groups in Organic Synthesis", Wiley (New York), 1981.

The products of the reactions described herein are isolated by conventional means such as extraction, distillation, chromatography, and the like.

Starting materials not described herein are available commercially, are known, or can be prepared by methods known in the art.

The salts of compounds II–NN described above are prepared by reacting the appropriate base or acid with a stoichiometric equivalent of the compounds of compounds II–NN.

Compounds of Genus VIII

One family of small molecule IgE inhibitors is defined by the following genus (Genus VIII):

Genus VIII

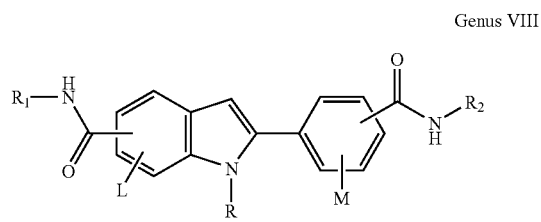

wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$–$C_5$ alkyl, benzyl, p-fluorobenzyl and di-alkylamino alkyl, wherein said $C_1$–$C_5$ alkyl is selected from the group consisting of a straight chain, branched or cyclic alkyl;

wherein $R_1$ and $R_2$ are independently selected from the group consisting of H, alkyl, substituted alkyl, $C_3$–$C_9$ cycloalkyl, substituted $C_3$–$C_9$ cycloalkyl, polycyclic aliphatic groups, substituted polycyclic aliphatic groups, phenyl, substituted phenyl, naphthyl, substituted naphthyl, heterocyclic, polycyclic heterocyclic, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1–3 substituents, wherein said substituent is selected from the group consisting of H, halogens, polyhalogens, alkoxy group, substituted alkoxy, alkyl, substituted alkyl, dialkylaminoalkyl, hydroxyalkyl, hydroxyamino, alkoxyamino, carbonyl, OH, $OCH_3$, COOH, COOR' COR', CN, $CF_3$, $OCF_3$, $NO_2$, NR'R', NHCOR', and CONR'R'; and wherein R' is selected from the group consisting of H, alkyl, substituted alkyl, $C_3$–$C_9$ cycloalkyl, substituted $C_3$–$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur.

Compounds of Genus VIII may be synthesized by any conventional reactions known in the art. Examples of syntheses include the following reactions, designated Synthetic Scheme VIII:

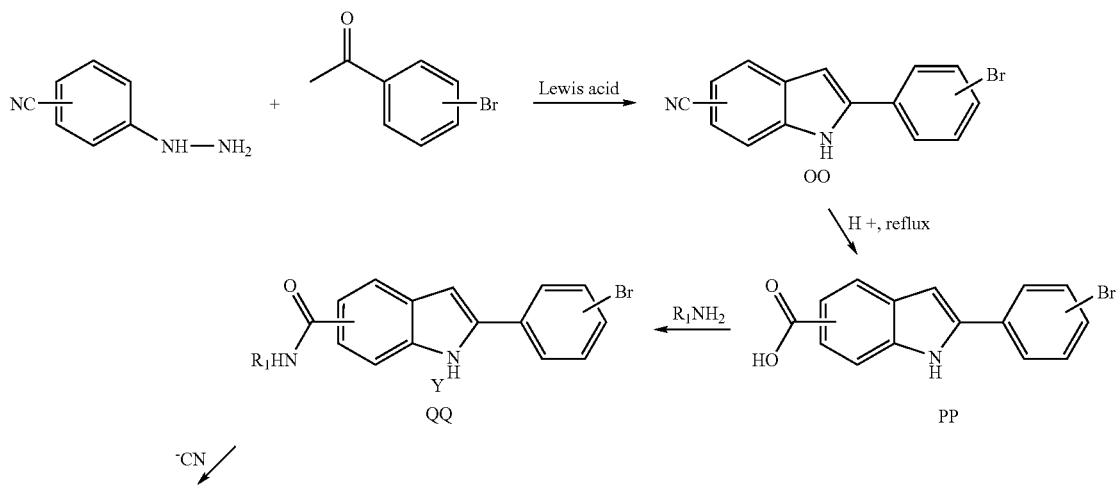

-continued

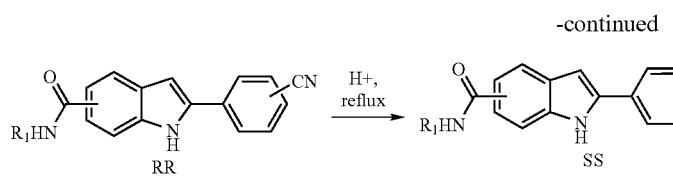 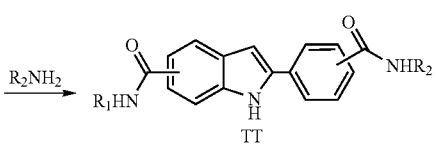

Synthesis of the Compounds of Genus VIII

Synthetic Scheme VIII shows one method that can be used to prepare the compounds of Genus VIII. One skilled in the art will appreciate that a number of different synthetic reaction schemes may be used to synthesize the compounds of Genus VIII. Further, one skilled in the art will understand that a number of different solvents, coupling agents and reaction conditions can be used in the syntheses reactions to yield comparable results.

Compound TT is representative of the compounds in Genus VIII.

One skilled in the art will appreciate variations in the sequence and further, will recognize variations in the appropriate reaction conditions from the analogous reactions shown or otherwise known which may be appropriately used in the processes above to make compounds OO–TT.

In the processes described herein for the preparation of compounds OO–TT of the preferred embodiments, the requirements for protective groups are generally well recognized by one skilled in the art of organic chemistry, and accordingly the use of appropriate protecting groups is necessarily implied by the processes of the schemes herein, although such groups may not be expressly illustrated. Introduction and removal of such suitable protecting groups are well known in the art of organic chemistry; see for example, T. W. Greene, "Protective Groups in Organic Synthesis", Wiley (New York), 1981.

The products of the reactions described herein are isolated by conventional means such as extraction, distillation, chromatography, and the like.

Starting materials not described herein are available commercially, are known, or can be prepared by methods known in the art.

The salts of compounds OO–TT described above are prepared by reacting the appropriate base or acid with a stoichiometric equivalent of the compounds OO–TT.

In Genera I–VIII, preferred substituents for $R_1$ and $R_2$ are independently selected from the following:

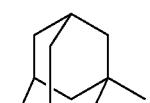

2

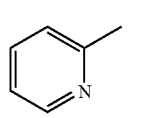

1

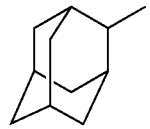

3

-continued

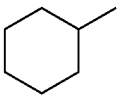

4

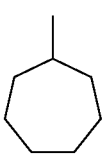

5

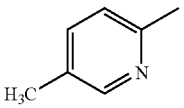

6

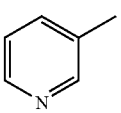

7

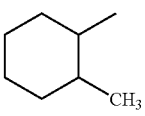

8

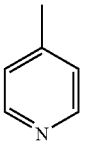

9

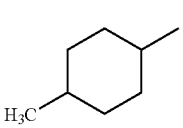

10

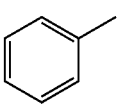

11

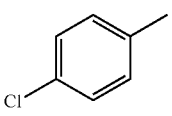

12

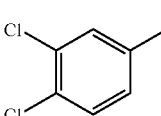

13

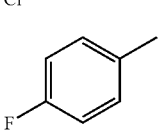

14

-continued
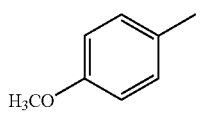
15
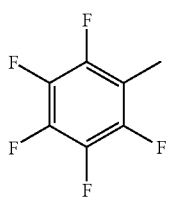
16
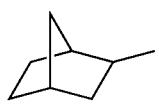
17
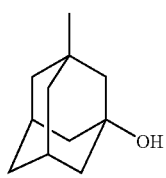
18
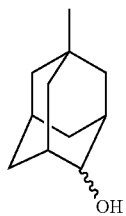
19
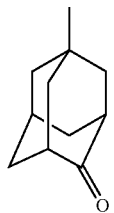
20
More preferably, substituents for R₁ and R₂ are selected from substituents 1–5 and 13.
The following specific compounds encompassed within Genera I and II are particularly preferred:
-continued
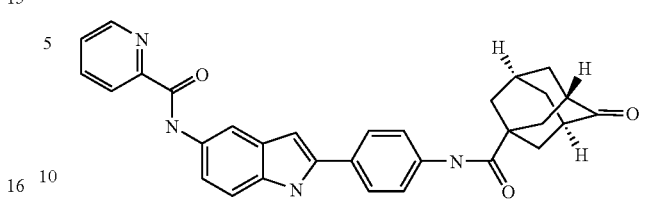
S-96
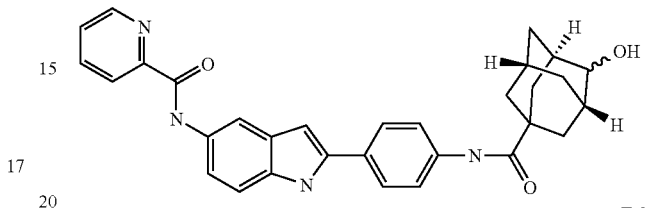
T-97
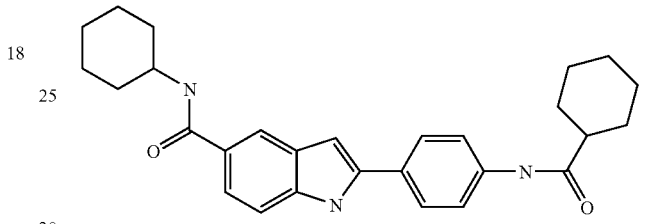
T-3
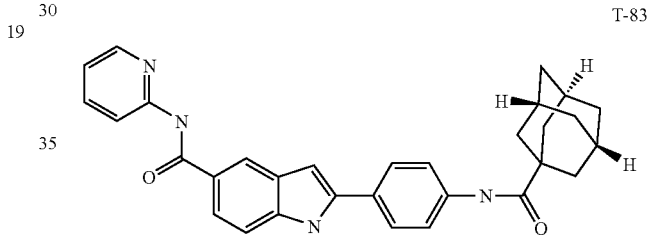
T-83
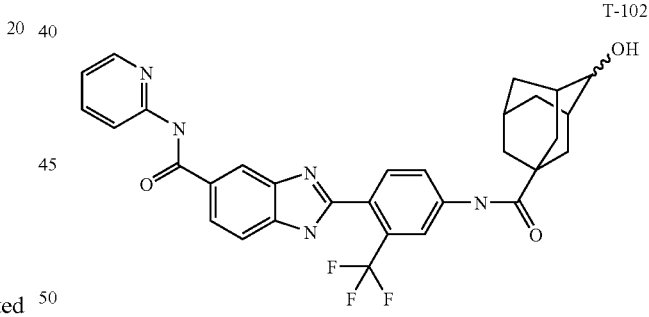
T-102
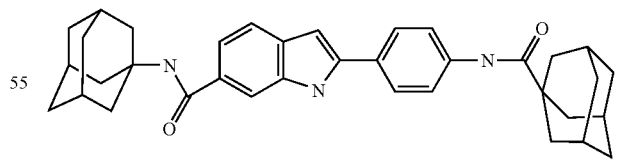
T-88
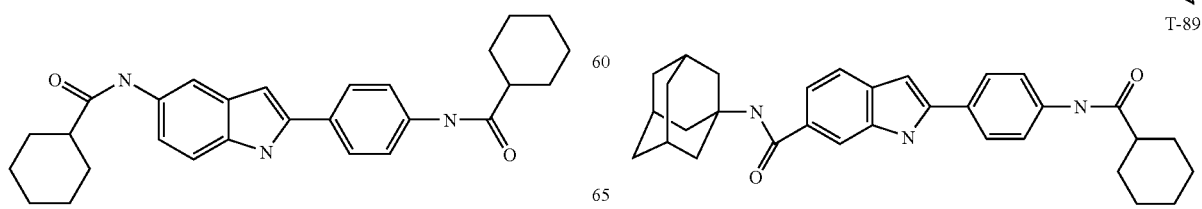
T-89
S-6

-continued

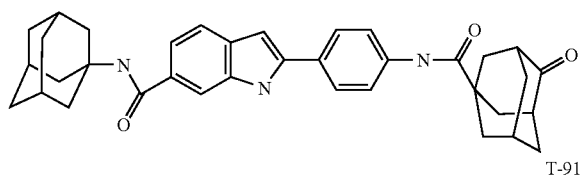

T-90

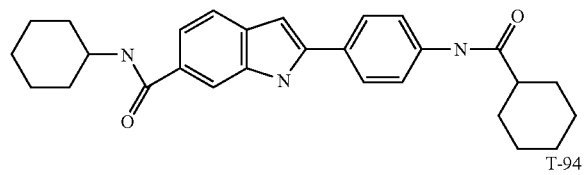

T-91

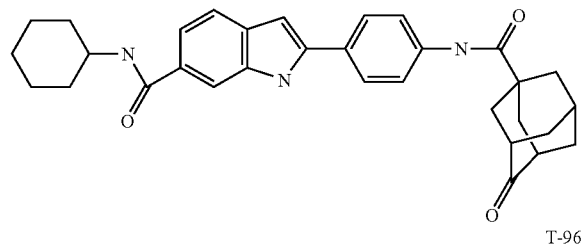

T-94

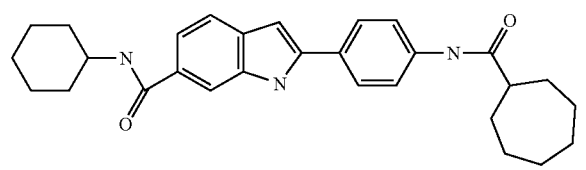

T-96

EXAMPLE 1

Syntheses of Preferred Compounds

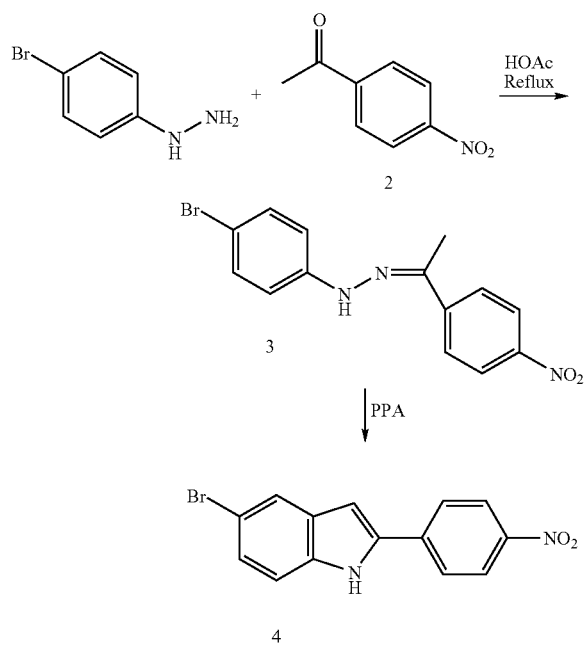

Hydrazone p-Bromophenylhydrazine hydrochloride (250.0 g, 1.12 mol) and p-Nitro-acetophenone (166.5 g, 1.00 mol) was suspended in acetic acid (1.95-L) in a 10 L R.B.flask. Ethanol (1.45L) was added into flask at room temperature under stirring. Slowly reaction mixture was heated to reflux and refluxed for 5 hours. Then water (3.5L) was added at 15° C. and stirred for 1 hour. Upon filtration followed by 200 ml, chilled water wash and drying in vacuo obtained dark red 246.8 g (66%) of pure product.

Step 2

To 1.0L of polyphosphoric acid at 82–85° C., hydrazone (100 g, 0.299 mol) was added[1] and stirred for 1 hour. The reaction mixture was cooled in an ice-bath then diluted with 3.0L of cold water followed by 1.0L of EtOAc. Reaction mixture was stirred for 1 hour and filtered. The obtained light yellow powder was dissolved in 4.0L of EtOAc and filtered. Filtrate was passed through Silica gel bed. Filtrate was concentrated in vacuo to give yellow colored crude product. It was recrystalized in methanol to give the target compound as an orange solid (35 g, 36% yield) which was shown to be pure by $^1$H-NMR and TLC. Caution! Exothermic reaction. Hydrazone should be added slowly to maintain reaction temperature.

Two-Step Synthesis of 5-Bromo-2-14-nitrophenyllindole

STEP 1: Synthesis of 3: A mixture of 1 hydrochloride (5.0 g, 22.4 mmol, 1.1 equiv) and 2 (3.3 g, 20.1 mmol, 1.0 equiv) in 50 mL acetic acid was heated at reflux for 5 hours then stirred at room temperature overnight. The reaction mixture was cooled in an ice-water bath and 100 ml H$_2$O was added. After stirring for 30 minutes, the red precipitate was filtered and washed with 20 ml cold H$_2$O. $^1$H-NMR and TLC analyses indicated that the hydrazone 3 is pure. Yield=4.9 g STEP 2: Synthesis of 4: The hydrazone 3 (4.0 g) in 25 ml Polyphosphoric acid (PPA) was heated at 85° C. for 1 hr. The reaction mixture was cooled in an ice-water bath then diluted with 200 ml H$_2$O and filtered. The solid was dissolved in 200 ml ethyl acetate then diluted with 200 ml hexanes and treated with 5 g silica gel. This was stirred for 30 minutes then filtered. The filtrate was concentrated to dryness then recrystallized from methanol to give an orange solid which is pure by $^1$H-NMR and TLC. Yield=26% (A TLC analysis of the mother liquor indicated the presence of a significant amount of indole 4.)

Synthesis of 2-(4-Nitrophenyl)-1H-indol-5-ylamine hydrochloride

An oven dried round bottom flask was charged with the bromoindole (100 mg, 0.315 mmol, 1.0 equiv) and Pd$_2$(dba)$_3$ (15 mg, 0.016 mmol, 0.05 equiv) then 5.0 ml THF. A solution of tri-t-butylphosphine in hexane (10% wt in hexane) (95 uL, 0.031 mmol, 0.1 equiv) was added followed by slow addition of Lithium bis(trimethylsilyl)amide (1.0M in THF) (0.95 ml, 0.95 mmol, 3.0 equiv). The resulting dark mixture was then heated at reflux for 1 hour. The reaction mixture was then cooled in an ice water bath and treated with 7 ml of 1:0M HCl (aq). After stirring for 15 minutes, 10 ml of hexanes was added and stirring was continued for 15 minutes. The suspension was filtered, washed with 10 ml of a 1:1 mixture of hexanes:ethyl acetate and then 10 ml cold H$_2$O. The precipitate was then washed with methanol. The filtrated was concentrated and dried under vacuo to give the title compound which was used for the next step without further purification.

2-(4-Nitro-phenyl)-1H-indol-5-ylamine hydrochloride

An oven dried argon cooled round bottom flask was charged with 5-Bromo-2-(4-nitrophenyl)-1H-indole (2.0 g, 6.31 mmol) and trisdibenzylideneacetone dipalladium(0.29 g, 0.32 mmol) then 100 ml THF. A solution of tri-tert-butyl phosphine (10 wt %) in hexane (1.93 mL, 0.63 mmol) was added followed by lithium hexamethyldisilazane (1.0M in THF) (18.9 ml, 18.9 mmol). The dark solution was heated at reflux for 1 hour then cooled to room temperature. This mixture was poured onto ice-cold 1.0M HCl (aq) (70 mL) and stirred vigorously. Hexanes was added and stirring was continued for 30 minutes. The precipitate was filtered, washed with 20 ml cold $H_2O$ and 20 mL 5% THF:95% Hexanes solution. The precipitate was washed with 200 ml methanol. The methanol washing was concentrated to give 1.5 g (82.4%) of the aminonitroindole.

2-(4-Nitro-phenyl)-1H-indole-5-carbonitrile

5-Bromo-2-(4-nitro-phenyl)-1H-indole (15.0 g, 47.3 mmol), $Pd_2(dba)_3$ (867 mg, 1.8 mmol Pd), $Zn(CN)_2$ (10.02 g, 85.3%) and zinc dust (372 mg, 0.7 mmol) were placed in a round bottom flask equipped with a condenser and stirbar. The system was purged under argon for several minutes and DMF was added (225 ml) followed by a solution of tri-tbutylphosphine in hexanes (5.8 ml, 10 wt %, 1.9 mmol). The mixture was stirred at room temperature for 15 minutes and then heated at 120° C. for 3 hours. The mixture was filtered through celite and the pad washed with DMF (20 ml). The filtrate was diluted with water (700 ml) resulting in the formation of a bright yellow precipitate. The precipitate was filtered and washed with water and dried under vacuo. Yield (13.1 g, quantitative).

2-(4-Nitro-phenyl'Y-1H-indole-5-carboxylic acid amide 2-(4-Nitro-phenyl)-1H-indole-5-carbonitrile (1.53 g, 5.80 mmol) and $LiOH.H_2O$ (1.46 g, 34.8 mmol) were placed in a 250 ml round bottom flask equipped with a stirbar and reflux condensor. The system was purged with argon and methanol (100 ml) was added. The solution mixture was placed in an oil bath at 40° C. and then 50% aqueous $H_2O_2$ added (2.34 ml, 40.6 mmol). The mixture was refluxed for 5 hours, cooled in an ice bath and diluted with 30 ml of 1.0M HCl(aq). The orange precipitate was filtered and washed with water. The product was dried at 110° C. under vacuo. Yield (1.25 g, 77%)

2-(4-Nitro-phenyl)-1H-indole-5-carboxylic acid methyl ester 2-(4-Nitro-phenyl)-1H-indole-5-carboxylic acid amide (9.95 g, 0.035 mol) was placed in a 2L round bottom flask equipped with a condensor and stirbar. The flask was purged with argon and methanol (1L) was added followed by concentrated HCl (300 mL). The mixture was refluxed for 5 days. The reaction mixture was concentrated, cooled at approximately 0° C. then filtered. The product was washed with water, collected and dried at 110° C. under vacuo. Yield: (8.15 g, 79%).

2-(4-Amino-phenyl)-1H-indole-5-carboxylic acid methyl ester

An oven dried 2L round bottom flask with magnetic stirbar under argon was charged with 2-(4-Nitro-phenyl)-1H-indole-5-carboxylic acid methyl ester (9.33 g, 31.52 mmol), methanol (600 mL), and THF (300 mL). The palladium catalyst (3.358, 10% wt, 3.152 mmol) was carefully added in portions then acetic acid (2 ml) was added. The mixture was evacuated then a balloon filled with $H_2$ (g) was placed over the mixture. The reaction mixture was stirred at room temperature overnight. The mixture was filtered through a pad of celite. The celite pad was washed with ethyl acetate. The filtrate was concentrated to about 250 ml then filtered through a plug of silica gel and eluted with 70% Ethyl acetate:30% Hexanes then with ethyl acetate. The filtrate was concentrated and slurried in about 70 ml boiling methanol. The crude product was then purified on silica gel using 7:3 ethylacetate:hexanes as eluant to give 4.5 g of the pure product. Yield (4.5 g, 53.7%)

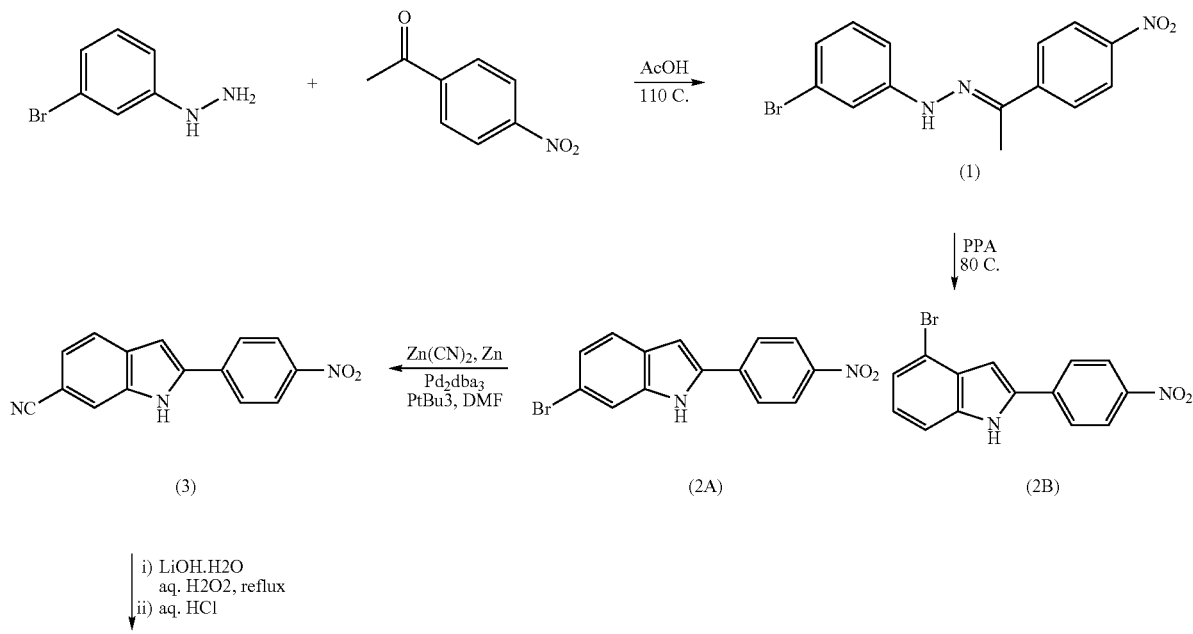

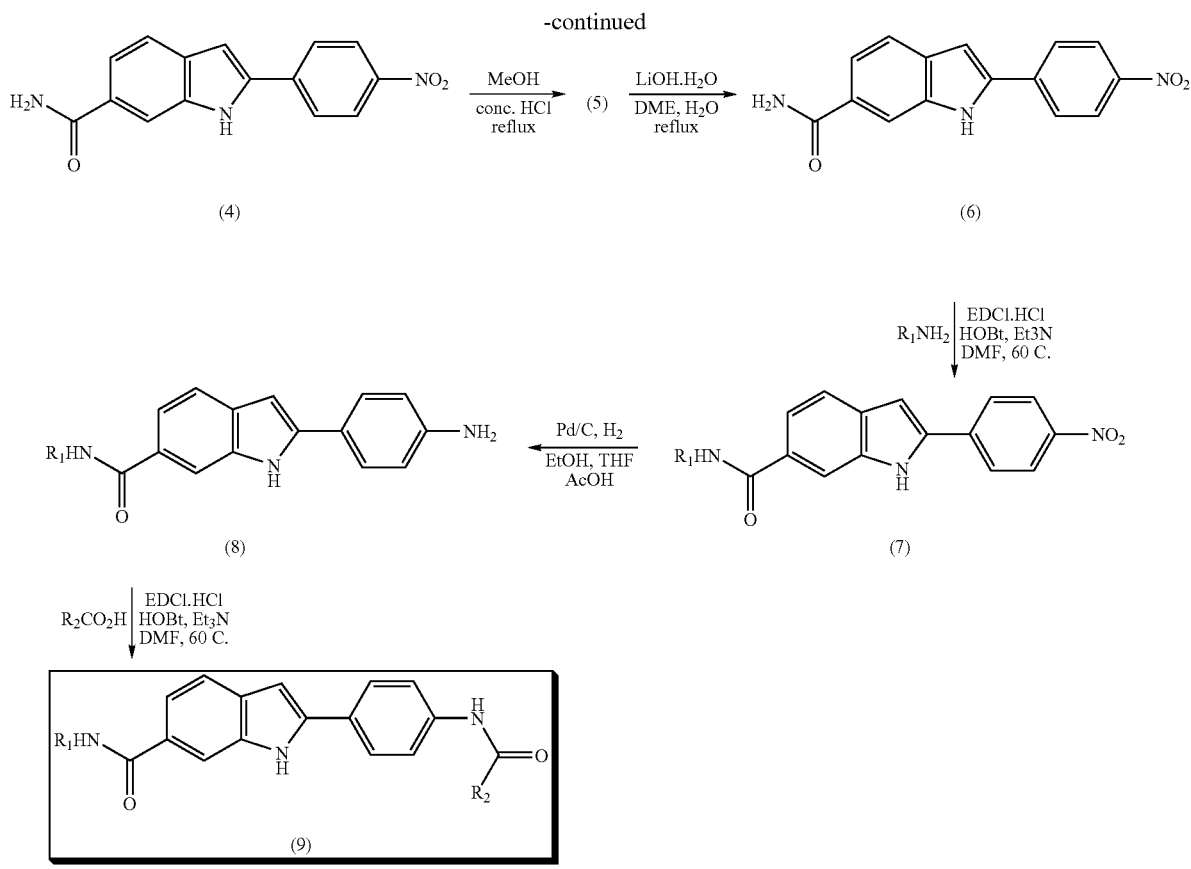

N-(3-Bromo-phenyl)-N'-[1-(4-nitro-phenyl)-ethylidene]-hydrazine (1):

To an oven dried Argon cooled 3-necked 1L flask, fitted with a magnetic stirring bar, a thermometer and condenser under Argon atmosphere, 20 gm. of 3-Bromo-phenyl hydrazine and 12.31 gm (1 eq) of 4-nitro-acetophenone were added followed by 350 mL of acetic acid. The mixture was heated at 110° C. for a period of 3.5 hrs. The mixture was left at room temperature for 18 hrs. The orange slurry was poured into ice water and the resulting precipitate was filtered, washed with water and dried to yield 18.33 gm of the desired hydrazone 1. Yield: 63%. The TLC showed essentially one product. This was directly used for the next step.

$^1$H NMR (DMSO): δ 9.81 (s, 1H, NH); 8.23 (d, 2H, J=9 Hz, aromatic H); 8.02 (d, 2H, J=9 Hz, aromatic H); 7.46 (s, 1H, aromatic H); 7.23 (m, 2H, aromatic H); 6.97 (m, 1H, aromatic H); 2.30 (s, 3H, $CH_3$).

6-Bromo-2-(4-nitro-phenyl)-1H-indole (2A):

To a 1L 3-necked oven dried flask fitted with a mechanical stirrer and thermometer, 9.4 gm of 1 was added followed by the addition of 250 mL of PPA with continuous stirring. The mixture was heated to 80° C. over 15 minutes and held at 80° C. for 30 minutes with vigorous stirring when TLC showed disappearance of the starting materials and appearance of two spots. The mixture was cooled and poured into 1L of ice water under vigorous stirring. The solid was collected by filtration, washed with water, then dissolved in ethyl acetate (leaving behind a residue on the filter), concentrated and dried to give a 50:50 mixture of the two regioisomers 2A and 2B. They were separated by chromatography on silica gel using 10–15% ethyl acetate in hexane. This yielded 1.8 gm of the 6-bromo isomer 2A.

$^1$H NMR (DMSO): δ 12.0 (br s, 1H, NH); 8.35 (d, 2H, J=8.7 Hz, aromatic H); 8.11 (d, 2H, J=8.7 Hz, aromatic H); 7.60 (s, 1H, aromatic H); 7.58 (d, 1H, J=8 Hz, aromatic H); 7.23 (s, 1H, aromatic H); 7.18 (d, 1H, J=8 Hz, aromatic H).

2-(4-Nitro-phenyl)-1H-indole-6-carbonitrile (3):

To an oven dried 250 mL flask, 2.77 g of 2A (1 eq), 1.85 g $Zn(CN)_2$ (1.8 eq), 68 mg of Zn powder and 160 mg (0.02 eq) of $Pd_2$ $dba_3$ were added followed by 75 mL of dry DMF. Under magnetic stirring, 1.07 mL of 10% hexane solution (0.04 eq) of $PtBu_3$ was added and the mixture was stirred at room temperature for a period of 30 min followed by heating at 100° C. for another 35 min. The mixture was cooled to room temperature and poured into ice water. The solid was collected, washed with water and dried. The product was dissolved in THF, filtered and concentrated to dryness to produce crude 3 that was used without purification in the next step.

$^1$H NMR (DMSO): δ 12.43 (br s, 1H, NH); 8.37 (d, 2H, J=9 Hz, aromatic H); 8.21 (d, 2H, J=9 Hz, aromatic H); 7.92 (s, 1H, aromatic H); 7.80 (m, 1H, aromatic H); 7.39 (m, 1H, aromatic H); 7.35 (s, 1H, aromatic H).

2-(4-Nitro-phenyl)-1H-indole-6-carboxylic acid amide (4):

To an oven dried 25 ml flask fitted with magnetic stirrer and condenser, 100 mg of 3, 96 mg. of $LiOH.H_2O$ (6 eq.) and 5 mL of methanol were added. Stirring under Argon, 0.155 mL of a 50% aqueous solution of hydrogen peroxide (7.2 eq) was introduced by a syringe and the mixture was refluxed. The reaction was complete after 2.5 hrs, when the mixture was cooled and poured into cold 1M HCl. The orange red precipitate was collected, washed with water and dried to yield 82 mg of the crude amide 4 that was further purified by chromatography on silica gel using 7.5% methanol in methylene chloride. Thus 53 mg of the pure 4 was obtained in 50% yield.

$^1$H NMR (DMSO): δ 12.08 (s, 1H, NH); 8.36 (d, 2H, J=9 Hz, aromatic H); 8.17 (d, 2H, J=9 Hz, aromatic H); 7.99 (s, 1H, aromatic H); 7.95 (s, 1H, aromatic H); 7.62 (m, 2H, aromatic H); 7.24 (m, 2H, aromatic H).

MS (APCI+ve): MH$^+$, 282, 100%

2-(4-Nitro-phenyl)-1H-indole-6-carboxylic acid (6):

A solution of 770 mg of the carboxamide 4 in 75 mL methanol containing 15 mL conc. HCl was heated under reflux for a period of 64 hrs when the hydrolysis was complete by TLC. The mixture was cooled, poured into ice water and the resulting precipitate was collected, washed with water and dried to produce 747 mg of the crude ester 5 that used without further purification.

To 635 mg of the ester 5 obtained above, in a flask fitted with condenser and magnetic stirrer, 901 mg of LiOH, 75 mL DME and 15 mL water were introduced and the mixture was refluxed under constant stirring for a period of 20 hrs. The cooled mixture was acidified to pH 1 by HCl and poured into ice water. The resulting precipitate was collected, washed with water and dried to produce 628 mg of the desired acid 6.

$^1$H NMR (DMSO): δ 12.65 (br s, 1H, CO$_2$H); 12.17 (s, 1H, NH); 8.36 (d, 2H, J=9 Hz, aromatic H); 8.20 (d, 2H, J=9 Hz, aromatic H); 8.08 (s, 1H, aromatic H); 7.66 (m, 2H, aromatic H); 7.29 (m, 2H, aromatic H).

MS (APCI-ve): M$^-$, 281, 100%

2-(4-Nitro-phenyl)-1H-indole-6-carboxylic acid adamantan-1-ylamide (7):

To an oven dried Argon cooled 100 mL flask, 605 mg acid 6, 493 mg EDCI.HCl, 348 mg of HOBt were added. While under Argon atmosphere, 30 mL of dry DMF and 1.79 mL of Et$_3$N were added and the mixture was stirred at room temperature for 15 min. After this, 389 mg of 1-adamantylamine was added and the resulting mixture was heated at 60° C. with continuous stirring for a period of 16 hrs when TLC indicated the reaction was complete. The mixture was cooled to 0° C. and poured into water. The resulting yellow solid was collected and filtered to give the crude amide that was further purified by chromatography over silica gel using 50–90% ethyl acetate in hexane as eluent. Evaporation of the solvent yielded 600 mg of pure 7.

$^1$H NMR (DMSO): δ 12.03 (s, 1H, NH); 8.34 (d, 2H, J=9 Hz, aromatic H); 8.15 (d, 2H, J=9 Hz, aromatic H); 7.88 (s, 1H); 7.61 (m, 1H): 7.52 (m, 2H); 7.25 (m, 1H); 1.65–2.12 (m, 15H).

MS (APCI+ve): MH$^+$, 416, 100%

2-(4-Amino-phenyl)-1H-indole-6-carboxylic acid adamantan-1-ylamide (8):

To 595 mg of 7 in a 250 mL flask purged with Argon, 40 mL of methanol and 40 mL of THF were introduced followed by 152 mg of 10% Pd/C. To this stirred mixture, 0.15 mL of acetic acid was added via a syringe. The flask was purged with hydrogen, evacuated and refilled with hydrogen (twice) and the mixture was stirred under hydrogen for 18 hr. The mixture was filtered over celite and silica gel. Removal of solvent and drying under vacuum yielded 675 mg of the essentially pure amine 8 that was used for the subsequent couplings.

MS (APCI+ve): MH$^+$, 386, 100%

General Procedure for the Reduction of the Nitro Group

An oven dried round bottom flask was charged with the nitroindole (1.0 equiv) and palladium on activated carbon (0.1 equiv). Methanol, THF (for complete dissolution) and a few drops of glacial acetic acid were added. The system was evacuated with a water aspirator and H$_2$(g) was let into the system via a balloon. The reaction mixture was stirred at room temperature for 16 hours (overnight) then filtered through a pad of celite/silica gel. The crude mixture was then purified by silica gel column chromatography to give the aniline.

General Procedure for Amide Formation

An oven dried round bottom flask was charged with the acid (1.1 equiv), HOBT (1.1 equiv) and EDCl(HCl) (1.1 equiv). DMF and triethylamine were added and the mixture was stirred at room temperature for 10 minutes. The amine (1.0 equiv) was added in one portion then the mixture was heated at 60° C. for 16 hours (overnight). After cooling in an ice water bath the mixture was treated with H$_2$O and stirred for 15 minutes. The precipitate was filtered and washed with cold H$_2$O.

EXAMPLE 2

Suppression of IgE Response

The inhibitory activity of the small molecules of the present invention were assayed using both the ex vivo and in vivo assays as described above. All of the compounds presented above were active in suppressing the IgE response. In the ex vivo assay, compounds in Genera I–IV produced 50% inhibition at concentrations ranging from 1 pM to 100 μM. In the in vivo assay, the compounds were effective at concentrations ranging from less than about 0.01 mg/kg/day to about 100 mg/kg/day, when administered in divided doses (e.g., two to four times daily) for at least two to seven consecutive days. Thus, the small molecule inhibitors of the preferred embodiments are disclosed as being useful in lowering the antigen-induced increase in IgE concentration, and consequently, in the treatment of IgE-dependent processes such as allergies in general and allergic asthma in particular.

EXAMPLE 3

Effects on Cellular Proliferation

A variety of experiments were performed in an effort to determine the effect of the phenyl-indole compounds on cellular proliferation. These experiments ultimately measured $^3$H-thymidine incorporation into proliferating cell DNA. The specific procedure varied with the cells and the stimuli. Cells derived from mouse spleen were cultured at 3 million per ml; cell lines were seeded at 0.1 to 1 million per ml. Splenic B cells were isolated by T cell depletion and stimulated with phorbol myristate acetate (PMA) (10 ng/ml) plus ionomycin (100 nM), or IL-4 (10 ng/ml) plus anti-CD40 Ab (100 ng/ml). T cells were depleted prior to culture by incubating spleen cells first with a cocktail of anti-Thy1 ascites (10%), anti-CD4 Ab (0.5 μg/ml) and anti-CD8 Ab (0.5 μg/ml), followed by guinea pig complement (adsorbed). Cell lines were unstimulated or stimulated with Human Epidermal Growth Factor (EGF) (100 ng/ml). All cells were cultured in 96-well plates for 2–3 days and pulsed for 6 to 14 hours with 50 μl of 3H-thymidine (50 μCi/ml).

In spleen cells, certain compounds of the preferred embodiments suppressed B cell proliferation responses to PMA/ionomycin and IL-4/anti-CD40 Ab (FIG. 1) with approximately the same potencies as it suppressed in vitro IgE responses to IL-4/anti-CD40 Ab. Similar inhibition potencies were obtained for certain compounds of the preferred embodiments in ConA-stimulated T cell proliferation and LPS-stimulated B cell proliferation (preformed by MDS Pharma), suggesting a lack of specificity in the action of these drugs. On the other hand, a battery of immunological tests performed with certain compounds of the preferred embodiments demonstrated little other effects other than inhibition of ConA-stimulated cytokine release.

In tumor cells, the results with splenic lymphocytes led to a further analysis of cellular proliferation by measuring the growth of tumor cells in the presence of these drugs. The initial analysis was performed with murine M12.4.1 lymphoma cells, either un-stimulated or stimulated with IL-4/anti-CD40 Ab. Certain compounds of the preferred embodiments suppressed the proliferation of M12.4.1 cells but with lower potency that observed in stimulated spleen cells. However, the potency of certain compounds of the preferred embodiments increased when the cells were cultured with IL-4/anti-CD40 Ab. This stimulation is known to induce the activity of NF-κB in M12.4.1 cells.

A similar approach was used to establish selectivity of the anti-proliferative activity by testing a battery of tumor lines derived from a variety of tissues, mostly human in origin. An attempt was made to generate proliferation data from at least 2 cell lines from each tissue selected. Only a handful of cell lines were inhibited by 100 nM or less of each compound while most the balance of the cells required much higher concentrations. Because of the known character of some of the tested cell lines and previous Western blot results with the compounds, there is evidence to suggest a link between NF-κB inhibition and the action of the drugs. Breast cancer cells offer a good model for testing this phenomenon because they are predominantly of 2 types; estrogen receptor (ER)-positive and ER-negative. The latter cells tend to be less differentiated, have a higher density of EGF receptor expression, and are more resilient to treatment. Proliferation of ER-negative/EGFR-positive cells also tends to be driven by NF-κB and thus a selection of these cells were tested for proliferation responses to drug in vitro. The proliferation of all of the EGF-responsive cell lines was potently inhibited by certain compounds of the preferred embodiments in vitro.

Certain compounds of the preferred embodiments exert an anti-proliferative activity to T and B lymphocytes exposed to a variety of immunogenic stimuli in vitro. These actions are highly potent and parallel their IgE-suppression activity. Although the mechanism of this action is unresolved, much is known about the mechanism of IL-4/anti-CD40 Ab-induced IgE production. A major factor in this response is the transcription activator, NF-κB. This factor has been implicated in the proliferation of a number of tumor cells and thus these drugs were tested for activity on the proliferation of various tumor cell lines in vitro. Our experiments revealed that a number of tumor cell lines are sensitive to the effects of certain compounds of the preferred embodiments, and that proliferation of many of the sensitive lines may be driven by NF-κB factors. However, other cell lines known to be driven by factors other than NF-κB (e.g., the ER-positive HCC 1500 and ZR-75-1). Thus, certain compounds of the preferred embodiments appear to selectively act on certain tumor cells. Other compounds disclosed in accordance with the preferred embodiments are also expected to exhibit similar characteristics, particularly those compounds which are structurally similar to certain compounds of the preferred embodiments.

Treatment Regimens

The amount of the phenyl-indole compounds which can be effective in treating a particular allergy or used as an anti-proliferation agent will depend on the nature of the disorder, and can be determined by standard clinical techniques. The precise dose to be employed in a given situation will also depend on the choice of compound and the seriousness of the condition, and should be decided according to the judgment of the practitioner and each patient's circumstances.

As an anti-allergy therapy, appropriate dosages can be determined and adjusted by the practitioner based on dose response relationships between the patient's IgE levels as well as standard indices of pulmonary and hemodynamic changes. Moreover, those skilled in the art will appreciate that dose ranges can be determined without undue experimentation by following the protocol(s) disclosed herein for ex vivo and in vivo screening (See for example Hasegawa et al., *J. Med. Chem.* 40: 395–407 (1997) and Ohmori et al., *Int. J. Immunopharmacol.* 15:573–579 (1993); employing similar ex vivo and in vivo assays for determining dose-response relationships for IgE suppression by naphthalene derivatives; incorporated herein by reference).

Initially, to exert anti-allergic or anti-asthmatic effects, suitable dosages of the compounds will generally range from about 0.001 mg to about 300 mg per kg body weight per day in divided doses, more preferably, between about 0.01 mg and 100 mg per kg body weight per day in divided doses. The compounds are preferably administered systemically as pharmaceutical formulations appropriate to such routes as oral, aerosol, intravenous, subcutaneously, or by any other route which may be effective in providing systemic dosing of the active compound. The compositions of pharmaceutical formulations are well known in the art. The treatment regimen preferably involves periodic administration. Moreover, long-term therapy may be indicated where allergic reactions appear to be triggered by continuous exposure to the allergen(s). Daily or twice daily administration has been effective in suppressing the IgE response to a single antigen challenge in animals when carried out continuously from a period of two to seven consecutive days. Thus, in a preferred embodiment, the compound is administered for at least two consecutive days at regular periodic intervals. However, the treatment regimen, including frequency of dosing and duration of treatment may be determined by the skilled practitioner, and modified as needed to provide optimal IgE down-regulation, depending on nature of the allergen, the dose, frequency, and duration of the allergen exposure, and the standard clinical indices.

In a preferred embodiment, an IgE-suppressing compound can be administered in conjunction with one or more of the other small molecule inhibitors disclosed, in order to produce optimal down-regulation of the patient's IgE response. Further, it is envisioned that one or more of the compounds of the preferred embodiments can be administered in combination with other drugs already known or later discovered for treatment of the underlying cause as well as the acute symptoms of allergy or asthma. Such combination therapies envisioned within the scope of the present invention include mixing of one or more of the small molecule IgE-inhibitors together with one or more additional ingredients, known to be effective in reducing at least one symptom of the disease condition. In a variation, the small molecule IgE-inhibitors herein disclosed can be administered separately from the additional drugs, but during the same course of the disease condition, wherein both the IgE-inhibitor(s) and the palliative compounds are administered in accordance with their independent effective treatment regimens.

As an anti-proliferative therapy, the appropriate dose of the phenyl-indole compounds disclosed herein can be determined by one skilled in the art. Pharmacologists and oncologists can readily determine the appropriate dose required for each individual patient without undue experimentation, based upon standard treatment techniques used for other anti-proliferation and chemotherapeutic agents.

Initially, suitable dosages of the anti-proliferation phenyl-indole compounds will generally range from about 0.001 mg to about 300 mg per kg body weight per day in divided doses, more preferably, between about 0.01 mg and 100 mg per kg body weight per day in divided doses. Most preferably, to exert anticancer effects, the dose will range from about 1 mg to 100 mg per kg body weight per day. The compounds are preferably administered systemically as pharmaceutical formulations appropriate to such routes as oral, aerosol, intravenous, subcutaneously, or by any other route which may be effective in providing systemic dosing of the active compound.

Ideally one or more phenyl-indole compounds of the preferred embodiments should be administered to achieve peak plasma concentrations of the active agent, as determined by one of skill in the art. To achieve adequate plasma levels, the pharmaceutical formulation can be injected intravenously in an appropriate solution, such as a saline solution or administered as a bolus of the active ingredient.

The treatment regimen used in accordance with preferred embodiments preferably involves periodic administration. Moreover, as with other chemotherapeutic agents, long-term therapy may be indicated. Weekly, daily or twice daily administration for a period of one to three years may be required for some patients. Thus, in a preferred embodiment, the compound is administered for at least six months at regular periodic intervals. However, the treatment regimen, including frequency of dosing and duration of treatment may be determined by the skilled practitioner, and modified as needed to provide optimal anti-proliferation effects, depending on nature of the disease, the extent of abnormal cell growth, the type of cancer, the tissues affected, and standard clinical indices.

One skilled in the art will understand that the ideal concentration of the anti-proliferation compounds in the formulation depends upon several pharmacokinetic parameters, such as, absorption, inactivation, metabolism and clearance rates of the drug as well as other known factors. One skilled in the art will also appreciate that the concentration will vary with the severity of the condition to be treated. Other factors which may affect the treatment dose include, tumor location, age and gender of the patient, other illnesses, prior exposure to other drugs, and the like. One skilled in the art will appreciate that for any particular patient, specific treatment regimens will be evaluated and adjusted over time according to the individual patient's requirements and according to the professional judgment of the medical practitioner administering the treatment.

In one preferred embodiment, compounds are orally administered. Preferably, oral formulations will include inert diluents or edible carriers. Oral dosages may be encapsulated in gelatin or formed into tablets. Oral administration may also be accomplished by using granules, grains or powders, syrups, suspensions, or solutions. One skilled in the art will understand that many acceptable oral compositions may be used in accordance with preferred embodiments. For example, the active compound may be combined with standard excipients, adjuvants, lubricants, sweetening agents, enteric coatings, buffers, stabilizing agents and the like.

In another embodiment, the active compound may be modified to include a targeting moiety that targets or concentrates the compound at the active site. Targeting moieties include, but are not limited to, antibodies, antibody fragments or derivatives, cytokines, and receptor ligands expressed on the cells to be treated.

In preferred embodiments, compounds are administered in conjunction with other active agents, which either supplement or facilitate the action of the phenyl-indole compound or cause other independent ameliorative effects. These additional active agents include, but are not limited to, antifungals, antivirals, antibiotics, anti-inflammatories, and anticancer agents. Protectants, which include carriers or agents which protect the active benzimidazole compound from rapid metabolism, degradation or elimination may also be used. Controlled release formulations can also be used in accordance with preferred embodiments.

In another embodiment, one or more anti-proliferation compounds may be administered in conjunction with one or more other anti-cancer agents or treatments to produce optimal anti-proliferative effects. Anti-cancer agents include, but are not limited to, alkylating agents (lomustine, carmustine, streptozocin, mechlorethamine, melphalan, uracil nitrogen mustard, chlorambucil cyclophosphamide, iphosphamide, cisplatin, carboplatin mitomycin thiotepa dacarbazine procarbazine, hexamethyl melamine, triethylene melamine, busulfan, pipobroman, and mitotane); anti-metabolites (methotrexate, trimetrexate pentostatin, cytarabine, ara-CMP, fludarabine phosphate, hydroxyurea, fluorouracil, floxuridine, chlorodeoxyadenosine, gemcitabine, thioguanine, and 6-mercaptopurine); DNA cutters (bleomycin); topoisomerase I poisons (topotecan irinotecan and camptothecin); topoisomerase II poisons (daunorubicin, doxorubicin, idarubicin, mitoxantrone, teniposide, and etoposide); DNA binders (dactinomycin, and mithramycin); and spindle poisons (vinblastine, vincristine, navelbine, paclitaxel, and docetaxel).

Further, it is envisioned that one or more of the compounds of the preferred embodiments can be administered in combination with other therapies, such as radiation, immunotherapy, gene therapy and/or surgery, in order to treat hyperproliferative diseases, including cancer. Such combination therapies envisioned within the scope of the present invention include mixing of one or more of the phenyl-indole compounds together with one or more additional ingredients, known to be effective in reducing at least one symptom of the disease condition. In a variation, the phenyl-indole compounds herein disclosed may be administered separately from the additional drugs, but during the same course of the disease condition, wherein both the phenyl-indole compound and the palliative compounds are administered in accordance with their independent effective treatment regimens.

While a number of preferred embodiments and variations thereof have been described in detail, other modifications and methods of use will be readily apparent to those of skill in the art. Accordingly, it should be understood that various applications, modifications and substitutions may be made of equivalents without departing from the spirit of the invention or the scope of the claims.

What is claimed is:

1. A compound or salt thereof having any one of the following formulas:

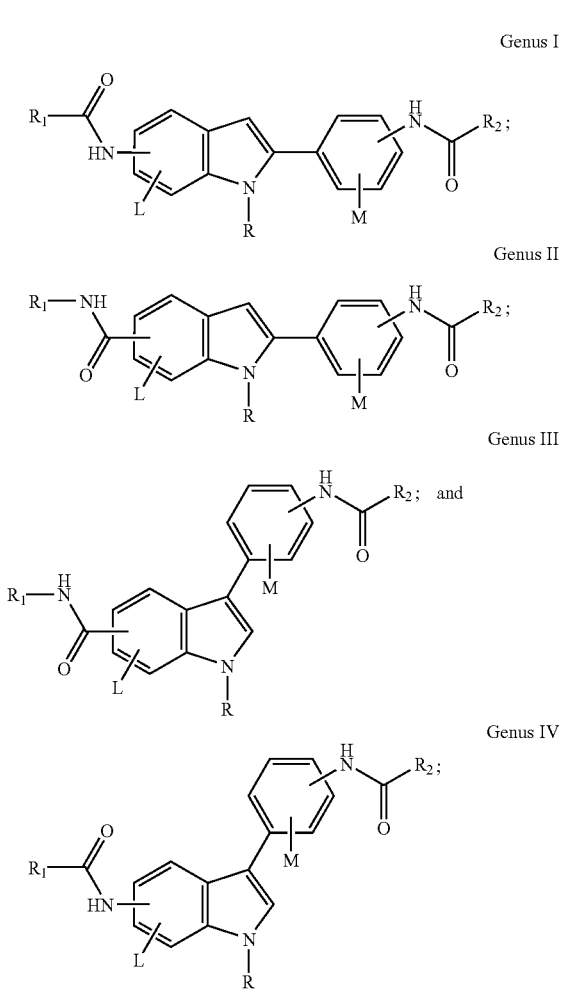

wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$–$C_5$ alkyl, benzyl, p-fluorobenzyl and di-alkylamino alkyl, wherein said $C_1$–$C_5$ alkyl is selected from the group consisting of a straight chain, branched or cyclic alkyl;

wherein $R_1$ and $R_2$ are independently selected from the group consisting of H, alkyl, substituted alkyl, $C_3$–$C_9$ cycloalkyl, substituted $C_3$–$C_9$ cycloalkyl, polycyclic aliphatic groups, substituted polycyclic aliphatic groups, phenyl, substituted phenyl, naphthyl, substituted naphthyl, heterocyclic, polycyclic heterocyclic, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1–3 substituents, wherein said substituent is selected from the group consisting of H, halogens, polyhalogens, alkoxy group, substituted alkoxy, alkyl, substituted alkyl, dialkylaminoalkyl, hydroxyalkyl, hydroxyamino, alkoxyamino, carbonyl, OH, $OCH_3$, COOH, COOR', COR', CN, $CF_3$, $OCF_3$, $NO_2$, NR'R', NHCOR', and CONR'R'; and wherein R' is selected from the group consisting of H, alkyl, substituted alkyl, $C_3$–$C_9$ cycloalkyl, substituted $C_3$–$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur.

2. The compound or salt thereof of claim 1, wherein said polycyclic aliphatic group is selected from the group consisting of adamantyl, bicycloheptyl, camphoryl, bicyclo[2,2,2]octanyl and norbornyl.

3. The compound or salt thereof of claim 1, wherein said heteroaryl and said substituted heteroaryl is selected from the group consisting of pyridines, thiazoles, isothiazoles, oxazoles, pyrimidines, pyrazines, furans, thiophenes, isoxazoles, pyrroles, pyridazines, 1,2,3-triazines, 1,2,4-triazines, 1,3,5-triazines, pyrazoles, imidazoles, indoles, quinolines, iso-quinolines, benzothiophines, benzofurans, parathiazines, pyrans, chromenes, pyrrolidines, pyrazolidines, imidazolidines, morpholines, thiomorpholines, and the corresponding heterocyclics.

4. The compound or salt thereof of claim 1, wherein $R_1$ and $R_2$ are independently selected from the following:

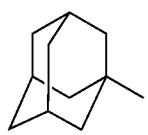

2

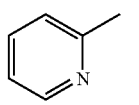

1

3

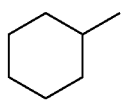

4

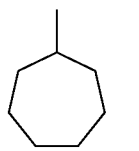

5

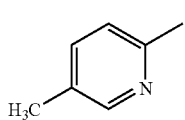

6

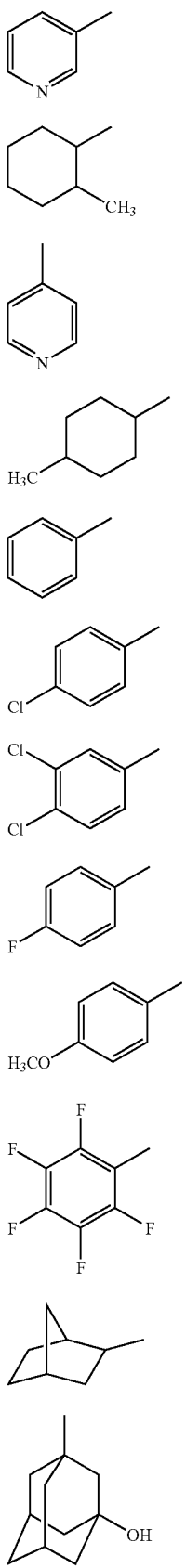
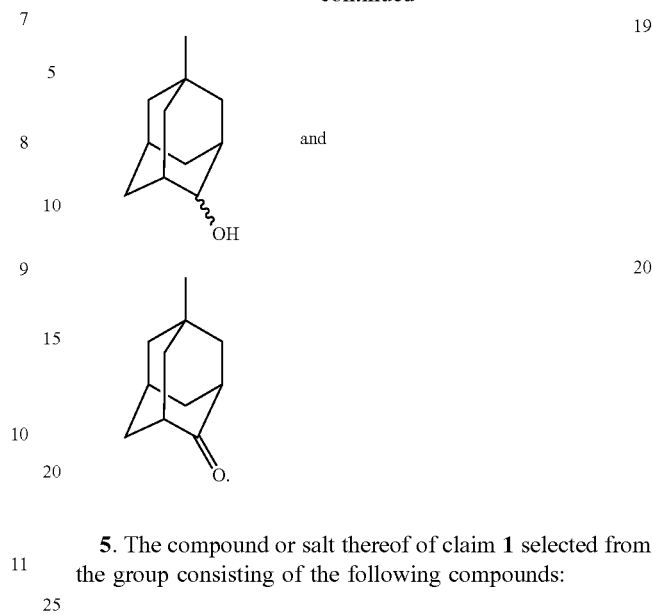
5. The compound or salt thereof of claim 1 selected from the group consisting of the following compounds:
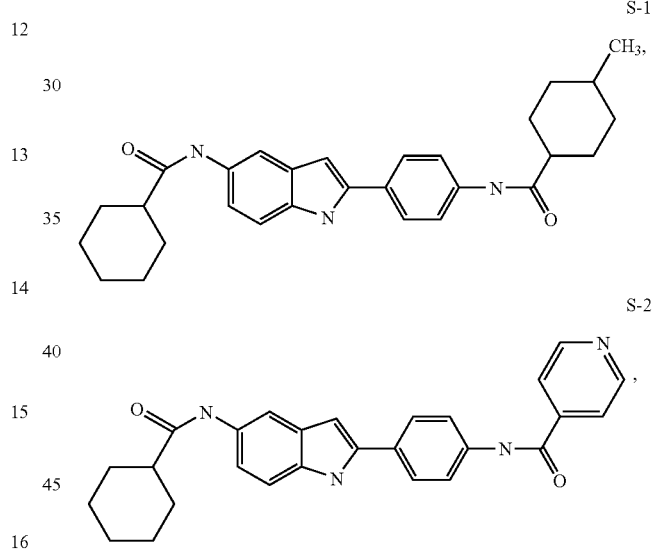
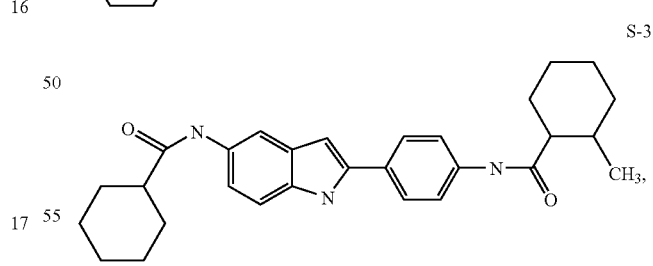
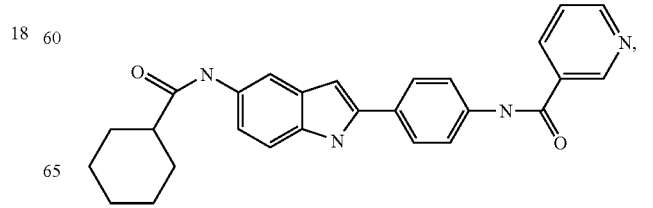

-continued
S-5
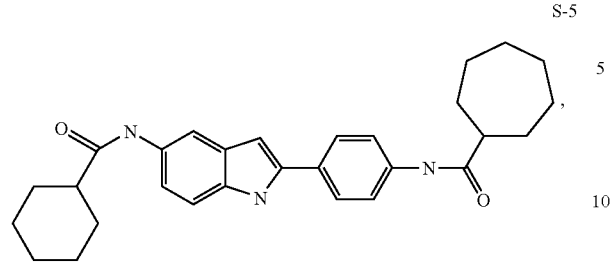
S-6
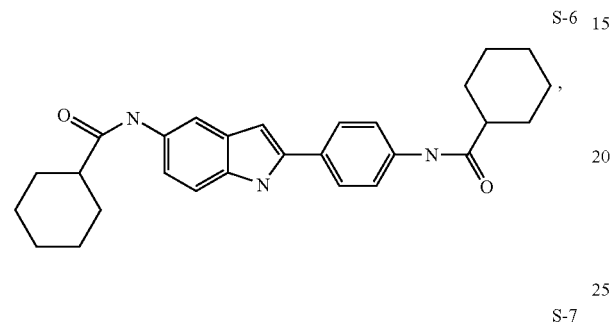
S-7
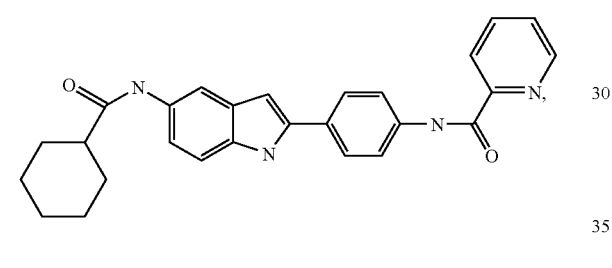
S-8
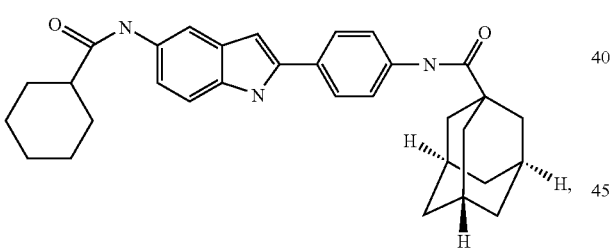
S-9
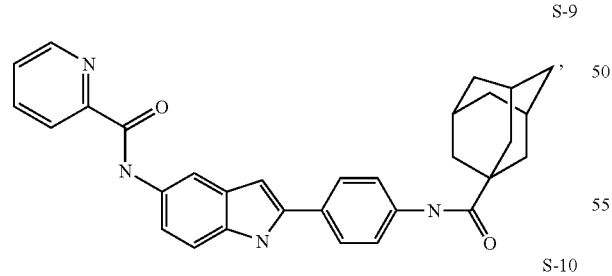
S-10
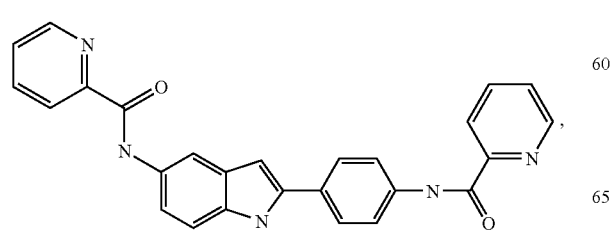
-continued
S-11
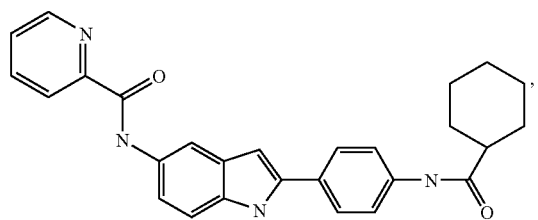
S-12
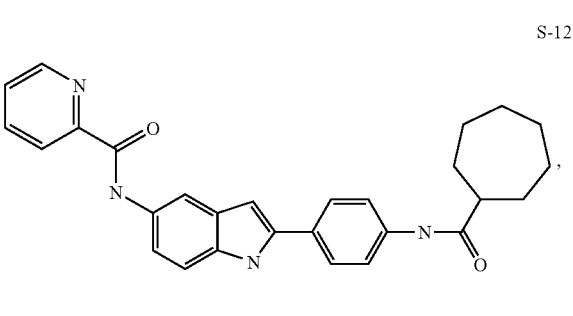
S-13
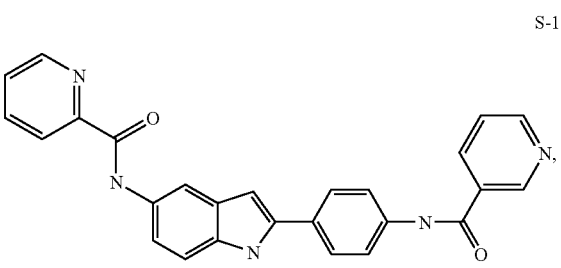
S-14
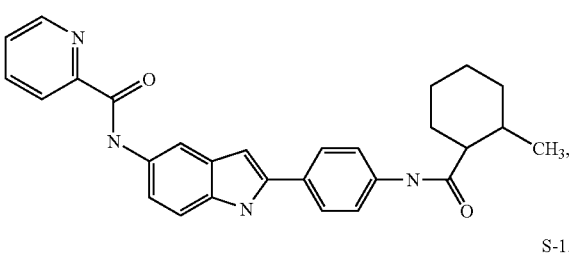
S-15
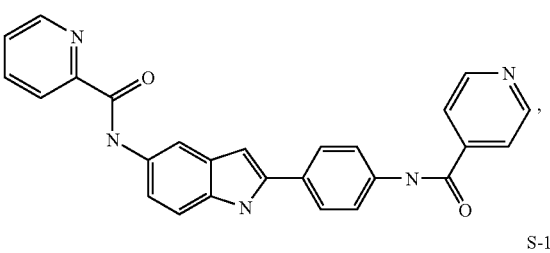
S-16
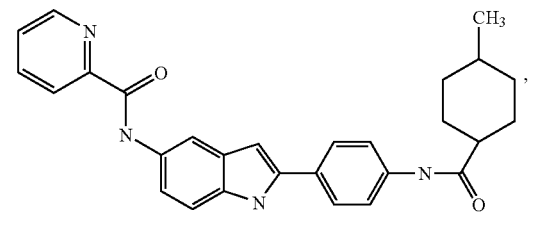

-continued
S-17
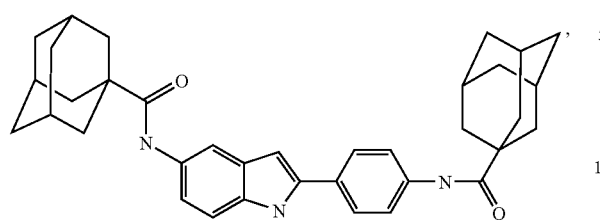
S-18
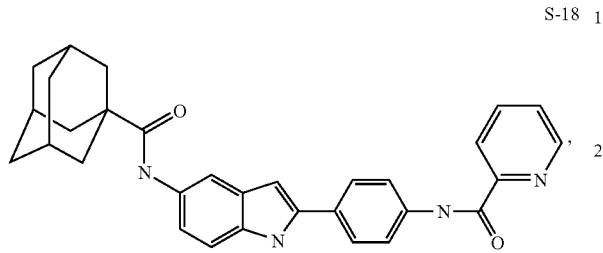
S-19
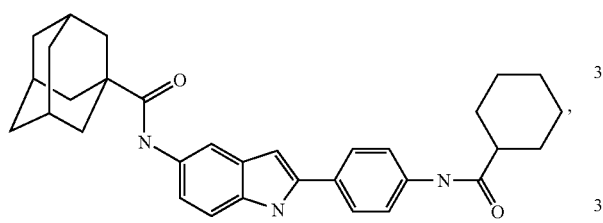
S-20
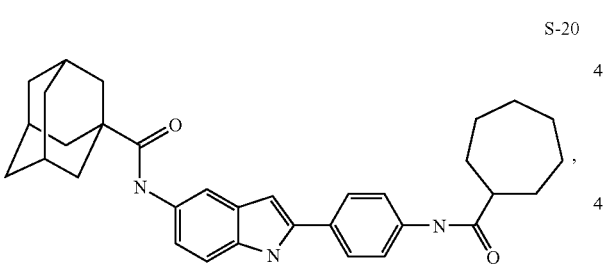
S-21
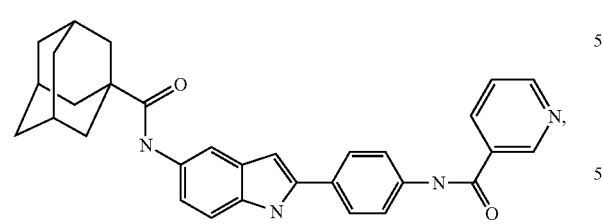
S-22
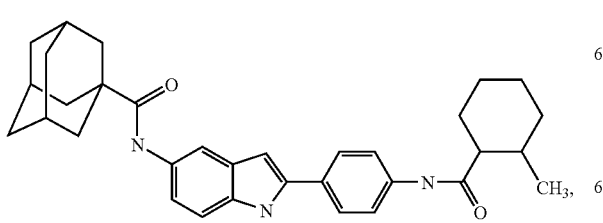
-continued
S-23
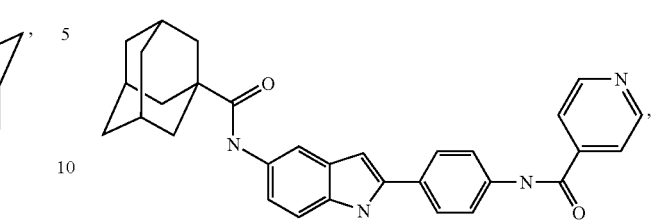
S-24
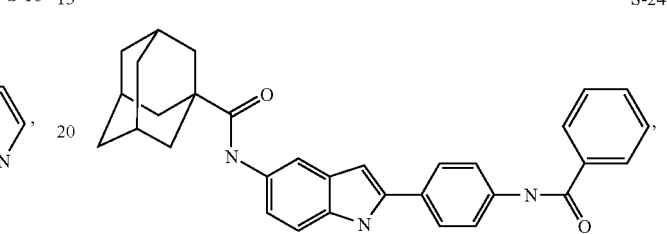
S-25
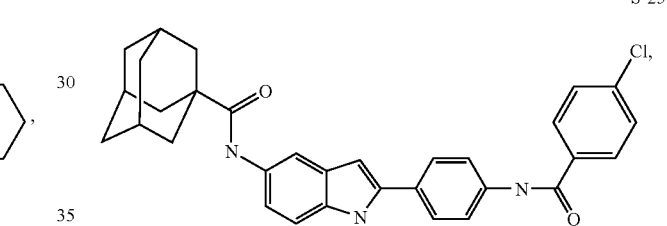
S-26
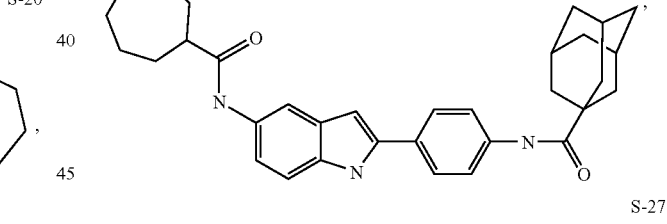
S-27
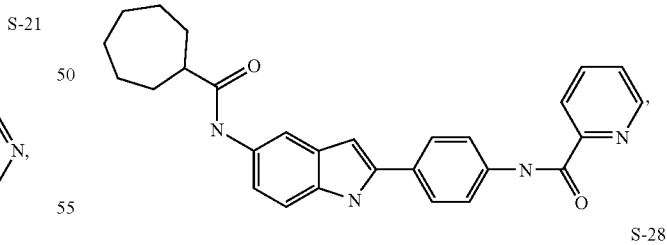
S-28
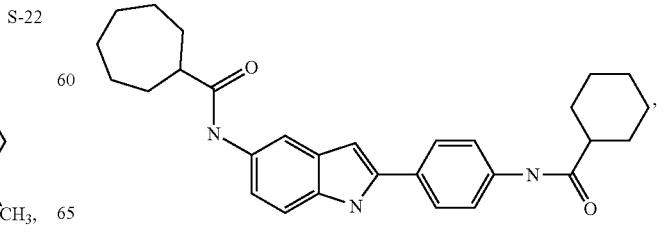

-continued
S-29
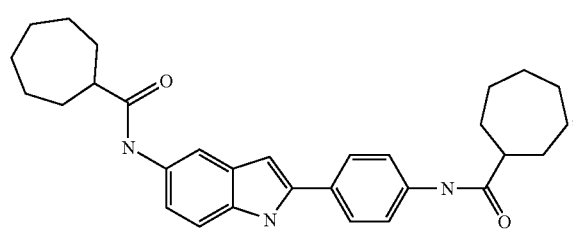
S-30
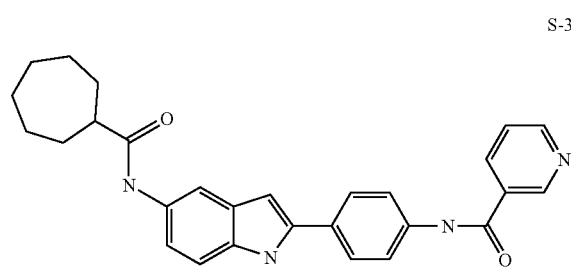
S-33
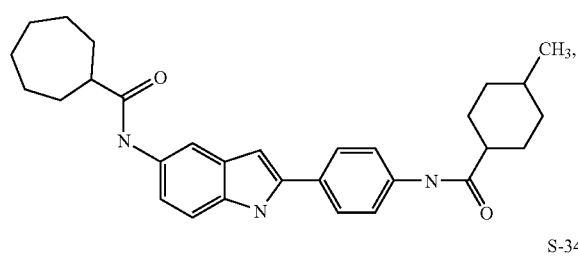
S-34
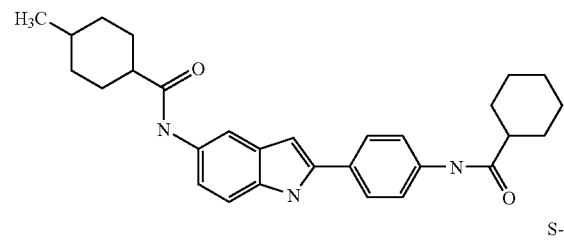
S-35
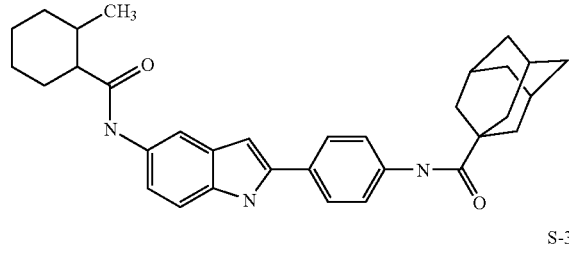
S-36
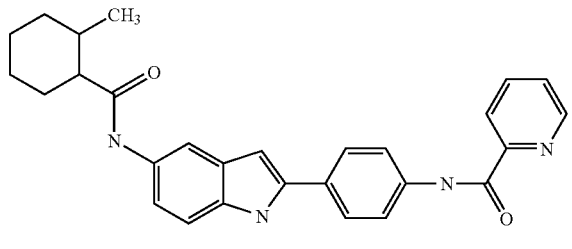
-continued
S-37
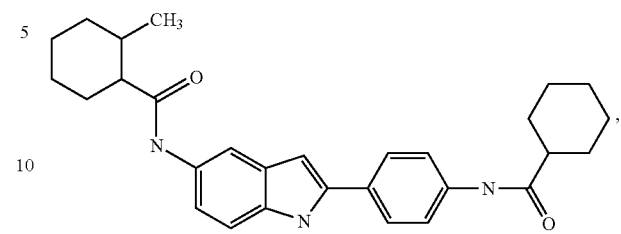
S-38
S-39
S-40
S-41
S-42

-continued
S-43
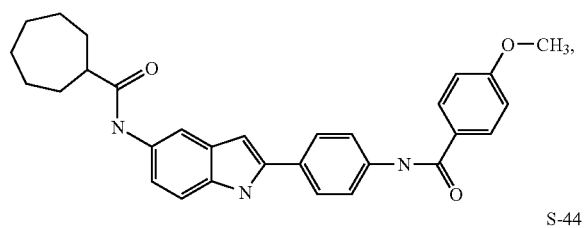
S-44
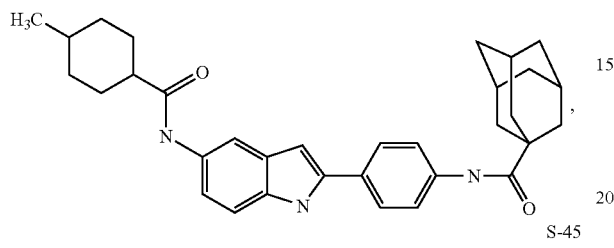
S-45
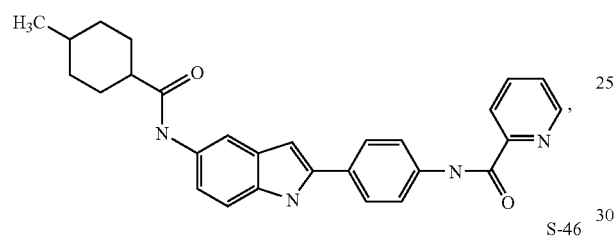
S-46
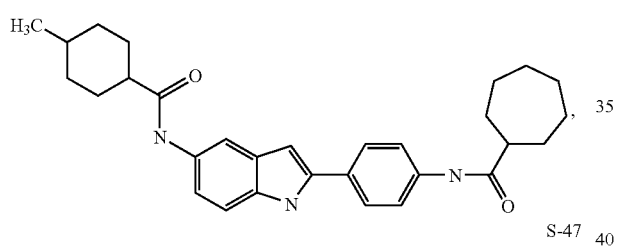
S-47
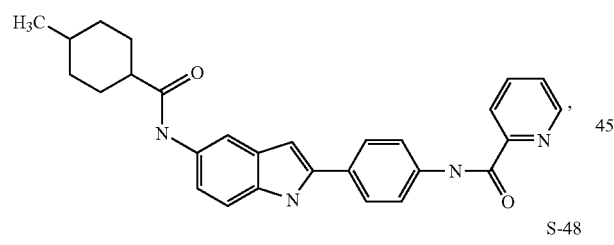
S-48
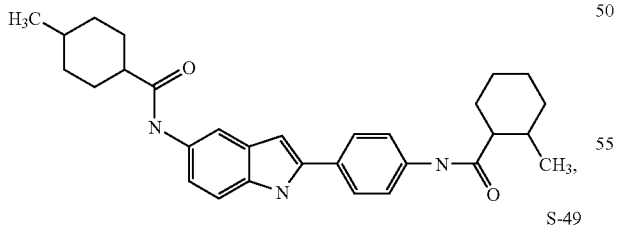
S-49
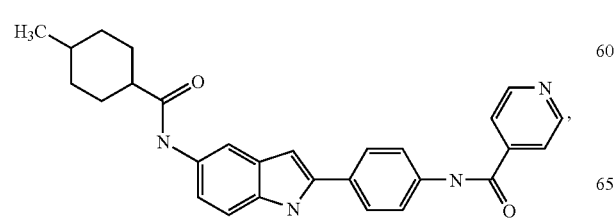
-continued
S-50
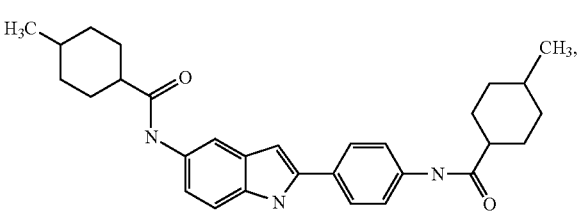
S-51
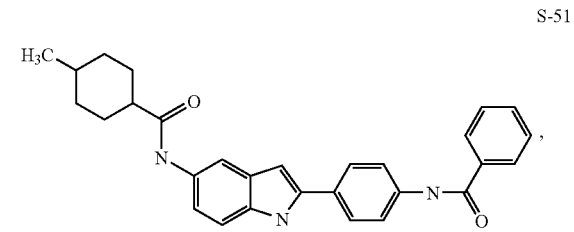
S-52
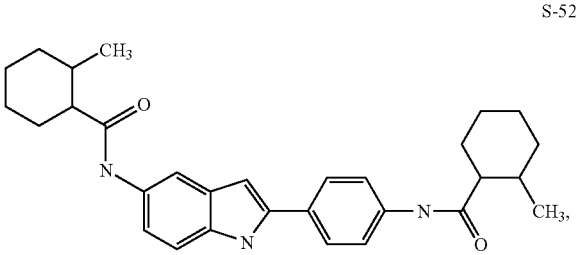
S-53
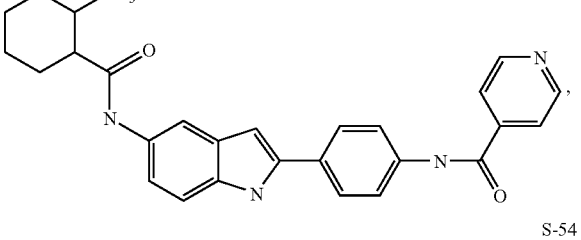
S-54
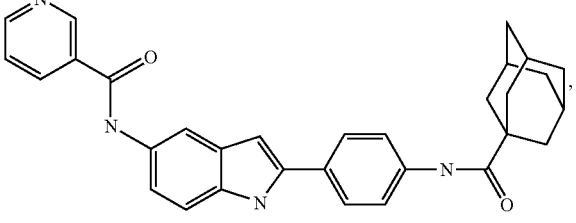
S-55
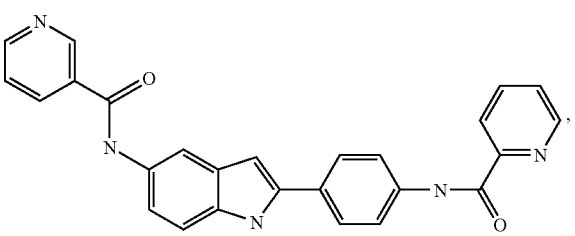

-continued
S-56
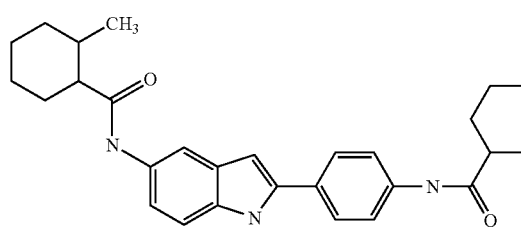
S-57
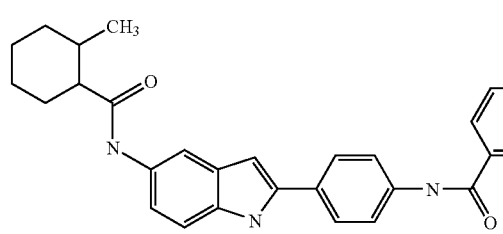
S-58
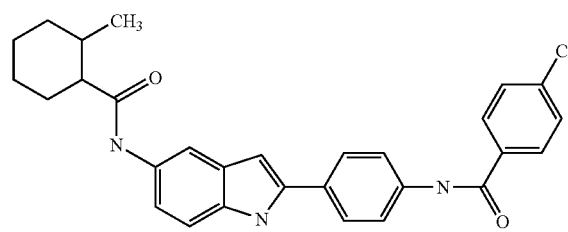
S-59
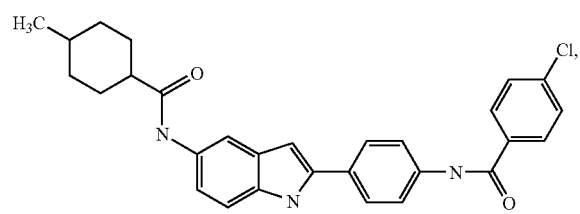
S-60
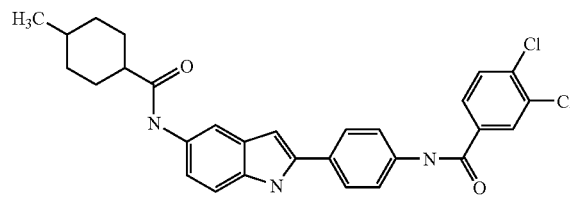
S-61
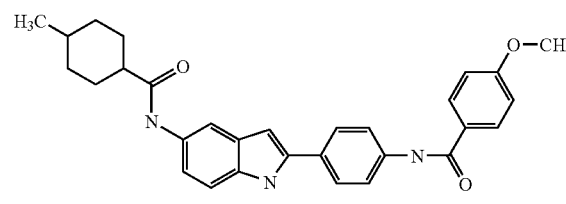
-continued
S-62
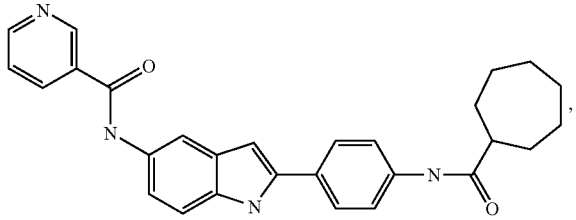
S-63
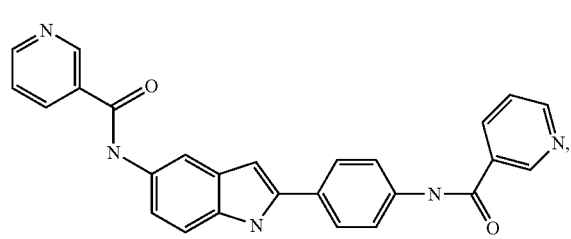
S-64
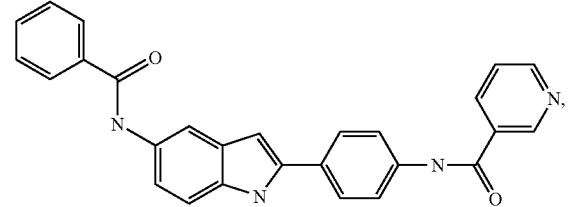
S-65
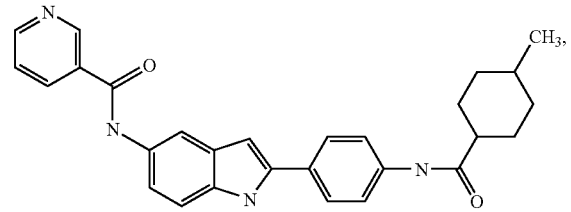
S-66
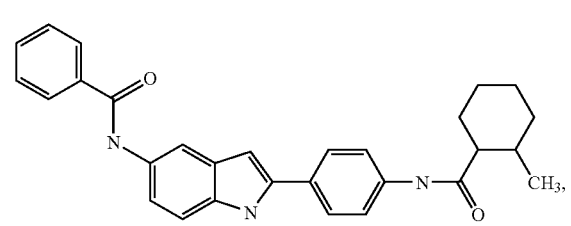
S-67

-continued
S-68
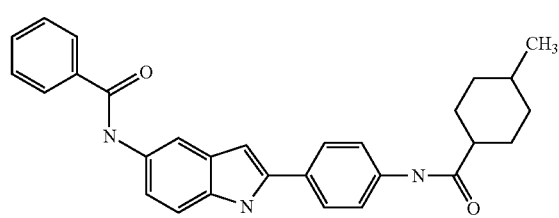
S-69
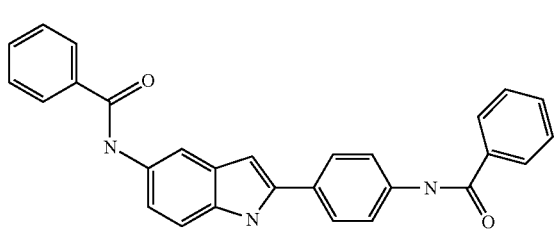
S-70
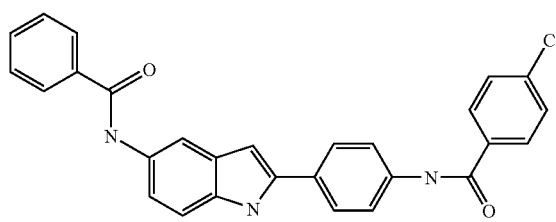
S-71
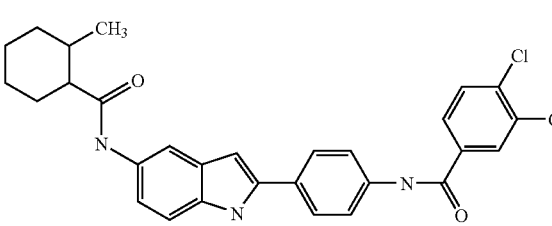
S-72
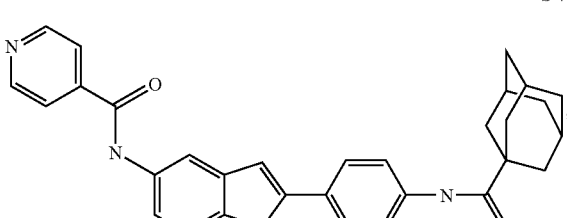
S-73
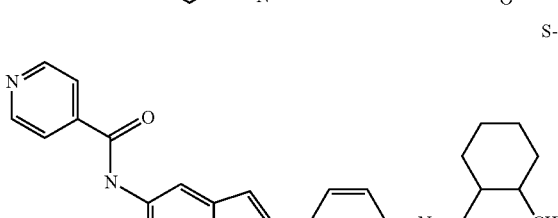
-continued
S-74
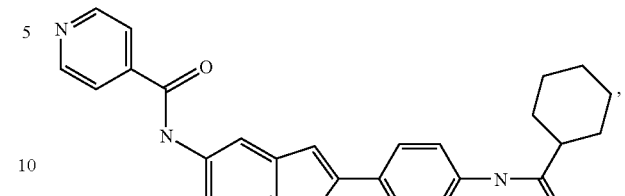
S-75
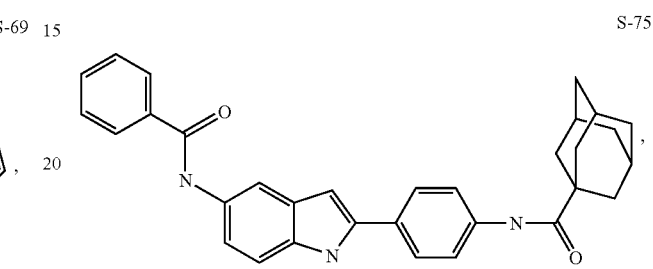
S-76
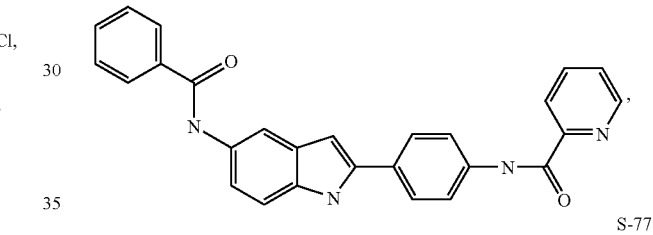
S-77
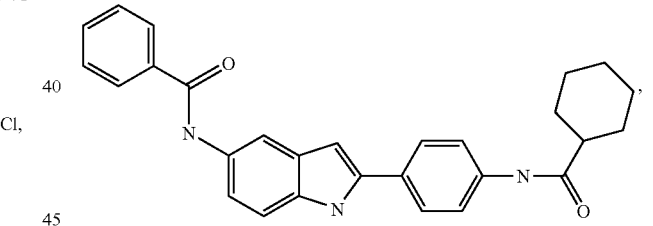
S-78
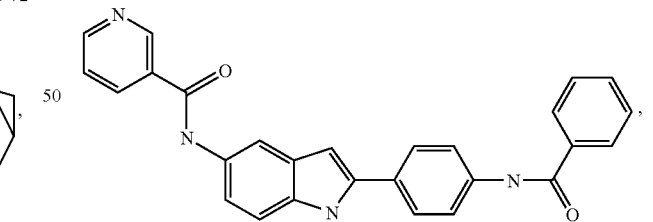
S-79
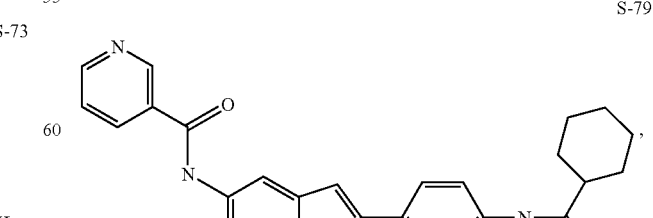

-continued

S-80, S-81, S-82, S-83, S-84, S-85, S-86, S-87, S-88, S-89, S-90, S-91, S-92

-continued

-continued
S-105
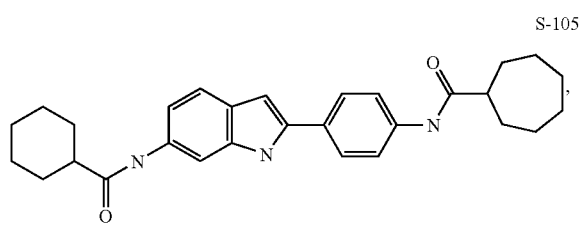
S-106
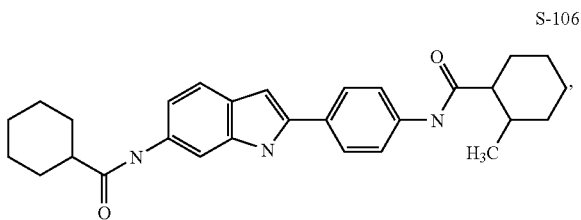
S-107
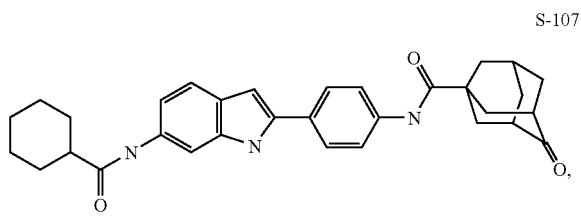
S-108
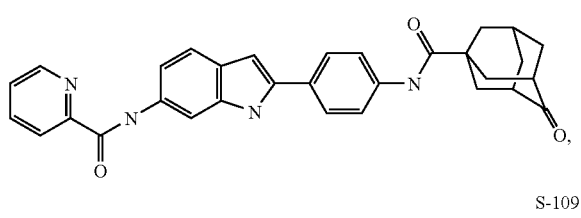
S-109
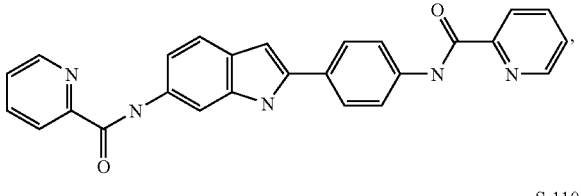
S-110
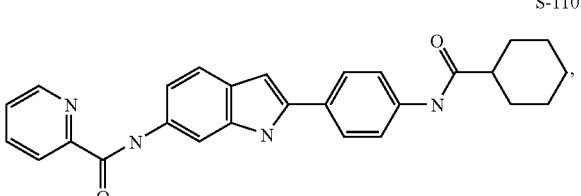
S-111
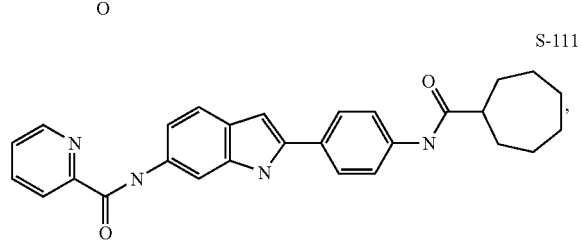
-continued
S-112
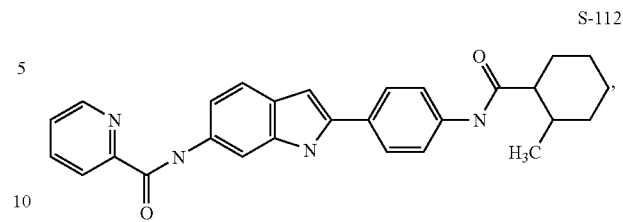
S-113
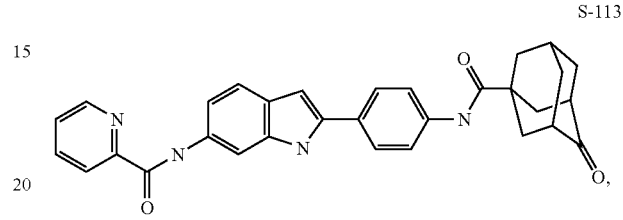
S-114
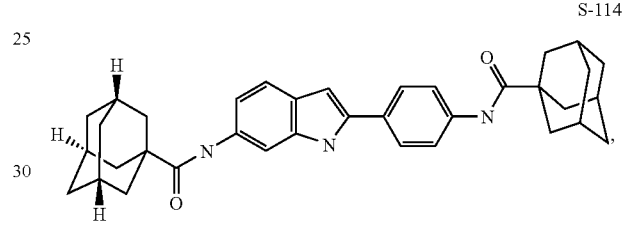
S-115
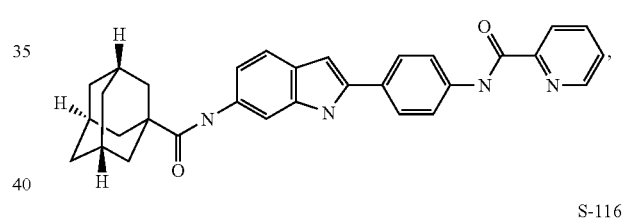
S-116
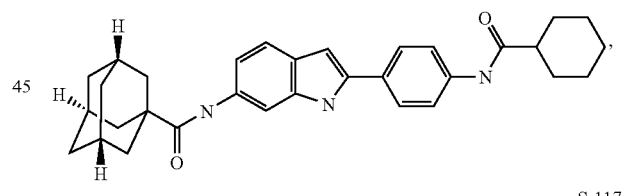
S-117
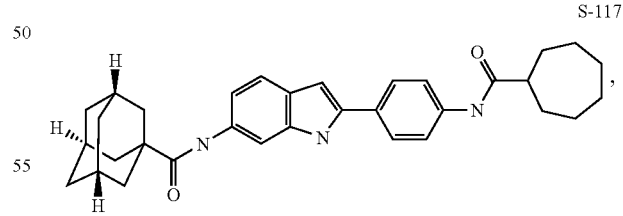
S-118
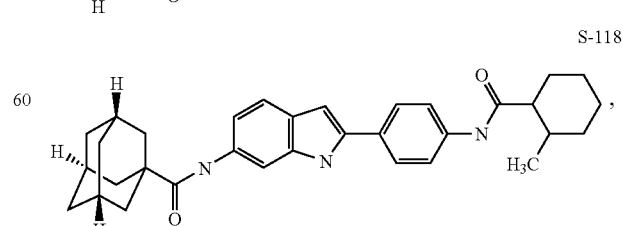

-continued
S-119
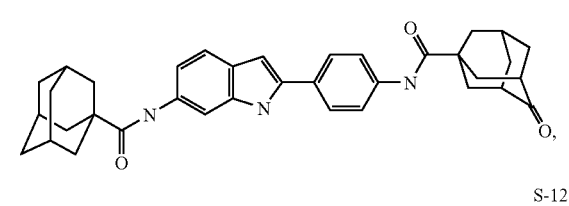
S-120
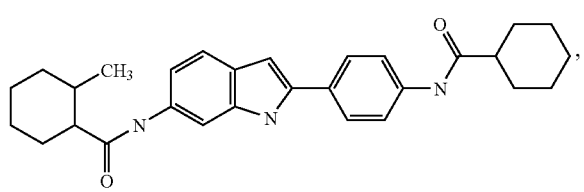
S-121
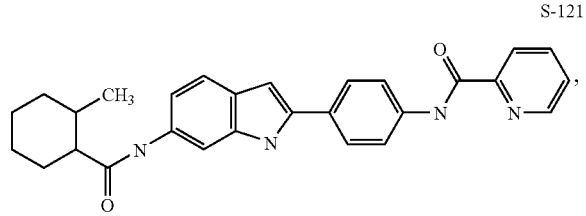
S-122
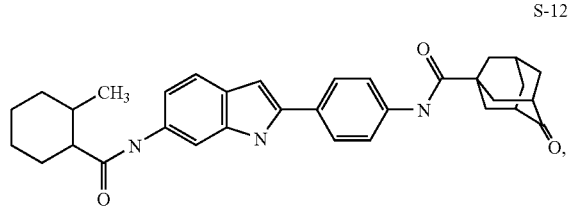
S-123
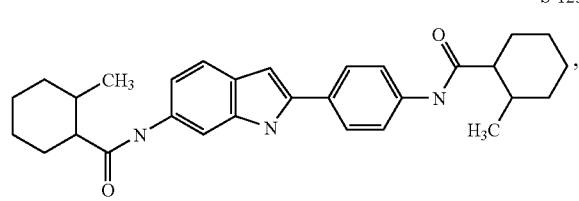
T-1
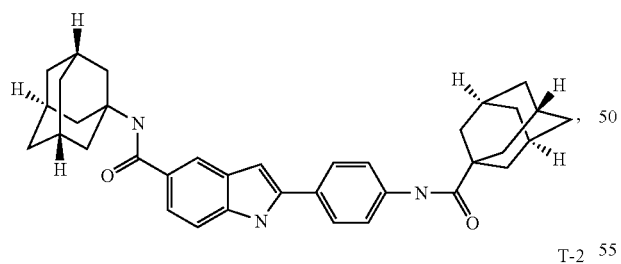
T-2
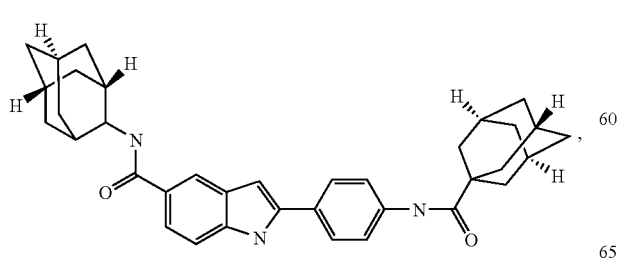
-continued
T-3
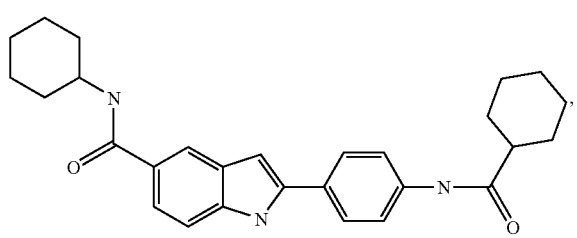
T-4
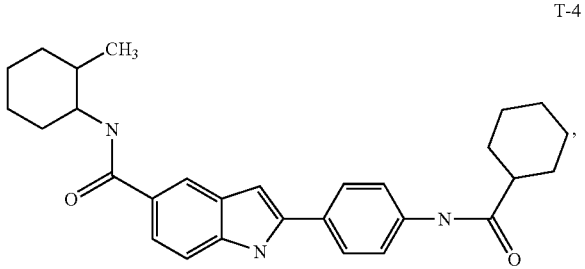
T-5
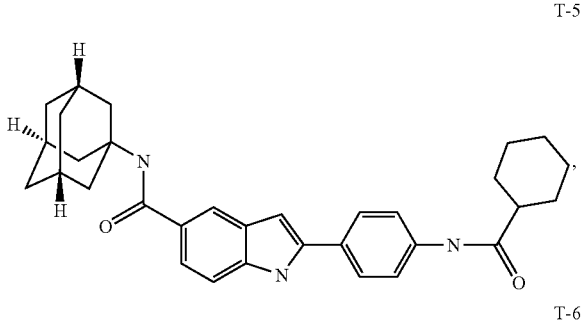
T-6
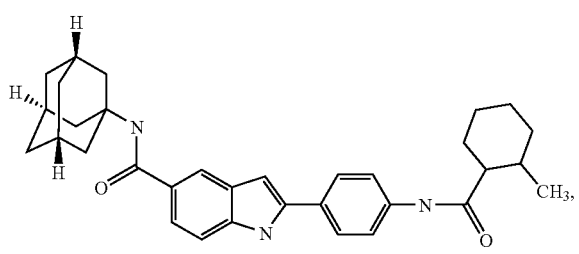
T-7
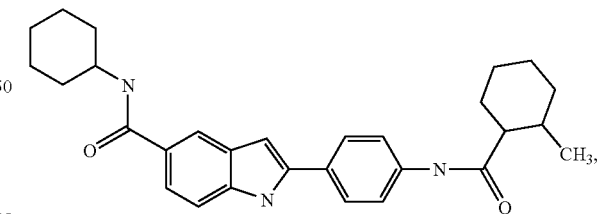
T-8
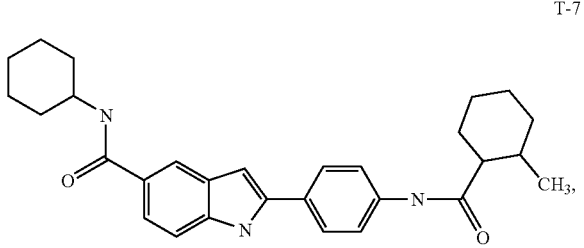

-continued
T-9
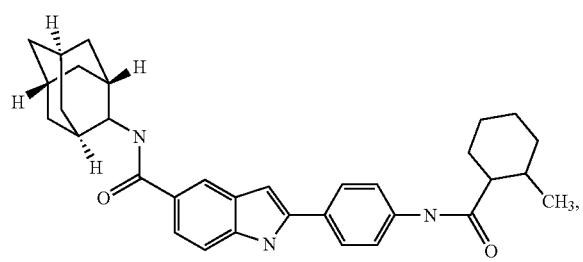
T-10
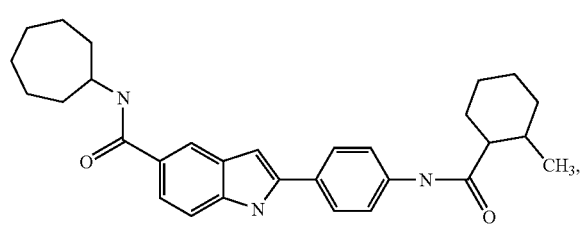
T-11
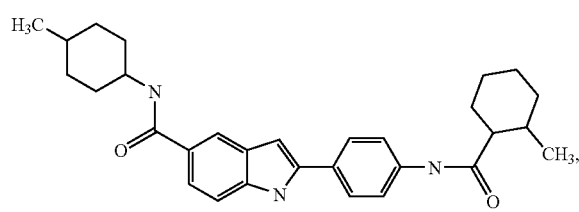
T-12
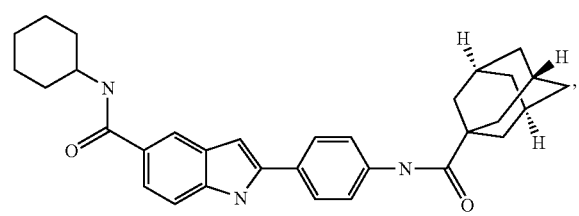
T-13
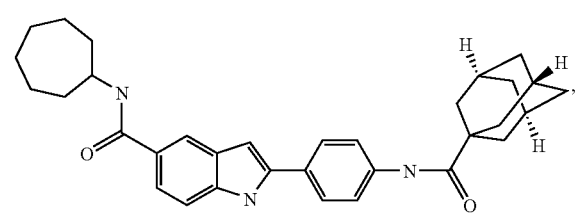
T-14
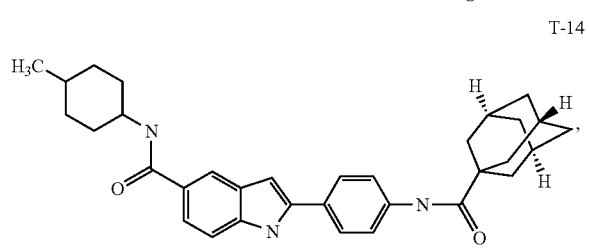
-continued
T-15
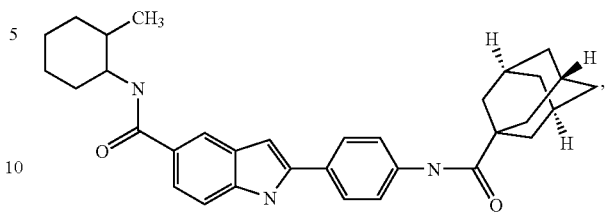
T-16
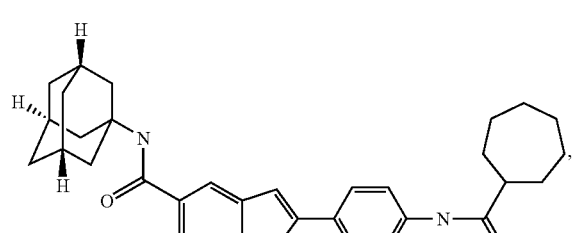
T-17
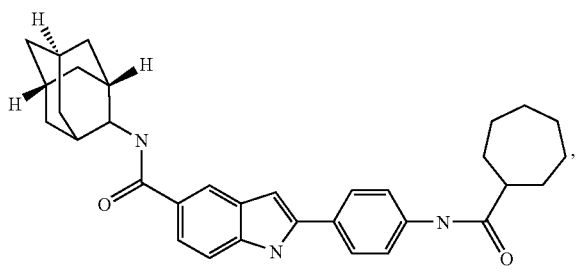
T-18
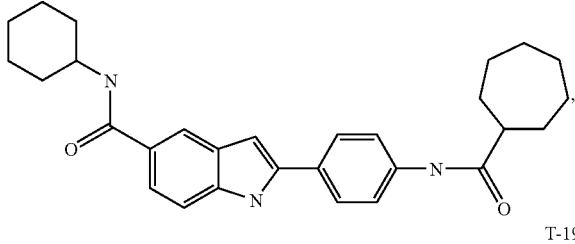
T-19
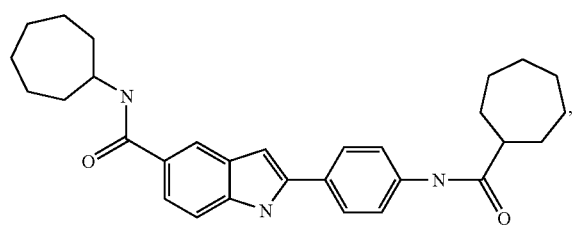
T-20
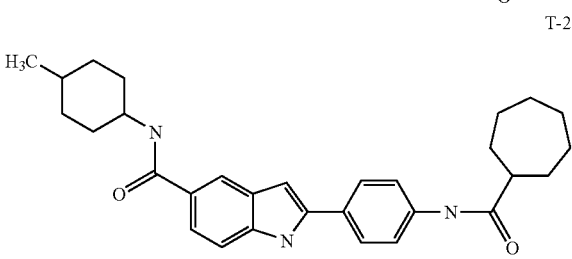

-continued
T-21
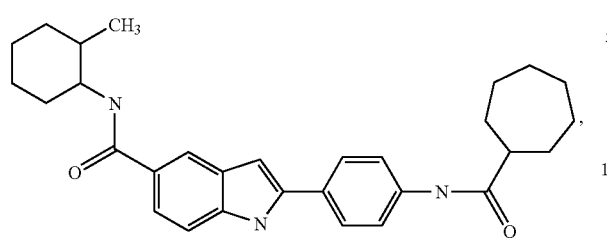
T-22
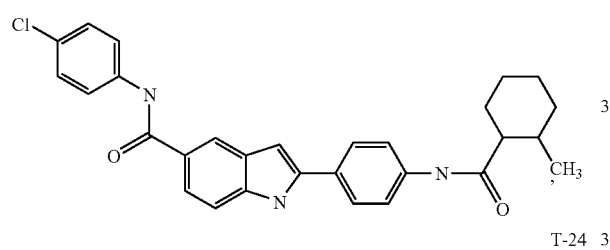
T-23
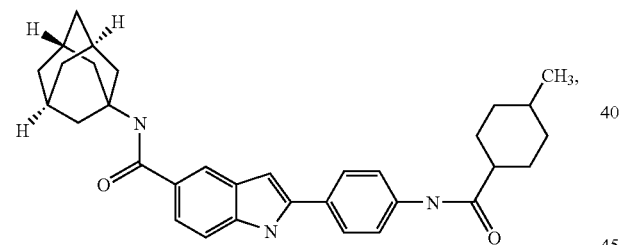
T-24
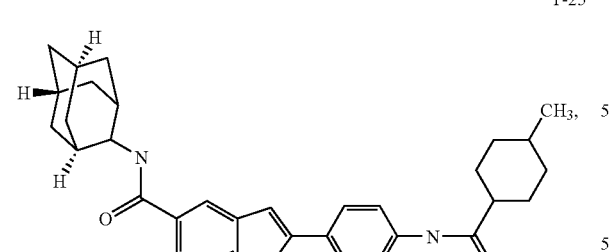
T-25
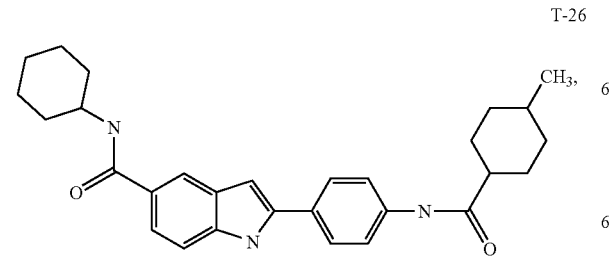
T-26
-continued
T-27
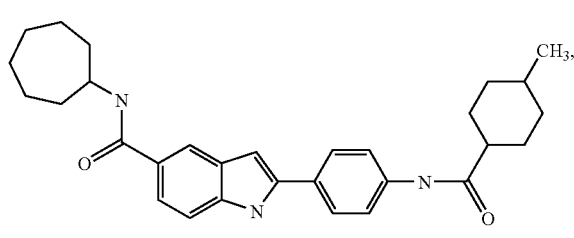
T-28
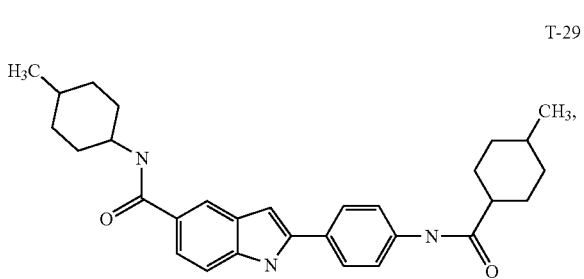
T-29
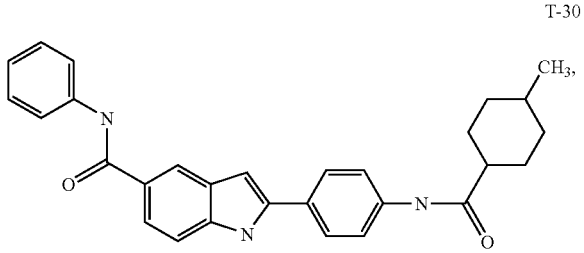
T-30
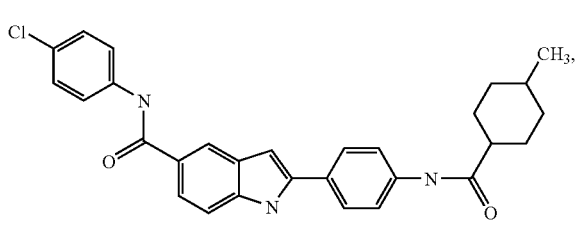
T-31
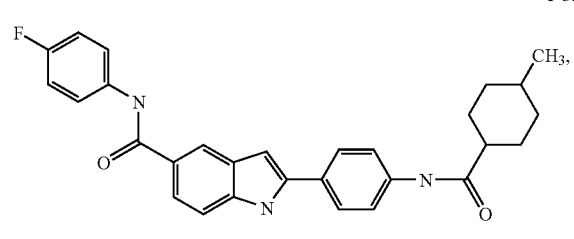
T-32

-continued
T-33
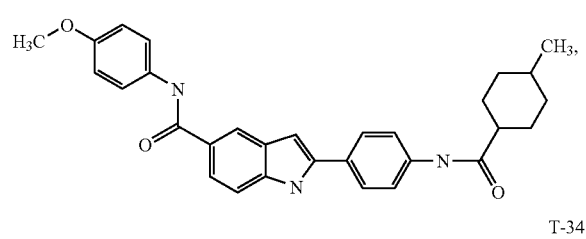
T-34
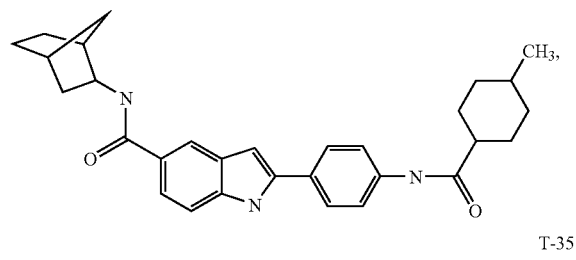
T-35
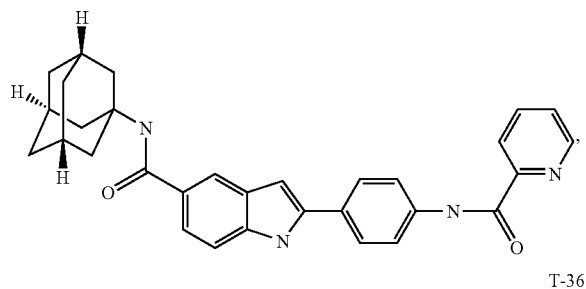
T-36
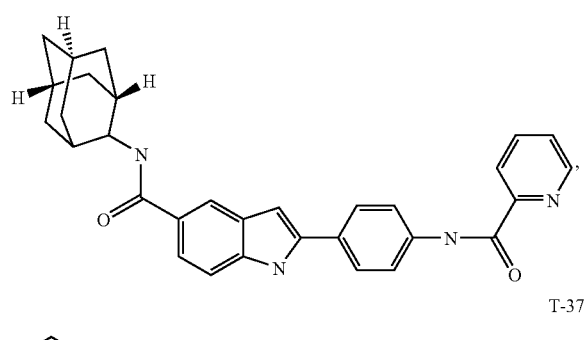
T-37
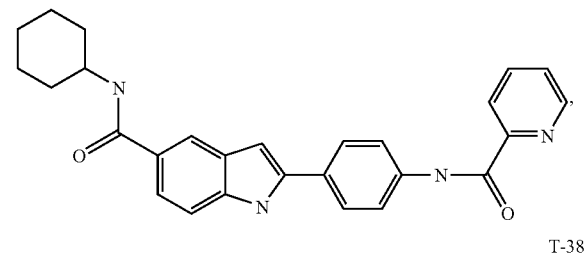
T-38
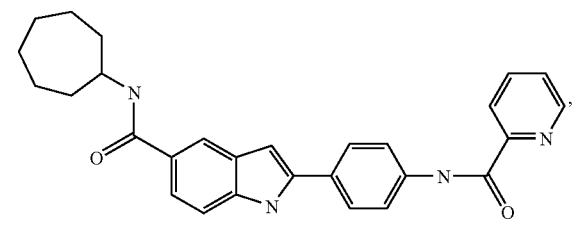
-continued
T-39
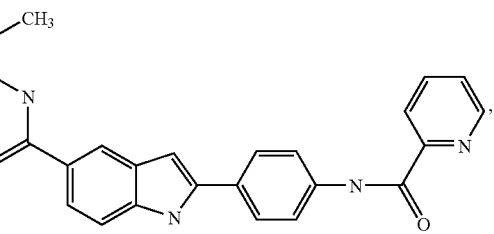
T-40
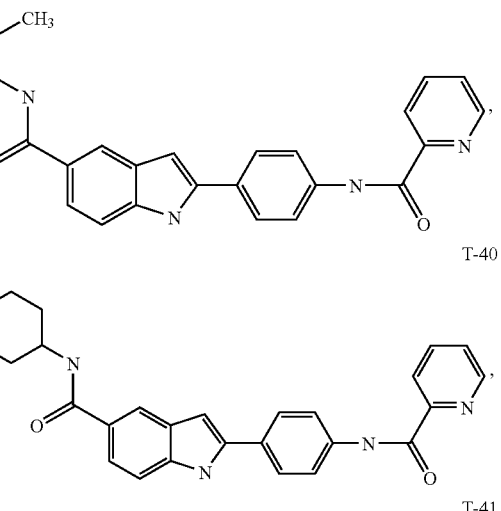
T-41
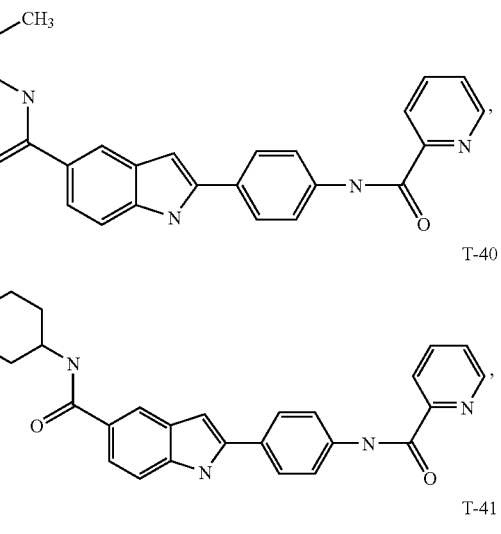
T-42
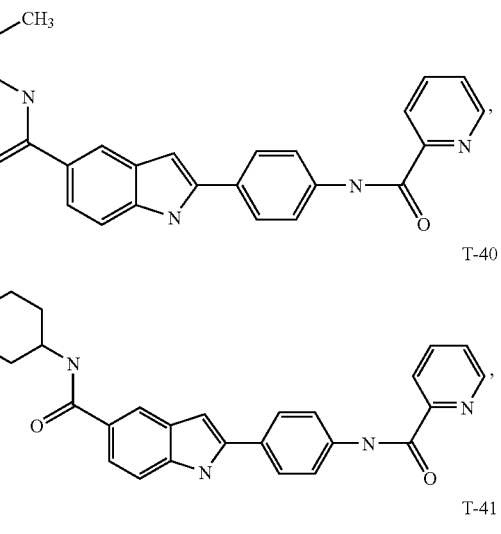
T-43
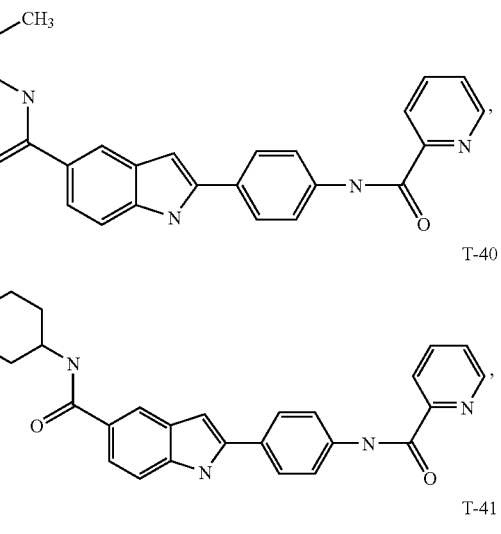
T-44
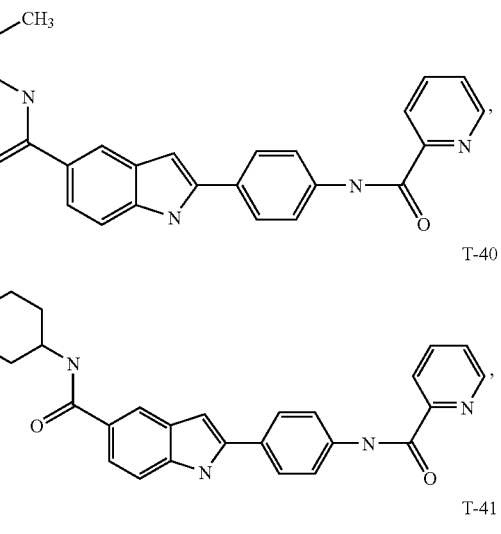

T-45
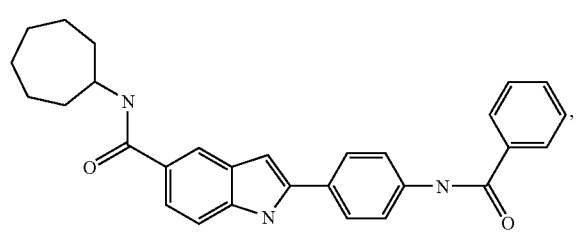
T-46
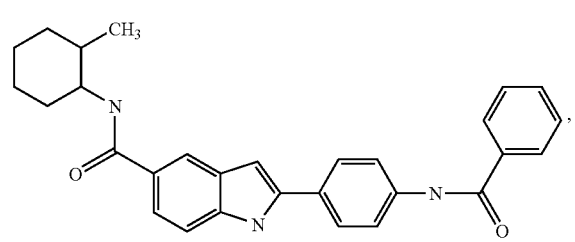
T-47
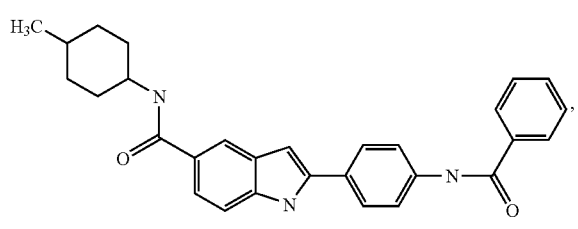
T-48
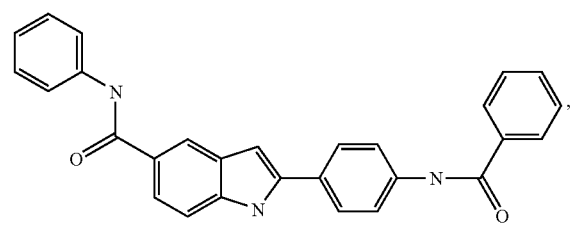
T-49
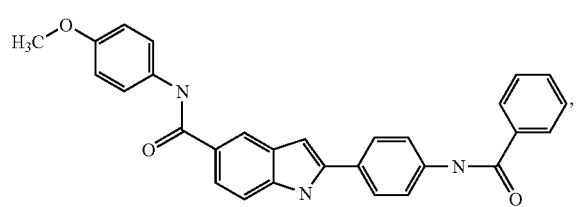
T-50
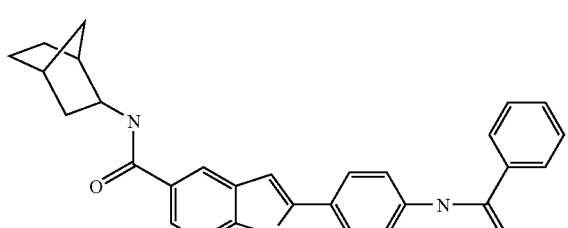
T-51
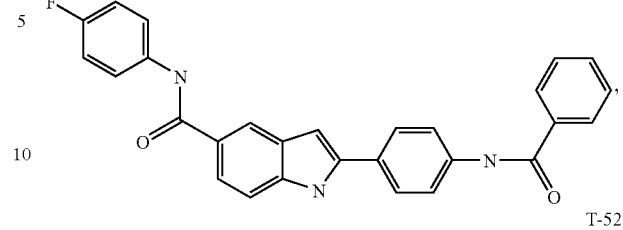
T-52
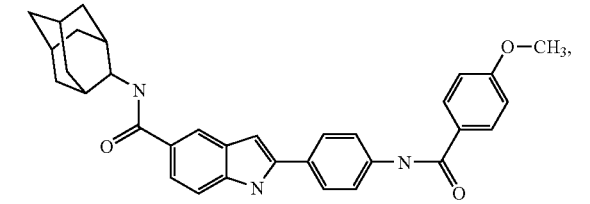
T-53
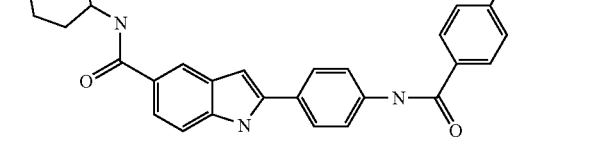
T-54
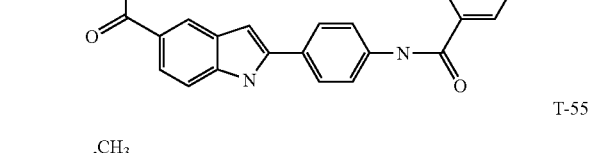
T-55
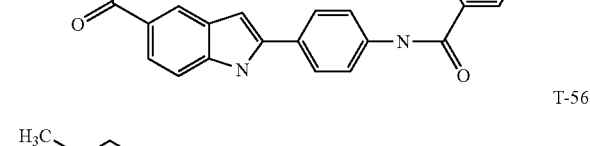
T-56
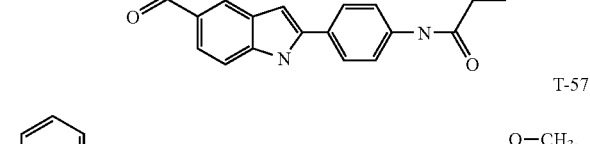
T-57
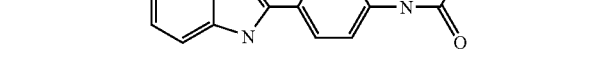

T-58
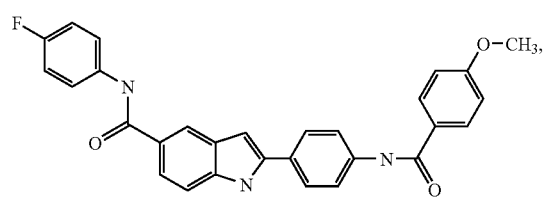
T-59
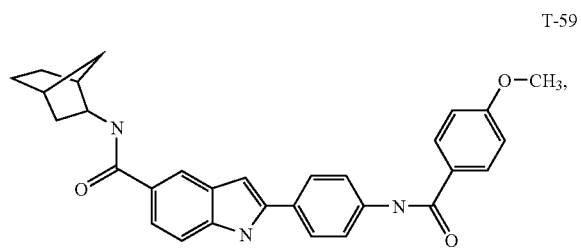
T-60
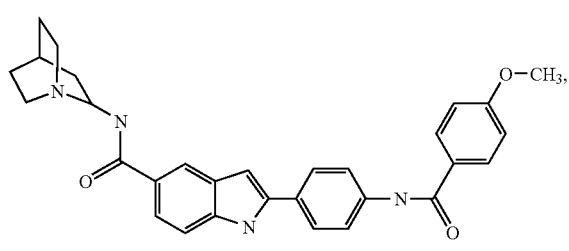
T-61
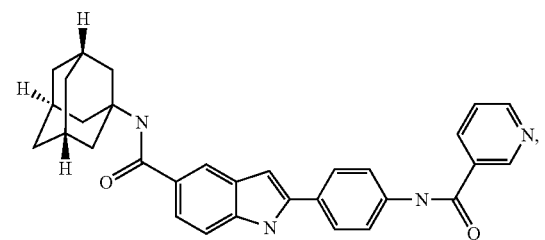
T-62
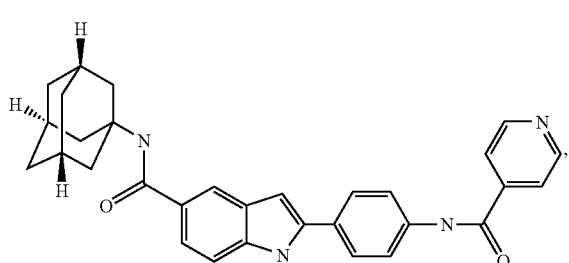
T-63
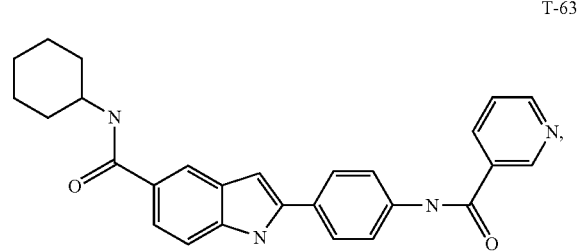
T-64
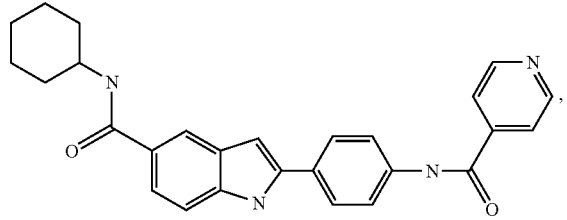
T-65
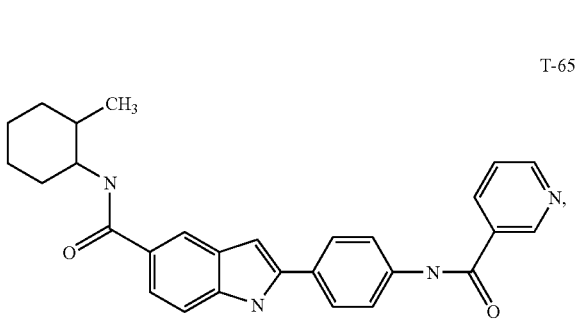
T-66
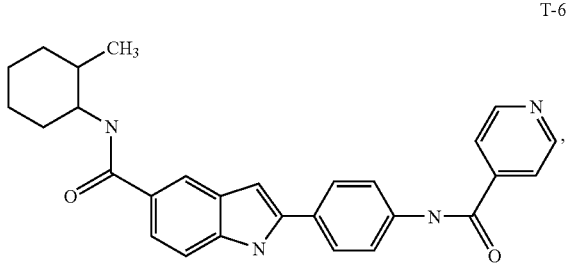
T-67
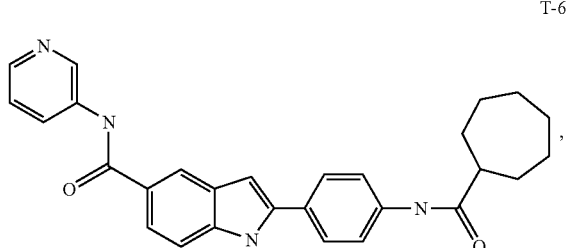
T-68
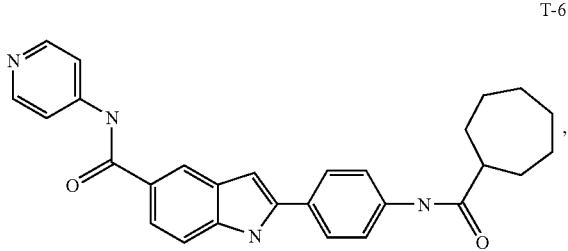
T-69
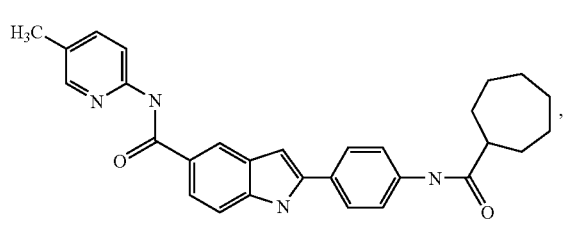

T-70
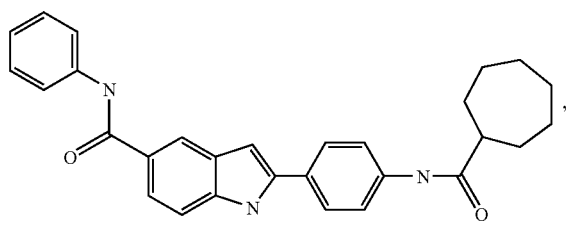
T-76
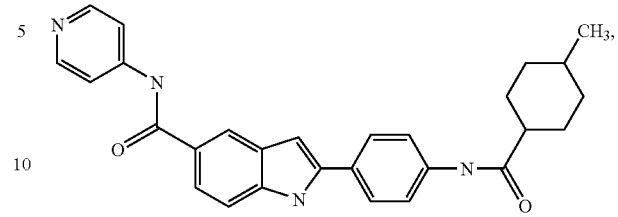
T-71
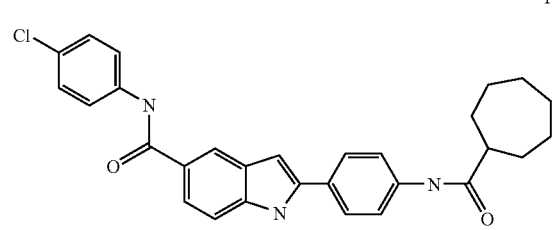
T-77
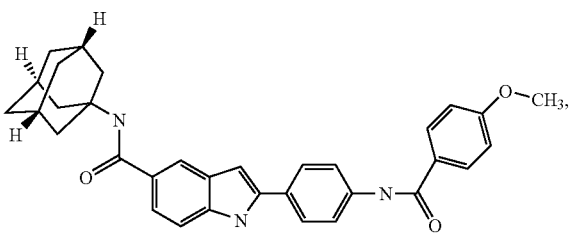
T-72
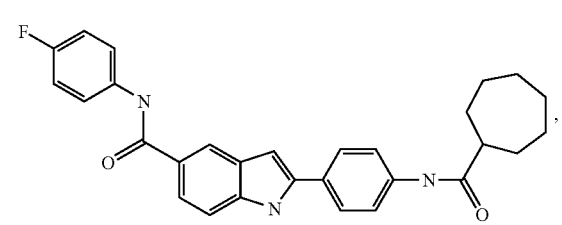
T-78
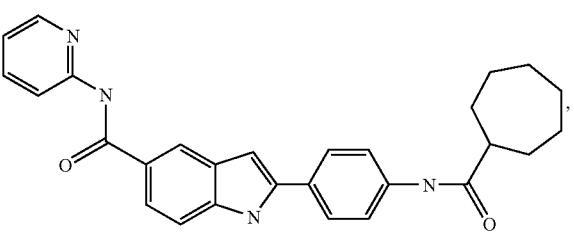
T-73
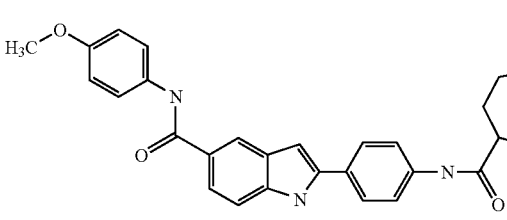
T-79
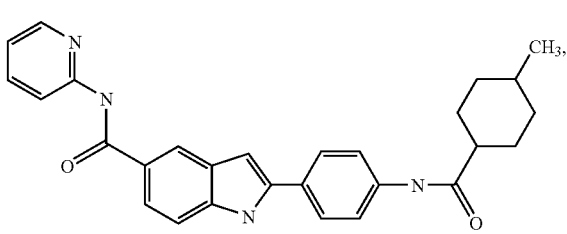
T-74
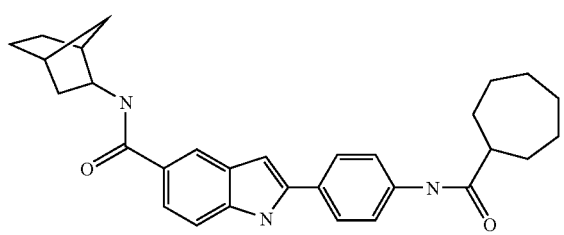
T-80
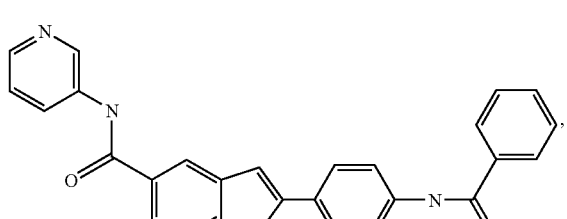
T-75
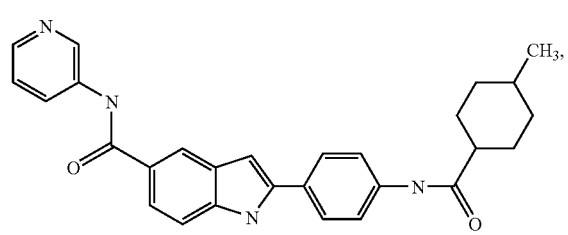
T-81

-continued

-continued
T-96
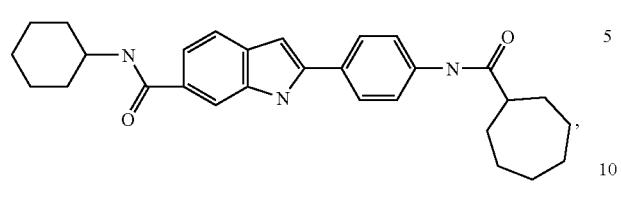
T-97
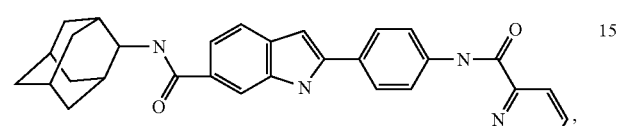
T-98
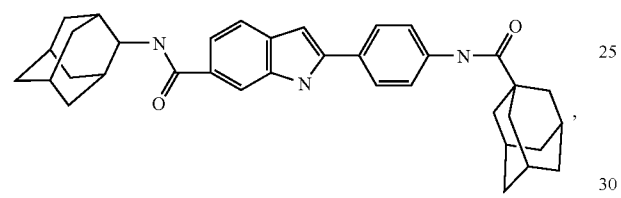
T-99
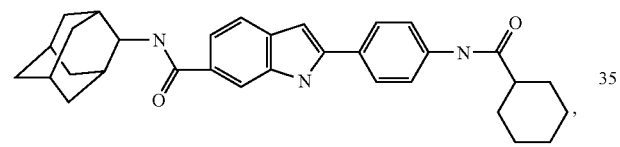
T-100
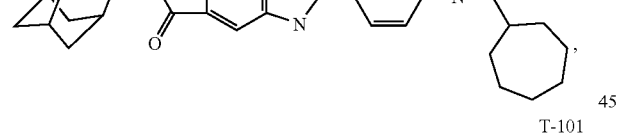
T-101
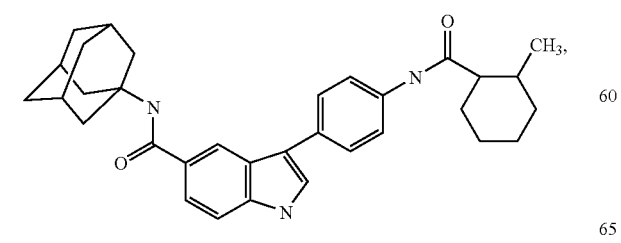
-continued
U-2
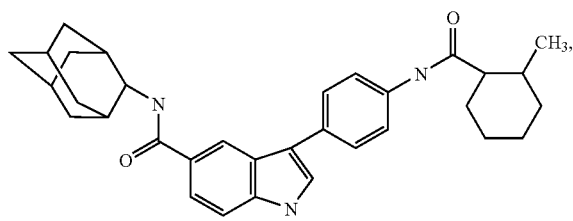
U-3
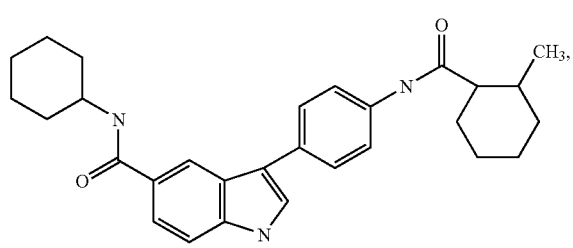
U-4
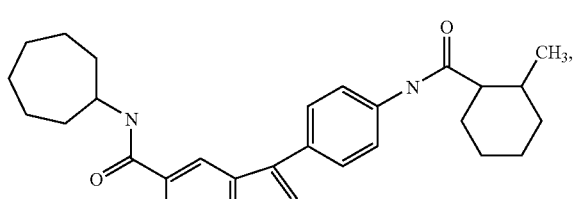
U-5
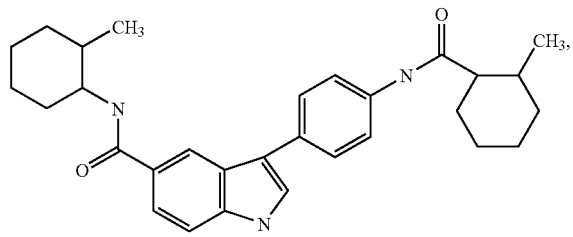
U-6
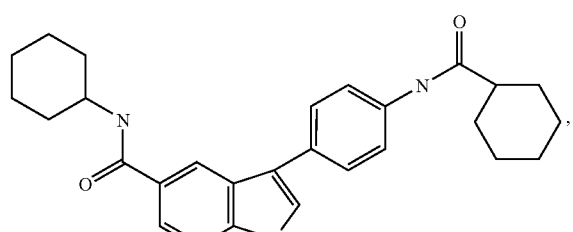
U-7
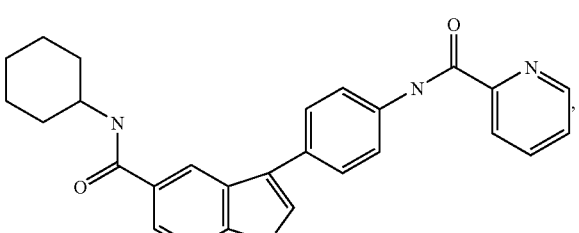

U-8
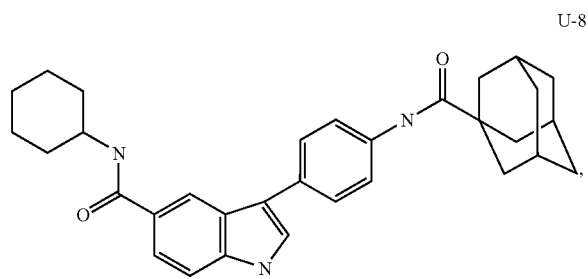
U-9
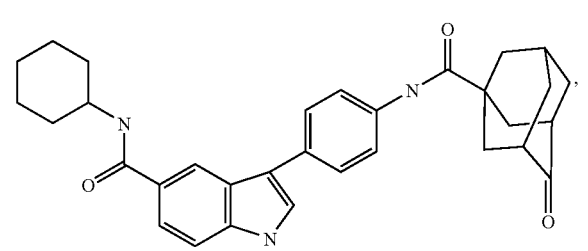
U-10
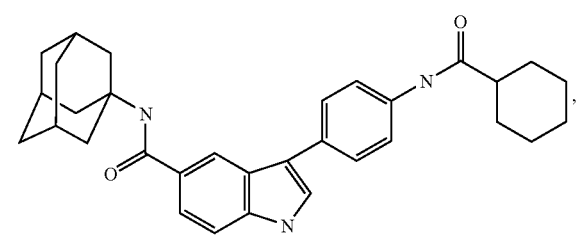
U-11
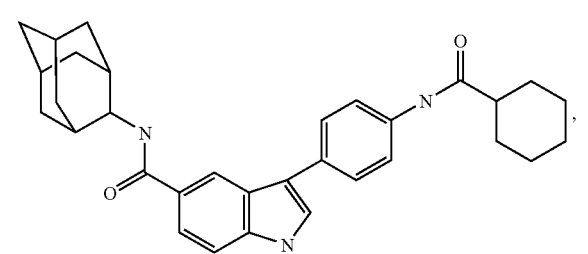
U-12
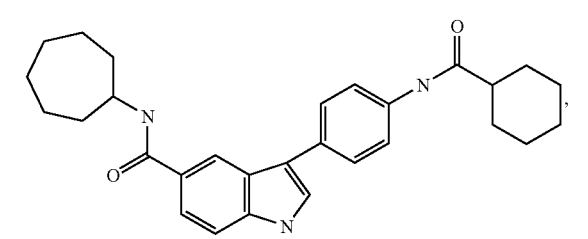
U-13
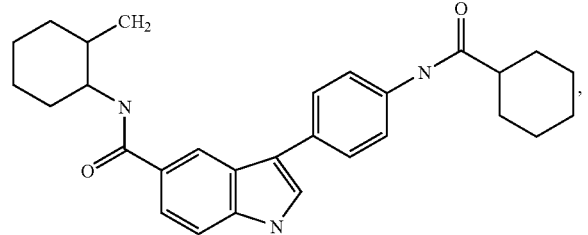
U-14
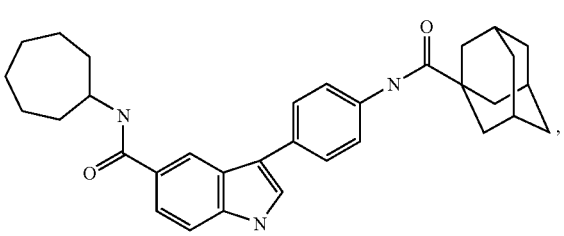
U-15
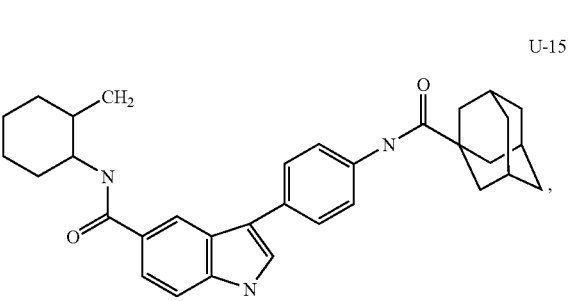
U-16
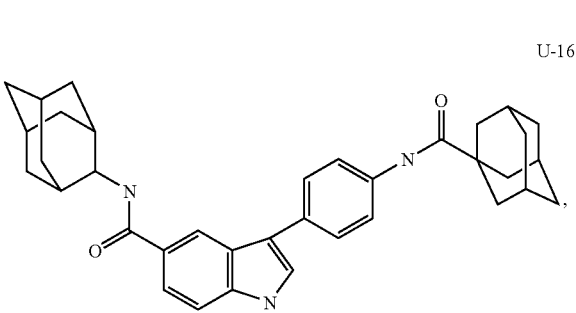
U-17
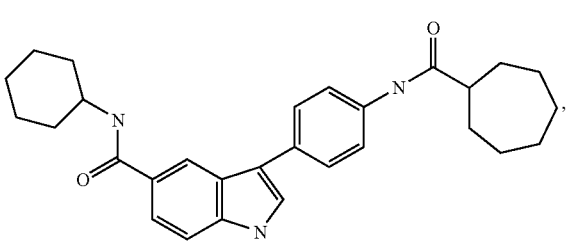
U-18
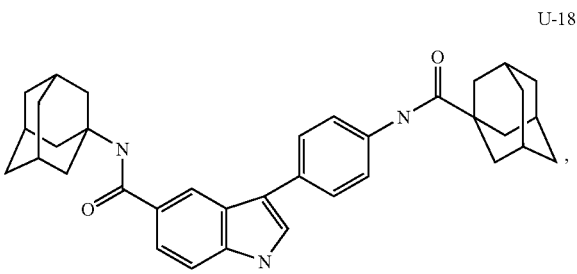

-continued
V-1
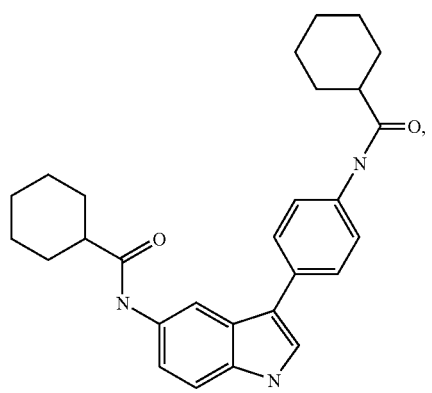
V-2
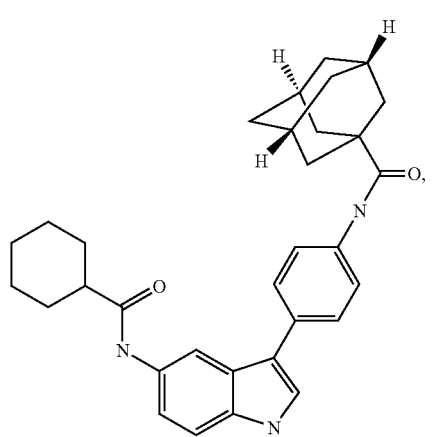
V-3
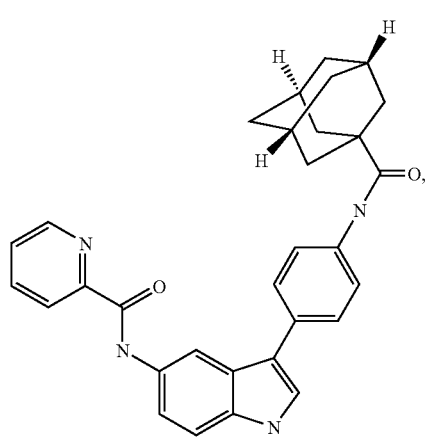
V-4
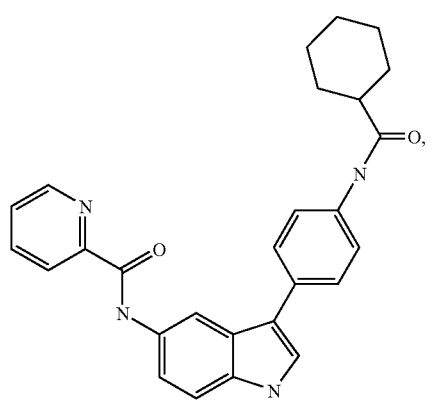
-continued
V-5
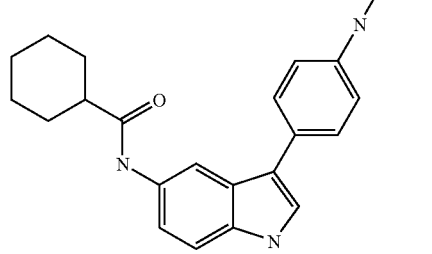
V-6
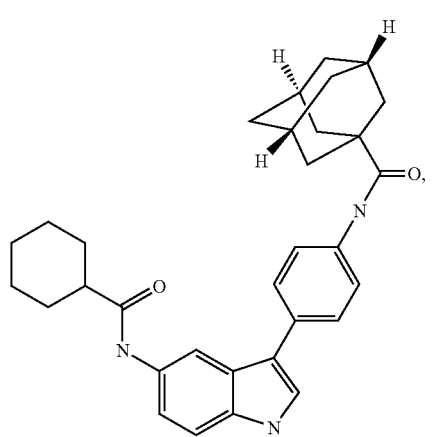
V-7
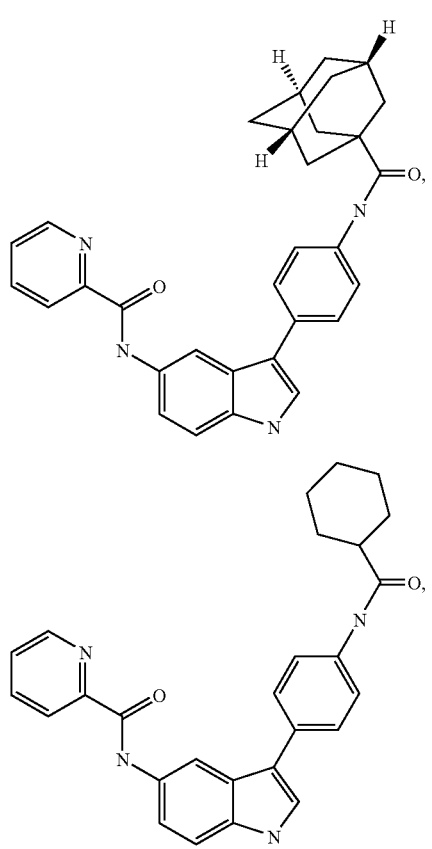
V-8
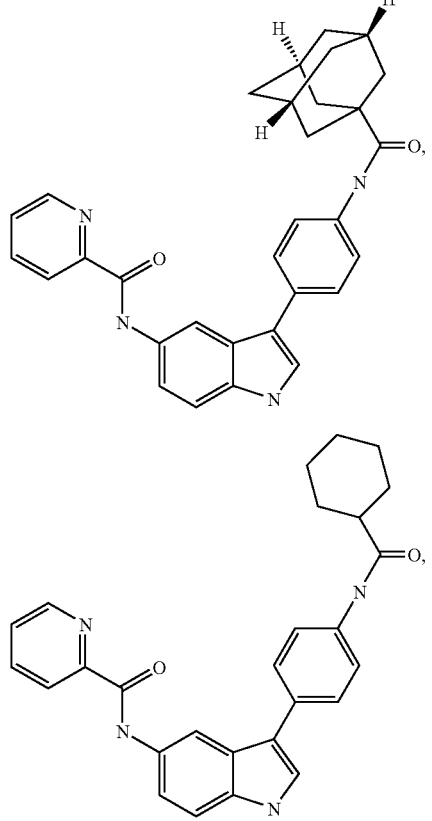

-continued
V-9
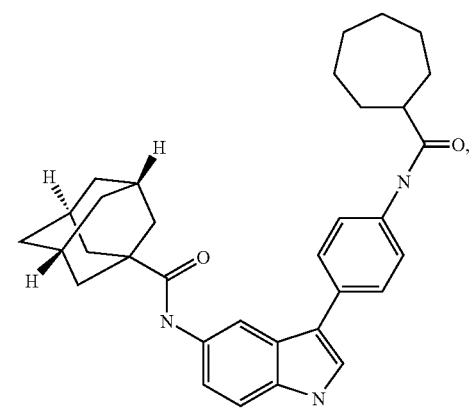
V-10
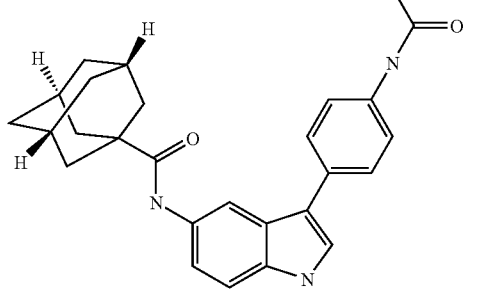
V-11
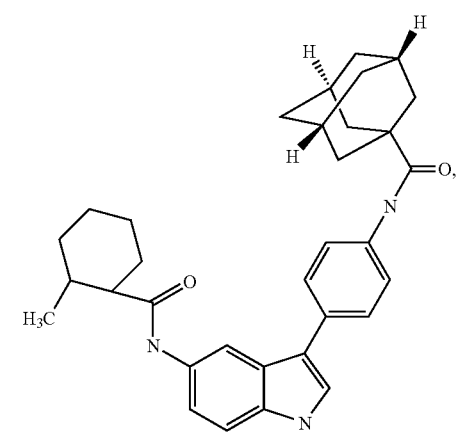
-continued
V-12
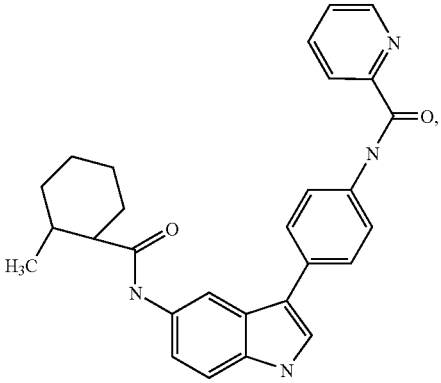
V-13
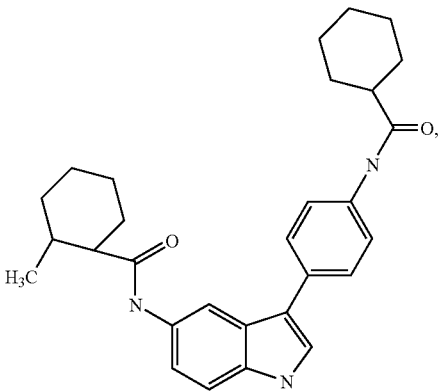
V-14
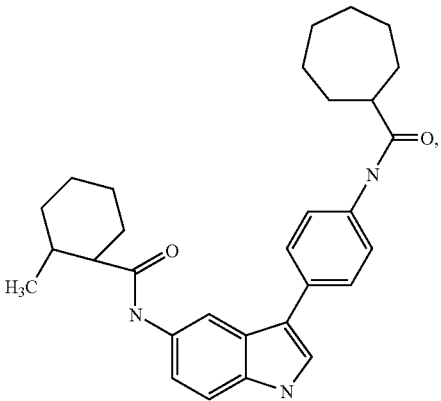
V-15
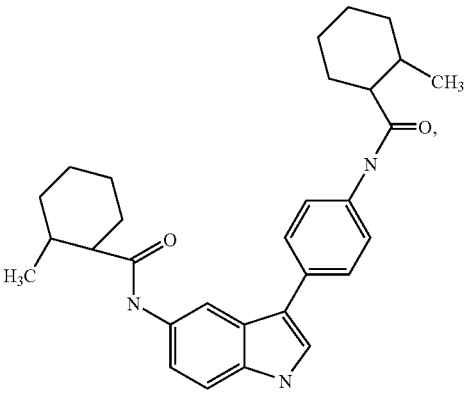

V-16
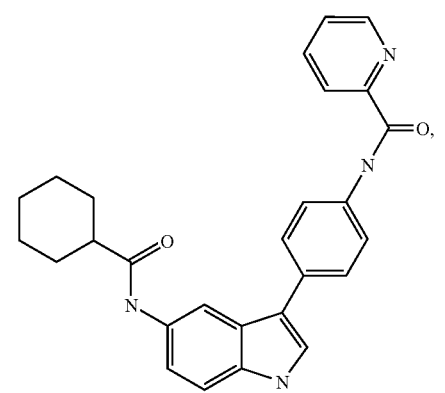
V-17
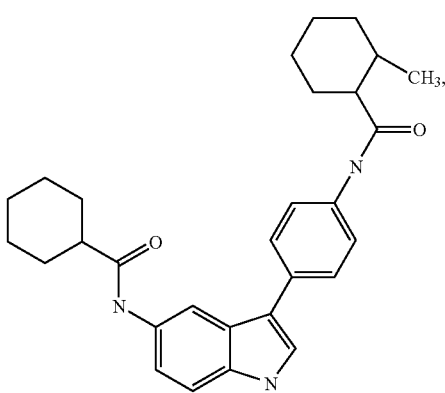
V-18
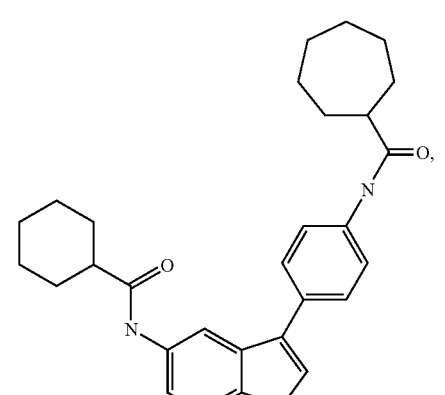
V-19
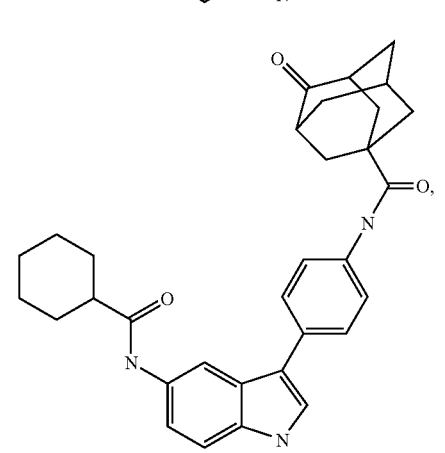
V-20
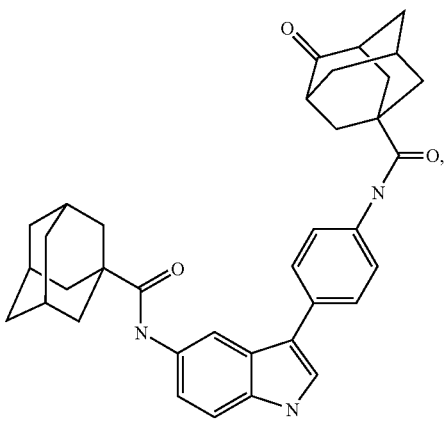
V-21
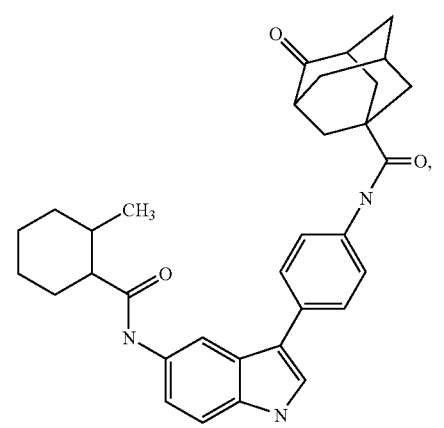
V-22
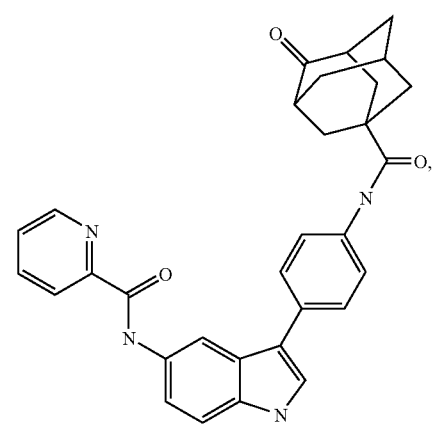

-continued

V-23
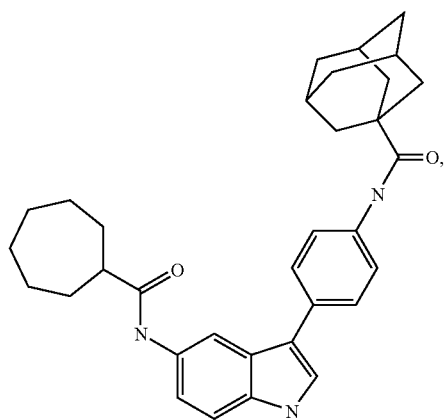

V-24
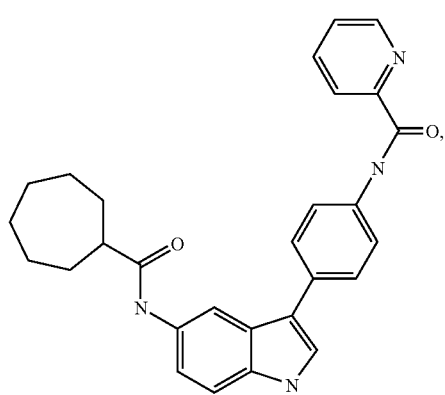

V-25
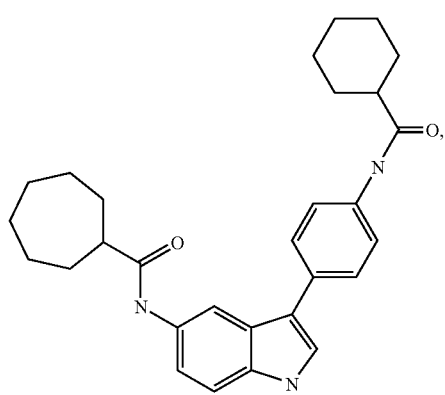

V-26
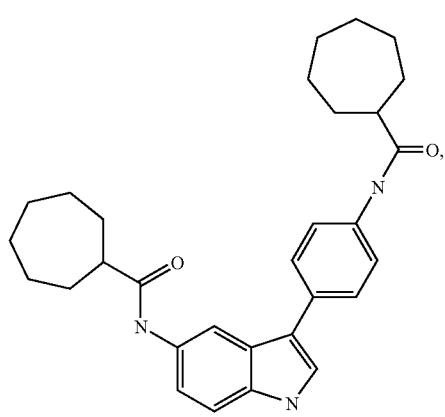

-continued

V-27
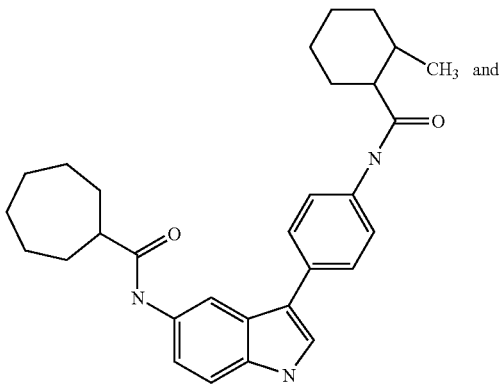

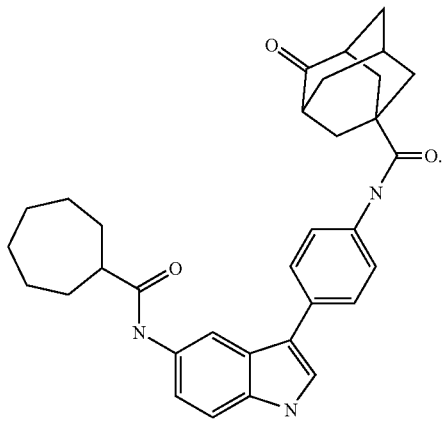

6. A compound or salt thereof represented by one of the following formulas:

Subgenus Ia wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$–$C_5$ alkyl, benzyl, p-fluorobenzyl and di-alkylamino alkyl, wherein said $C_1$–$C_5$ alkyl is selected from the group consisting of a straight chain, branched or cyclic alkyl;

wherein $R_1$ and $R_2$ are independently selected from the group consisting of H, alkyl, substituted alkyl, $C_3$–$C_9$ cycloalkyl, substituted $C_3$–$C_9$ cycloalkyl, polycyclic aliphatic groups, substituted polycyclic aliphatic groups, phenyl, substituted phenyl, naphthyl, substituted naphthyl, heterocyclic, polycyclic heterocyclic, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1–3 substituents, wherein said substituent is selected from the group consisting of H, halogens, polyhalogens, alkoxy group, substituted alkoxy, alkyl, substituted alkyl, dialkylaminoalkyl, hydroxyalkyl, hydroxyamino, alkoxyamino, carbonyl, OH, OCH$_3$, COOH, COOR' COR', CN, CF$_3$, OCF$_3$, NO$_2$, NR'R', NHCOR', and CONR'R'; and wherein R' is selected from the group consisting of H, alkyl, substituted alkyl, C$_3$–C$_9$ cycloalkyl, substituted C$_3$–C$_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur.

7. The compound or salt thereof of claim 6 selected from the group consisting of the following compounds:

S-6

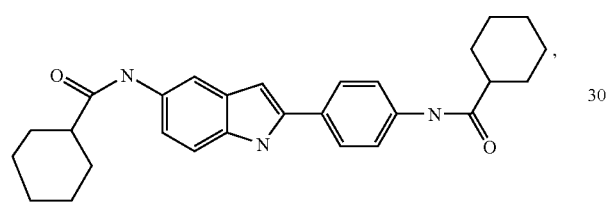

S-96

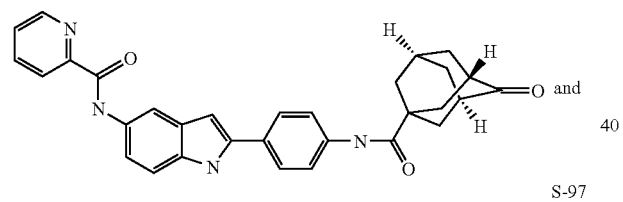

S-97

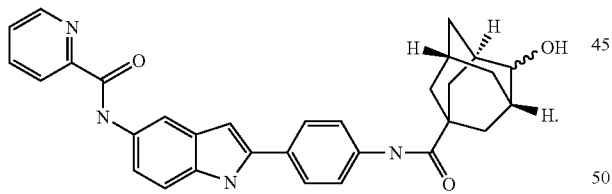

8. A compound or salt thereof represented by one of the following formulas:

Subgenus IIa

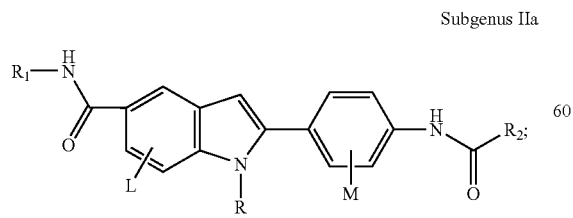

wherein L and M are independently selected from the group consisting of H, alkyl, alkoxy, aryl, substituted aryl, hydroxy, halogen, amino, alkylamino, nitro, cyano, CF$_3$, OCF$_3$, CONH$_2$, CONHR and NHCOR$_1$;

wherein R is selected from the group consisting of H, C$_1$–C$_5$ alkyl, benzyl, p-fluorobenzyl and di-alkylamino alkyl, wherein said C$_1$–C$_5$ alkyl is selected from the group consisting of a straight chain, branched or cyclic alkyl;

wherein R$_1$ and R$_2$ are independently selected from the group consisting of H, alkyl, substituted alkyl, C$_3$–C$_9$ cycloalkyl, substituted C$_3$–C$_9$ cycloalkyl, polycyclic aliphatic groups, substituted polycyclic aliphatic groups, phenyl, substituted phenyl, naphthyl, substituted naphthyl, heterocyclic, polycyclic heterocyclic, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1–3 substituents, wherein said substituent is selected from the group consisting of H, halogens, polyhalogens, alkoxy group, substituted alkoxy, alkyl, substituted alkyl, dialkylaminoalkyl, hydroxyalkyl, hydroxyamino, alkoxyamino, carbonyl, OH, OCH$_3$, COOH, COOR' COR', CN, CF$_3$, OCF$_3$, NO$_2$, NR'R', NHCOR', and CONR'R'; and wherein R' is selected from the group consisting of H, alkyl, substituted alkyl, C$_3$–C$_9$ cycloalkyl, substituted C$_3$–C$_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur.

9. The compound or salt thereof of claim 8 selected from the group consisting of the following compounds:

T-3

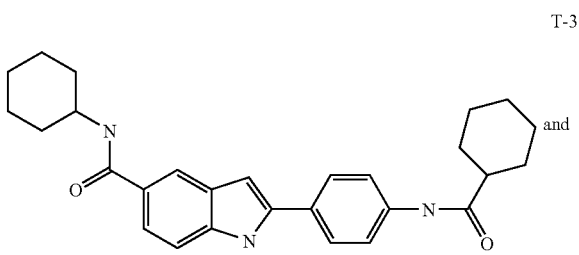

T-83

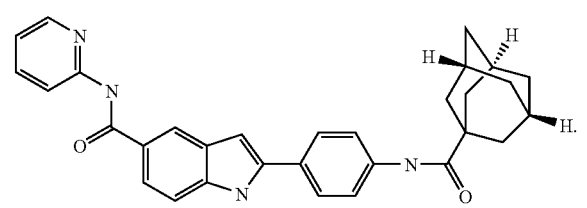

10. A compound or salt thereof represented by one of the following formulas:

Subgenus IIb

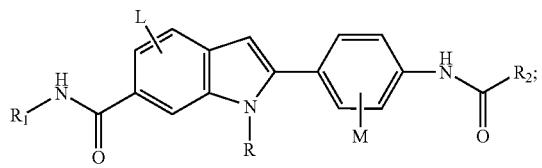

wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$–$C_5$ alkyl, benzyl, p-fluorobenzyl and di-alkylamino alkyl, wherein said $C_1$–$C_5$ alkyl is selected from the group consisting of a straight chain, branched or cyclic alkyl;

wherein $R_1$ and $R_2$ are independently selected from the group consisting of H, alkyl, substituted alkyl, $C_3$–$C_9$ cycloalkyl, substituted $C_3$–$C_9$ cycloalkyl, polycyclic aliphatic groups, substituted polycyclic aliphatic groups, phenyl, substituted phenyl, naphthyl, substituted naphthyl, heterocyclic, polycyclic heterocyclic, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1–3 substituents, wherein said substituent is selected from the group consisting of H, halogens, polyhalogens, alkoxy group, substituted alkoxy, alkyl, substituted alkyl, dialkylaminoalkyl, hydroxyalkyl, hydroxyamino, alkoxyamino, carbonyl, OH, $OCH_3$, COGH, COOR' COR', CN, $CF_3$, $OCF_3$, $NO_2$, NR'R', NHCOR', and CONR'R'; and wherein R' is selected from the group consisting of H, alkyl, substituted alkyl, $C_3$–$C_9$ cycloalkyl, substituted $C_3$–$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur.

11. The compound or salt thereof of claim 10 selected from the group consisting of the following compounds:

T-88

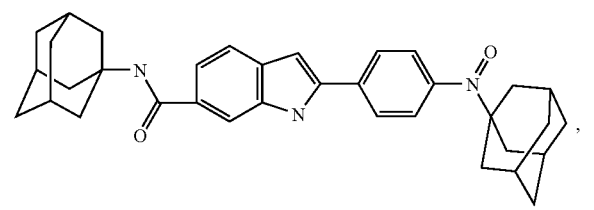

T-89

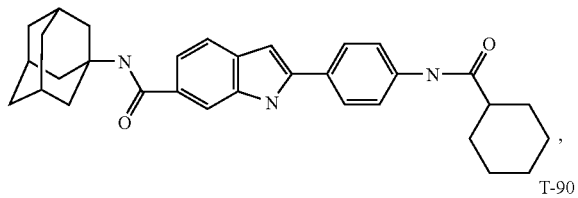

T-90

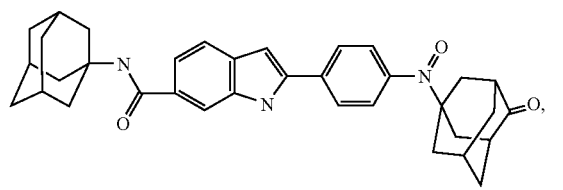

T-91

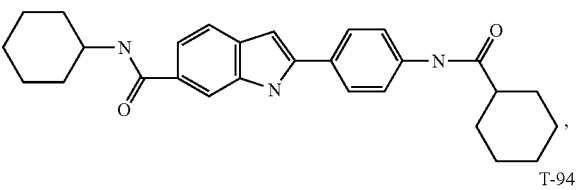

T-94

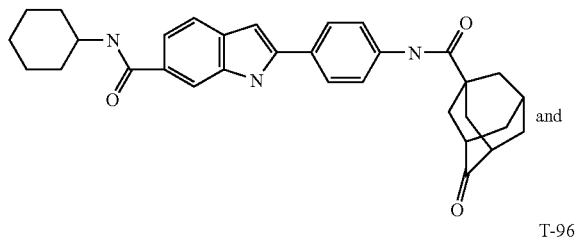

and

T-96

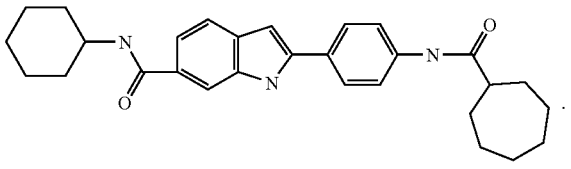

12. A method of preparing a compound or salt thereof of Genus I as defined in claim 1 comprising: reacting a compound having formula:

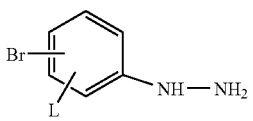

with a compound having formula:

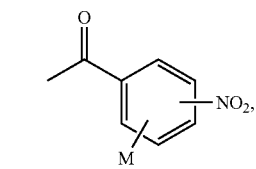

thereby forming a first intermediate having formula:

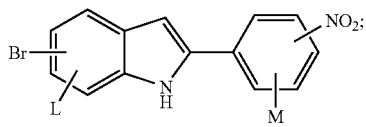

performing a reductive amination to said first intermediate, thereby forming a second intermediate having formula:

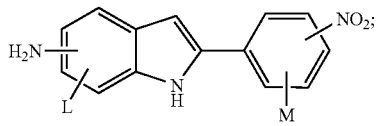

reacting an acyl chloride with said second intermediate, thereby forming a third intermediate having formula:

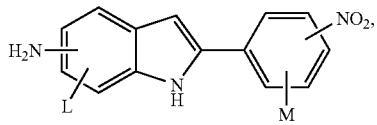

reducing said third intermediate, thereby forming a fourth intermediate having formula:

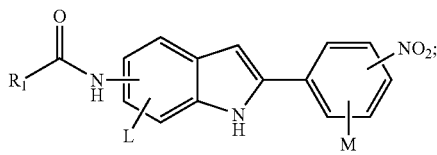

and
reacting an acyl chloride with the said fourth intermediate, thereby forming a compound or salt thereof of Genus I.

13. A method of preparing a compound or salt thereof of Genus II as defined in claim 1 comprising: reacting a compound having formula

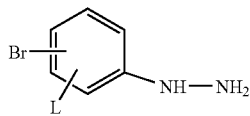

with a compound having formula

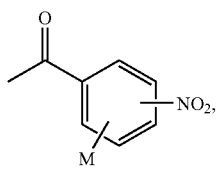

thereby forming a first intermediate;

reacting said first intermediate with cyanide ion, thereby forming a second intermediate having formula:

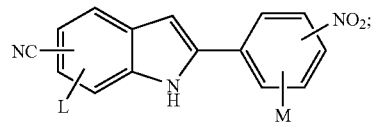

performing hydrolysis on said second intermediate, thereby forming a third intermediate having formula:

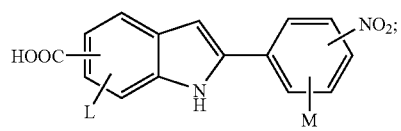

reacting said third intermediate with an alkylamine, thereby forming a fourth intermediate having formula:

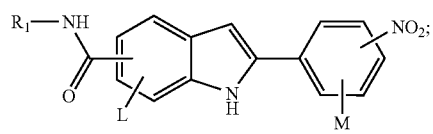

reducing said fourth intermediate; thereby forming a fifth intermediate having formula:

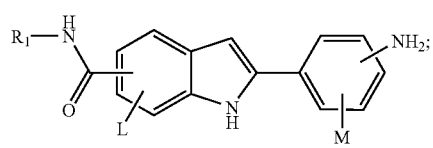

and
reacting an acyl chloride with said fifth intermediate; thereby forming a compound or salt thereof of Genus II.

14. A method of preparing a compound or salt thereof of Genus III as defined in claim 1 comprising: reacting a compound having formula:

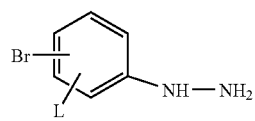

with a compound having formula:

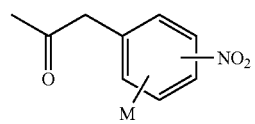

in the presence of a Lewis acid, thereby forming a first intermediate having formula:

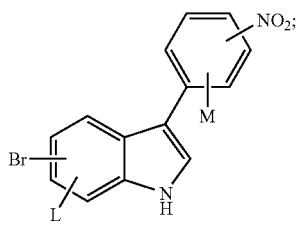

reacting said first intermediate with a cyanide ion, thereby forming a second intermediate having formula:

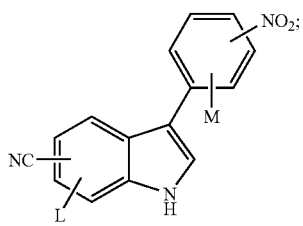

performing hydrolysis on said second intermediate, thereby forming a third intermediate having formula:

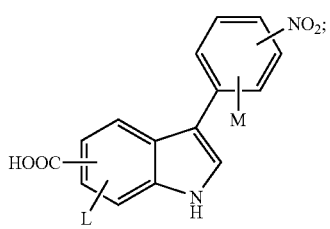

reacting said third intermediate with an alkylamine, thereby forming a fourth intermediate having formula:

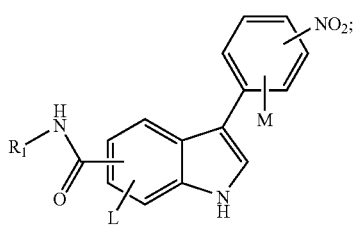

reducing said fourth intermediate; thereby forming a fifth intermediate having formula:

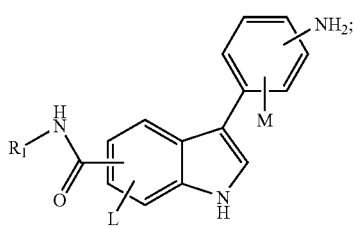

and
reacting an acyl chloride with said fifth intermediate; thereby forming a compound or salt thereof of Genus III.

15. A method of preparing a compound or salt thereof of Genus IV as defined in claim 1 comprising:
reacting a compound having formula:

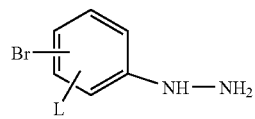

with a compound having formula:

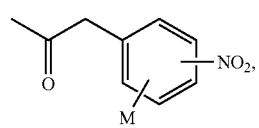

thereby forming a first intermediate having formula:

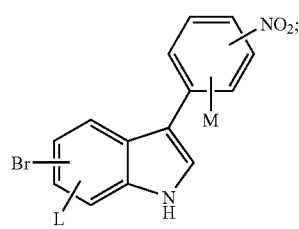

performing a reductive amination to said first intermediate, thereby forming a second intermediate having formula:

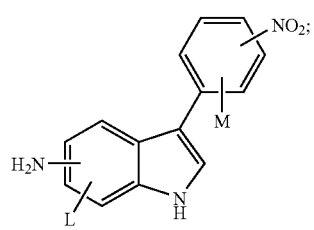

reacting an acyl chloride with said second intermediate, thereby forming a third intermediate having formula:

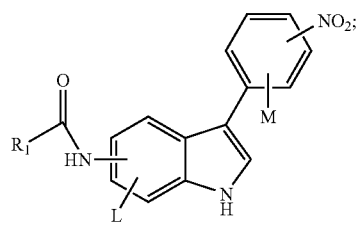

reducing said third intermediate, thereby forming a fourth intermediate having formula:

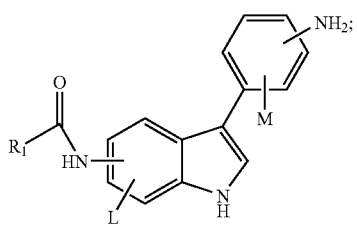
and
reacting an acyl chloride with said fourth intermediate, thereby forming a compound or salt thereof of Genus IV.